US007575928B2

(12) United States Patent
Lin et al.

(10) Patent No.: US 7,575,928 B2
(45) Date of Patent: Aug. 18, 2009

(54) GENES FOR DIAGNOSING COLORECTAL CANCER

(75) Inventors: Shiu-Ru Lin, Kaohsiung (TW); Jaw-Yuan Wang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 142 days.

(21) Appl. No.: 10/786,148

(22) Filed: Feb. 26, 2004

(65) Prior Publication Data

US 2005/0191634 A1 Sep. 1, 2005

(51) Int. Cl.

| | |
|---|---|
| ***G01N 33/48*** | (2006.01) |
| ***C12Q 1/68*** | (2006.01) |
| ***A61B 5/055*** | (2006.01) |
| *C12N 15/867* | (2006.01) |

(52) U.S. Cl. .............. 436/64; 435/6; 435/4; 424/9.351; 424/9.1

(58) Field of Classification Search ................... 436/64; 435/6, 4; 424/9.351, 9

See application file for complete search history.

(56) References Cited

U.S. PATENT DOCUMENTS

2004/0146921 A1* 7/2004 Eveleigh et al. ................ 435/6
2005/0287544 A1* 12/2005 Bertucci et al. ................ 435/6

FOREIGN PATENT DOCUMENTS

WO 00/55351 9/2000

* cited by examiner

*Primary Examiner*—T. D. Wessendorf
(74) *Attorney, Agent, or Firm*—WPAT, P.C.; Anthony King

(57) ABSTRACT

This invention relates to provide the genes for diagnosing colorectal cancer, the gene sequences searching comprise the steps of: (1) deriving epithelium cells from normal intestines, polypus of intestines and colorectal cancer tissue; (2) collecting genes with highly differential gene expression by Suppression Subtractive Hybridization (SSH), and building library; (3) deriving colonies with relatively high signal intensities from cancer tissue; (4) collecting more clinically cancer tissues by Northern Hybridization, real-time Polymerase Chain Reaction (PCR) combined with analysis of bioinformation to affirm variation between differential gene expression; and (5) selecting the most suitable genes from said library, and using the gene sequence as reagent provides the effects of early diagnosis, specificity, highly sensitivity and safety.

1 Claim, 8 Drawing Sheets

Genes of colorectal cancer

Forming plasmid or other vectors of genes for diagnosing colorectal cancer

Plasmid transfer to transgene or further forming gene recombined cell antibody

GENES FOR DIAGNOSING COLORECTAL CANCER

REFERENCE CITED

1. WO005531

FIELD OF THE INVENTION

This invention relates to genes for diagnosing colorectal cancer, particularly provided a method of clinical diagnosis for colorectal cancer which enables the effects of early diagnosis, specificity, highly sensitivity and safety.

BACKGROUND OF THE INVENTION

Colorectal cancer is one of the most common malignant tumors of the world; it is the second most frequent cause of malignant tumor related mortality in developed countries. In developed countries, mortality rate caused by colorectal cancer seems have a progressively descending tendency in the past 20 years. There are motivations for early diagnosis and for improvement in methods of therapy and medicines. In Taiwan, the rate of suffering for colorectal cancer is rising constantly, furthermore, there is evidence of an age-descending tendency.

According to a 2002 survey by the Department of Health (DOH), the highest level of the executive branch in Taiwan, on the top ten related cancer of Taiwanese population, colorectal cancer (CRC) is the third leading cause of cancer-related death for male and female. About 6681 new cases of colorectal cancer were diagnosed according to statistical data by DOH in 1999, and 3649 patients died in Taiwan due to colorectal cancer according to statistical data by DOH in 2002. The average age of colorectal cancer patient is lower than other countries. In other words, twenty-year-old or thirty-year-old people suffer from the colorectal cancer in Taiwan. Therefore, we can't ignore the possibility of the colorectal cancer occurring in younger populations.

Although methods of diagnosis and surgical operation treatment have improved for colorectal cancer patients, when one makes a comparison between early diagnosis with later period diagnosis by surgical operation, treatment is able to probably overcome colorectal cancer in early diagnosis, but is not able to absolutely overcome colorectal cancer in later period diagnosis. Thus far metastasis are the main problem in the treatment for the colorectal cancer, therefore, a method with high sensitivity, high specificity and easy diagnosis that can detect arly and potentially curable CRC would be a novel target for CRC diagnosis and therapy.

The present invention is to provide functional genetic method, for diagnostic genes of colorectal cancer consist of 71 types of genes, that can be applied for early diagnosing possibility of recurrence and metastasis for colorectal patients. Simultaneously, tracing of 100 colorectal cancer cases have found a 92% genes variation in colorectal tissue. In the process of tracing 100 colorectal cancer cases simultaneously, mutation of genes is found in 92% colorectal cancer tissues. In the tracing process, although CEA of 16 patients remained in normal value range, the method can detect early tumor cells in blood by using genes variation testing.

In WO0055351, ROSEN CRAIG A et. al., entitled "Human Colon Cancer Associated Gene Sequences And Polypeptides", disclose colon cancer related polynucleotides and the polypeptides encoded by the polynucleotides herein collectively known as "colon cancer antigens", screening methods for identifying agonists and antagonists of colon cancer antigens of the invention. But, the present invention is to provide SSH and cDNA microarray technology to identify candidate marker genes which are overexpressed continuously from colorectal proliferous polypus to colorectal oncogene, detecting overexpressed genes are selected from up regulation genes which related intently in colorectal cancer oncogene, and down regulation genes which related in colorectal cancer oncogene. The total 71 genes are used to diagnosing early colorectal cancer.

SUMMARY OF THE INVENTION

Therefore, the main purpose according to the present invention is to provide methods of clinical diagnosis for colorectal cancer for early diagnosis, specificity, highly sensitivity and safety.

For the purpose stated above, the method comprises the steps of: (1) deriving epithelium cells from normal intestines, polypus of intestines and colorectal cancer tissue; (2) collecting genes with highly differential gene expression by Suppression Subtractive Hybridization (SSH), and building library; (3) deriving colonies with relatively high signal intensities from cancer tissue; (4) collecting more clinically cancer tissues by Northern Hybridization, real-time Polymerase Chain Reaction (PCR) combined with analysis of bioinformation to affirm variation between differential gene expression; and (5) selecting the most suitable genes from said library. Moreover, the reagent uses the gene sequence as method of clinical diagnosis for colorectal cancer to the early diagnosis.

BRIEF DESCRIPTION OF THE DRAWINGS

The present invention will be better understood from the following detailed description of preferred embodiments of the invention, taken in conjunction with the accompanying drawings, in which.

Table 1 is a table showing the result of clinical examination of colorectal cancer biochip.

DESCRIPTION OF THE PREFERRED EMBODIMENTS

Figure 1:
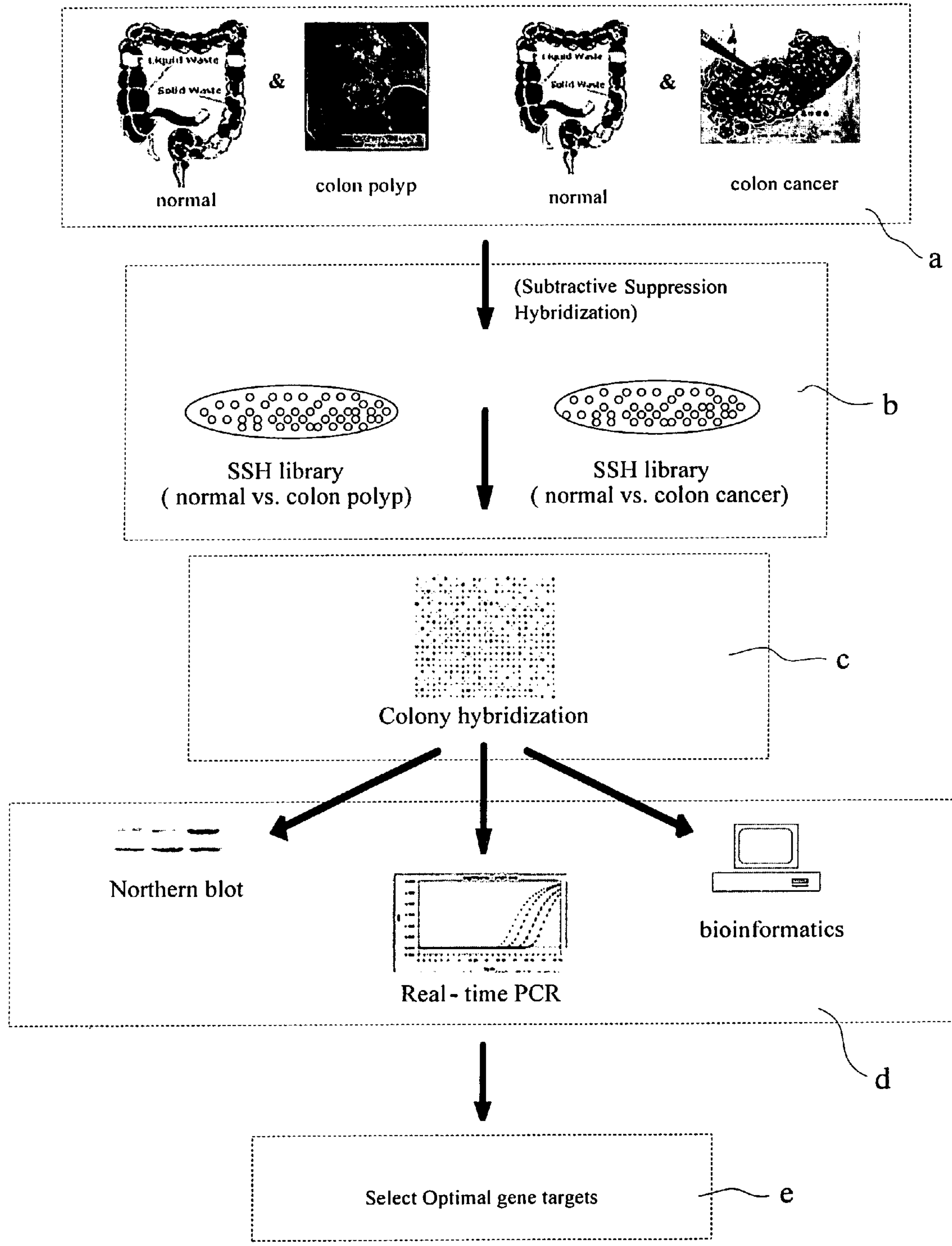
FIG. 1 is a view showing the procedure of deriving genes according to the present invention.

The following descriptions of the preferred embodiments are provided to understand the methods and the procedures of the present invention. Please refer to FIG. 1, showing the procedure of searching genes according to the present invention. Said procedure comprise the steps of: (1) deriving epithelium cells from normal intestines, polypus of intestines and colorectal cancer tissue; (2) collecting genes with highly differential gene expression by Suppression Subtractive Hybridization (SSH), and building library; (3) deriving colonies with relatively high signal intensities from cancer tissue; (4) collecting more clinically cancer tissues by Northern Hybridization, real-time Polymerase Chain Reaction (PCR) combined with analysis of bioinformation to affirm variation between differential gene expression; and (5) selecting the most suitable genes from said library. Moreover, by using the gene sequence as a reagent, this enables clinical diagnosis for colorectal cancer to the effects of early diagnosis, specificity, highly sensitivity and safety.

The genes for diagnosing colorectal cancer, the specific oligonucleotides sequence are selected from the group consisting of:

| No | Hs ID | ACC No | Discription | Definition | Oligo sequence |
|---|---|---|---|---|---|
| 1 | Hs.107213 | BC027178 (SEQUENCE LISTING 72) | FNBP3 Formin binding protein 3 | *Homo sapiens*, formin binding protein 3, clone MGC: 16979 IMAGE: 4343048, mRNA, complete cds | CATCATAGGAA ACGTTCCCGCT CTCGATCGGGG TCAGATTCAGAT GATGATG (SEQUENCE LISTING 1) |
| 2 | Hs.123107 | NM_002257 (SEQUENCE LISTING 73) | KLK1 Kallikrein 1, renal/pancreas/ salivary | *Homo sapiens* kallikrein 1, renal/pancreas/ salivary (KLK1), mRNA. | GCCTTCTGTCG CCGTCAGAGTG CTGTCTTATGTG AAGTGGATCGA GGACA (SEQUENCE LISTING 2) |
| 3 | Hs.1369 | NM_000574 (SEQUENCE LISTING 74) | DAF Decay accelerating factor for complement (CD55, Cromer blood group system) | *Homo sapiens* decay accelerating factor for complement (CD55, Cromer blood group system) (DAF), mRNA | GGGCAGTCAAT GGTCAGATATT GAAGAGTTCTG CAATCGTAGCT GCGAGGTG (SEQUENCE LISTING 3) |
| 4 | Hs.151254 | NM_005046 (SEQUENCE LISTING 75) | KLK7 Kallikrein 7 (chymotryptic, stratum corneum) | *Homo sapiens* kallikrein 7 (chymotryptic, stratum corneum) (KLK7), transcript vari-ant 1, mRNA. | TGGAACCACCT GTACTGTCTCC GGCTGGGGCAC TACCACGA (SEQUENCE LISTING 4) |
| 5 | Hs.1526 | NM_001681 (SEQUENCE LISTING 76) | ATP2A2 ATPase, Ca++ transporting, cardiac muscle, slow twitch 2 | *Homo sapiens* ATPase, Ca++ transporting, cardiac muscle, slow twitch 2 (ATP2A2), mRNA | CATCGGCATCT TCGGGCAGGAT GAGGACGTGAC GTCAAAAGCTTT CACAG (SEQUENCE LISTING 5) |
| 6 | Hs.184270 | NM_006135 (SEQUENCE LISTING 77) | CAPZA1 Capping protein actin) filament) muscle Z-line, alpha 1 | *Homo sapiens* capping protein (actin filament) muscle Z-line, alpha 1 (CAPZA1), mRNA. | TGACCACTTAC GGAAAGAAGCA AGTGACCCCCA GCCAGAAGAAG CAGATG (SEQUENCE LISTING 6) |
| 7 | Hs.2043 | NM_001151 (SEQUENCE LISTING 78) | SLC25A4 Solute carrier family 25 (mitochondrial carrier adenine nucleotide translocator), member 4 | *Homo sapiens* solute carrier family 25 (mitochondrial carrier; adenine nucleotide translocator), member 4 (SLC25A4), nuclear gene encoding mitochondrial protein, mRNA. | AGATCTTCAAGT CTGATGGCCTG AGGGGGCTCTA CCAGGGTTTCA ACGTC (SEQUENCE LISTING 7) |
| 8 | Hs.267871 | NM_005177 (SEQUENCE LISTING 79) | ATP6V0A1 ATPase, H+ transporting, lysosomal V0 | *Homo sapiens* ATPase, H+ transporting, lysosomal V0 | GGACAGAAAGG AATTCAGTGTTT CCTGGTAGTGG TTGCACTACTGT |

-continued

| No Hs ID | ACC No | Discription | Definition | Oligo sequence |
|---|---|---|---|---|
| | | subunit a isoform 1 | subunit a isoform 1 (ATP6V0A1), mRNA. | GTGTACCTTGG (SEQUENCE LISTING 8) |
| 9 Hs.4935 | D79998 (SEQUENCE LISTING 80) | KIAA0176 KIAA0176 protein | Human mRNA for KIAA0176 gene, partial cds | GGAAAGGATAC GGGACAATGAG AACAGAACTTCA CAAGGCCCCGT GAAGC (SEQUENCE LISTING 9) |
| 10 Hs.5509 | NM_006495 (SEQUENCE LISTING 81) | EVI2B Ecotropic viral integration site 2B | *Homo sapiens* ecotropic viral integration site 2B (EVI2B), mRNA. | GCCCCTGCCAC CAGTAGATTTA TGAAAAACCAA GAAGATTCCAA CCTTGAGATCC AGTGTC (SEQUENCE LISTING 10) |
| 11 Hs.5662 | NM_006098 (SEQUENCE LISTING 82) | GNB2L1 Guanine nucleotide binding protein (G protein), beta polypeptide 2-like 1 | *Homo sapiens* guanine nucleotide binding protein (G protein), beta polypeptide 2-like 1 (GNB2L1), mRNA. | ATGACTGAGCA GATGACCCTTC GTGGCACCCTC AAGGGCCACAA C (SEQUENCE LISTING 11) |
| 12 Hs.75990 | NM_005143 (SEQUENCE LISTING 83) | HP Haptoglobin | *Homo sapiens* haptoglobin (HP), mRNA. | AGGCTGTTGGA GATAAACTTCCT GAATGTGAAGC AGATGACGGCT GCCCG (SEQUENCE LISTING 12) |
| 13 Hs.83384 | NM_006272 (SEQUENCE LISTING 84) | S100B S100 calcium binding protein, beta (neural) | *Homo sapiens* S100 calcium binding protein, beta (neural) (S100B), mRNA | CCGAACTCAAG GAGCTCATCAA CAATGAGCTTTC CCATTTCTTAGA GGAAATCAAAG AGCAGGAG (SEQUENCE LISTING 13) |
| 14 Hs.10029 | NM_001814 (SEQUENCE LISTING 85) | CTSC Cathepsin C | *Homo sapiens* cathepsin C (CTSC), mRNA | CACCGGAAAGA AGGTGGGAACT GCCTCTGAGAA TGTGTATGTCAA CACAGC (SEQUENCE LISTING 14) |
| 15 Hs. 103982 | NM_005409 (SEQUENCE LISTING 86) | SCYB11 Small inducible cytokine subfamily B (Cys-X-Cys), member 11 | *Homo sapiens* small inducible cytokine subfamily B (Cys-X-Cys), member 11 (SCYB11), mRNA. | GGGCATGGCTA TAGCCTTGGCT GTGATATTGTGT GCTACAGTTGTT CAAGGC (SEQUENCE LISTING 15) |
| 16 Hs.12314 | AL049397 (SEQUENCE LISTING 87) | *Homo sapiens* mRNA; cDNA DKFZp586C1019 (from clone DKFZp586C1019) | *Homo sapiens* mRNA; cDNA DKFZp586C1019 (from clone DKFZp586C1019) | CAACACCACAG ACAGCTGCAGG ACTCGATATCCA TGGCTTCTTTCC ATCAC (SEQUENCE LISTING 16) |
| 17 Hs.150557 | NM_001206 (SEQUENCE | BTEB1 Basic transcription | *Homo sapiens* basic | TTCCACCCCAG CATGATCAAGC |

-continued

| No Hs ID | ACC No | Discription | Definition | Oligo sequence |
|---|---|---|---|---|
| | LISTING 88) | element binding protein 1 | transcription element binding protein 1 (BTEB1), mRNA. | GATCGAAAAAG GCGCTGGCCAA CGCTTT (SEQUENCE LISTING 17) |
| 18 Hs.169266 | NM_000909 (SEQUENCE LISTING 89) | NPY1R Neuropeptide Y receptor Y1 | *Homo sapiens* neuropeptide Y receptor Y1 (NPY1R), mRNA. | CCGGTCTCGGG ATGATGATTATG AAACAATAGCC ATGTCCACGAT GCACACAG (SEQUENCE LISTING 18) |
| 19 Hs.1827 | NM_002507 (SEQUENCE LISTING 90) | NGFR Nerve growth factor receptor (TNFR superfamily, member 16) | *Homo sapiens* nerve growth factor receptor (TNFR superfamily, member 16) (NGFR), mRNA. | CAAGCGGGAGG AGGTGGAGAAG CTTCTCAACGG CTCTGCG (SEQUENCE LISTING 19) |
| 20 Hs.1869 | NM_002633 (SEQUENCE LISTING 91) | PGM1 Phosphoglucomu-tase 1 | *Homo sapiens* phosphoglucomu-tase 1 (PGM1), mRNA. | GCCAACGGGAT CGGTCGCTTGG TTATCGGACAG AATGGAATCCT CTCCA (SEQUENCE LISTING 20) |
| 21 Hs.194148 | NM_005433 (SEQUENCE LISTING 92) | YES1 V-yes-1 Yamaguchi sarcoma viral oncogene homolog 1 | *Homo sapiens* v-yes-1 Yamaguchi sarcoma viral oncogene homolog 1(YES1), mRNA | CAAGTGTGAGC CATTATGGAGC AGAACCCACTA CAGTGTCACCA TGTCCG (SEQUENCE LISTING 21) |
| 22 Hs.2352 | X74210 (SEQUENCE LISTING 93) | ADCY2 Adenylate cyclase 2 (brain) | *H. sapiens* mRNA for adenylyl cyclase | TCGTCTGCTTTG CTGGACAGCTT CTGCAATGCAG CAAAAAAGCCT CTCCC (SEQUENCE LiSTING 22) |
| 23 Hs.246885 | NM_017958 (SEQUENCE LISTING 94) | FLJ20783 Hypothetical protein FLJ20783 | *Homo sapiens* hypothetical protein FLJ20783 (FLJ20783), mRNA. | CCAAGATTCTA GGACAAACACA GCGTATGTGGG CTCTGCAGTCA TGACCG (SEQUENCE LISTING 23) |
| 24 Hs.29665 | NM_014944 (SEQUENCE LISTING 95) | CLSTN1 Calsyntenin 1 | *Homo sapiens* calsyntenin 1 (CLSTN1), mRNA. | CACGAGCCCTT CTCTGTGACTG AGGATTACCCG CTCCATCCATC CAAGAT (SEQUENCE LISTING 24) |
| 25 Hs.3235 | NM_002272 (SEQUENCE LISTING 96) | KRT4 Keratin 4 | *Homo sapiens* keratin 4 (KRT4), mRNA | TTCAGCTGTGG CTCGGCCATTG TAGGCGGTGGC AAGAGAGGT (SEQUENCE LISTING 25) |
| 26 Hs.55209 | AF327354 (SEQUENCE LISTING 97) | *Homo sapiens* DMR protein mRNA, complete cds | *Homo sapiens* DMR protein mRNA, complete cds | TAAAGTGGGCT CATTGTCATCCC CAAGCCAGGCC AGTTCTCCAGG TGGAA (SEQUENCE LISTING 26) |

-continued

| No Hs ID | ACC No | Discription | Definition | Oligo sequence |
|---|---|---|---|---|
| 27 Hs.585 | NM_000384 (SEQUENCE LISTING 98) | APOB Apolipoprotein B (including Ag(x) antigen) | *Homo sapiens* apolipoprotein B (including Ag(x) antigen) (APOB), mRNA | GCCCAAGGCCA CAGGGGTCCTT TATGATTATGTC AACAAGTACCA CTGGG (SEQUENCE LISTING 27) |
| 28 Hs.62187 | AF022913 (SEQUENCE LISTING 99) | PIGK Phosphati-dylinositol glyan, class K | *Homo sapiens* GPI transamidase mRNA, complete cds | TCTTGTCCTTCG GCAGCGTGGCC GCTAGTCATATC GAGGATCAAGC AGAA (SEQUENCE LISTING 28) |
| 29 Hs.63290 | NM_012260 (SEQUENCE LISTING 100) | HPCL2 2-hydroxyphy-tanoyl-CoA lyase | *Homo sapien* 2-hydroxyphy-tanoyl-CoA lyase (HPCL2), mRNA | CATGAACTGCT GGCCCTTGCTT GTGATTGGTGG TTCCTCTGAAAG AAACCAAG (SEQUENCE LISTING 29) |
| 30 Hs.699 | NM_000942 (SEQUENCE LISTING 101) | PPIB Peptidylprolyl isomerase B (cyclophilin B) | *Homo sapiens* peptidylprolyl isomerase B (cyclophilin B) (PPIB), mRNA | AGCCGGGATAA ACCCCTGAAGG ATGTGATCATC GCAGACTGCGG CAAGAT (SEQUENCE LISTING 30) |
| 31 Hs.74111 | NM_007367 (SEQUENCE LISTING 102) | RALY RNA binding protein (autoantigen-ic, hnRNP-associated with lethal yellow) | *Homo sapiens* RNA binding protein (autoantigenic, hnRNP-associated with lethal yellow) (RALY) transcript vari-ant 2, mRNA | AGCGAGGAAGA GCTGGAACACA GCCAGGACACA GACGCGGATGA T (SEQUENCE LISTING 31) |
| 32 Hs.75103 | NM_003406 (SEQUENCE LISTING 103) | YWHAZ Tyrosine 3-monooxygen-ase/tryptophan 5-monooxygen-ase activation protein, zeta polypeptide | *Homo sapiens* tyrosine 3-monooxygenase/ /tryptophan 5-monooxygenase activation protein, zeta polypeptide (YWHAZ), mRNA | CGGAAGGTGCT GAGAAAAAACA GCAGATGGCTC GAGAATACAGA GAGAAAATTGA GACGG (SEQUENCE LISTING 32) |
| 33 Hs.75117 | NM_004515 (SEQUENCE LISTING 104) | ILF2 Interleukin enhancer binding factor 2, 45 kD | *Homo sapiens* interleukin enhancer binding factor 2, 45 kD (ILF2), mRNA | TGACTTCTATTT GTGTGAAATGG CCTTTCCCCGG GTCAAGCCAGC ACCTG (SEQUENCE LISTING 33) |
| 34 Hs.75236 | NM_021952 (SEQUENCE LISTING 105) | ELAVL4 ELAV (embryonic lethal, abnormal vision, | *Homo sapiens* ELAV (embryonic lethal, abnormal vision, Drosophila)-like | GCACCATGGAG CCTCAGGTGTC AAATGGTCCGA CATCCAATACAA GCAATG (SEQUENCE |

-continued

| No Hs ID | ACC No | Discription | Definition | Oligo sequence |
|---|---|---|---|---|
| | | Drosophila)-like 4 (Hu antigen D) | 4 (Hu antigen D) (ELAVL4), mRNA | LISTING 34) |
| 35 Hs.75258 | NM_004893 (SEQUENCE LISTING 106) | H2AFY H2A histone family, member Y | *Homo sapiens* H2A histone family, member Y (H2AFY), transcript vari-ant 2, mRNA | CACCGAAGCCA GGAAGCCCCGT TTGTAAGCGTG TGTTGTGGTGC TTTATT (SEQUENCE LISTING 35) |
| 36 Hs.75498 | NM_004591 (SEQUENCE LISTING 107) | SCYA20 Small inducible cytokine subfamily A (Cys—Cys), member 20 | *Homo sapiens* small inducible cytokine subfamily A (Cys—Cys), member 20 (SCYA20), mRNA | GCTACTCCACC TCTGCGGCGAA TCAGAAGCAGC AAGCAACTTTGA CTGCT (SEQUENCE LISTING 36) |
| 37 Hs.76913 | NM_002790 (SEQUENCE LISTING 108) | PSMA5 Proteasome (prosome, macropain) subunit, alpha type, 5 | *Homo sapiens* proteasome (prosome, macropain) subunit, alpha type, 5 (PSMA5), mRNA | GTTTCTTACCCG GTCTGAGTACG ACAGGGGCGTG AATACTTTTTCT CCCG (SEQUENCE LISTING 37) |
| 38 Hs.79889 | NM_012329 (SEQUENCE LISTING 109) | MMD Monocyte to macrophage differentiation-associated | *Homo sapiens* monocyte to macrophage differentiation-associated (MMD), mRNA | GCTATGAACAT GCTGCTAACTG TTACACACACG CATTCCTCATTG TTCCGGCC (SEQUENCE LiSTING 38) |
| 39 Hs.82173 | NM_005655 (SEQUENCE LISTING 110) | TIEG TGFB inducible early growth response | *Homo sapiens* TGFB inducible early growth response (TIEG) Mrna | TTTGTGGTACC CCAGCCCGTTG TGCAGAGTTCA AAGCCTCCGGT G (SEQUENCE LISTING 39) |
| 40 Hs.84072 | NM_004616 (SEQUENCE LISTING 111) | TM4SF3 Transmembrane 4 superfamily member 3 | *Homo sapiens* transmembrane 4 superfamily member 3 (TM4SF3), mRNA | GCAATGACTCT CAAGCAATTTTT GGTTCTGAAGA TGTAGGCTCTA GCTCCTACGTT GCTGTG (SEQUENCE LISTING 40) |
| 41 Hs.85146 | NM_005239 (SEQUENCE LISTING 112) | ETS2 V-ets erythroblastosis virus E26 oncogene homolog 2 (avian) | *Homo sapiens* v-ets erythroblastosis virus E26 oncogene homolog 2 (avian) (ETS2), mRNA | CTCATGACTCC GCCAACTGTGA ATTGCCTTTGTT AACCCCGTGCA GCAAG (SEQUENCE LISTING 41) |
| 42 Hs.85844 | NM_002529 (SEQUENCE LISTING 113) | NTRK1 Neurotrophic tyrosine kinase, receptor, type | *Homo sapiens* neurotrophic tyrosine kinase, receptor, type 1 (NTRK1), mRNA | TTCATGGACAA CCCTTTCGAGTT CAACCCCGAGG ACCCCATCCCT GTCT |

-continued

| No Hs ID | ACC No | Discription | Definition | Oligo sequence |
|---|---|---|---|---|
| | | 1 | | (SEQUENCE LISTING 42) |
| 43 Hs.88219 | NM_003454 (SEQUENCE LISTING 114) | ZNF200 Zinc finger protein 200 | *Homo sapiens* zinc finger protein 200 (ZNF200), mRNA | CCCAGTCAGAA AGTCAAGGAGA CCTTGGTTATTA TGAAAGATGTG AGCTCAAGCCT TCAGAACAG (SEQUENCE LISTING 43) |
| 44 Hs.9914 | NM_006350 (SEQUENCE LISTING 115) | FST Follistatin | *Homo sapiens* follistatin (FST), transcript variant FST317, mRNA | CCCTGACAGTA AGTCGGATGAG CCTGTCTGTGC CAGTGACAATG CCACTT (SEQUENCE LISTING 44) |
| 45 Hs.169319 | NM_003419 (SEQUENCE LISTING 116) | ZNF345 Zinc finger protein 345 | *Homo sapiens* zinc finger protein 345 (ZNF345), mRNA | CAGGGATCTCA GGAAGGACATT TCAGTGAAATG ATATTTACTCCT GAAGACATGCC CACTTTCAG (SEQUENCE LISTING 45) |
| 46 Hs.72805 | NM_030921 (SEQUENCE LISTING 117) | DC42 Hypothetical protein DC42 | *Homo sapiens* hypothetical protein DC42 (DC42), mRNA | GGCATGGCAGC AAATGCCAACAT TTTGTGGAATAG CAGCAAATCTA CAAGAGACCCT GG (SEQUENCE LISTING 46) |
| 47 HS.108301 | NM_003297 (SEQUENCE LISTING 118) | NR2C1 Nuclear receptor subfamily 2, group C, member 1 | *Homo sapiens* nuclear receptor subfamily 2, group C, member 1 (NR2C1), mRNA | GACACCTACAG GTTATCCAGACT ACTACTCAGATT GCCAGCTTTAA GACTGATGAAT GCTACCATC (SEQUENCE LISTING 47) |
| 48 Hs.177926 | NM_030941 (SEQUENCE LISTING 119) | LOC81691 Exonuctease NEF-sp | *Homo sapiens* exonuclease NEF-sp (LOC81691), mRNA | CCCAGTGACGA CCAAACTCAAA GATGTACAGAG GCAGTTAAAAG CACTGCTTCCT C (SEQUENCE LISTING 48) |
| 49 Hs.194746 | NM_018896 (SEQUENCE LISTING 120) | CACNA1G Calcium channel, voltage-dependent, alpha 1G subunit | *Homo sapiens* calcium channel, voltage-dependent, alpha 1G subunit (CACNA1G), mRNA | ACGTCAGAGAT TGTGTCTGAAC CGTCCTGCTCT CTAGCTCTGAC GGATGA (SEQUENCE LISTING 49) |
| 50 Hs.209061 | NM_003831 (SEQUENCE LISTING 121) | SUDD SudD suppressor of bimD6 | *Homo sapiens* sudD suppressor of | TCACGGCCTGG AGTTCTTGTTCC GGGACTGCAGG |

-continued

| No Hs ID | ACC No | Discription | Definition | Oligo sequence |
|---|---|---|---|---|
| | | homolog (A. nidulans) | bimD6 homolog (A. nidulans) (SUDD), mRNA | AATGTCTCGCA GTT (SEQUENCE LISTING 50) |
| 51 Hs.25087 | NM_006070 (SEQUENCE LISTING 122) | TFG TRK-fused gene | *Homo sapiens* TRK-fused gene (TFG), mRNA | TAATCCTTATGC GCGTAACCGTC CTCCCTTTGGT CAGGGCTATAC CCAAC (SEQUENCE LISTING 51) |
| 52 Hs.3017 | NM_003284 (SEQUENCE LISTING 123) | TNP1 Transition protein 1 (during histone to protamine replacement) | *Homo sapiens* transition protein 1 (during histone to protamine replacement) (TNP1), mRNA | GATCAAAGCCA GAGAGGAGCCT ATGGAATGTGG ATCAAATGCCA GTTGTGACG (SEQUENCE LISTING 52) |
| 53 Hs.283664 | NM_032466 (SEQUENCE LISTING 124) | ASPH Aspartate beta-hydroxylase | *Homo sapiens* aspartate beta-hydroxylase (ASPH), transcript variant 3, mRNA | GAACCACAACA AGAGGATGATG AGTTTCTTATGG CGACTGATGTA GATGATAGATTT GAGACCCTGG (SEQUENCE LISTING 53) |
| 54 Hs.283664 | NM_032467 (SEQUENCE LISTING 125) | ASPH Aspartate beta-hydroxylase | *Homo sapiens* aspartate beta-hydroxylase (ASPH), transcript variant 4, mRNA | CTCAGGGAGAT GGATTTGCTCG TTGTTTTCTTCC CTCCTTCCCCTT CCTG (SEQUENCE LISTING 54) |
| 55 Hs.171992 | NM_002843 (SEQUENCE LISTING 126) | PTPRJ Protein tyrosine phosphatase, receptor type, J | *Homo sapiens* protein tyrosine phosphatase, receptor type, J (PTPRJ), mRNA | CCGTGGATGTG TATGGGATTGT GTATGACCTTC GAATGCATAGG CCTTTAATGGTG C (SEQUENCE LISTING 55) |
| 56 Hs.155172 | NM_003664 (SEQUENCE LISTING 127) | AP3B1 | adaptor-related protein complex 3, beta 1 subunit | GCCCAGCTTAT CATAAACACTGA GAAAACTGTGA TTGGCTCTGTTC TGCTGCGGG (SEQUENCE LISTING 56) |
| 57 Hs.183418 | M37712 (SEQUENCE LISTING 128) | CDC2L2 | cell dividion cycle2-like2 | CGAGAAAATGA AAACCACCTCTT GGTTGTTCCAG AGTCACGGTTC GACCGAG (SEQUENCE LISTING 57) |
| 58 Hs.244473 | NM_031900 (SEQUENCE LISTING 129) | AGXT2 | alanine-glyoxylate aminotransferase 2 | TCCGGGATTGT TACTGTCAGTGT TGGCCATTGCC ACCCAAAGGTG |

-continued

| No Hs ID | ACC No | Discription | Definition | Oligo sequence |
|---|---|---|---|---|
| | | | | AATGC (SEQUENCE LISTING 58) |
| 59 Hs.12835 | NM_004842 (SEQUENCE LISTING 130) | AKAP7 | A kinase (PRKA) anchor protein 7 | GAGCCCGATGA CGCTGAACTAG TAAGGCTCAGT AAGAGGCTGGT GGAGAA (SEQUENCE LISTING 59) |
| 60 Hs.1650 | NM_000111 (SEQUENCE LISTING 131) | SLC26A3 | solute carrier family 26, member 3 | TCAGCCCCCTA TTACACCTGAC GTGGAGACTTT CCAAAACACCG TAGGAG (SEQUENCE LISTING 60) |
| 61 Hs.29981 | NM_000112 (SEQUENCE LISTING 132) | SLC26A2 | solute carrier family 26 (sulfate transporter), member 2 | CAGCAGGGATC CACACACTGAA AGAAGTTCGCA GAGATTATGAA GCCATTGGAAT CC (SEQUENCE LISTING 61) |
| 62 Hs.2246 | NM_001308 (SEQUENCE LISTING 133) | CPN1 | carboxypeptidase N, polypeptide 1, 50 kD | TCAAGTAAGCC CTGTGAGGAGA GCTCCCAGCAG AAGGCACGGAG T (SEQUENCE LISTING 62) |
| 63 Hs.267871 | NM_005177 (SEQUENCE LISTING 134) | ATP6V0A1 | ATPase, H+ transporting, lysosomal V0 subunit a isoform 1 | AAATGCTTGATT GCAGAGGTCTG GTGCCCTGTCA CCGACCTTGAC TCCAT (SEQUENCE LISTING 63) |
| 64 Hs.75445 | NM_004684 (SEQUENCE LISTING 135) | SPARCL1 | SPARC-like 1 (mast9, hevin) | CTGCGAGCATC TCTGGTGCCCA TGGAACACTGC ATAACCCGTTTC TTTGA (SEQUENCE LISTING 64) |
| 65 Hs.39957 | NM_016445 (SEQUENCE LISTING 136) | PLEK2 | pleckstrin 2 (mouse) homolog | TGGCGTTCCCA CTGGGGTTAAA GGGAATGTCCA GGGAAACCTCT TCAAAG (SEQUENCE LISTING 65) |
| 66 Hs.65029 | NM_002048 (SEQUENCE LISTING 137) | GAS1 | growth arrest-specific 1 | CGACTACTACG ATGAGGACTAC GATGACGAGCA GCGCACCGG (SEQUENCE LISTING 66) |
| 67 Hs.239926 | NM_006745 (SEQUENCE | SC4MOL | sterol-C4-methyl oxidase-like | GCTGGTTCTCG GCATCATGATTT |

-continued

| No Hs ID | ACC No | Discription | Definition | Oligo sequence |
|---|---|---|---|---|
| | LISTING 138) | | | CCACCACATGA ACTTCATTGGAA ACTATGCTTCAA C (SEQUENCE LISTING 67) |
| 68 Hs.59271 | NM_006758 (SEQUENCE LISTING 139) | U2AF1 | U2(RNU2) small nuclear RNA auxillary factor 1 | TCTGTGACAAC CTGGGAGACCA CCTGGTGGGGA ACGTGTACGTC AAGTTT (SEQUENCE LISTING 68) |
| 69 Hs.8867 | NM_001554 (SEQUENCE LISTING 140) | CYR61 | cysteine-rich, angiogenic inducer, 61 | CAAAACGCAGC CCTGCGACCAC ACCAAGGGGCT GGAATGCAACT T (SEQUENCE LISTING 69) |
| 70 Hs.50123 | NM_003452 (SEQUENCE LISTING 141) | ZNF189 | zinc finger protein 189 | CAACAGCGCAG TCTTGTCAACCA TCAGATGATCC ATGCAGAGGTG AAAACCC (SEQUENCE LISTING 70) |
| 71 Hs.82071 | NM_006079 (SEQUENCE LISTING 142) | CITED2 | Cbp/p300-interacting transactivator, with Glu/Asp-rich carboxy-terminal domain, 2 | CACCAGATGAA CGGGACAAACC AGCACTTCCGA GATTGCAACCC CAAGCA (SEQUENCE LISTING 71) |

From the above table, the HS ID of the 71 genes comprises:

Hs. 107213 Hs. 123107 Hs. 1369 Hs. 151254 Hs. 1526 Hs. 184270 Hs. 2043 Hs. 267871 Hs. 4935 Hs. 5509 Hs. 5662 Hs. 75990 Hs. 83384 Hs. 10029 Hs. 103982 Hs. 12314 Hs. 150557 Hs. 169266 Hs. 1827 Hs. 1869 Hs. 194148 Hs. 2352 Hs. 246885 Hs. 29665 Hs. 3235 Hs. 55209 Hs. 585 Hs. 62187 Hs. 63290 Hs. 699 Hs. 74111 Hs. 75103 Hs. 75117 Hs. 75236 Hs. 75258 Hs. 75498 Hs. 76913 Hs. 79889 Hs. 82173 Hs. 84072 Hs. 85146 Hs. 85844 Hs. 88219 Hs. 9914 Hs. 169319 Hs. 72805 Hs. 108301 Hs. 177926 Hs. 194746 Hs. 209061 Hs. 25087 Hs. 3017 Hs. 283664 Hs. 283664 Hs. 171992 Hs. 155172 Hs. 183418 Hs. 244473 Hs. 12835 Hs. 1650 Hs. 29981 Hs. 2246 Hs. 267871 Hs. 75445 Hs. 39957 Hs. 65029 Hs. 239926 Hs. 59271 Hs. 8867 Hs. 50123 Hs. 82071 etc.

We obtain said specific oligonucleotides sequences by using analysis of OMP (Oligonucleotide Modeling Platform, DNA Software, Inc., Ann Arbor, Mich.) DNA software, Said gene sequences can act as a reagent, a biochip and a medicine for detecting colorectal cancer shown in table 1.

Figure 2A:
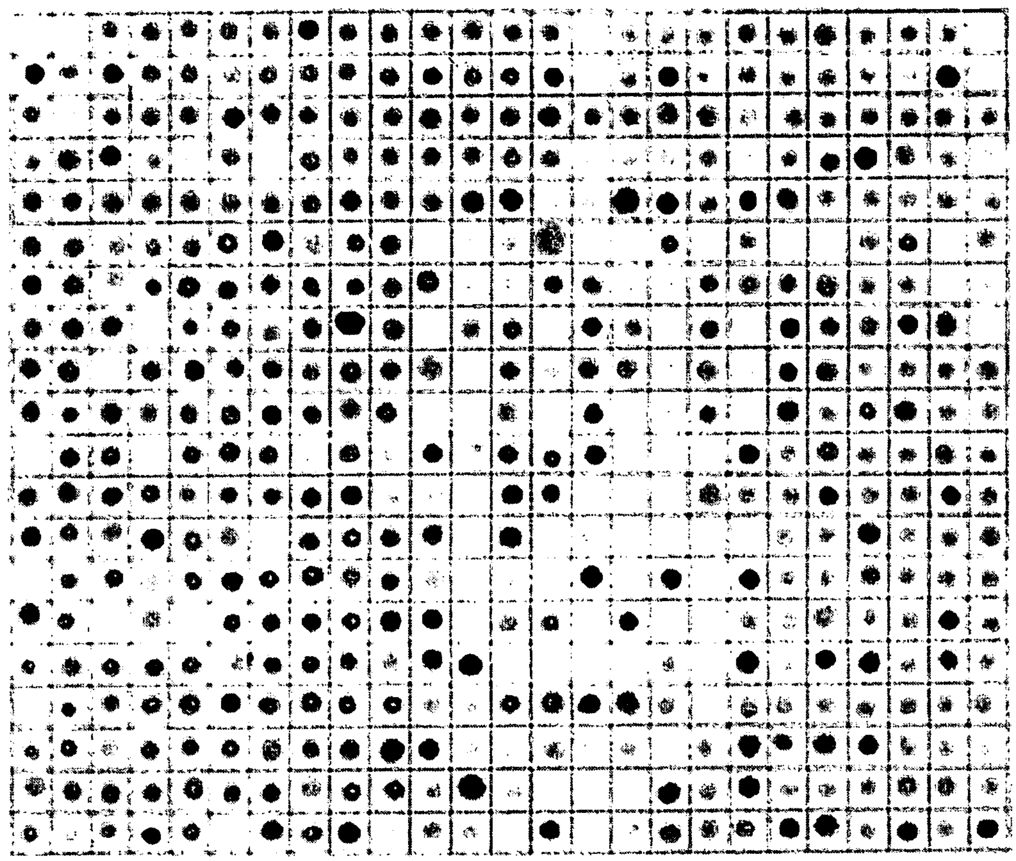
FIG. 2*a* and FIG. 2*b* are views showing the primary screening according to the present invention.
Figure 2B:
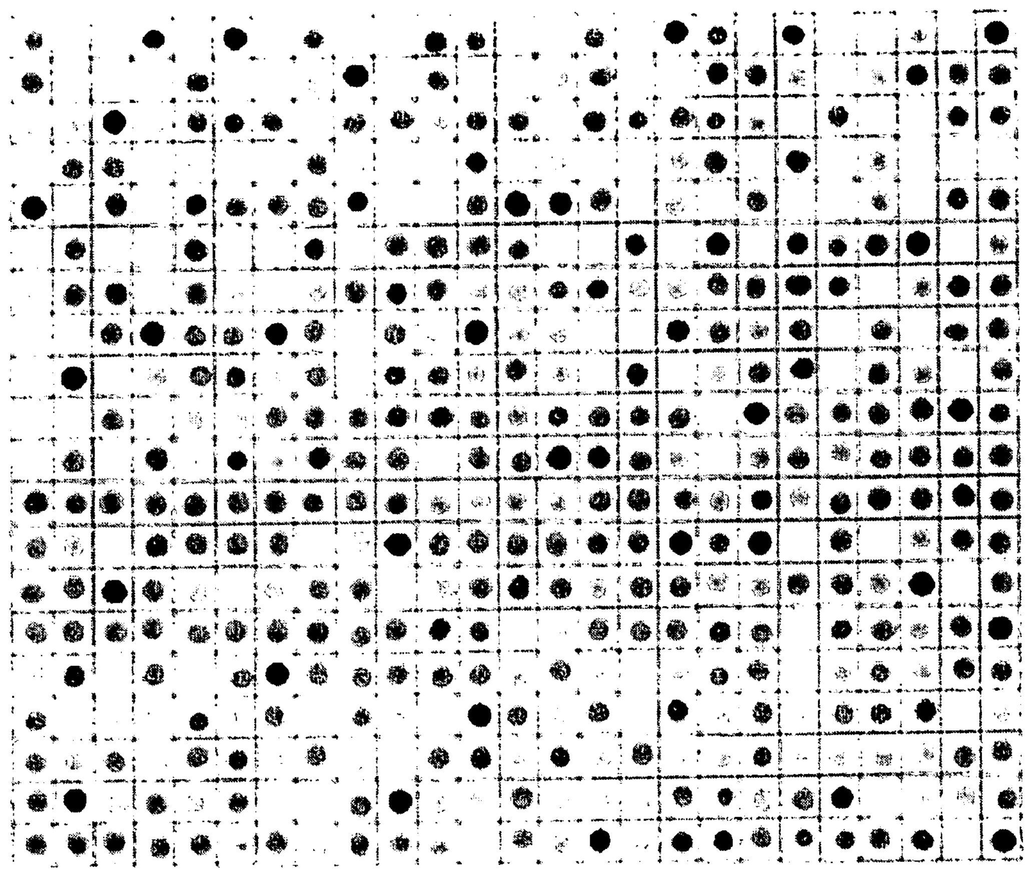
Figure 3A:
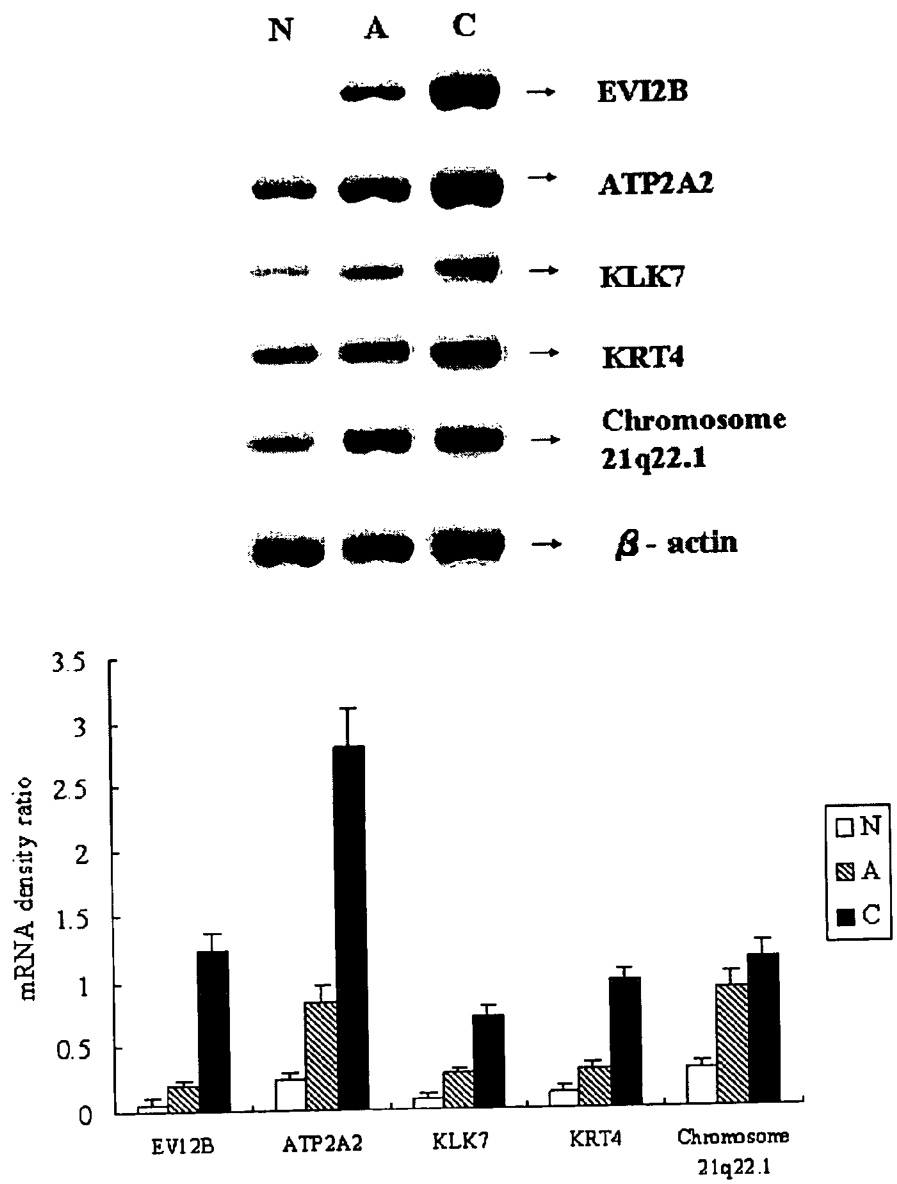
FIG. 3*a* and FIG. 3*b* are views showing affirmation to genes using Northern Blotting method according to the present invention.
Figure 3B:
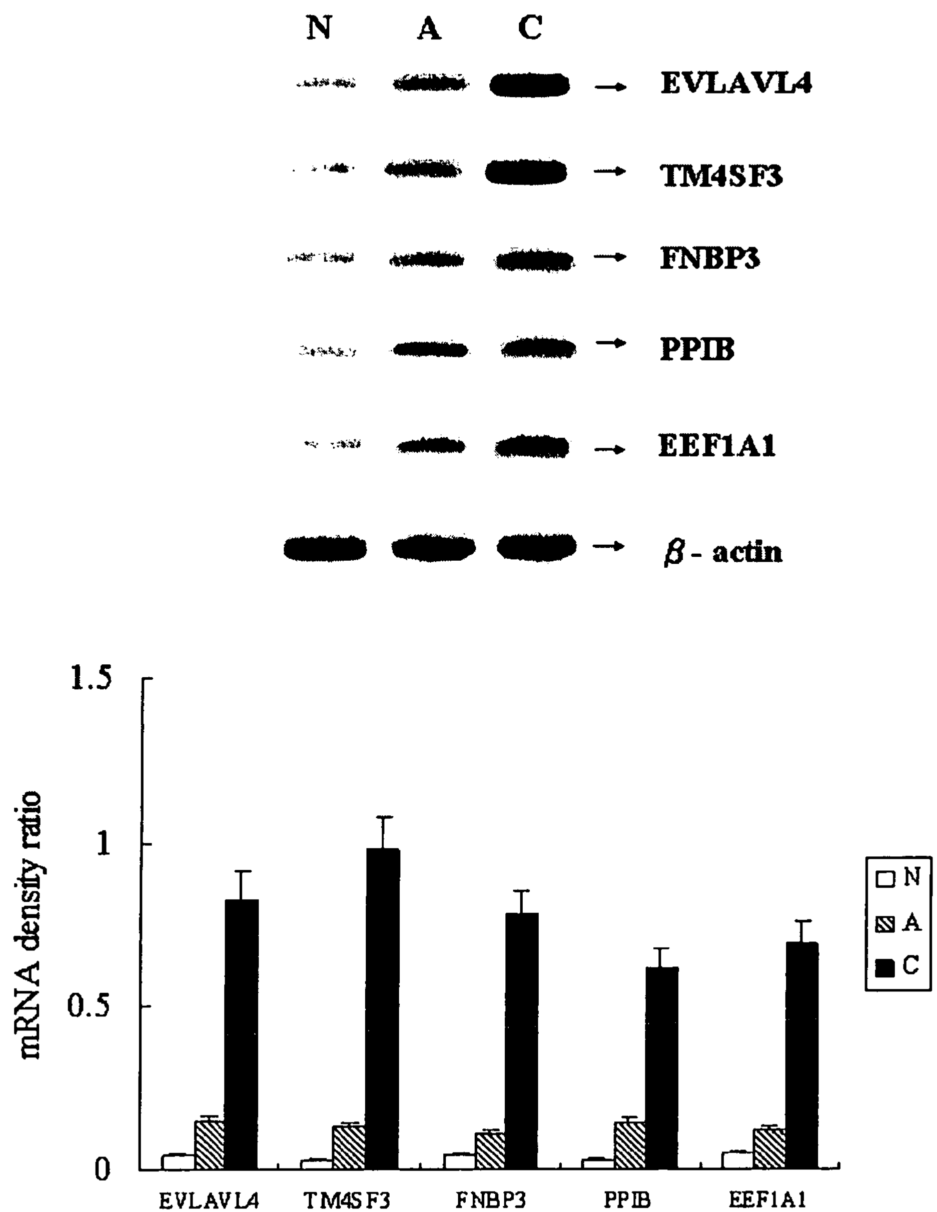
Figure 4A:
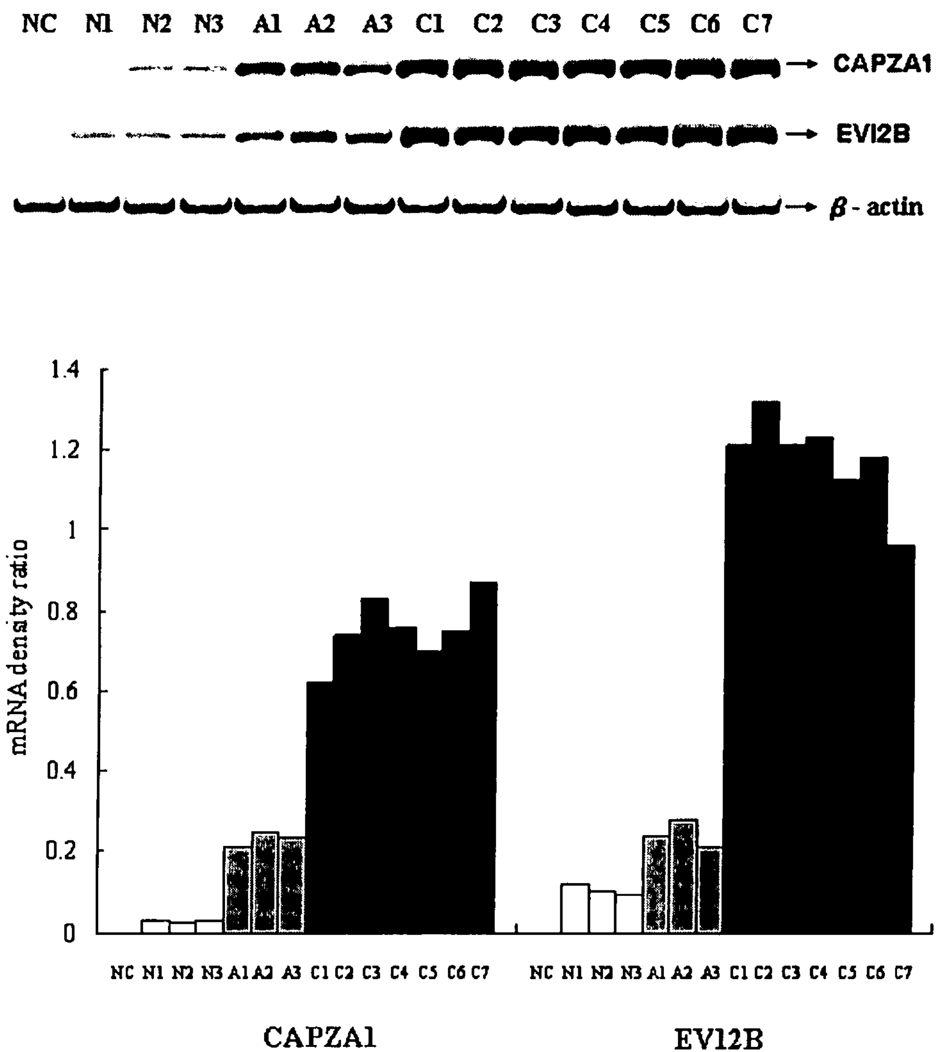
FIGS. 4*a* and 4*b* are views showing quantity expression of cancer tissue according to the present invention.
Figure 4B:
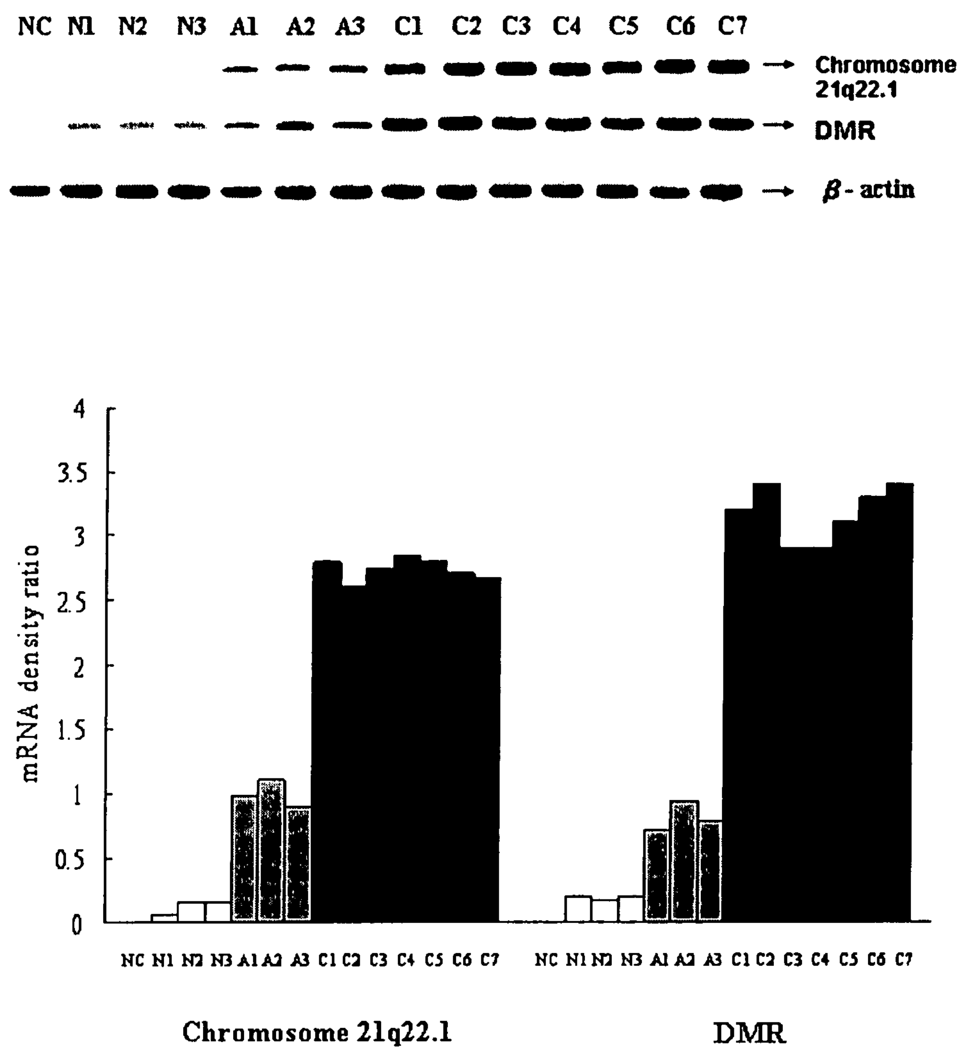

According to the present invention, FIG. 2*a* and FIG. 2*b* are views showing the primary screening. FIG. 3*a* and FIG. 3*b* are views showing affirmation to genes using Northern Blotting method. FIGS. 4*a* and 4*b* are views showing quantity expression of cancer tissue we search over progressive distinctive new genes among the carcinoma process of colorectal cancer by using SSH method to build up CRA libraries and CRC libraries which make the comparison between adenoma, adenocarcinoma and normal tissue, that obtain over 5000 clones in per library; then randomly select about 3000 clones of cDNA from per library to dot on nylon membrane as pre-screen by using Colony Hybridization shown in FIG. 2*a* and FIG. 2*b*. The high expression colonies in colorectal cancer and adenoma are selected by the Colony Hybridization and then the nucleic acid of cDNA after purification spot on glass chip by using microarray testing.

The expression profiles of the cDNA chips were derived from a set of cDNA probes including adenoma, adenocarcinoma and the corresponding normal tissue from the same patient. Genes exhibiting at least three-fold greater intensities in the adenocarcinoma or adenoma than in corresponding normal tissue samples were considered significant. The significant up-regulated genes were then further confirmed by Northern blot (FIG. 3*a* and FIG. 3*b*) and subsequently sequenced. Northern analysis of each set of cDNA genes on the chip revealed that 36 genes were detected as up-regulated in adenoma compared to normal, and 54 genes were detected as up-regulated in carcinoma as compared to the normal control. A set of 23 genes with serial increase of genes expression from adenoma to carcinoma was identified.

Further, comparison is made by using EMBL/GenBank libraries of NCBI/BLAST program, there are 3 unknown functional genes among 23 identified genes including ectopic viral integration site 2B (Genbank accession no.NM-006495) Homo sapiens chromosome 21q22.1 anonymous mRNA sequence (Genebank accession no.AF003738) and Homo sapiens DMR protein mRNA (Genbank accession no.AF327354), and another 20 functional genes. Among these 20 functional genes, 6 genes are CRC-related (such as TM4SF3), 14 genes are CRC-unrelated (such as ATP2A2). Moreover, we obtain cDNAs of three patients who suffer from adenoma and adenocarcinama simultaneously and four colorectal cancer patients to affirm variation of 23 identified genes, result shown that were at least 3-fold higher in mRNA expression level in the adenocarcinoma tissues compared with normal samples, and the level gradually increased from colorectal adenomas to adenocarcinomas shown in FIG. 4*a* and FIG. 4*b*.

Now, methods of clinical diagnosis for detecting colorectal cancer are fecal occult blood test, image test, tumor label and colonoscopy. In each of these methods, we can generalize purpose of the present invention according to disadvantage of these methods.

1. Early Diagnosis

If patient undergo colorectal cancer before tumor cells spread out, five-year survival rate can be achieved over 90%. A certain number of tumor cells are needed for traditional detection by using tumor label method. In the case of image test, normally, correctly affirmation can be made easier when tumor become large. It is high invasion and price to make low acceptance for the patient in the colonoscopy that can not suitable for early diagnosis. Because of the process of circulating of tumor cells, different expression certainly happen among the genes. In the process of proliferation of early tumor cells, the dying cells cause molecule of ribonucleic acid to release into blood circulation. And, early diagnosis can be offered by the detection of using the constructed oligonucleotide biochip which is discharged from small number of tumor cells in the peripheral blood.

2. Specificity and Sensitivity

Fecal occult blood test has shortcomings for high false positives and false negatives to low specificity and sensitivity of the method, therefore the method is merely a first screening tool and the tumor label method is also not high specificity and sensitivity. But, we use these genes to detect peripheral blood of 100 CRC patients, peripheral blood of 50 healthy people and 40 other cancer-related patients as controls shown in FIG. 1, these genes can detect 88 colorectal cancer patients for remarkable sensitivity of 88% (88/100) and specificity of 90% (90/100) in the clinical analysis.

3. Safety

The colonoscopy has high invasion and price to make low acceptance for patient in the mass screening tool of early diagnosis. Because sample collection is convenience and low invasion, Peripheral blood test of patient is a diagnosis method of genes, that is suitable to mass screening clinical application.

Figure 5:
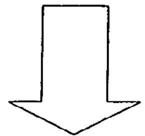
FIG. 5 is a diagram showing second preferred embodiments according to the present invention.
Figure 5:
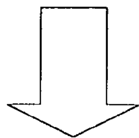

Please refer to FIG. 5, showing another preferred embodiment according to the present invention. We choose genes of colorectal cancer and vector that express simultaneously in eukaryotic and prokaryotic to form recombination genes, and then form eukaryotic transformant cell by using and further form prokaryotic transfectant cell, and then obtain secreted protein by using extract of genes having said recombination genes, and obtain antibody from said secreted protein immune animals for making of protein testing reagent, colorectal vaccine and colorectal protein medicine for colorectal cancer.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

TABLE 1

Assessment of clinical testing result for colorectal cancer biochip

| No. | Age | Sex | diagnosis | Stage | result |
|---|---|---|---|---|---|
| 1 | 43 | F | Colon cancer | C1 | P |
| 2 | 35 | F | Colon cancer | B2 | P |
| 3 | 68 | M | Colon adenoma | | P |
| 4 | 56 | F | Colon cancer | C2 | P |
| 5 | 32 | F | Colon cancer | B1 | N |
| 6 | 65 | M | Colon cancer | B2 | P |
| 7 | 46 | M | Colon cancer | C1 | P |
| 8 | 67 | M | Colon cancer | C1 | P |
| 9 | 58 | F | Colon cancer | C1 | P |
| 10 | 45 | M | Colon cancer | B2 | P |
| 11 | 62 | F | Colon adenoma | | P |
| 12 | 64 | F | Colon cancer | C2 | P |
| 13 | 58 | F | Colon cancer | A | N |
| 14 | 76 | M | Colon cancer | C1 | P |
| 15 | 38 | M | Colon cancer | B2 | P |
| 16 | 67 | M | Colon cancer | C1 | P |
| 17 | 86 | F | Colon adenoma | | P |
| 18 | 47 | F | Colon cancer | C2 | P |
| 19 | 56 | M | Colon cancer | B1 | P |
| 20 | 67 | F | Colon cancer | B2 | P |
| 21 | 43 | F | Colon adenoma | | P |
| 22 | 65 | M | Colon cancer | A | P |
| 23 | 43 | F | Colon cancer | C2 | P |
| 24 | 54 | M | Colon cancer | B1 | P |
| 25 | 34 | F | Colon cancer | B2 | P |
| 26 | 76 | F | Colon adenoma | | P |
| 27 | 66 | M | Colon cancer | B2 | P |
| 28 | 78 | F | Colon cancer | B1 | P |
| 29 | 57 | M | Colon cancer | B2 | P |
| 30 | 74 | M | Colon adenoma | | P |
| 31 | 65 | F | Colon cancer | B1 | P |
| 32 | 64 | F | Colon cancer | B2 | P |
| 33 | 62 | M | Colon cancer | B1 | P |
| 34 | 46 | M | Colon cancer | B2 | P |
| 35 | 54 | F | Colon cancer | B1 | P |
| 36 | 58 | F | Colon cancer | B1 | P |
| 37 | 64 | F | Colon adenoma | | P |
| 38 | 56 | M | Colon cancer | B1 | P |
| 39 | 67 | M | Colon cancer | B2 | P |
| 40 | 48 | F | Colon cancer | B1 | P |
| 41 | 55 | M | Colon cancer | B1 | P |
| 42 | 64 | F | Colon adenoma | | P |
| 43 | 58 | F | Colon cancer | C1 | P |
| 44 | 65 | M | Colon cancer | C1 | P |
| 45 | 66 | M | Colon cancer | C2 | P |
| 46 | 43 | M | Colon cancer | C1 | P |
| 47 | 26 | F | Colon cancer | C2 | P |
| 48 | 54 | M | Colon cancer | C1 | P |
| 49 | 59 | F | Colon cancer | C2 | P |
| 50 | 71 | F | Colon adenoma | | N |
| 51 | 37 | M | Colon cancer | C1 | P |
| 52 | 47 | F | Colon cancer | C1 | P |
| 53 | 62 | M | Colon cancer | C2 | P |
| 54 | 47 | M | Colon adenoma | | P |
| 55 | 55 | F | Colon cancer | B2 | P |
| 56 | 48 | M | Colon cancer | B1 | P |
| 57 | 66 | F | Colon cancer | B2 | P |
| 58 | 64 | M | Colon cancer | B1 | N |
| 59 | 30 | M | Colon cancer | B1 | P |
| 60 | 56 | F | Colon cancer | B2 | P |
| 61 | 46 | M | Colon cancer | B1 | P |
| 62 | 67 | F | Colon cancer | B2 | P |
| 63 | 35 | M | Colon cancer | B1 | P |
| 64 | 45 | F | Colon cancer | B1 | P |
| 65 | 86 | F | Colon cancer | B2 | P |

TABLE 1-continued

Assessment of clinical testing result for colorectal cancer biochip

| No. | Age | Sex | diagnosis | Stage | result |
|---|---|---|---|---|---|
| 66 | 54 | M | Colon cancer | B1 | P |
| 67 | 57 | M | Colon cancer | C1 | P |
| 68 | 76 | F | Colon cancer | C2 | P |
| 69 | 46 | M | Colon cancer | C1 | P |
| 70 | 68 | M | Colon cancer | B2 | P |
| 71 | 45 | F | Colon cancer | B1 | P |
| 72 | 87 | M | Colon cancer | B1 | P |
| 73 | 53 | M | Colon cancer | C1 | P |
| 74 | 58 | F | Colon cancer | A | P |
| 75 | 54 | M | Colon cancer | B1 | P |
| 76 | 67 | F | Colon cancer | C2 | P |
| 77 | 56 | F | Colon cancer | A | N |
| 78 | 35 | M | Colon adenoma | | P |
| 79 | 79 | F | Colon cancer | B2 | P |
| 80 | 82 | M | Colon cancer | C2 | P |
| 81 | 76 | M | Colon cancer | C2 | P |
| 82 | 54 | F | Colon cancer | C1 | P |
| 83 | 42 | M | Colon cancer | B1 | P |
| 84 | 68 | M | Colon cancer | B1 | P |
| 85 | 27 | M | Colon cancer | B2 | P |
| 86 | 67 | F | Colon cancer | B2 | P |
| 87 | 46 | M | Colon adenoma | | N |
| 88 | 76 | F | Colon cancer | B1 | P |
| 89 | 44 | MF | Colon cancer | B1 | P |
| 90 | 56 | F | Colon cancer | B2 | P |
| 91 | 65 | M | Colon cancer | C2 | P |
| 92 | 57 | F | Colon cancer | C1 | P |
| 93 | 67 | M | Colon cancer | B1 | P |
| 94 | 78 | F | Colon adenoma | | P |
| 95 | 56 | F | Colon cancer | C1 | P |
| 96 | 56 | M | Colon cancer | C1 | P |
| 97 | 45 | F | Colon cancer | B1 | P |
| 98 | 63 | F | Colon cancer | B2 | P |
| 99 | 62 | M | Colon cancer | C2 | P |
| 100 | 54 | F | Colon cancer | C1 | P |

Controls

| NO | Age | Sex | Diagnosis | result |
|---|---|---|---|---|
| 1 | 76 | F | Breast cancer | N |
| 2 | 35 | F | Breast cancer | N |
| 3 | 74 | F | Breast cancer | P |
| 4 | 57 | F | Gastric cancer | N |
| 5 | 87 | F | Breast cancer | N |
| 6 | 55 | M | Gastic cancer | N |
| 7 | 35 | M | NPC | N |
| 8 | 78 | F | Breast cancer | N |
| 9 | 65 | M | NPC | N |
| 10 | 55 | F | Breast cancer | N |
| 11 | 54 | M | NPC | N |
| 12 | 67 | F | normal | N |
| 13 | 86 | M | Gastic cancer | P |
| 14 | 53 | F | NPC | N |
| 15 | 58 | F | normal | N |
| 16 | 78 | F | Breast cancer | N |
| 17 | 45 | M | normal | N |
| 18 | 78 | F | normal | N |
| 19 | 87 | F | normal | N |
| 20 | 45 | M | normal | N |

What is claimed is:

1. A method for diagnosing colorectal cancer comprising:

contacting a gene consisting of a gene sequence of SEQ ID NO: 76 with a colorectal cancer containing cells; and detecting molecules of ribonucleic acid released in a peripheral blood by said colorectal cancer containing cells which reacted with SEQ ID NO: 76, thereby diagnosing the colorectal cancer containing cells.

* * * * *

SEQUENCE LISTING

```
<160> NUMBER OF SEQ ID NOS: 142

<210> SEQ ID NO 1
<211> LENGTH: 52
<212> TYPE: DNA
<213> ORGANISM: Homo sapiens

<400> SEQUENCE: 1

catcatagga aacgttcccg ctctcgatcg gggtcagatt cagatgatga tg            52


<210> SEQ ID NO 2
<211> LENGTH: 50
<212> TYPE: DNA
<213> ORGANISM: Homo sapiens

<400> SEQUENCE: 2

gccttctgtc gccgtcagag tgctgtctta tgtgaagtgg atcgaggaca              50


<210> SEQ ID NO 3
<211> LENGTH: 52
<212> TYPE: DNA
<213> ORGANISM: Homo sapiens

<400> SEQUENCE: 3

gggcagtcaa tggtcagata ttgaagagtt ctgcaatcgt agctgcgagg tg            52
```

<210> SEQ ID NO 4
<211> LENGTH: 41
<212> TYPE: DNA
<213> ORGANISM: Homo sapiens

<400> SEQUENCE: 4
tggaaccacc tgtactgtct ccggctgggg cactaccacg a 41

<210> SEQ ID NO 5
<211> LENGTH: 50
<212> TYPE: DNA
<213> ORGANISM: Homo sapiens

<400> SEQUENCE: 5
catcggcatc ttcgggcagg atgaggacgt gacgtcaaaa gctttcacag 50

<210> SEQ ID NO 6
<211> LENGTH: 50
<212> TYPE: DNA
<213> ORGANISM: Homo sapiens

<400> SEQUENCE: 6
tgaccactta cggaaagaag caagtgaccc ccagccagaa gaagcagatg 50

<210> SEQ ID NO 7
<211> LENGTH: 50
<212> TYPE: DNA
<213> ORGANISM: Homo sapiens

<400> SEQUENCE: 7
agatcttcaa gtctgatggc ctgagggggc tctaccaggg tttcaacgtc 50

<210> SEQ ID NO 8
<211> LENGTH: 57
<212> TYPE: DNA
<213> ORGANISM: Homo sapiens

<400> SEQUENCE: 8
ggacagaaag gaattcagtg tttcctggta gtggttgcac tactgtgtgt accttgg 57

<210> SEQ ID NO 9
<211> LENGTH: 50
<212> TYPE: DNA
<213> ORGANISM: Homo sapiens

<400> SEQUENCE: 9
ggaaaggata cgggacaatg agaacagaac ttcacaaggc cccgtgaagc 50

<210> SEQ ID NO 10
<211> LENGTH: 62
<212> TYPE: DNA
<213> ORGANISM: Homo sapiens

<400> SEQUENCE: 10
gcccctgcca ccagtagatt ttatgaaaaa ccaagaagat tccaaccttg agatccagtg 60
tc 62

<210> SEQ ID NO 11
<211> LENGTH: 45
<212> TYPE: DNA
<213> ORGANISM: Homo sapiens

<400> SEQUENCE: 11

-continued atgactgagc agatgaccct tcgtggcacc ctcaagggcc acaac 45

<210> SEQ ID NO 12
<211> LENGTH: 50
<212> TYPE: DNA
<213> ORGANISM: Homo sapiens

<400> SEQUENCE: 12
aggctgttgg agataaactt cctgaatgtg aagcagatga cggctgcccg 50

<210> SEQ ID NO 13
<211> LENGTH: 65
<212> TYPE: DNA
<213> ORGANISM: Homo sapiens

<400> SEQUENCE: 13
ccgaactcaa ggagctcatc aacaatgagc tttcccattt cttagaggaa atcaaagagc 60
aggag 65

<210> SEQ ID NO 14
<211> LENGTH: 51
<212> TYPE: DNA
<213> ORGANISM: Homo sapiens

<400> SEQUENCE: 14
caccggaaag aaggtgggaa ctgcctctga gaatgtgtat gtcaacacag c 51

<210> SEQ ID NO 15
<211> LENGTH: 52
<212> TYPE: DNA
<213> ORGANISM: Homo sapiens

<400> SEQUENCE: 15
gggcatggct atagccttgg ctgtgatatt gtgtgctaca gttgttcaag gc 52

<210> SEQ ID NO 16
<211> LENGTH: 51
<212> TYPE: DNA
<213> ORGANISM: Homo sapiens

<400> SEQUENCE: 16
caacaccaca gacagctgca ggactcgata tccatggctt ctttccatca c 51

<210> SEQ ID NO 17
<211> LENGTH: 50
<212> TYPE: DNA
<213> ORGANISM: Homo sapiens

<400> SEQUENCE: 17
ttccacccca gcatgatcaa gcgatcgaaa aaggcgctgg ccaacgcttt 50

<210> SEQ ID NO 18
<211> LENGTH: 53
<212> TYPE: DNA
<213> ORGANISM: Homo sapiens

<400> SEQUENCE: 18
ccggtctcgg gatgatgatt atgaaacaat agccatgtcc acgatgcaca cag 53

<210> SEQ ID NO 19
<211> LENGTH: 40
<212> TYPE: DNA
<213> ORGANISM: Homo sapiens

<400> SEQUENCE: 19
caagcgggag gaggtggaga agcttctcaa cggctctgcg 40

<210> SEQ ID NO 20
<211> LENGTH: 49
<212> TYPE: DNA
<213> ORGANISM: Homo sapiens

<400> SEQUENCE: 20
gccaacggga tcggtcgctt ggttatcgga cagaatggaa tcctctcca 49

<210> SEQ ID NO 21
<211> LENGTH: 50
<212> TYPE: DNA
<213> ORGANISM: Homo sapiens

<400> SEQUENCE: 21
caagtgtgag ccattatgga gcagaaccca ctacagtgtc accatgtccg 50

<210> SEQ ID NO 22
<211> LENGTH: 50
<212> TYPE: DNA
<213> ORGANISM: Homo sapiens

<400> SEQUENCE: 22
tcgtctgctt tgctggacag cttctgcaat gcagcaaaaa agcctctccc 50

<210> SEQ ID NO 23
<211> LENGTH: 50
<212> TYPE: DNA
<213> ORGANISM: Homo sapiens

<400> SEQUENCE: 23
ccaagattct aggacaaaca cagcgtatgt gggctctgca gtcatgaccg 50

<210> SEQ ID NO 24
<211> LENGTH: 50
<212> TYPE: DNA
<213> ORGANISM: Homo sapiens

<400> SEQUENCE: 24
cacgagccct tctctgtgac tgaggattac ccgctccatc catccaagat 50

<210> SEQ ID NO 25
<211> LENGTH: 42
<212> TYPE: DNA
<213> ORGANISM: Homo sapiens

<400> SEQUENCE: 25
ttcagctgtg gctcggccat tgtaggcggt ggcaagagag gt 42

<210> SEQ ID NO 26
<211> LENGTH: 50
<212> TYPE: DNA
<213> ORGANISM: Homo sapiens

<400> SEQUENCE: 26
taaagtgggc tcattgtcat ccccaagcca ggccagttct ccaggtggaa 50

<210> SEQ ID NO 27
<211> LENGTH: 50
<212> TYPE: DNA

<213> ORGANISM: Homo sapiens

<400> SEQUENCE: 27
gcccaaggcc acaggggtcc tttatgatta tgtcaacaag taccactggg 50

<210> SEQ ID NO 28
<211> LENGTH: 50
<212> TYPE: DNA
<213> ORGANISM: Homo sapiens

<400> SEQUENCE: 28
tcttgtcctt cggcagcgtg gccgctagtc atatcgagga tcaagcagaa 50

<210> SEQ ID NO 29
<211> LENGTH: 53
<212> TYPE: DNA
<213> ORGANISM: Homo sapiens

<400> SEQUENCE: 29
catgaactgc tggcccttgc ttgtgattgg tggttcctct gaaagaaacc aag 53

<210> SEQ ID NO 30
<211> LENGTH: 50
<212> TYPE: DNA
<213> ORGANISM: Homo sapiens

<400> SEQUENCE: 30
agccgggata aacccctgaa ggatgtgatc atcgcagact gcggcaagat 50

<210> SEQ ID NO 31
<211> LENGTH: 45
<212> TYPE: DNA
<213> ORGANISM: Homo sapiens

<400> SEQUENCE: 31
agcgaggaag agctggaaca cagccaggac acagacgcgg atgat 45

<210> SEQ ID NO 32
<211> LENGTH: 54
<212> TYPE: DNA
<213> ORGANISM: Homo sapiens

<400> SEQUENCE: 32
cggaaggtgc tgagaaaaaa cagcagatgg ctcgagaata cagagagaaa attg 54

<210> SEQ ID NO 33
<211> LENGTH: 50
<212> TYPE: DNA
<213> ORGANISM: Homo sapiens

<400> SEQUENCE: 33
tgacttctat ttgtgtgaaa tggcctttcc ccgggtcaag ccagcacctg 50

<210> SEQ ID NO 34
<211> LENGTH: 51
<212> TYPE: DNA
<213> ORGANISM: Homo sapiens

<400> SEQUENCE: 34
gcaccatgga gcctcaggtg tcaaatggtc cgacatccaa tacaagcaat g 51

<210> SEQ ID NO 35
<211> LENGTH: 50

-continued

<212> TYPE: DNA
<213> ORGANISM: Homo sapiens

<400> SEQUENCE: 35
caccgaagcc aggaagcccc gtttgtaagc gtgtgttgtg gtgctttatt 50

<210> SEQ ID NO 36
<211> LENGTH: 50
<212> TYPE: DNA
<213> ORGANISM: Homo sapiens

<400> SEQUENCE: 36
gctactccac ctctgcggcg aatcagaagc agcaagcaac tttgactgct 50

<210> SEQ ID NO 37
<211> LENGTH: 50
<212> TYPE: DNA
<213> ORGANISM: Homo sapiens

<400> SEQUENCE: 37
gtttcttacc cggtctgagt acgacagggg cgtgaatact ttttctcccg 50

<210> SEQ ID NO 38
<211> LENGTH: 53
<212> TYPE: DNA
<213> ORGANISM: Homo sapiens

<400> SEQUENCE: 38
gctatgaaca tgctgctaac tgttacacac acgcattcct cattgttccg gcc 53

<210> SEQ ID NO 39
<211> LENGTH: 45
<212> TYPE: DNA
<213> ORGANISM: Homo sapiens

<400> SEQUENCE: 39
tttgtggtac cccagcccgt tgtgcagagt tcaaagcctc cggtg 45

<210> SEQ ID NO 40
<211> LENGTH: 62
<212> TYPE: DNA
<213> ORGANISM: Homo sapiens

<400> SEQUENCE: 40
gcaatgactc tcaagcaatt tttggttctg aagatgtagg ctctagctcc tacgttgctg 60
tg 62

<210> SEQ ID NO 41
<211> LENGTH: 50
<212> TYPE: DNA
<213> ORGANISM: Homo sapiens

<400> SEQUENCE: 41
ctcatgactc cgccaactgt gaattgcctt tgttaacccc gtgcagcaag 50

<210> SEQ ID NO 42
<211> LENGTH: 49
<212> TYPE: DNA
<213> ORGANISM: Homo sapiens

<400> SEQUENCE: 42
ttcatggaca accctttcga gttcaacccc gaggacccca tccctgtct 49

<210> SEQ ID NO 43
<211> LENGTH: 65
<212> TYPE: DNA
<213> ORGANISM: Homo sapiens

<400> SEQUENCE: 43
cccagtcaga aagtcaagga gaccttggtt attatgaaag atgtgagctc aagccttcag 60
aacag 65

<210> SEQ ID NO 44
<211> LENGTH: 50
<212> TYPE: DNA
<213> ORGANISM: Homo sapiens

<400> SEQUENCE: 44
ccctgacagt aagtcggatg agcctgtctg tgccagtgac aatgccactt 50

<210> SEQ ID NO 45
<211> LENGTH: 65
<212> TYPE: DNA
<213> ORGANISM: Homo sapiens

<400> SEQUENCE: 45
cagggatctc aggaaggaca tttcagtgaa atgatattta ctcctgaaga catgcccact 60
ttcag 65

<210> SEQ ID NO 46
<211> LENGTH: 59
<212> TYPE: DNA
<213> ORGANISM: Homo sapiens

<400> SEQUENCE: 46
ggcatggcag caaatgccaa cattttgtgg aatagcagca aatctacaag agaccctgg 59

<210> SEQ ID NO 47
<211> LENGTH: 66
<212> TYPE: DNA
<213> ORGANISM: Homo sapiens

<400> SEQUENCE: 47
gacacctaca ggttatccag actactactc agattgccag ctttaagact gatgaatgct 60
accatc 66

<210> SEQ ID NO 48
<211> LENGTH: 56
<212> TYPE: DNA
<213> ORGANISM: Homo sapiens

<400> SEQUENCE: 48
cccagtgacg accaaactca aagatgtaca gaggcagtta aaagcactgc ttcctc 56

<210> SEQ ID NO 49
<211> LENGTH: 50
<212> TYPE: DNA
<213> ORGANISM: Homo sapiens

<400> SEQUENCE: 49
acgtcagaga ttgtgtctga accgtcctgc tctctagctc tgacggatga 50

<210> SEQ ID NO 50
<211> LENGTH: 48

-continued

<212> TYPE: DNA
<213> ORGANISM: Homo sapiens

<400> SEQUENCE: 50
tcacggcctg gagttcttgt tccgggactg caggaatgtc tcgcagtt 48

<210> SEQ ID NO 51
<211> LENGTH: 50
<212> TYPE: DNA
<213> ORGANISM: Homo sapiens

<400> SEQUENCE: 51
taatccttat gcgcgtaacc gtcctccctt tggtcagggc tatacccaac 50

<210> SEQ ID NO 52
<211> LENGTH: 53
<212> TYPE: DNA
<213> ORGANISM: Homo sapiens

<400> SEQUENCE: 52
gatcaaagcc agagaggagc ctatggaatg tggatcaaat gccagttgtg acg 53

<210> SEQ ID NO 53
<211> LENGTH: 67
<212> TYPE: DNA
<213> ORGANISM: Homo sapiens

<400> SEQUENCE: 53
gaaccacaac aagaggatga tgagtttctt atggcgactg atgtagatga tagatttgag 60
accctgg 67

<210> SEQ ID NO 54
<211> LENGTH: 50
<212> TYPE: DNA
<213> ORGANISM: Homo sapiens

<400> SEQUENCE: 54
ctcagggaga tggatttgct cgttgttttc ttccctcctt ccccttcctg 50

<210> SEQ ID NO 55
<211> LENGTH: 57
<212> TYPE: DNA
<213> ORGANISM: Homo sapiens

<400> SEQUENCE: 55
ccgtggatgt gtatgggatt gtgtatgacc ttcgaatgca taggccttta atggtgc 57

<210> SEQ ID NO 56
<211> LENGTH: 55
<212> TYPE: DNA
<213> ORGANISM: Homo sapiens

<400> SEQUENCE: 56
gcccagctta tcataaacac tgagaaaact gtgattggct ctgttctgct gcggg 55

<210> SEQ ID NO 57
<211> LENGTH: 52
<212> TYPE: DNA
<213> ORGANISM: Homo sapiens

<400> SEQUENCE: 57
cgagaaaatg aaaaccacct cttggttgtt ccagagtcac ggttcgaccg ag 52

-continued

<210> SEQ ID NO 58
<211> LENGTH: 50
<212> TYPE: DNA
<213> ORGANISM: Homo sapiens

<400> SEQUENCE: 58
tccgggattg ttactgtcag tgttggccat tgccacccaa aggtgaatgc 50

<210> SEQ ID NO 59
<211> LENGTH: 50
<212> TYPE: DNA
<213> ORGANISM: Homo sapiens

<400> SEQUENCE: 59
gagcccgatg acgctgaact agtaaggctc agtaagaggc tggtggagaa 50

<210> SEQ ID NO 60
<211> LENGTH: 50
<212> TYPE: DNA
<213> ORGANISM: Homo sapiens

<400> SEQUENCE: 60 tcagcccct attacacctg acgtggagac tttccaaaac accgtaggag 50

<210> SEQ ID NO 61
<211> LENGTH: 57
<212> TYPE: DNA
<213> ORGANISM: Homo sapiens

<400> SEQUENCE: 61
cagcagggat ccacacactg aaagaagttc gcagagatta tgaagccatt ggaatcc 57

<210> SEQ ID NO 62
<211> LENGTH: 45
<212> TYPE: DNA
<213> ORGANISM: Homo sapiens

<400> SEQUENCE: 62
tcaagtaagc cctgtgagga gagctcccag cagaaggcac ggagt 45

<210> SEQ ID NO 63
<211> LENGTH: 50
<212> TYPE: DNA
<213> ORGANISM: Homo sapiens

<400> SEQUENCE: 63
aaatgcttga ttgcagaggt ctggtgccct gtcaccgacc ttgactccat 50

<210> SEQ ID NO 64
<211> LENGTH: 50
<212> TYPE: DNA
<213> ORGANISM: Homo sapiens

<400> SEQUENCE: 64
ctgcgagcat ctctggtgcc catggaacac tgcataaccc gtttctttga 50

<210> SEQ ID NO 65
<211> LENGTH: 50
<212> TYPE: DNA
<213> ORGANISM: Homo sapiens

<400> SEQUENCE: 65
tggcgttccc actggggtta aagggaatgt ccagggaaac ctcttcaaag 50

<210> SEQ ID NO 66
<211> LENGTH: 42
<212> TYPE: DNA
<213> ORGANISM: Homo sapiens

<400> SEQUENCE: 66
cgactactac gatgaggact acgatgacga gcagcgcacc gg 42

<210> SEQ ID NO 67
<211> LENGTH: 59
<212> TYPE: DNA
<213> ORGANISM: Homo sapiens

<400> SEQUENCE: 67
gctggttctc ggcatcatga tttccaccac atgaacttca ttggaaacta tgcttcaac 59

<210> SEQ ID NO 68
<211> LENGTH: 50
<212> TYPE: DNA
<213> ORGANISM: Homo sapiens

<400> SEQUENCE: 68
tctgtgacaa cctgggagac cacctggtgg ggaacgtgta cgtcaagttt 50

<210> SEQ ID NO 69
<211> LENGTH: 45
<212> TYPE: DNA
<213> ORGANISM: Homo sapiens

<400> SEQUENCE: 69
caaaacgcag ccctgcgacc acaccaaggg gctggaatgc aactt 45

<210> SEQ ID NO 70
<211> LENGTH: 52
<212> TYPE: DNA
<213> ORGANISM: Homo sapiens

<400> SEQUENCE: 70
caacagcgca gtcttgtcaa ccatcagatg atccatgcag aggtgaaaac cc 52

<210> SEQ ID NO 71
<211> LENGTH: 50
<212> TYPE: DNA
<213> ORGANISM: Homo sapiens

<400> SEQUENCE: 71
caccagatga acgggacaaa ccagcacttc cgagattgca accccaagca 50

<210> SEQ ID NO 72
<211> LENGTH: 1424
<212> TYPE: DNA
<213> ORGANISM: Homo sapiens

<400> SEQUENCE: 72
gatgaaacga aaagaatctg catttaagag tatgttaaaa caagctgctc ctccgataga 60
attggatgct gtctgggaag atatccgtga gagatttgta aaagagccag catttgagga 120
cataactcta gaatctgaaa gaaaacgaat atttaaagat tttatgcatg tgcttgagca 180
tgaatgtcag catcatcatt caaagaacaa gaaacattct aagaaatcta aaaaacatca 240
taggaaacgt tcccgctctc gatcggggtc agattcagat gatgatgata gccattcaaa 300

```
gaaaaaaaga cagcgatcag agtctcgttc tgcttcagaa cattcttcta gtgcagagtc    360

tgagagaagt tataaaaagt caaaaaagca taagaagaaa agtaagaaga ggagacataa    420

atctgactct ccagaatccg atgctgagcg agagaaggat aaaaaagaaa aagatcggga    480

aagtgaaaaa gacagaacta gacaaagatc agaatcaaaa cacaaatcgc ctaagaaaaa    540

gactggaaag gattctggta attgggatac ttctggcagc gaactgagtg aaggggaatt    600

ggaaaagcgc agaagaaccc ttttggagca actggatgat gatcaataaa ttataccaaa    660

tatatgttta cagtatgatt taaagtctga ttcagaccag ggactctatt ttaagttcaa    720

ctgaaataac actgggtttt aattatatca caggaaaaaa aaagtgcatt taagtattgt    780

tatcgtggac tttataaaag caaaggaaat tgaaagtaac ttttgattct gtatcaagaa    840

tcatattttc atacagtcat aactgtcttt ctgtgaccct ttcacagggc actgtaggat    900

ggattaaagg tggcaattta ctgataactg cagatgtctc tactttgttc taaaatctaa    960

gtcataaggt gatttgattt actttataga agctggattt tgaagatcta atgaaaaatt   1020

ttttgataat atagtagtac aaaaaaagca ccagcaactg ataaaaattg ctttttttgtg   1080

cgctacccaa ctggttaaag ccaatgtgat cttttatggt gaaactccta agaaacaggt   1140

ggttttgctg gaaacttggt agacccttaa ttatagtggt gctaatgagc actactgtaa   1200

tataaagcca ccattatttt ttatcaaaca tctgaataca ttttacaaag gctattgtga   1260

gggcattatt ttgagcatct attttgaggt gatgtttaaa aaaactttaa catcaaatca   1320

aattgtaaat taatttaaat atattgcctt aaggacctac taaagaatgt gccaccagac   1380

tttaagtgat agttgcaata tccttgtcta aaaaaaaaaa aaaa                      1424
```

<210> SEQ ID NO 73
<211> LENGTH: 874
<212> TYPE: DNA
<213> ORGANISM: Homo sapiens

<400> SEQUENCE: 73

```
agttcctcca cctgctggcc cctggacacc tctgtcacca tgtggttcct ggttctgtgc     60

ctcgccctgt ccctgggggg gactggtgct gcgcccccga ttcagtcccg gattgtggga    120

ggctgggagt gtgagcagca ttcccagccc tggcaggcgg ctctgtacca tttcagcact    180

ttccagtgtg gggcatcct ggtgcaccgc cagtgggtgc tcacagctgc tcattgcatc    240

agcgacaatt accagctctg gctgggtcgc cacaacttgt ttgacgacga aaacacagcc    300

cagtttgttc atgtcagtga gagcttccca caccctggct tcaacatgag cctcctggag    360

aaccacaccc gccaagcaga cgaggactac agccacgacc tcatgctgct ccgcctgaca    420

gagcctgctg ataccatcac agatgctgtg aaggtcgtgg agttgcccac cgaggaaccc    480

gaagtgggga gcacctgttt ggcttccggc tggggcagca tcgaaccaga gaatttctca    540

tttccagatg atctccagtg tgtggacctc aaaatcctgc ctaatgatga gtgcaaaaaa    600

gcccacgtcc agaaggtgac agacttcatg ctgtgtgtcg gacacctgga aggtggcaaa    660

gacacctgtg tgggtgattc aggggggcccg ctgatgtgtg atggtgtgct ccaaggtgtc    720

acatcatggg gctacgtccc ttgtggcacc cccaataagc cttctgtcgc cgtcagagtg    780

ctgtcttatg tgaagtggat cgaggacacc atagcggaga actcctgaac gcccagccct    840

gtcccctacc cccagtaaaa tcaaatgtgc atcc                                 874
```

<210> SEQ ID NO 74
<211> LENGTH: 2308

-continued

<212> TYPE: DNA
<213> ORGANISM: Homo sapiens

<400> SEQUENCE: 74

```
cccggggcgt atgacgccgg agccctctga ccgcacctct gaccacaaca aacccctact     60
ccacccgtct tgtttgtccc acccttggtg acgcagagcc ccagcccaga ccccgcccaa    120
agcactcatt taactggtat tgcggagcca cgaggcttct gcttactgca actcgctccg    180
gccgctgggc gtagctgcga ctcggcggag tcccggcggc gcgtccttgt tctaacccgg    240
cgcgccatga ccgtcgcgcg gccgagcgtg cccgcggcgc tgcccctcct cggggagctg    300
ccccggctgc tgctgctggt gctgttgtgc ctgccggccg tgtggggtga ctgtggcctt    360
cccccagatg tacctaatgc ccagccagct ttggaaggcc gtacaagttt tcccgaggat    420
actgtaataa cgtacaaatg tgaagaaagc tttgtgaaaa ttcctggcga gaaggactca    480
gtgatctgcc ttaagggcag tcaatggtca gatattgaag agttctgcaa tcgtagctgc    540
gaggtgccaa caaggctaaa ttctgcatcc ctcaaacagc cttatatcac tcagaattat    600
tttccagtcg gtactgttgt ggaatatgag tgccgtccag gttacagaag agaaccttct    660
ctatcaccaa aactaacttg ccttcagaat ttaaaatggt ccacagcagt cgaattttgt    720
aaaaagaaat catgccctaa tccgggagaa atacgaaatg gtcagattga tgtaccaggt    780
ggcatattat ttggtgcaac catctccttc tcatgtaaca cagggtacaa attatttggc    840
tcgacttcta gtttttgtct tatttcaggc agctctgtcc agtggagtga cccgttgcca    900
gagtgcagag aaatttattg tccagcacca ccacaaattg acaatggaat aattcaaggg    960
gaacgtgacc attatggata tagacagtct gtaacgtatg catgtaataa aggattcacc   1020
atgattggag agcactctat ttattgtact gtgaataatg atgaaggaga gtggagtggc   1080
ccaccacctg aatgcagagg aaaatctcta acttccaagg tcccaccaac agttcagaaa   1140
cctaccacag taaatgttcc aactacagaa gtctcaccaa cttctcagaa aaccaccaca   1200
aaaaccacca caccaaatgc tcaagcaaca cggagtacac ctgtttccag gacaaccaag   1260
cattttcatg aaacaacccc aaataaagga agtggaacca cttcaggtac tacccgtctt   1320
ctatctgggc acacgtgttt cacgttgaca ggtttgcttg ggacgctagt aaccatgggc   1380
ttgctgactt agccaaagaa gagttaagaa gaaaatacac acaagtatac agactgttcc   1440
tagtttctta gacttatctg catattggat aaaataaatg caattgtgct cttcatttag   1500
gatgctttca ttgtctttaa gatgtgttag gaatgtcaac agagcaagga gaaaaaaggc   1560
agtcctggaa tcacattctt agcacaccta cacctcttga aaatagaaca acttgcagaa   1620
ttgagagtga ttcctttcct aaaagtgtaa gaaagcatag agatttgttc gtatttagaa   1680
tgggatcacg aggaaaagag aaggaaagtg atttttttcc acaagatctg taatgttatt   1740
tccacttata aaggaaataa aaaatgaaaa acattatttg gatatcaaaa gcaaataaaa   1800
acccaattca gtctcttcta agcaaaattg ctaaagagag atgaaccaca ttataaagta   1860
atctttggct gtaaggcatt ttcatctttc cttcgggttg gcaaaatatt ttaaaggtaa   1920
aacatgctgg tgaaccaggg gtgttgatgg tgataaggga ggaatataga atgaaagact   1980
gaatcttcct ttgttgcaca aatagagttt ggaaaaagcc tgtgaaaggt gtcttctttg   2040
acttaatgtc tttaaaagta tccagagata ctacaatatt aacataagaa aagattatat   2100
attatttctg aatcgagatg tccatagtca aatttgtaaa tcttattctt ttgtaatatt   2160
tatttatatt tatttatgac agtgaacatt ctgattttac atgtaaaaca agaaaagttg   2220
```

-continued

```
aagaagatat gtgaagaaaa atgtattttt cctaaataga aataaatgat cccatttttt   2280

ggtaaaaaaa aaaaaaaaaa aaaaaaaa                                       2308


<210> SEQ ID NO 75
<211> LENGTH: 1927
<212> TYPE: DNA
<213> ORGANISM: Homo sapiens

<400> SEQUENCE: 75

tgccagccca agtcggaact tggatcacat cagatcctct cgagctccag caggagaggc     60

ccttcctcgc ctggcagccc ctgagcggct cagcagggca ccatggcaag atcccttctc    120

ctgcccctgc agatcttact gctatcctta gccttggaaa ctgcaggaga agaagcccag    180

ggtgacaaga ttattgatgg cgccccatgt gcaagaggct cccacccatg gcaggtggcc    240

ctgctcagtg gcaatcagct ccactgcgga ggcgtcctgg tcaatgagcg ctgggtgctc    300

actgccgccc actgcaagat gaatgagtac accgtgcacc tgggcagtga tacgctgggc    360

gacaggagag ctcagaggat caaggcctcg aagtcattcc gccaccccgg ctactccaca    420

cagacccatg ttaatgacct catgctcgtg aagctcaata gccaggccag gctgtcatcc    480

atggtgaaga aagtcaggct gccctcccgc tgcgaacccc ctggaaccac ctgtactgtc    540

tccggctggg gcactaccac gagcccagat gtgacctttc cctctgacct catgtgcgtg    600

gatgtcaagc tcatctcccc ccaggactgc acgaaggttt acaaggactt actggaaaat    660

tccatgctgt gcgctggcat ccccgactcc aagaaaaacg cctgcaatgg tgactcaggg    720

ggaccgttgg tgtgcagagg taccctgcaa ggtctggtgt cctggggaac tttcccttgc    780

ggccaaccca atgacccagg agtctacact caagtgtgca agttcaccaa gtggataaat    840

gacaccatga aaaagcatcg ctaacgccac actgagttaa ttaactgtgt gcttccaaca    900

gaaaatgcac aggagtgagg acgccgatga cctatgaagt caaatttgac tttacctttc    960

ctcaaagata tatttaaacc aacctcatgc cctgttgata aaccaatcaa attggtaaag   1020

acctaaaacc aaaacaaata aagaaacaca aaaccctcag tgctggagaa gagtcagtga   1080

gaccagcact ctcaaacact ggaactggac gttcgtacag tctttacgga agacacttgg   1140

tcaacgtaca ccgagaccct tattcaccac ctttgaccca gtaactctaa tcttaggaag   1200

aacctactga aacaaaaaaa atccaaaatg tagaacaaga cttgaattta ccatgatatt   1260

atttatcaca gaaatgaagt gaaaccatca aacatgttcc aaaagtacca gatggcttaa   1320

ataatagtct ggcttggcac aacgatgttt tttttctttg agacagagtc tctgttgctt   1380

gggctgcaat gcagtgatgc aatcttggct cactgcaacc tccgcctcct gggttcaagt   1440

gattctcgtg cttcagcctc ccaagtacct gggactacag gtgtgcacca ccacaccagg   1500

ctaatttttt gtgtattttt actagagaca gggtttcacc atgttggcca gcgtggtctt   1560

gaacgcctga cctcagatga tccacccacc ttggcctccc aaagtgctgg gattacaggc   1620

atgagccacc acggccagcc cacaatgata ttacaaacct attaaaaatg atacttagac   1680

agaattgtca gtattattca agaacattta ggctatagga tgttaaatga caaaaggaag   1740

gacaaaaata tatatgtatg tgaccctacc cataaaaaat gaaatattca cagaatcaga   1800

tctgaaaaca catgtcccag actgcatact ggggtcgtca tgaggtgtct ccttccttct   1860

gtgtactttt ccttgaatgt gcacttttat aacatgaaaa ataaaggtgg ggaaaaaagt   1920

ctgaaga                                                              1927
```

-continued

<210> SEQ ID NO 76
<211> LENGTH: 3942
<212> TYPE: DNA
<213> ORGANISM: Homo sapiens

<400> SEQUENCE: 76

```
gggtgattca gcgcccggcg aggcggaagc ggccgcaaga ggaggagggg agagcccgtc     60
cgcgcctggg ctcccggggt ggcacgagcc cgcggccgga gtgcgaggcg gaggcgagga    120
ggccgcgggg acgggaggcg aggccggccg ggcccccgaa gccatggaga acgcgcacac    180
caagacggtg gaggaggtgc tgggccactt cggcgtcaac gagagtacgg ggctgagcct    240
ggaacaggtc aagaagctta aggagagatg ggctccaaac gagttaccgg ctgaagaagg    300
aaaaaccttg ctggaacttg tgattgagca gtttgaagac ttgctagtta ggattttatt    360
actggcagca tgtatatctt ttgttttggc ttggtttgaa gaaggtgaag aaacaattac    420
agcctttgta gaaccttttg taattttact catattagta gccaatgcaa ttgtgggtgt    480
atggcaggaa agaaatgctg aaaatgccat cgaagccctt aaggaatatg agcctgaaat    540
gggcaaagtg tatcgacagg acagaaagag tgtgcagcgg attaaagcta aagacatagt    600
tcctggtgat attgtagaaa ttgctgttgg tgacaaagtt cctgctgata taaggttaac    660
ttccatcaaa tctaccacac taagagttga ccagtcaatt ctcacaggtg aatctgtctc    720
tgtcatcaag cacactgatc ccgtccctga cccacgagct gtcaaccaag ataaaaagaa    780
catgctgttt tctggtacaa acattgctgc tgggaaagct atgggagtgg tggtagcaac    840
tggagttaac accgaaattg gcaagatccg ggatgaaatg gtggcaacag aacaggagag    900
aacacccctt cagcaaaaac tagatgaatt tggggaacag ctttccaaag tcatctccct    960
tatttgcatt gcagtctgga tcataaatat tgggcacttc aatgacccgg ttcatggagg   1020
gtcctggatc agaggtgcta tttactactt taaaattgca gtggccctgg ctgtagcagc   1080
cattcctgaa ggtctgcctg cagtcatcac cacctgcctg gctcttggaa ctcgcagaat   1140
ggcaaagaaa aatgccattg ttcgaagcct cccgtctgtg gaaacccttg gttgtacttc   1200
tgttatctgc tcagacaaga ctggtacact tacaacaaac cagatgtcag tctgcaggat   1260
gttcattctg gacagagtgg aaggtgatac ttgttccctt aatgagttta ccataactgg   1320
atcaacttat gcacctattg gagaagtgca taaagatgat aaaccagtga attgtcacca   1380
gtatgatggt ctggtagaat tagcaacaat ttgtgctctt tgtaatgact ctgctttgga   1440
ttacaatgag gcaaagggtg tgtatgaaaa agttggagaa gctacagaga ctgctctcac   1500
ttgcctagta gagaagatga atgtatttga taccgaattg aagggtcttt ctaaaataga   1560
acgtgcaaat gcctgcaact cagtcattaa acagctgatg aaaaaggaat tcactctaga   1620
gttttcacgt gacagaaagt caatgtcggt ttactgtaca ccaaataaac caagcaggac   1680
atcaatgagc aagatgtttg tgaagggtgc tcctgaaggt gtcattgaca ggtgcaccca   1740
cattcgagtt ggaagtacta aggttcctat gacctctgga gtcaaacaga agatcatgtc   1800
tgtcattcga gagtggggta gtggcagcga cacactgcga tgcctggccc tggccactca   1860
tgacaaccca ctgagaagag aagaaatgca ccttgaggac tctgccaact ttattaaata   1920
tgagaccaat ctgaccttcg ttggctgcgt gggcatgctg gatcctccga gaatcgaggt   1980
ggcctcctcc gtgaagctgt gccggcaagc aggcatccgg gtcatcatga tcactgggga   2040
caacaagggc actgctgtgg ccatctgtcg ccgcatcggc atcttcgggc aggatgagga   2100
cgtgacgtca aaagctttca caggccggga gtttgatgaa ctcaacccct ccgcccagcg   2160
```

-continued

```
agacgcctgc ctgaacgccc gctgttttgc tcgagttgaa ccctcccaca agtctaaaat   2220

cgtagaattt cttcagtctt ttgatgagat tacagctatg actggcgatg gcgtgaacga   2280

tgctcctgct ctgaagaaag ccgagattgg cattgctatg ggctctggca ctgcggtggc   2340

taaaaccgcc tctgagatgg tcctggcgga tgacaacttc tccaccattg tggctgccgt   2400

tgaggagggg cgggcaatct acaacaacat gaaacagttc atccgctacc tcatctcgtc   2460

caacgtcggg gaagttgtct gtattttcct gacagcagcc cttggatttc ccgaggcttt   2520

gattcctgtt cagctgctct gggtcaatct ggtgacagat ggcctgcctg ccactgcact   2580

ggggttcaac cctcctgatc tggacatcat gaataaacct ccccggaacc caaaggaacc   2640

attgatcagc gggtggctct tttccgtta cttggctatt ggctgttacg tcggcgctgc   2700

taccgtgggt gctgctgcat ggtggttcat tgctgctgac ggtggtccaa gagtgtcctt   2760

ctaccagctg agtcatttcc tacagtgtaa agaggacaac ccggactttg aaggcgtgga   2820

ttgtgcaatc tttgaatccc catacccgat gacaatggcg ctctctgttc tagtaactat   2880

agaaatgtgt aacgccctca acagcttgtc cgaaaaccag tccttgctga ggatgccccc   2940

ctgggagaac atctggctcg tgggctccat ctgcctgtcc atgtcactcc acttcctgat   3000

cctctatgtc gaacccttgc cactcatctt ccagatcaca ccgctgaacg tgacccagtg   3060

gctgatggtg ctgaaaatct ccttgcccgt gattctcatg gatgagacgc tcaagtttgt   3120

ggcccgcaac tacctggaac ctgcaatact ggagtaaccg cttcctaaac cattttgcag   3180

aaatgtaagg gtgttcggtt gcgtgcatgt gcgtttttag caacacatct accaaccctg   3240

tgcatgactg atgttgggga aaaagaaaag taaaaaactt cccaactcac tttgtgttat   3300

gtggaggaaa tgtgtattac caatggggtt gttagctttt aaatcaaaat actgattaca   3360

gatgtacaat ttagcttaat cagaaagcct ctccagagaa gtttggtttc tttgctgcaa   3420

gaggaatgag gctctgtaac cttatctaag aacttggaag ccgtcagcca agtcgccaca   3480

tttctctgca aaatgtcata gcttatataa atgtacagta ttcaattgta atgcatgcct   3540

tcggttgtaa gtagccagat ccctctccag tgacattgga acatgctact ttttaattgg   3600

ccctgtacag tttgcttatt tataaattca ttaaaaacac tacaggtgtt gaatggttaa   3660

aatgtaggcc tccagttcat tttcagttat tttctgagtg tgcagacagc tatttcgcac   3720

tgtattaaat gtaacttatt taatgaaatc agaagcagta gacagatgtt ggtgcaatac   3780

aaatattgtg atgcatttat cttaataaaa tgctaaatgt caatttatca ctgcgcatgt   3840

ttgactttag actgtaaata gagatcagtt tgtttctttc tgtgctggta acaatgagcg   3900

tcgcacagac atggtttcag gtaaataaat ctattctatg at                      3942
```

<210> SEQ ID NO 77
<211> LENGTH: 2385
<212> TYPE: DNA
<213> ORGANISM: Homo sapiens

<400> SEQUENCE: 77

```
atggccgact tcgatgatcg tgtgtcggat gaggagaagg tacgcatagc tgctaaattc     60

atcactcatg cacccccagg ggaatttaat gaagtattca atgacgttcg gctactactt    120

aataatgaca atctcctcag ggaaggggca gcacatgcat ttgcccagta taacatggat    180

cagttcacgc ctgtgaagat agaaggatat gaagatcagg tcttaattac agagcacggt    240

gacctgggta atagcagatt tttagatcca agaaacaaaa tttcctttaa atttgaccac    300

ttacggaaag aagcaagtga cccccagcca gaagaagcag atggaggtct gaagtcttgg    360
```

-continued

```
agagaatcct gtgacagtgc tttaagagcc tatgtgaaag accattattc caacggcttc    420
tgtactgttt atgctaaaac tatcgatggg caacagacta ttattgcatg tattgaaagc    480
caccagtttc agcctaaaaa cttctggaat ggtcgttgga gatcagagtg gaagttcacc    540
atcacaccac ctacagccca ggtggttggc gtgcttaaga ttcaggttca ctattatgaa    600
gatggcaatg ttcagttggt tagtcataaa gatgtacagg attcactaac tgtttcgaat    660
gaagcccaaa ctgccaagga gtttattaaa atcatagaga atgcagaaaa tgagtatcag    720
acagcaatta gtgaaaacta tcaaacaatg tcagatacca cattcaaggc cttgcgccgc    780
cagcttccag ttacccgcac caaaatcgac tggaacaaga tactcagcta caagattggc    840
aaagaaatgc agaatgctta aaggctgaat gtaggattct tcagtatgtg gaaagacaag    900
gattcaacgt gtggtcatat gataaataag tgatttataa acaagagtga tattttgcta    960
gggctttcaa agttaaccgg ttttctagcc tcatggaata ctgttgaacc tatagcgttg   1020
tcttgattct tttgtgttct ctgccttgta attttctgtt actgctatat ctacgtgtaa   1080
atcttttttt cttttttttt tttttttttt ttcttttttg gttaattctg ccacatttaa   1140
tgttggtgag agagtgatct atcctaatga catttactgt ttaaaaaagt ttcctagcca   1200
tgaagccctg ctactgattt agacaaggta ttatggtcat tactttgtac ccctatcctt   1260
ccaagcactt ctggtacttc agtcgttttt actgatccac caacacctaa agaggctatg   1320
ctacagtctc tagctaaatg gaagacacat tcatccttct ccctctgact gctttgatca   1380
tcatttattg catcgtcata tcatatttat cgcatctcat aactaacttt ctaaagtttg   1440
gattgggact tttcaggtcc tttttggagg gcaaaggaag ttccagcttc tctggggaac   1500
ttgtttttaa atccaaagac ttgaaccaca ttccctgcac atgaacatgt ttgcttttat   1560
cccttctctc attggctcct tcccatctta gtaccattgt agttatacat ctgcattttt   1620
tagaagcatt ttacccattt atttttttaa acattcaaga actgctgacg tactgtggat   1680
gtagagtata aaacttgaaa aatgcagatg ttgaaggaat aataggtatc ttgtgcttta   1740
atactttatg gcaggattgt actataagca aatgaattaa acagctatgt aaatcataaa   1800
gaaaaactaa aaatgaacca aagtgaaagg ataacttcca ggcagtatct ttctattgta   1860
acctgttatt taaggaaata ctagtgattt cttctaaata ggatgtaaac ttctttcaaa   1920
ttactcttcc tcagtctgcc tgccaagaac tcaagtgtaa ctgtgataaa ataacctttc   1980
ccaggtatat tcggcaggta tgtgtgtaat ctcagaatac acaggtgaca tagatatgat   2040
atgacaactg gtaatggtgg attcatttac attgtttaca cttctatgac caggccttaa   2100
gggaaggtca gtttttttaaa aaaccaagta gtgtcttcct acctatctcc agatacatgt   2160
caaaaagaaa aggtgtttgt gctccgtttt gtttctgctc agtaatatag tcaagcaagt   2220
ttgttccagg tgacccattg agctgtgtat gcatttttgt ttatttcaat aaaatatatt   2280
tgtattattt gtccttcata ctatccatcc ataccacact atcttctgta tcaggtagtc   2340
taatagaaat atacctgttt tgttctaaaa aaaaaaaaaa aaaaa                   2385
```

<210> SEQ ID NO 78
<211> LENGTH: 1320
<212> TYPE: DNA
<213> ORGANISM: Homo sapiens

<400> SEQUENCE: 78

```
cccccctagcg tcgcgcaggg tcggggactg cgcgcggtgc caggccgggc gtgggcgaga     60
```

-continued

```
gcacgaacgg gctgctgcgg gctgagagcg tcgagctgtc accatgggtg atcacgcttg    120
gagcttccta aaggacttcc tggccggggc ggtcgccgct gccgtctcca agaccgcggt    180
cgccccccatc gagagggtca aactgctgct gcaggtccag catgccagca aacagatcag    240
tgctgagaag cagtacaaag ggatcattga ttgtgtggtg agaatcccta aggagcaggg    300
cttcctctcc ttctggaggg gtaacctggc caacgtgatc cgttacttcc ccacccaagc    360
tctcaacttc gccttcaagg acaagtacaa gcagctcttc ttagggggtg tggatcggca    420
taagcagttc tggcgctact ttgctggtaa cctggcgtcc ggtggggccg ctggggccac    480
ctccctttgc tttgtctacc cgctggactt tgctaggacc aggttggctg ctgatgtggg    540
caggcgcgcc cagcgtgagt tccatggtct gggcgactgt atcatcaaga tcttcaagtc    600
tgatggcctg agggggctct accagggttt caacgtctct gtccaaggca tcattatcta    660
tagagctgcc tacttcggag tctatgatac tgccaagggg atgctgcctg accccaagaa    720
cgtgcacatt tttgtgagct ggatgattgc ccagagtgtg acggcagtcg cagggctgct    780
gtcctacccc tttgacactg ttcgtcgtag aatgatgatg cagtccggcc ggaaaggggc    840
cgatattatg tacacgggga cagttgactg ctggaggaag attgcaaaag acgaaggagc    900
caaggccttc ttcaaaggtg cctggtccaa tgtgctgaga ggcatgggcg gtgcttttgt    960
attggtgttg tatgatgaga tcaaaaaata tgtctaatgt aattaaaaca caagttcaca   1020
gatttacatg aacttgatct acaagttcac agatccattg tgtggtttaa tagactattc   1080
ctaggggaag taaaaagatc tgggataaaa ccagactgaa aggaatacct cagaagagat   1140
gcttcattga gtgttcatta aaccacacat gtattttgta tttattttac atttaaattc   1200
ccacagcaaa tagaaataat ttatcatact tgtacaatta actgaagaat tgataataac   1260
tgaatgtgaa acatcaataa agaccactta atgcacaaaa aaaaaaaaaa aaaaaaaaaa   1320
```

<210> SEQ ID NO 79
<211> LENGTH: 4139
<212> TYPE: DNA
<213> ORGANISM: Homo sapiens

<400> SEQUENCE: 79

```
ggcggcgcag gggcggggct ttacggacgc aagcacgtcg aagcgctgct cctggagccg     60
cggagggtgc gggtttggct gcggtggttt ctgtggcggt tgctgtggcg gagtttggag    120
gttggagaga aatccaggta ctcactagac tggtaccttc tgccaccatg gggggagcttt    180
tccggagtga agaaatgaca ctggcccagc tttttctaca gtcagaggct gcttattgtt    240
gtgtcagtga attaggagaa cttggaaagg ttcagtttcg tgacttaaat ccagatgtga    300
atgttttcca acggaaattt gtgaatgaag ttagaagatg tgaagaaatg gatcgaaagc    360
ttcgatttgt tgagaaagag ataagaaaag ctaacattcc gattatggac accggtgaaa    420
acccagaggt tcccttcccc cgggacatga ttgacttaga ggccaatttt gagaagattg    480
aaaatgaact gaaggaaatc aacacaaacc aggaagctct gaagagaaac ttcctggaac    540
tgaccgaatt aaaatttata cttcgcaaaa ctcagcaatt ttttgatgag atggcggatc    600
cagacttgtt ggaagagtcc tcatccctct tggagccaag tgagatggga agaggcactc    660
ctttaagact tggcttcgtg gctggtgtca ttaaccggga gcgcatccct actttttgagc    720
gcatgctttg gcgggtatgc cggggaaatg tgttcctgcg acaggctgaa atcgagaacc    780
ccctggagga tcctgtgact ggcgactacg tgcacaagtc tgtgtttatc attttcttcc    840
aaggcgatca gctgaaaaac agagtcaaga aaatctgtga agggttccga gcctcactct    900
```

-continued

```
atccctgtcc tgagacacca caggagagga aggaaatggc ttctggagtg aataccagga    960
ttgatgatct ccaaatggtt ctgaatcaaa cggaggatca ccgccagagg gttctgcagg   1020
cagctgctaa gaacatccgt gtctggttca tcaaagtgcg gaagatgaag gccatctatc   1080
acaccctgaa cctgtgcaac atagatgtga ctcagaaatg cttgattgca gaggtctggt   1140
gccctgtcac cgaccttgac tccatccagt ttgcactcag aaggggcacg gaacacagtg   1200
gttccactgt accttccatt ttgaacagga tgcagacaaa ccagactccc ccaacctata   1260
acaaaaccaa caagtttacc tatggctttc agaacatagt agatgcttat ggaattggaa   1320
cttaccgaga gataaatcca gctccgtata ctattatcac gttccctttt ctatttgctg   1380
tgatgtttgg agacttcggt catggcattt taatgaccct tttgctgtg tggatggtac   1440
tgagggagag ccggatcctt tcccagaaga atgagaatga gatgtttagc actgtgttca   1500
gtggtcgata cattatttta ttgatgggtg tgttctccat gtacactggc ctcatctaca   1560
atgattgctt ttccaagtct cttaatatct ttgggtcatc ctggagtgta cggccgatgt   1620
ttacttataa ttggactgaa gagacgcttc gggggaaccc tgttctacag ctgaacccag   1680
ccctccctgg agtgtttggt ggaccatacc cttttggcat tgatccaatt tggaacattg   1740
ctaccaataa actgacgttc ttgaactcct ttaagatgaa gatgtctgtt atccttggta   1800
tcatccatat gctgtttgga gtcagcctga gtctgttcaa ccatatctat ttcaagaagc   1860
ccctgaatat ctactttgga tttattcctg aaataatctt catgacctct ttgtttggct   1920
atttggttat ccttattttt tacaagtgga cggcctatga tgctcatacc tctgagaatg   1980
caccaagcct tctgatccat ttcataaaca tgttcctctt ttcctaccca gagtctggtt   2040
attcaatgtt gtattctgga cagaaaggaa ttcagtgttt cctggtagtg gttgcactac   2100
tgtgtgtacc ttggatgctg ctgtttaaac cattggtcct tcgccgtcag tatttgagga   2160
gaaagcattt gggaactctc aactttggtg ggatcagggt gggcaacgga ccgacagagg   2220
aggatgctga gattattcag catgaccagc tctccaccca ctcagaggac gcagacgagt   2280
ttgactttgg ggacaccatg gtccaccagg ccatccacac catcgagtac tgcctgggct   2340
gcatctccaa cactgcctcc tacttgcggc tctgggccct cagcctcgct catgcgcagc   2400
tgtctgaggt gctttggacc atggtgatcc acatcggcct gagcgtgaag agcttggcgg   2460
gaggtttggt gctgttcttc ttcttcactg cctttgccac cctgaccgtg gccatcctcc   2520
tgatcatgga gggcctctcg gcctttctcc acgcactgcg cttacactgg gttgagttcc   2580
agaataaatt ctacagcggg accggtttca agttcttacc cttctccttc gagcatattc   2640
gggaaggaa gtttgaagag tgagtccctg tgagggccgt gtgccccatg ctaccctccc   2700
cgcctccctc cacagtgatc agctgtgcct ctctgcctgt tggttgtgat ctgtgggcac   2760
cagctcattc gtgtcaccct gtctgtgagt catttagata gaatagtcct ccttgggtct   2820
cccaccaccc ctagctttgt gtgtagtgta gtgattttct ggctgtcact catactcact   2880
gggcaccagc cttgccctct tagcctccat ccatccagac agcccttccc acctcctggt   2940
ggtgagccag tctgcattcc cacgccatcc caaagccctt tcatcttccc cgtgcattgt   3000
agatggaagg agcacccatg ccattcaccc atctagactt tgagttccct gcatctgcca   3060
ccgtagtttc tagcaggagt agtgggggga gtaatacaga ttcttcccta gaaggggaca   3120
ctggtaacat gtcccactct tggattagca ggggtgggtc caggaagatg atatttgcgt   3180
cttttgccca ccccccctggc attcagctgg acccaactag gccatcatga gtggcttctc   3240
```

-continued

```
cctgtcatcc ccaggggtca taggatatct acaccgcctt tctgacccca ccctgcactc   3300

ccatcctttc ctctctcccc gttcatgccc tgcactacat agcacagccg ggatgcttgg   3360

aacagaggcc ttggctgctc cgcagtgcac agggcttccc tctctcgggg ttggcttctt   3420

cccaggcctt gcatgggccc tgcccacaag cacaccctca ggccgagggt gcagactgat   3480

gctcttccct gatggagacc ctgagatctt ccccaccccc aatcatgatg tcttcagtgt   3540

gggactgggg tcctcttggt tctgcctgca gcctgcctgg ctccgcccct agtgccccct   3600

cctcaccaca ctggccccag gtctcaggag gggtgtcctg ggcagggaag gtcagtgtca   3660

ctgatggttt gctgtttgga agccattggc agggctgccg tgcatgtggc tgtgagggct   3720

gcacagtcct gccaaggggc ttcctccttg tcaccccgaa ccttgtaatc gtgtgctggc   3780

gtggcagccc tggctaagtt aatccccacc gctttcagtg gtagaaagaa ttccctgagt   3840

gggccaggct ggtgccctcc tcctaccctg gcttttctga gtgagctgcc tggagccctc   3900

atcccctctc ccaggctggg ctggccctgg gcggggccac tgtgtgctgg cccactgtga   3960

cctgacccga ccttgtgcag ccccccctgcc ctggtgtcct gggttttcgt gatgatcttt   4020

gctctgtttc cagtggggtt tgaagcagag ttcagggaac cctgcccaag gtcctcctgt   4080

tcagacattc ctatgttgaa taaagtatgt ttgacttccc cggaaaaaaa aaaaaaaaa   4139
```

```
<210> SEQ ID NO 80
<211> LENGTH: 3635
<212> TYPE: DNA
<213> ORGANISM: Homo sapiens

<400> SEQUENCE: 80

tccaagatgg cggaactgca gctggacccg gcgatggcgg ggctgggagg gggcggcggg     60

agtggggtgg gcgacggggg tggcccagtc cgcgggcccc ccagcccacg cccggctggc    120

cccacgcccc gcgggcacgg ccgcccggct gccgccgtcg cgcagcgatt ggagccgggt    180

cccggaccac ccgagcgggc agggggcggc ggcgcggccc gctgggtcag gctgaacgtg    240

ggaggcacct acttcgtgac caccagacag accttaggcc gggagcccaa gtcatttctc    300

tgccgcctct gctgccagga ggacccggag ctggactcag acaaggatga gacaggagcc    360

tatctgattg acagggaccc cacctacttt ggtcctatcc tcaactacct ccgccacggg    420

aaactcatca tcactaagga gttggcagaa gaaggtgtgc tggaggaagc ggagttttac    480

aacatcgcgt cccttgtgcg gctggttaag gaaaggatac gggacaatga gaacagaact    540

tcacaaggcc ccgtgaagca cgtgtacaga gtcctgcagt gtcaggaaga agagctcacg    600

cagatggtgt ccacgatgtc cgacggctgg aaattcgaac agctcatcag catcggatct    660

tcctataact acggcaatga ggatcaggca gaattcctct gtgttgtctc cagagaacta    720

aataattcta ccaatggcat cgtcatagag ccgagcgaaa aggcgaagat tcttcaggag    780

agaggatcgc ggatgtaaac taagaccccg aaaactccag accttcagga gagcagtcag    840

cagagcccct ctgtgaagtg aaaccttact cctgtccagt gaccgagcca ctgcaaagca    900

cagctgatcc tggccccctg tgaagaagtg ttctggtcaa aactaaagga actccctccc    960

cacctgcagg actccgaaga cagtgcgact tctggctgca gaatacccttt tcagaaacct   1020

gctttcattt gcttagccag tattagaaca gatctttaca acagcagctg ggctgggttc   1080

ccagtcggag cctttcgggg atctggggga tgagggcgga aggcctagct ccttggaaat   1140

ggcctgtact ttaaggacgc tggagccaag aggattgttc ccgtgccgtg ccatggtttc   1200

accctatgtg tgccacaatg gacgttagca gctgcttcgg aacaccgtcc ctcctatgca   1260
```

-continued

```
ccctccaaga cctgcagcag atgcaaaggg ttctagctgc agtttgtcga attgaggttt   1320
taggtaaagc atagagttgc cagagtaccc cgcattccca tgaatagagc ctccaaggaa   1380
agggaggatg gggtgtcctt tgttgtggtt ggaggttggt gatcattgct ctggatttgg   1440
ggctcccggc tgccaccaca tgcagctttg cctcagcttt ctccagcagc cgggaccctc   1500
tggagagctt gttttccctc caagaagagg tttgagacag gcggcatcct gcactgagtc   1560
agacaagtgg gagctgtagg aactgcacct gcagcctctt cttactcccc attgaccctg   1620
tcttccttcc ctggcttttt caactggacc aaagatgaag gcacttatgg accctttgat   1680
ggcttggagt ggggaaggct gtttctttga aagttgccaa atgtgttacg ttgtgtctca   1740
gagagagtta tttctgtgac tctcttggaa atgccttgac tgaatgtgca atatttgtgt   1800
ctcttggttt ctaaccttgg cggacctgct cccctctgta ctgtccccag tggtatgtat   1860
gtatgtgcta ggcagtctgg ggacccccctg tgtctctgac cacccccctg acccccgcca   1920
ttactttctt ttctggagtg ccatgctggc gaggatccgg atgcggcagc accctctttc   1980
gggctgcatc cacagagttt gtgtccacac tttctctccg agcatgtggg tctcgctgag   2040
cagtcatgga atgcggtaga gccaggggac cctgtctgcc ccgaataact ttcagtagta   2100
tggcagatgg cacagagaaa gggaaggggc tctggggact tctccttcta tgaaagccgc   2160
ctcgagccag gtgctcctgg gcaccttcag aagtgatgtc ctgtgtgctc cacagctcac   2220
ctgcttgcca aggtacgtct gggtagtagt ttctggaaat gactgcagac tgtgccaaat   2280
gtcttttgag cttctgacct gaccatgccc agatggcata acttttccct aggaccctca   2340
gtctccttgt ttctctgtat ctgtagcata gcatagaacc cggtatacag ggtttctgc   2400
tgacacatca acgtctaaac acctatgcgc cacattttac agctgtaaag tgttagatga   2460
actgccgtcc tcagtaaaag cagccacccc ttcaagagtc acaggcatcc atccagtcgt   2520
atctttcaga gaaaaaaaaa gttagatgta gccaaggaaa gtagtgatca cgggaaggac   2580
tgctctgagc cgggtaggat ggaggacttt ggaagaggcg ctccttggcc aggtccaatg   2640
agtaacatca gactgacaga ggaaaagcag cttggtttgc ggccttgtgc ccagtctcgt   2700
tgaggcgctt gtccctgtct gctttcctgg ggcatgcctg atcagcgtgg gctggagctc   2760
ctagaccaac cccagctttc tcaccaggtt cagcaaggag gcctgggggt cagacaccaa   2820
tgttgagcac ctcctgaggg cgccgtttcc ttcattcctc ttagattcca tagttgccgc   2880
catgaaaaga ctgctcttga gccccaaggc acaggcacgt gctctgggaa atagacagga   2940
gtggtatttc cgccctctcg gagggctggt gttcaccaag tttccctcct cgctgcaacc   3000
caatgacacc tgtattgttc cagcgctcca ggactctggg ttcttaagat ttctgggagc   3060
gttgttcacc cacccccttt aggaaccagg ctggtgttct tgcttgaaag cgttgtgccc   3120
tctgagtgtc tggctgatca catcagagag gtctgcgtgg cagtttgggg ctgtcacgtg   3180
accagtgacc cacactctct gctgcccagt actgccaagt ggggagggtc ctgccttttt   3240
ctctgcccca ggtctgggac gcaggtgatg ccagccaggc ccaggagtgc ccagcatccc   3300
ccaactgatg acacagtagc actgattctg tcttttcctc agaatctggc ctttttccat   3360
ggcaatgagg tggggcccag cctcctctaa agtgactttg tttctgcaca gttgtaactg   3420
ctcttgggga tgtcagtgag gctgggagca gggagccacg ggatgctgag agaggaggcc   3480
cgagaggaca ccccaccctc cagcgtggcc tttgatccag acttagggac gaggctgtca   3540
ctggtgggca ccctctgttc ctgtttgtgt gtttgaatag tctgaaatgc tgtgactttt   3600
```

-continued

```
tttgtgtgaa taaagatatg aaacttctga atctc                             3635


<210> SEQ ID NO 81
<211> LENGTH: 1983
<212> TYPE: DNA
<213> ORGANISM: Homo sapiens

<400> SEQUENCE: 81

gaattgaacc acccattttc ctttcttagc caaatcacca aaatgtccag ttagaacaag     60

aatttagcat tctgcaaaag aagttaacag ctgagataac gaggaaatat tctgaaatgg    120

atcccaaata tttcatctta attttgtttt gtggacacct gaacaataca ttttttttcaa    180

agacagagac aattacaaca gagaagcagt cacagcctac cttattcaca tcatcaatgt    240

cacaggtatt ggctaattct caaaacacaa cagggaatcc tttgggtcaa ccaacacaat    300

tcagcgacac tttttctgga caatcaatat cacctgccaa agtcactgct ggacaaccaa    360

caccagctgt ctatacctct tctgaaaaac cagaagcaca tacttctgct ggacaaccac    420

ttgcctacaa caccaaacaa ccaacaccaa tagccaacac ctcctcccag caagccgtgt    480

tcacctctgc cagacaacta ccatctgccc gtacttctac cacacaacca ccaaagtcat    540

ttgtctatac ttttactcaa caatcatcat ctgtccagat cccttctaga aaacaaataa    600

ctgttcataa tccatccaca caaccaacat caactgtcaa aaattcacct aggagtacac    660

caggatttat cttagatact accagtaaca aacaaacccc acaaaaaaac aattataatt    720

caatagctgc catactaatt ggtgtacttc tgacttctat gttggtagct ataatcatca    780

ttgtactttg gaaatgctta aggaaaccag ttttaaatga tcaaaattgg gcaggtagat    840

ctccatttgc tgatggagaa acccctgaca tttgtatgga taacatcaga gaaaatgaaa    900

tatccacaaa acgtacatca atcatttcac ttacaccctg gaaaccaagc aaaagcacac    960

ttttagcaga tgacttagaa attaagttgt ttgaatcaag tgaaaacatt gaagactcca   1020

acaaccccaa aacagagaaa ataaaagatc aagtaaatgg tacatcagaa gatagtgctg   1080

atggttcaac agttggaact gctgtttctt cttcagatga tgcaggtctg cctccaccac   1140

ctccccttct ggatttggaa ggacaggaaa gtaaccaatc tgacaaaccc acaatgacaa   1200

ttgtatctcc tcttccaaat gattctacta gtctccctcc atctctggac tgtctcaatc   1260

aagactgtgg agatcataaa tctgagataa tacaatcatt tccaccgctt gactcactta   1320

acttgcccct gccaccagta gattttatga aaaaccaaga agattccaac cttgagatcc   1380

agtgtcagga gttctctatt cctcccaact ctgatcaaga tcttaatgaa tccctgccac   1440

ctccacctgc agaactgtta taaatattac aacttgcttt ttagctgatc ttccatcctc   1500

aaatgactct tttttcttta tatgttaaca tatataaaat ggcaactgat agtcaatttt   1560

gatttttatt caggaactat ctgaaatctg ctcagagcct atgtgcatag atgaaacttt   1620

tttttaaaaa aagttattta acagtaatct atttactaat tatagtacct atctttaaag   1680

tatagtacat tttacatatg taaatggtat gtttcaataa tttaagaact ctgaaacaat   1740

ctacatatac ttattaccca gtacagtttt ttttcccctg aaaagctgtg tataaaatta   1800

tggtgaataa acttttatgt ttccatttca aagaccaggg tggagaggaa taagagacta   1860

agtatatgct tcaagtttta aattaatacc tcaagtatta aataaatatt ccaagtttgt   1920

gggaatggga gattaaaatg catgtttgag agtaaaaaaa aaaaaaaaaa aaaaaaaaaa   1980

aaa                                                                 1983
```

<210> SEQ ID NO 82
<211> LENGTH: 1093
<212> TYPE: DNA
<213> ORGANISM: Homo sapiens

<400> SEQUENCE: 82

```
ctgcaaggcg gcggcaggag aggttgtggt gctagtttct ctaagccatc cagtgccatc     60
ctcgtcgctg cagcgacacc gctctcgccg ccgccatgac tgagcagatg acccttcgtg    120
gcaccctcaa gggccacaac ggctgggtaa cccagatcgc tactaccccg cagttcccgg    180
acatgatcct ctccgcctct cgagataaga ccatcatcat gtggaaactg accagggatg    240
agaccaacta tggaattcca cagcgtgctc tgcggggtca ctcccacttt gttagtgatg    300
tggttatctc ctcagatggc cagtttgccc tctcaggctc ctgggatgga accctgcgcc    360
tctgggatct cacaacgggc accaccacga ggcgatttgt gggccatacc aaggatgtgc    420
tgagtgtggc cttctcctct gacaaccggc agattgtctc tggatctcga gataaaacca    480
tcaagctatg gaataccctg ggtgtgtgca aatacactgt ccaggatgag agccactcag    540
agtgggtgtc ttgtgtccgc ttctcgccca acagcagcaa ccctatcatc gtctcctgtg    600
gctgggacaa gctggtcaag gtatggaacc tggctaactg caagctgaag accaaccaca    660
ttggccacac aggctatctg aacacggtga ctgtctctcc agatggatcc ctctgtgctt    720
ctggaggcaa ggatggccag gccatgttat gggatctcaa cgaaggcaaa cacctttaca    780
cgctagatgg tggggacatc atcaacgccc tgtgcttcag ccctaaccgc tactggctgt    840
gtgctgccac aggccccagc atcaagatct gggatttaga gggaaagatc attgtagatg    900
aactgaagca agaagttatc agtaccagca gcaaggcaga accaccccag tgcacttccc    960
tggcctggtc tgctgatggc cagactctgt ttgctggcta cacggacaac ctggtgcgag   1020
tgtggcaggt gaccattggc acacgctaga agtttatggc agagctttac aaataaaaaa   1080
aaaatggctt ttc                                                      1093
```

<210> SEQ ID NO 83
<211> LENGTH: 1412
<212> TYPE: DNA
<213> ORGANISM: Homo sapiens

<400> SEQUENCE: 83

```
ctcttccaga ggcaagacca accaagatga gtgccttggg agctgtcatt gccctcctgc     60
tctggggaca gctttttgca gtggactcag gcaatgatgt cacggatatc gcagatgacg    120
gctgcccgaa gccccccgag attgcacatg gctatgtgga gcactcggtt cgctaccagt    180
gtaagaacta ctacaaactg cgcacagaag gagatggagt atacacctta aatgataaga    240
agcagtggat aaataaggct gttggagata aacttcctga atgtgaagca gatgacggct    300
gcccgaagcc ccccgagatt gcacatggct atgtggagca ctcggttcgc taccagtgta    360
agaactacta caaactgcgc acagaaggag atggagtgta caccttaaac aatgagaagc    420
agtggataaa taaggctgtt ggagataaac ttcctgaatg tgaagcagta tgtgggaagc    480
ccaagaatcc ggcaaaccca gtgcagcgga tcctgggtgg acacctggat gccaaaggca    540
gctttccctg gcaggctaag atggtttccc accataatct caccacaggt gccacgctga    600
tcaatgaaca atggctgctg accacggcta aaaatctctt cctgaaccat tcagaaaatg    660
caacagcgaa agacattgcc cccactttaa cactctatgt ggggaaaaag cagcttgtag    720
agattgagaa ggttgttcta caccctaact actcccaagt agatattggg ctcatcaaac    780
```

-continued

```
tcaaacagaa ggtgtctgtt aatgagagag tgatgcccat ctgcctacca tccaaggatt    840

atgcagaagt agggcgtgtg ggttatgttt ctggctgggg gcgaaatgcc aattttaaat    900

ttactgacca tctgaagtat gtcatgctgc ctgtggctga ccaagaccaa tgcataaggc    960

attatgaagg cagcacagtc cccgaaaaga agacaccgaa gagccctgta ggggtgcagc   1020

ccatactgaa tgaacacacc ttctgtgctg gcatgtctaa gtaccaagaa gacacctgct   1080

atggcgatgc gggcagtgcc tttgccgttc acgacctgga ggaggacacc tggtatgcga   1140

ctgggatctt aagctttgat aagagctgtg ctgtggctga gtatggtgtg tatgtgaagg   1200

tgacttccat ccaggactgg gttcagaaga ccatagctga gaactaatgc aaggctggcc   1260

ggaagccctt gcctgaaagc aagatttcag cctggaagag ggcaaagtgg acgggagtgg   1320

acaggagtgg atgcgataag atgtggtttg aagctgatgg gtgccagccc tgcattgctg   1380

agtcaatcaa taaagagctt tcttttgacc ca                                 1412
```

<210> SEQ ID NO 84
<211> LENGTH: 1095
<212> TYPE: DNA
<213> ORGANISM: Homo sapiens

<400> SEQUENCE: 84

```
tgccgcccag gacccgcagc agagacgacg cctgcagcaa ggagaccagg aaggggtgag     60

acaaggaaga ggatgtctga gctggagaag gccatggtgg ccctcatcga cgtttttccac   120

caatattctg gaagggaggg agacaagcac aagctgaaga aatccgaact caaggagctc    180

atcaacaatg agctttccca tttcttagag gaaatcaaag agcaggaggt tgtggacaaa    240

gtcatggaaa cactggacaa tgatggagac ggcgaatgtg acttccagga attcatggcc    300

tttgttgcca tggttactac tgcctgccac gagttctttg aacatgagtg agattagaaa    360

gcagccaaac ctttcctgta acagagacgg tcatgcaaga aagcagacag caagggcttg    420

cagcctagta ggagctgagc tttccagccg tgttgtagct aattaggaag cttgatttgc    480

tttgtgattg aaaaattgaa aacctctttc caaaggctgt tttaacggcc tgcatcattc    540

tttctgctat attaggcctg tgtgtaagct gactggcccc agggactctt gttaacagta    600

acttaggagt caggtctcag tgataaagcg tgcaccgtgc agcccgccat ggccgtgtag    660

accctaaccc ggagggaacc ctgactacag aaattacccc ggggcaccct taaaacttcc    720

actaccttta aaaaacaaag ccttatccag cattatttga aacactgct gttctttaaa    780

tgcgttcctc atccatgcag ataacagctg gttggccggt gtggccctgc aagggcgtgg    840

tggcttcggc ctgcttcccg ggatgcgcct gatcaccagg tgaacgctca gcgctggcag    900

cgtcctggaa aaagcaactc catcagaact cgcaatccga gccagctctg gggctccag    960

cgtggcctcc gtgacccatg cgattcaagt cgcggctgca ggatccttgc ctccaacgtg   1020

cctccagcac atgcggcttc cgagggcact accgggggct ctgagccacc gcgagggcct   1080

gcgttcaata aaaag                                                    1095
```

<210> SEQ ID NO 85
<211> LENGTH: 1904
<212> TYPE: DNA
<213> ORGANISM: Homo sapiens

<400> SEQUENCE: 85

```
agctatttca aggcgcgcgc ctcgtggtgg actcaccgct agcccgcagc gctcggcttc     60

ctggtaattc ttcacctctt ttctcagctc cctgcagcat gggtgctggg ccctccttgc    120
```

-continued

```
tgctcgccgc cctcctgctg cttctctccg gcgacggcgc cgtgcgctgc gacacacctg    180

ccaactgcac ctatcttgac ctgctgggca cctgggtctt ccaggtgggc tccagcggtt    240

cccagcgcga tgtcaactgc tcggttatgg gaccacaaga aaaaaaagta gtggtgtacc    300

ttcagaagct ggatacagca tatgatgacc ttggcaattc tggccatttc accatcattt    360

acaaccaagg ctttgagatt gtgttgaatg actacaagtg gtttgccttt tttaagtata    420

aagaagaggg cagcaaggtg accacttact gcaacgagac aatgactggg tgggtgcatg    480

atgtgttggg ccggaactgg gcttgtttca ccggaaagaa ggtgggaact gcctctgaga    540

atgtgtatgt caacacagca caccttaaga attctcagga aaagtattct aataggctct    600

acaagtatga tcacaacttt gtgaaagcta tcaatgccat tcagaagtct tggactgcaa    660

ctacatacat ggaatatgag actcttaccc tgggagatat gattaggaga agtggtggcc    720

acagtcgaaa aatcccaagg cccaaacctg caccactgac tgctgaaata cagcaaaaga    780

ttttgcattt gccaacatct tgggactgga gaaatgttca tggtatcaat tttgtcagtc    840

ctgttcgaaa ccaagcatcc tgtggcagct gctactcatt tgcttctatg ggtatgctag    900

aagcgagaat ccgtatacta accaacaatt ctcagacccc aatcctaagc cctcaggagg    960

ttgtgtcttg tagccagtat gctcaaggct gtgaaggcgg cttcccatac cttattgcag   1020

gaaagtacgc ccaagatttt gggctggtgg aagaagcttg cttcccctac acaggcactg   1080

attctccatg caaaatgaag gaagactgct ttcgttatta ctcctctgag taccactatg   1140

taggaggttt ctatggaggc tgcaatgaag ccctgatgaa gcttgagttg gtccatcatg   1200

ggcccatggc agttgctttt gaagtatatg atgacttcct ccactacaaa aaggggatct   1260

accaccacac tggtctaaga gaccctttca accccttga gctgactaat catgctgttc   1320

tgcttgtggg ctatggcact gactcagcct ctgggatgga ttactggatt gttaaaaaca   1380

gctggggcac cggctggggt gagaatggct acttccggat ccgcagagga actgatgagt   1440

gtgcaattga gagcatagca gtggcagcca caccaattcc taaattgtag ggtatgcctt   1500

ccagtatttc ataatgatct gcatcagttg taaaggggaa ttggtatatt cacagactgt   1560

agactttcag cagcaatctc agaagcttac aaatagattt ccatgaagat atttgtcttc   1620

agaattaaaa ctgcccttaa ttttaatata cctttcaatc ggccactggc catttttttc   1680

taagtattca attaagtggg aattttctgg aagatggtca gctatgaagt aatagagttt   1740

gcttaatcat ttgtaattca aacatgctat attttttaaa atcaatgtga aaacatagac   1800

ttatttttaa attgtaccaa tcacaagaaa ataatggcaa taattatcaa aacttttaaa   1860

atagatgctc atatttttaa aataaagttt taaaaataac tgca                    1904
```

<210> SEQ ID NO 86
<211> LENGTH: 1493
<212> TYPE: DNA
<213> ORGANISM: Homo sapiens

<400> SEQUENCE: 86

```
ttcctttcat gttcagcatt tctactcctt ccaagaagag cagcaaagct gaagtagcag     60

caacagcacc agcagcaaca gcaaaaaaca aacatgagtg tgaagggcat ggctatagcc    120

ttggctgtga tattgtgtgc tacagttgtt caaggcttcc ccatgttcaa aagaggacgc    180

tgtctttgca taggccctgg ggtaaaagca gtgaaagtgg cagatattga gaaagcctcc    240

ataatgtacc caagtaacaa ctgtgacaaa atagaagtga ttattaccct gaaagaaaat    300
```

-continued

```
aaaggacaac gatgcctaaa tcccaaatcg aagcaagcaa ggcttataat caaaaaagtt    360

gaaagaaaga atttttaaaa atatcaaaac atatgaagtc ctggaaaagg gcatctgaaa    420

aacctagaac aagtttaact gtgactactg aaatgacaag aattctacag taggaaactg    480

agacttttct atggttttgt gactttcaac ttttgtacag ttatgtgaag gatgaaaggt    540

gggtgaaagg accaaaaaca gaaatacagt cttcctgaat gaatgacaat cagaattcca    600

ctgcccaaag gagtccagca attaaatgga tttctaggaa aagctacctt aagaaaggct    660

ggttaccatc ggagtttaca aagtgctttc acgttcttac ttgttgtatt atacattcat    720

gcatttctag gctagagaac cttctagatt tgatgcttac aactattctg ttgtgactat    780

gagaacattt ctgtctctag aagttatctg tctgtattga tctttatgct atattactat    840

ctgtggttac agtggagaca ttgacattat tactggagtc aagcccttat aagtcaaaag    900

catctatgtg tcgtaaagca ttcctcaaac atttttcat gcaaatacac acttctttcc     960

ccaaatatca tgtagcacat caatatgtag ggaaacattc ttatgcatca tttggtttgt   1020

tttataacca attcattaaa tgtaattcat aaaatgtact atgaaaaaaa ttatacgcta   1080

tgggatactg gcaacagtgc acatatttca taaccaaatt agcagcaccg gtcttaattt   1140

gatgtttttc aacttttatt cattgagatg ttttgaagca attaggatat gtgtgtttac   1200

tgtacttttt gttttgatcc gtttgtataa atgatagcaa tatcttggac acatttgaaa   1260

tacaaaatgt ttttgtctac caaagaaaaa tgttgaaaaa taagcaaatg tatacctagc   1320

aatcactttt actttttgta attctgtctc ttagaaaaat acataatcta atcaatttct   1380

ttgttcatgc ctatatactg taaaatttag gtatactcaa gactagttta aagaatcaaa   1440

gtcatttttt tctctaataa actaccacaa cctttctttt ttaaaaaaaa aaa          1493
```

<210> SEQ ID NO 87
<211> LENGTH: 1737
<212> TYPE: DNA
<213> ORGANISM: Homo sapiens

<400> SEQUENCE: 87

```
gcggacgcgt gggggaaaa taaaccttgg gttataagca ttagcctgag gacaatgaag      60

ccacttaacc taatttatgc tttcgactgt tctgtttcca gagaggaaag cctttacaaa    120

ttactctcag ttctttaggg gcagaaggct tgtttcaaga ggtttgacag aagaaaggaa    180

tatatgaact taatgagatg tcgacttggt tcaggtctaa aaatgagggc aaaacactaa    240

ggctctagca gtgacttgtt cactaaaaag agagagtcct gtccccagac ggttagtaca    300

aagccttgga tacagtttgc ttgtaatatt tttaataatg tgaggagtac agtgttttct    360

aattcattca agtatatatg atttaaacct gggctactga cacacacaca gtagccatta    420

gttagactct tcttagtgaa tatcaggaac atcccatctg tgcttaacca gaatccagca    480

agtcagcaca caagtgattt tattgttatt ttgttgtatt tacttgcatt tgttgtattt    540

actttcatct gcagcatttg gagtttaaaa ataatgtaaa gggttctagt agaaatagtg    600

tcctaaggcc aattacctac catactaaca atcagcagat aaaattctgg acgtgagatt    660

ccttataatc taattatacc tgaggttgag caagaaatgt cttcctttag aaaatctcat    720

tcaagtcagg ttcttctcta cagttcaaaa ttgagaatgg atttaattaa ctagcattta    780

gccagctttt tcttgccctt ggagaaaaag aatcattctc aacctgataa tctgttaaga    840

aaaatcccat atgaacaatc tggtcattaa catacatatg atacggagtc tctttgttgt    900

caccaagtga acatacttct catggtgggt tggacagtaa tacatgttag agggtcagaa    960
```

-continued

```
gcttctggtt tctgctgttt gctttaaata cccttggggt ttttttttta aacccttaca   1020

aggggagcat cagctttgga aagtgtgact ctgtaggagt gtagaaggca gtggtgtatg   1080

atcttagcct cgtcctgatg cctgaatcca gccagctgtt gctctgaccc acagcaatag   1140

agcaagttac ccatcaccag catttgtaca gagcagggaa ttctggtttt agtccattgg   1200

tagcattgtg tgtatgagga gattcaacac cacagacagc tgcaggactc gatatccatg   1260

gcttctttcc atcacaaaac gggtagaaac acattcactg cttcagggtt ctaatctgtg   1320

tgtctcctta tgactccatt tctgtaagct actctgtaac tttgatatat gctgtatttt   1380

ctttctttaa aagatttaga tgtttttttca gcaagctagc catacaacca ttgtatctct   1440

ttctcttcag tatggtttag agcccagatc agttagtagg ctttcgttgt cttctctttc   1500

aatacatgta catctttact gtttgaaaag tgttacagct gtcaaagaat cttcatggac   1560

ctgaagataa tttcttgtga agttgaatgc aagtgtactg tcattcatag tgtttatatc   1620

aaaataccag gaatcttcac ttttgctacc ttgatatagc attgggctat catgttacaa   1680

cattgaaata cattgattta ttaaaaaata cttttataag aaaaaaaaaa aaaaaaa      1737
```

<210> SEQ ID NO 88
<211> LENGTH: 4859
<212> TYPE: DNA
<213> ORGANISM: Homo sapiens

<400> SEQUENCE: 88

```
cacgttgggt gacataatgg ggttttttta attatagatt cacactgcat ttattcatca     60

cccctgtcct ctcatccata actcaaattt actaccagca acacaaaata caaagatgtg    120

tccagtttca ctacagctct tcgcgtttac aagtgtcgag cgcttgcttt cggaacgccc    180

ttgtgattgg ccgagccaat gccagtgaca tcaaccaact tacttttgat tggaaggctg    240

gttgctggga ctgtagcgtt tgcaggaagt cacttaactg tttgggagct ggaaaaccga    300

agctgaagtt ctcttttgcc ataggaacga gcgcaactga ctaggaaaga tgtgtcccaa    360

agctccgcaa gctggaacgt gagccaggag gcccggaccg gccacgggac cgcgaggcac    420

tccgaaagtg tgcggctgcc ccttccctgc ctcccagctg ttaccctttt aaatgtcagt    480

gttcgaggct gtaggggtag cacgaggcag cgaaacggaa cagtcggatt ggccgcacgc    540

ctcagttcta gacgcacctc tccaccgaag ccgttctgac tggcaggggg agaaagtaaa    600

cagagttgaa tcaccctccc cactggccaa ttggaggggg tttggtttgt gacgtgatgg    660

gattctgcga aattgttact gagcaagaga atgccggaac gtgcggaccg gccggagcag    720

gggttcagaa gccgtcagtg gactcgggaa aaagtgtctc ttagacctgg cgctcggcgg    780

ggccctcgcc acccgcgtcg gggtgatcgg gtgaatgtcc tggggctttg gctcgacggc    840

gaggcggccg agggcgtgca cctctcttgc agtttcctct cccagcgcct cgggggcgtt    900

ttcagtcgaa taaacttgcg accgccacgt gtggcatctt tccaagggag ccggctcaga    960

ggggccggcg cgcccgtcgg gggatcgcgg ccggcgcggg gcaggggcgg cggctagagg   1020

cggcggcgcg gcggagcccg gggccgtgga tgctgcgtgc ggaggcgctg ccggttacgt   1080

aaagatgagg ggctgaggtc gcctcggcgc tcctgcgagt cggaagcgcc ccgcgccccc   1140

gccccccttgg ccgccgcgcc gtgccgggcg ggcgggtcgt cgtccgaggc cagggagggc   1200

gagccgaacc tccgcagcca ccgccaagtt tgtccgcgcc gcctgggctg ccgtcgcccg   1260

caccatgtcc gcggccgcct acatggactt cgtggctgcc cagtgtctgg tttccatttc   1320
```

-continued

```
gaaccgcgct gcggtgccgg agcatggggt cgctccggac gccgagcggc tgcgactacc   1380

tgagcgcgag gtgaccaagg agcacggtga cccgggggac acctggaagg attactgcac   1440

actggtcacc atcgccaaga gcttgttgga cctgaacaag taccgaccca tccagacccc   1500

ctccgtgtgc agcgacagtc tggaaagtcc agatgaggat atgggatccg acagcgacgt   1560

gaccaccgaa tctgggtcga gtccttccca cagcccggag gagagacagg atcctggcag   1620

cgcgcccagc ccgctctccc tcctccatcc tggagtggct gcgaagggga aacacgcctc   1680

cgaaaagagg cacaagtgcc cctacagtgg ctgtgggaaa gtctatggaa aatcctccca   1740

tctcaaagcc cattacagag tgcatacagg tgaacggccc ttcccctgca cgtggccaga   1800

ctgccttaaa aagttctccc gctcagacga gctgacccgc cactaccgga cccacactgg   1860

ggaaaagcag ttccgctgtc cgctgtgtga gaagcgcttc atgaggagtg accacctcac   1920

aaagcacgcc cggcggcaca ccgagttcca ccccagcatg atcaagcgat cgaaaaaggc   1980

gctggccaac gctttgtgag gtgctgcccg tggaagccag ggagggatgg accccgaaag   2040

gacaaaagta ctcccaggaa acagacgcgt gaaaactgag ccccagaaga ggcacacttg   2100

acggcacagg aagtcactgc tctttggtca atattctgat tttcctctcc ctgcattgtt   2160

tttaaaaagc acattgtagc ctaagatcaa agtcaacaac actcggtccc cttgaagagg   2220

caactctctg aacccgtctc tgactgttgg agggaaggca aatgcttttg ggtttttttgg   2280

tttttgtttt tgtttttttt tctcctttta tttttttgcg ggggagggta gggagtgggt   2340

gggggggagg gggtaaggcc aagactgggt agattttaaa gattcaacac tggtgtacat   2400

atgtccgctg ggtgagttga cctgtggcct cgcacagtga ttctaggccc tttatgcttg   2460

ctgtctctca gaattgtttt cttacctttt aatgtaatga cgagtgtgct tcagtttgtt   2520

tagcaaaacc actctcttga atcacgttaa cttttgagat taaaaaaaaa aacgccatag   2580

cacagctgtc tttatgcaag caagagcaca tctactccag catgatctgt catctaaaga   2640

cttgaaaaca aaaaacagtt acttatagtc aatgggtaag cagagtctga atttatacta   2700

atcaagacaa acctttgaaa ggttacacta agtacagaac ttttaaacct tgctttgtat   2760

gagttgtact ttttgaacat aagctgcact tttattttct aatgcagagg atgaataagt   2820

taaatacatg ctttgaggat agaagcagat gttctgtttg gcaccacgtt ataatctgct   2880

tattttacaa tatacacgtt tccctaagaa atcatgcgca gagatgtgag ggcagaatat   2940

acacaacaga tgctgaagga gaaggagggt agtgttttgc aaaagaaaaa gaaaagaacc   3000

aacagaattt taactctatt aacttttcca aattttccta tgcttttagt taacatcatt   3060

attgtatcct aatgccacta ggggagagag cttttgactc tgttgggttt tatttgaatg   3120

tgtgcataac agtaatgaga tctggaaaca cctatttttt ggggaaaaag gtttgttggt   3180

ctccttcctg tgttcctaca aaactcccac tctcaggtgc aagagttatg tagaaggaaa   3240

gggagctgaa ataggaacag aaaaatcaac ccctataact agtgaacacc aagggaaaat   3300

accacaatga tttcagagga gactctgcaa aatcgtccct tgtggagaat gcaggcaaca   3360

tggaatacta cgaatgaaat cacatcactg tatcttttac atcaatagcc tcaccactaa   3420

tatatcttgt atctaggtgt ctataatggc tgaaaccact acatccatct atgccattta   3480

cctgaaaact taactgtggc ctttatgagg ccagaaaagt gaactgagtt ttgtagttaa   3540

gacctcaaat gaggggagtc agcagtgatc atgggggaaa tgtttacatt tttttttct   3600

tcagaagtaa cgctttctga tgattttatc tgatatttaa aacagggagc tatggtgcac   3660

tctagtttat acttgcgctc tgaaatgtgt aaacataggg tgcctaccta tttcacctga   3720
```

```
cccatactcg tttctgattc agaatcagtg tgggctcctg cagtgggcgc gggtcacggc   3780

tgactccaac ttccaataca acagccatca ctagcacagt gtttttttgt ttaaccaacg   3840

tagtgttatt agtagttcta taaagagaac tgcttttaac attagggact gggagcagtc   3900

catgggataa aaaggaaagt gttttctcac gagaaaacat gtcaggaaaa ataaagaaca   3960

ctttctacct ctgtttcaga tttttgaaac acttatttta aaccaaattt taatttctgt   4020

gtccaaaata agttttaagg acatctgttc ttccatacga aataggttag gctgcctatt   4080

tctcactgag ctcatggaat ggttctgctt atgatactct gcacgctgcc ttttagtgag   4140

tgaggagttt ggggttgcct agcacttgct aacttgtaaa aagtcatctt tccctcacag   4200

aaagaaacga aagaaagcaa agcaaagtca gtgaaagaca atctttatag tttcaggagt   4260

aaatctaaat gtggcttttg tcaagcactt agatggatat aaatgcagca acttgtttta   4320

aaaaaatgca catttacttc ccaaaaaagt tgttacttgc cttttcaagt gtgacaaact   4380

cacatttgat attctcttat atgttatagt aatgtaacgt ataaactcaa gccttttat    4440

tctttgtgat taaatcctgt tttaaaatgt cacaaaacag gaaccagcat tctaattaga   4500

tttactatat caagatatgg ttcaaatagg actactagag ttcattgaac actaaaacta   4560

tgaaacaatt actttttata ttaaaaagac catggattta acttatgaaa atccaaatgc   4620

aggatagtaa tttttgttta cttttttaac caaactgaat ttttgaaaga ctattgcagg   4680

tgtttaaaaa gaaagaaaag ttgttttatc taatactgta agtagttgtc atattctgga   4740

aaatttaata gttttagagt taagatatct cctctctttg gttagggaag aagaaagccc   4800

ttcaccattg tggaatgatg ccctggcttt aaggtttagc tccacatcat gcttctctt    4859
```

<210> SEQ ID NO 89
<211> LENGTH: 2775
<212> TYPE: DNA
<213> ORGANISM: Homo sapiens

<400> SEQUENCE: 89

```
aatctttagg atctgagcag gagaaatacc agcggatctt ccccactctg ctcccttcca     60

ttcccaccct tccttcttta ataagcagga gcgaaaaaga caaattccaa agaggattgt    120

tcagttcaag ggaatgaaga attcagaata attttggtaa atggattcca atatggggaa    180

taagaataag ctgaacagtt gacctgcttt gaagaaacat actgtccatt tgtctaaaat    240

aatctataac aaccaaacca atcaaaatga attcaacatt attttcccag gttgaaaatc    300

attcagtcca ctctaatttc tcagagaaga atgcccagct tctggctttt gaaaatgatg    360

attgtcatct gcccttggcc atgatattta ccttagctct tgcttatgga gctgtgatca    420

ttcttggtgt ctctggaaac ctggccttga tcataatcat cttgaaacaa aaggagatga    480

gaaatgttac caacatcctg attgtgaacc tttccttctc agacttgctt gttgccatca    540

tgtgtctccc ctttacattt gtctacacat taatggacca ctgggtcttt ggtgaggcga    600

tgtgtaagtt gaatcctttt gtgcaatgtg tttcaatcac tgtgtccatt ttctctctgg    660

ttctcattgc tgtggaacga catcagctga taatcaaccc tcgagggtgg agaccaaata    720

atagacatgc ttatgtaggt attgctgtga tttgggtcct tgctgtggct tcttctttgc    780

ctttcctgat ctaccaagta atgactgatg agccgttcca aaatgtaaca cttgatgcgt    840

acaaagacaa atacgtgtgc tttgatcaat ttccatcgga ctctcatagg ttgtcttata    900

ccactctcct cttggtgctg cagtattttg gtccactttg ttttatattt atttgctact    960
```

-continued

```
tcaagatata tatacgccta aaaaggagaa acaacatgat ggacaagatg agagacaata   1020

agtacaggtc cagtgaaacc aaaagaatca atatcatgct gctctccatt gtggtagcat   1080

ttgcagtctg ctggctccct cttaccatct ttaacactgt gtttgattgg aatcatcaga   1140

tcattgctac ctgcaaccac aatctgttat tcctgctctg ccacctcaca gcaatgatat   1200

ccacttgtgt caaccccata ttttatgggt tcctgaacaa aaacttccag agagacttgc   1260

agttcttctt caacttttgt gatttccggt ctcgggatga tgattatgaa acaatagcca   1320

tgtccacgat gcacacagat gtttccaaaa cttctttgaa gcaagcaagc ccagtcgcat   1380

ttaaaaaaat caacaacaat gatgataatg aaaaaatctg aaactactta tagcctatgg   1440

tcccggatga catctgttta aaaacaagca caacctgcaa catactttga ttacctgttc   1500

tcccaaggaa tggggttgaa atcatttgaa aatgactaag attttcttgt cttgcttttt   1560

actgcttttg ttgtagttgt cataattaca tttggaacaa aaggtgtggg ctttggggtc   1620

ttctggaaat agttttgacc agacatcttt gaagtgcttt ttgtgaattt atgcatataa   1680

tataaagact tttatactgt acttattgga atgaaatttc tttaaagtat tactattaac   1740

tgacttcaga agtacctgcc atccaatacg gtcattagat tgggtcatct tgattagatt   1800

agattagatt agattgtcaa cagattgggc catccttact ttatgatagg catcatttta   1860

gtgtgttaca atagtaacag tatgcaaaag cagcattcag gagccgaaag atagtctgaa   1920

gtcattcaga agtggtttga ggtttctgtt ttttggtggt ttttgtttgt tttttttttt   1980

tttcacctta agggaggatt taatttgctc ccaactgatt gtcacttaaa tgaaaattta   2040

aaaatgaata aaaagacata cttctcagct gcaaatatta tggagaattg ggcacccac    2100

aggaatgaag agagaaagca gctccctaac ttcaaaacca ttttggtacc tgacaacaag   2160

agcattttag agtaattaat ttaataaagt aaattagtat tgctgcaaat agttaaatta   2220

tatttatttg aattgatggt caagagattt tccatttttt ttacagactg ttcagtgttt   2280

gtcaagcttt ctggcataaa tatgtactca aaaggcattt ccgcttacaa tttgtagaaa   2340

cacaaaatgc gttttccata cagcagtgcc tatatagtga ctgattttta actttcaatg   2400

tccatctttc aaaggaagta acaccaaggt acaatgttaa aggaatattc actttaccta   2460

gcagggaaaa atacacaaaa actgcagata cttcatatag cccattttaa cttgtataaa   2520

ctgtgtgact tgtggcgtct tataaataat gcactgtaaa gattactgaa tagttgtgtc   2580

atgttaatgt gcctaatttc atgtatcttg taatcatgat tgagcctcag aatcatttgg   2640

agaaactata ttttaaagaa caagacatac ttcaatgtat tatacagata aagtattaca   2700

tgtgtttgat tttaaaaggg cggacatttt attaaaatca atattgtttt tgctttttca   2760

aaaaaaaaaa aaaaa                                                    2775
```

```
<210> SEQ ID NO 90
<211> LENGTH: 3386
<212> TYPE: DNA
<213> ORGANISM: Homo sapiens

<400> SEQUENCE: 90

gccgcggcca gctccggcgg gcaggggggg cgctggagcg cagcgcagcg cagccccatc     60

agtccgcaaa gcggaccgag ctggaagtcg agcgctgccg cgggaggcgg gcgatggggg    120

caggtgccac cggccgcgcc atggacgggc cgcgcctgct gctgttgctg cttctggggg    180

tgtcccttgg aggtgccaag gaggcatgcc cccacaggcct gtacacacac agcggtgagt   240

gctgcaaagc ctgcaacctg ggcgagggtg tggcccagcc ttgtggagcc aaccagaccg    300
```

-continued

```
tgtgtgagcc ctgcctggac agcgtgacgt tctccgacgt ggtgagcgcg accgagccgt    360
gcaagccgtg caccgagtgc gtggggctcc agagcatgtc ggcgccgtgc gtggaggccg    420
acgacgccgt gtgccgctgc gcctacggct actaccagga tgagacgact gggcgctgcg    480
aggcgtgccg cgtgtgcgag gcgggctcgg gcctcgtgtt ctcctgccag gacaagcaga    540
acaccgtgtg cgaggagtgc cccgacggca cgtattccga cgaggccaac cacgtggacc    600
cgtgcctgcc ctgcaccgtg tgcgaggaca ccgagcgcca gctccgcgag tgcacacgct    660
gggccgacgc cgagtgcgag gagatccctg gccgttggat tacacggtcc acacccccag    720
agggctcgga cagcacagcc cccagcaccc aggagcctga ggcacctcca gaacaagacc    780
tcatagccag cacggtggca ggtgtggtga ccacagtgat gggcagctcc cagcccgtgg    840
tgacccgagg caccaccgac aacctcatcc ctgtctattg ctccatcctg gctgctgtgg    900
ttgtgggcct tgtggcctac atagccttca agaggtggaa cagctgcaag cagaacaagc    960
aaggagccaa cagccggcca gtgaaccaga cgcccccacc agagggagaa aaactccaca   1020
gcgacagtgg catctccgtg gacagccaga gcctgcatga ccagcagccc cacacgcaga   1080
cagcctcggg ccaggccctc aagggtgacg gaggcctcta cagcagcctg cccccagcca   1140
agcgggagga ggtggagaag cttctcaacg gctctgcggg ggacacctgg cggcacctgg   1200
cgggcgagct gggctaccag cccgagcaca tagactcctt tacccatgag gcctgccccg   1260
ttcgcgccct gcttgcaagc tgggccaccc aggacagcgc cacactggac gccctcctgg   1320
ccgccctgcg ccgcatccag cgagccgacc tcgtggagag tctgtgcagt gagtccactg   1380
ccacatcccc ggtgtgagcc caaccgggga gcccccgccc cgccccacat tccgacaacc   1440
gatgctccag ccaacccctg tggagcccgc acccccaccc tttggggggg gcccgcctgg   1500
cagaactgag ctcctctggg caggacctca gagtccaggc cccaaaacca cagccctgtc   1560
agtgcagccc gtgtggcccc ttcacttctg accacacttc ctgtccagag agagaagtgc   1620
ccctgctgcc tccccaaccc tgcccctgcc ccgtcaccat ctcaggccac ctgcccccctt   1680
ctcccacact gctaggtggg ccagcccctc ccaccacagc aggtgtcata tatgggggc    1740
caacaccagg gatggtacta gggggaagtg acaaggcccc agagactcag agggaggaat   1800
cgaggaacca gagccatgga ctctacactg tgaacttggg gaacaagggt ggcatcccag   1860
tggcctcaac cctccctcag cccctcttgc cccccacccc agcctaagat gaagaggatc   1920
ggaggcttgt cagagctggg aggggttttc gaagctcagc ccaccccccct catttttggat   1980
ataggtcagt gaggcccagg gagaggccat gattcgccca aagccagaca gcaacgggga   2040
ggccaagtgc aggctggcac cgccttctct aaatgagggg cctcaggttt gcctgagggc   2100
gaggggaggg tggcaggtga ccttctggga aatggcttga agccaagtca gctttgcctt   2160
ccacgctgtc tccagacccc cacccttcc ccactgcctg cccacccgtg gagatgggat    2220
gcttgcctag ggcctggtcc atgatggagt caggtttggg gttcgtggaa agggtgctgc   2280
ttccctctgc ctgtccctct caggcatgcc tgtgtgacat cagtggcatg gctccagtct   2340
gctgccctcc atcccgacat ggacccggag ctaacactgg cccctagaat cagcctaggg   2400
gtcagggacc aaggacccct caccttgcaa cacacagaca cacgcacaca cacacacagg   2460
aggagaaatc tcacttttct ccatgagttt tttctcttgg gctgagactg gatactgccc   2520
ggggcagctg ccagagaagc atcggaggga attgaggtct gctcggccgt cttcactcgc   2580
ccccgggttt ggcgggccaa ggactgccga ccgaggctgg agctggcgtc tgtcttcaag   2640
```

-continued

```
ggcttacacg tggaggaatg ctcccccatc ctccccttcc ctgcaaacat ggggttggct   2700

gggcccagaa ggttgcgatg aagaaaagcg ggccagtgtg ggaatgcggc aagaaggaat   2760

tgacttcgac tgtgacctgt ggggatttct cccagctcta gacaaccctg caaaggactg   2820

ttttttcctg agcttggcca gaagggggcc atgaggcctc agtggacttt ccacccccctc   2880

cctggcctgt tctgttttgc ctgaagttgg agtgagtgtg gctcccctct atttagcatg   2940

acaagcccca ggcaggctgt gcgctgacaa ccaccgctcc ccagcccagg gttcccccag   3000

ccctgtggaa gggactagga gcactgtagt aaatggcaat tctttgacct caacctgtga   3060

tgaggggagg aaactcacct gctggcccct cacctgggca cctggggagt gggacagagt   3120

ctgggtgtat ttattttcct ccccagcagg tggggagggg gtttggtggc ttgcaagtat   3180

gttttagcat gtgtttggtt ctggggcccc tttttactcc ccttgagctg agatggaacc   3240

cttttggccc ccagctgggg gccatgagct ccagaccccc agcaaccctc ctatcacctc   3300

ccctccttgc ctcctgtgta atcatttctt gggccctcct gaaacttaca cacaaaacgt   3360

taagtgatga acattaaata gcaaag                                        3386
```

```
<210> SEQ ID NO 91
<211> LENGTH: 2487
<212> TYPE: DNA
<213> ORGANISM: Homo sapiens

<400> SEQUENCE: 91

cctttcccct cccgccggac ctgccaggag gtgggctggc gcggagggag ggccctgtcc     60

cctgtccctt taaggaggag ggccaaacgc cggcctagag tgcggcgtag cccccacccg    120

ccgtgccctc accccagagc agctgcagcc tcagccggcc gcccctccgc cagccaagtc    180

cgccgctctg acccccggca gcaagtcgcc accatggtga agatcgtgac agttaagacc    240

caggcgtacc aggaccagaa gccgggcacg agcgggctgc ggaagcgggt gaaggtgttc    300

cagagcagcg ccaactacgc ggagaacttc atccagagta tcatctccac cgtggagccg    360

gcgcagcggc aggaggccac gctggtggtg ggcggggacg gccggttcta catgaaggag    420

gccatccagc tcatcgctcg catcgctgcc gccaacggga tcggtcgctt ggttatcgga    480

cagaatggaa tcctctccac ccctgctgta tcctgcatca ttagaaaaat caaagccatt    540

ggtgggatca ttctgacagc cagtcacaac ccagggggcc ccaatggaga ttttggaatc    600

aaattcaata tttctaatgg aggtcctgct ccagaagcaa taactgataa aattttccaa    660

atcagcaaga caattgaaga atatgcagtt tgccctgacc tgaaagtaga ccttggtgtt    720

ctgggaaagc agcagtttga cttggaaaat aagttcaaac ccttcacagt ggaaattgtg    780

gattcggtag aagcttatgc tacaatgctg agaagcatct ttgatttcag tgcactgaaa    840

gaactacttt ctgggccaaa ccgactgaag atccgtattg atgctatgca tggagttgtg    900

ggaccgtatg taaagaagat cctctgtgaa gaactcggtg cccctgcgaa ctcggcagtt    960

aactgcgttc ctctggagga ctttggaggc caccaccctg accccaacct cacctatgca   1020

gctgacctgg tggagaccat gaagtcagga gagcatgatt ttggggctgc ctttgatgga   1080

gatggggatc gaaacatgat tctgggcaag catgggttct ttgtgaaccc ttcagactct   1140

gtggctgtca ttgctgccaa catcttcagc attccgtatt tccagcagac tggggtccgc   1200

ggctttgcac ggagcatgcc cacgagtggt gctctggacc gggtggctag tgctacaaag   1260

attgctttgt atgagacccc aactggctgg aagtttttg ggaatttgat ggacgcgagc   1320

aaactgtccc tttgtgggga ggagagcttc gggaccggtt ctgaccacat ccgtgagaaa   1380
```

-continued

```
gatggactgt gggctgtcct tgcctggctc tccatcctag ccacccgcaa gcagagtgtg   1440

gaggacattc tcaaagatca ttggcaaaag tatggccgga atttcttcac caggtatgat   1500

tacgaggagg tggaagctga gggcgcaaac aaaatgatga aggacttgga ggccctgatg   1560

tttgatcgct cctttgtggg gaagcagttc tcagcaaatg acaaagttta cactgtggag   1620

aaggccgata actttgaata cagcgaccca gtggatggaa gcatttcaag aaatcagggc   1680

ttgcgcctca ttttcacaga tggttctcga atcgtcttcc gactgagcgg cactgggagt   1740

gccggggcca ccattcggct gtacatcgat agctatgaga aggacgttgc caagattaac   1800

caggaccccc aggtcatgtt ggcccccctt atttccattg ctctgaaagt gtcccagctg   1860

caggagagga cgggacgcac tgcacccact gtcatcacct aagaagacag gcctgatgtg   1920

gtacgtccct ccaccccccgg acccatccaa gtcatctgat tgaagagcat gacagaaaca   1980

aaatgtattc accaagcatt ttaggatttg actttttcac taaccagttg acgagcagtg   2040

catttacaag gcactgccaa acaagatgcc cttgggagct gtgagggaaa gaggacctgc   2100

gggcttagat caatctcaat tccttttcat gccctcctgc attgctgctg cgtgggtatt   2160

tgtctcctta gccatcaggt acagtttaca ctacaatgta agctataggt ggagcatcag   2220

cagtgagtga ggccattctt catccttagg atgtggcaat gaaatgatgg tgcaagttcc   2280

tttctctttt gtgaatcttt ccccccattt cctgtttaca tgtaacccaa caaaatgcaa   2340

tttctagtgc cttctgtcca atcagttctt tcctctgagt gagacgtact tggctacaga   2400

tttctgcctt gttttgcgac attgtcccat tcacacagat attttgggat aataaaggaa   2460

aataagctac aaaaaaaaaa aaaaaaa                                       2487
```

<210> SEQ ID NO 92
<211> LENGTH: 4343
<212> TYPE: DNA
<213> ORGANISM: Homo sapiens

<400> SEQUENCE: 92

```
agatttgata atgggctgca ttaaaagtaa agaaaacaaa agtccagcca ttaaatacag     60

acctgaaaat actccagagc ctgtcagtac aagtgtgagc cattatggag cagaacccac    120

tacagtgtca ccatgtccgt catcttcagc aaagggaaca gcagttaatt tcagcagtct    180

ttccatgaca ccatttggag gatcctcagg ggtaacgcct tttggaggtg catcttcctc    240

attttcagtg gtgccaagtt catatcctgc tggtttaaca ggtggtgtta ctatatttgt    300

ggccttatat gattatgaag ctagaactac agaagacctt tcatttaaga agggtgaaag    360

atttcaaata attaacaata cggaaggaga ttggtgggaa gcaagatcaa tcgctacagg    420

aaagaatggt tatatcccga gcaattatgt agcgcctgca gattccattc aggcagaaga    480

atggtatttt ggcaaaatgg ggagaaaaga tgctgaaaga ttacttttga atcctggaaa    540

tcaacgaggt attttcttag taagagagag tgaaacaact aaaggtgctt attccctttc    600

tattcgtgat tgggatgaga taaggggtga caatgtgaaa cactacaaaa ttaggaaact    660

tgacaatggt ggatactata tcacaaccag agcacaattt gatactctgc agaaattggt    720

gaaacactac acagaacatg ctgatggttt atgccacaag ttgacaactg tgtgtccaac    780

tgtgaaacct cagactcaag gtctagcaaa agatgcttgg gaaatccctc gagaatcttt    840

gcgactagag gttaaactag gacaaggatg tttcggcgaa gtgtggatgg gaacatggaa    900

tggaaccacg aaagtagcaa tcaaaacact aaaaccaggt acaatgatgc cagaagcttt    960
```

-continued

```
ccttcaagaa gctcagataa tgaaaaaatt aagacatgat aaacttgttc cactatatgc   1020

tgttgtttct gaagaaccaa tttacattgt cactgaattt atgtcaaaag gaagcttatt   1080

agatttcctt aaggaaggag atggaaagta tttgaagctt ccacagctgg ttgatatggc   1140

tgctcagatt gctgatggta tggcatatat tgaaagaatg aactatattc accgagatct   1200

tcgggctgct aatattcttg taggagaaaa tcttgtgtgc aaaatagcag actttggttt   1260

agcaaggtta attgaagaca atgaatacac agcaagacaa ggtgcaaaat ttccaatcaa   1320

atggacagct cctgaagctg cactgtatgg tcggtttaca ataaagtctg atgtctggtc   1380

atttggaatt ctgcaaacag aactagtaac aaagggccga gtgccatatc caggtatggt   1440

gaaccgtgaa gtactagaac aagtggagcg aggatacagg atgccgtgcc ctcagggctg   1500

tccagaatcc ctccatgaat tgatgaatct gtgttggaag aaggaccctg atgaaagacc   1560

aacatttgaa tatattcagt ccttcttgga agactacttc actgctacag agccacagta   1620

ccagccagga gaaaatttat aattcaagta gcctatttta tatgcacaaa tctgccaaaa   1680

tataaagaac ttgtgtagat tttctacagg aatcaaaaga agaaaatctt ctttactctg   1740

catgttttta atggtaaact ggaatcccag atatggttgc acaaaaccac tttttttttcc   1800

ccaagtatta aactctaatg taccaatgat gaatttatca gcgtatttca gggtccaaac   1860

aaaatagagc taagatactg atgacagtgt gggtgacagc atggtaatga aggacagtga   1920

ggctcctgct tatttataaa tcatttcctt tcttttttttc cccaaagtca gaattgctca   1980

aagaaaatta tttattgtta cagataaaac ttgagagata aaaagctata ccataataaa   2040

atctaaaatt aaggaatatc atgggaccaa ataattccat tccagttttt taaagtttct   2100

tgcatttatt attctcaaaa gtttttttcta agttaaacag tcagtatgca atcttaatat   2160

atgctttctt ttgcatggac atgggccagg tttttcaaaa ggaatataaa caggatctca   2220

aacttgatta aatgttagac cacagaagtg gaatttgaaa gtataatgca gtacattaat   2280

attcatgttc atggaactga aagaataaga actttttcac ttcagtcctt ttctgaagag   2340

tttgacttag aataatgaag gtaactagaa agtgagttaa tcttgtatga ggttgcattg   2400

attttttaag gcaatatata attgaaacta ctgtccaatc aaaggggaaa tgttttgatc   2460

tttagatagc atgcaaagta agacccagca ttttaaaagc ccttttttaaa aactagactt   2520

cgtactgtga gtattgctta tatgtcctta tggggatggg tgccacaaat agaaaatatg   2580

accagatcag ggacttgaat gcacttttgc tcatggtgaa tatagatgaa cagagaggaa   2640

aatgtattta aaagaaatac gagaaaagaa aatgtgaaag ttttacaagt tagagggatg   2700

gaaggtaatg tttaatgttg atgtcatgga gtgacagaat ggctttgctg gcactcagag   2760

ctcctcactt agctatattc tgagactttg aagagttata aagtataact ataaaactaa   2820

tttttcttac acactaaatg ggtatttgtt caaaataatg aagttatggc ttcacattca   2880

ttgcagtggg atatggtttt tatgtaaaac atttttagaa ctccagtttt caaatcatgt   2940

ttgaatctac attcactttt ttttgttttc tttttttgaga cggagtctcg ctctgccgcc   3000

caggctggag tgcagtggcg cgatctcggc tcactgcaag ctctgcctcc caggttcaca   3060

ccattctcct gcctcagcct cccgagtagc tgggactaca ggtgcccacc accacgcctg   3120

gctagttttt tgtattttta gtagagacgc agtttcaccg tgttagccag gatggtctcg   3180

atctcctgac cttgtgatct gcccgcctcg gcctcccaaa gtgctgggat tacaggcgtg   3240

agccaccgcg cccagcctac attcacttct aaagtctatg taatggtggt catttttttcc   3300

cttttagaat acattaaatg gttgatttgg ggaggaaaac ttattctgaa tattaacggt   3360
```

```
ggtgaaaagg ggacagtttt taccctaaag tgcaaaagtg aaacatacaa aataagacta   3420

atttttaaga gtaactcagt aatttcaaaa tacagatttg aatagcagca ttagtggttt   3480

gagtgtctag caaaggaaaa attgatgaat aaaatgaagg tctggtgtat atgttttaaa   3540

atactctcat atagtcacac tttaaattaa gccttatatt aggcccctct attttcagga   3600

tataattctt aactatcatt atttacctga ttttaatcat cagattcgaa attctgtgcc   3660

atggcgtata tgttcaaatt caaaccattt ttaaaatgtg aagatggact tcatgcaagt   3720

tggcagtggt tctggtacta aaaattgtgg ttgtttttc tgtttacgta acctgcttag   3780

tattgacact ctctaccaag agggtcttcc taagaagagt gctgtcatta tttcctctta   3840

tcaacaactt gtgacatgag atttttaag ggctttatgt gaactatgat attgtaattt   3900

ttctaagcat attcaaaagg gtgacaaaat tacgtttatg tactaaatct aatcaggaaa   3960

gtaaggcagg aaaagttgat ggtattcatt aggttttaac tgaatggagc agttccttat   4020

ataataacaa ttgtatagta gggataaaac actaacttaa tgtgtattca ttttaaattg   4080

ttctgtattt ttaaattgcc aagaaaaaca actttgtaaa tttggagata ttttccaaca   4140

gcttttcgtc ttcagtgtct taatgtggaa gttaaccctt accaaaaaag gaagttggca   4200

aaaacagcct tctagcacac ttttttaaat gaataatggt agcctaaact taatattttt   4260

ataaagtatt gtaatattgt tttgtggata attgaaataa aaagttctca ttgaatgcac   4320

ctattaaaaa aaaaaaaaaa aaa                                           4343
```

<210> SEQ ID NO 93
<211> LENGTH: 2110
<212> TYPE: DNA
<213> ORGANISM: Homo sapiens

<400> SEQUENCE: 93

```
attgtgcaga ttctcgtgct gccaaaaacg tctgtcctgg gcatctcctt tggggctgcg     60

tttctcttgc tggccttcat cctcttcgtc tgctttgctg gacagcttct gcaatgcagc    120

aaaaaagcct ctcccctgct catgtggctt ttgaagtcct cgggcatcat tgccaaccag    180

ccctggccac ggatctctct cacgatcatc accacagcca tcatattaat gatggccgtg    240

ttcaacatgt ttttcctgag tgactcagag gaaacaatcc ctccaactgc caacacaaca    300

aacacaagct tttcagcctc aaataatcag gtggcgattc tgcgtgcgca gaatttattt    360

ttcctcccgt actttatcta cagctgcatt ctgggactga tatcctgttc cgtgttcctg    420

cgggtaaact atgagctgaa gatgttgatc atgatggtgg ccttggtggg ctacaacacc    480

atcctactcc acacccacgc ccacgtcctg ggcgactaca gccaggtctt atttgagaga    540

ccaggcattt ggaaagacct gaagaccatg ggctctgtgt ctctctctat attcttcatc    600

acactgcttg ttctgggtag acagaatgaa tattactgta ggttagactt cttatggaag    660

aacaaattca aaaaagagcg ggaggagata gagaccatgg agaacctgaa ccgcgtgctg    720

ctggagaacg tgcttcccgc gcacgtggct gagcacttcc tggccaggag cctgaagaat    780

gaggagctat accaccagtc ctatgactgc gtctgcgtca tgtttgcctc cattccggat    840

ttcaaagaat tttatacaga atccgacgtg aacaaggagg gcttggaatg ccttcggctc    900

ctgaacgaga tcatcgctga ctttgatgat cttctttcca agccaaaatt cagtggagtt    960

gaaaagatta agaccattgg cagcacatac atggcagcaa caggtctgag cgctgtgccc   1020

agccaggagc actcccagga gcccgagcgg cagtacatgc acattggcac catggtggag   1080
```

-continued

```
tttgcttttg ccctggtagg gaagctggat gccatcaaca agcactcctt caacgacttc   1140

aaattgcgag tgggtattaa ccatggacct gtgatagctg gtgtgattgg agctcagaag   1200

ccacaatatg atatctgggg caacactgtc aatgtggcca gtaggatgga cagcaccgga   1260

gtcctggaca aaatacaggt taccgaggag acgagcctcg tcctgcagac cctcggatac   1320

acgtgcacct gtcgaggaat aatcaacgtg aaaggaaagg gggacctgaa gacgtacttt   1380

gtaaacacag aaatgtcaag gtccctttcc cagagcaacg tggcatcctg aagagtcacc   1440

ttcattttgg caagaagact gtattttcag gaaggtatca cacactttct gactgcaact   1500

tctgtccctt gtttttgatg tgcgtgctgt ctgtcctatg gagcctctgc agactcgttc   1560

tcgtgaccca gtggcatacc gtttggtgtc tgatgtgtgc ccagatcgtt ctgccacttg   1620

cactgtgctt gctcctaagc aaaagggaaa aggagcgcgc gtgatagaag aaaagcactg   1680

ggagaactaa cagaggagaa aggtgaaaca cacacacatt cttaaggcaa taaaactagg   1740

gggtgtatat tatcttctgg tgcatgttct tttctggaaa atatggtagc tcgccaaccg   1800

catctgctca tctgatattc aaacacacag tattcgtgaa taagttgatt ctgtccccca   1860

cgtggactct gtgctcaccc attgtctcat tgccagtggt gtccaagggc ccccgttggg   1920

acccacggct ctcgtccctc tgctccgtgt gtctcatgcc agcagcacgt cgccatccgt   1980

caccagaatt agtcctcaca gcctaggacc agttttgtat caaactcgtc tgatgttttg   2040

atgccatttg tcttttgtaa agttaattca ttaaaagttt tatgtacttt gaaaaaaaaa   2100

aaaaaaaaaa                                                          2110
```

<210> SEQ ID NO 94
<211> LENGTH: 1778
<212> TYPE: DNA
<213> ORGANISM: Homo sapiens

<400> SEQUENCE: 94

```
agttgcaggc gagcaggcga ggaatcgccg tggcgtcttg gtgttctcca cgctggttcg     60

caggtgaaga gatggcgttt gtgaagagtg gctggttgct gcgacagagt actattttga    120

agcgctggaa gaagaactgg tttgatctgt ggtcggatgg tcacctgatc tattatgatg    180

accagactcg gcagaatatc gaggataagg tccacatgcc aatggactgc atcaacatcc    240

gcacggggca ggaatgtcgg gatactcagc cccggatgg aaagtcaaaa gactgcatgc     300

tccagattgt ttgtcgagat gggaaaacaa ttagtctttg tgcagaaagc acagatgatt    360

gcttggcctg gaaatttaca ctccaagatt ctaggacaaa cacagcgtat gtgggctctg    420

cagtcatgac cgatgagaca tccgtggttt cctcacctcc accatacacg gcctatgctg    480

caccggcccc tgaggcttat ggctatgggc catacggtgg tgcgtacccg ccaggaactc    540

aagttgtcta cgctgcgaat gggcaggcgt atgccgtgcc ccaccagtac ccatatgcag    600

gactttatgg acagcagcct gctaaccaag tcatcattcg agagcgctat cgagacaacg    660

acagcgacct ggcactgggc atgctggcag gagcagccac gggcatggcc ttagggtctc    720

tattttgggt cttctagggg cctcaaggtc ttgatgtgca tagcttctga taaccctgtg    780

tgcaataata tgatttgcag ggcatttctg tttgtgacaa aagtttttaa taatagtttt    840

aatcattcct ttgaaagtag tgatgtcata attgtactaa tccacataag taccacagag    900

aagggtttga actgtgctat tttgttcaaa tgttgactct ccgggggcac tggctcattc    960

caagactgtt cttgtgcaac tctcagaata ccttatttga gcatacctgt tttgaaaggc   1020

attttctttt tagagttagg tgtagtgctt aagggttaat ttattttcat gttatgccag   1080
```

-continued

```
taatatagtg ttgtatgcct attgagtgat tgtggcaaga aaagctacag cttctttgcg   1140

tttaactttt tcaaaccaca gaccagaact ggttgcatgt tactttagga gttgtgggtt   1200

ggtaagctcc caggtacttc ccgaggctat ggtgtgagag cccccgtcct gccctctggg   1260

gctccacagg cccctggcaa ggccgatggc tcaggatgat ggggcacagc ccgcctttga   1320

acaatcatgc ttcagaaatc tgcctgaccc tagctgctgc tgctgctcac tttattcttg   1380

tatggctttg gtaggcatac ttggagaaca tatcccacat taggaattga tttaagcctg   1440

agagtttgag ggctttaatc ctttaaaact tggagaagct ggctgggcgc ggtggctcac   1500

gcctgtaatc ccagcacttt gagagaccga ggcgggcgga tcacgaggtc aggagatcga   1560

gaccatcctg gctaacacgg tgaaacccca tctctactaa aaatacaaaa aattagctgg   1620

gcgtggtggc aggcgcctgt ggtcccagct actcgggagg ctgaggcagg agaatagtgt   1680

gaacccagga ggcggagctt gcagtgagcc aagatagtgc cactgcactt cagcctgggt   1740

gacagagtga gactctgtct caaaaaaaaa aaaaaaaa                           1778
```

<210> SEQ ID NO 95
<211> LENGTH: 4965
<212> TYPE: DNA
<213> ORGANISM: Homo sapiens
<220> FEATURE:
<221> NAME/KEY: misc_feature
<222> LOCATION: (3757)..(3757)
<223> OTHER INFORMATION: n stands for any base
<220> FEATURE:
<221> NAME/KEY: misc_feature
<222> LOCATION: (3810)..(3810)
<223> OTHER INFORMATION: n stands for any base
<220> FEATURE:
<221> NAME/KEY: misc_feature
<222> LOCATION: (3881)..(3881)
<223> OTHER INFORMATION: n stands for any base
<220> FEATURE:
<221> NAME/KEY: misc_feature
<222> LOCATION: (3882)..(3882)
<223> OTHER INFORMATION: n stands for any base
<220> FEATURE:
<221> NAME/KEY: misc_feature
<222> LOCATION: (3892)..(3892)
<223> OTHER INFORMATION: n stands for any base

<400> SEQUENCE: 95

```
acctctactg gggagacgag gaccccgagg ttctgggggg cgacgcgacc tgcccgaagt     60

gacaagggtc ctgggccgca ctgctccgcc ggggtctgcg ctcctcggcg gagcgggtgg    120

gaaggatgag tcctcggggt ggagaaggag gagcgggtcc ccgggtaccg ctcacccggc    180

cttaggagcc cgggagcgcg cgtagggacg cggagttgag gctctccatc tgcggccagg    240

gaaagggata cagtccccg ggcccctccc ggccgctcgg aacccacccc aggcgcgtcc    300

ccgcgggcgc gcgctccagg cggggccgac gggctcggag gcgcgcgccc gctgccgggt    360

ccgccgcgcg cgctccctcc gctcctctcc cccgcccctc ccgggcccgc gcgctcccag    420

ggtccgccgc gcgcgcgcct cgcgtcgctc cccatccccg cccctcccgc cgccaccccg    480

cccccggccg ggtaccctcg ccggacccga gagagagcgc cgccgccatc ttagttgctg    540

ccgctgcctt cagcaagacg ctgctctgag gcggggaggg cgccgcgtcc tgagcgcgcg    600

gcccagcgtc acggcggcgg cggcggcggc tcctccttgg acccccggag ctccccgcgc    660

cgcggagcag ctggccccag gcccctagag ccccgagagc tccgagagct ccgctcggcg    720

tcccgcgcgc ctccctgccg ctcccgcccc gggctggcga tgctgcgccg ccccgctccc    780
```

-continued

```
gcgctggccc cggccgcccg gctgctgctg gccgggctgc tgtgcggcgg cggggtctgg    840
gccgcgcgag ttaacaagca caagccctgg ctggagccca cctaccacgg catagtcaca    900
gagaacgaca acaccgtgct cctcgacccc ccactgatcg cgctggataa agatgcgcct    960
ctgcgatttg caggtgagat ttgtggattt aaaattcacg ggcagaatgt ccccttttgat   1020
gcagtggtag tggataaatc cactggtgag ggagtcattc gctccaaaga gaaactggac   1080
tgtgagctgc agaaagacta ttcattcacc atccaggcct atgattgtgg gaagggacct   1140
gatggcacca acgtgaaaaa gtctcataaa gcaactgttc atattcaggt gaacgacgtg   1200
aatgagtacg cgcccgtgtt caaggagaag tcctacaaag ccacggtcat cgagggggaag   1260
cagtacgaca gcattttgag ggtggaggcc gtggatgccg actgctcccc tcagttcagc   1320
cagatttgca gctacgaaat catcactcca gacgtgccct ttactgttga caaagatggt   1380
tatataaaaa acacagagaa attaaactac gggaaagaac atcaatataa gctgaccgtc   1440
actgcctatg actgtgggaa gaaaagagcc acagaagatg ttttggtgaa gatcagcatt   1500
aagcccacct gcacccctgg gtggcaagga tggaacaaca ggattgagta tgagccgggc   1560
accggcgcgt tggccgtctt tccaaatatc cacctggaga catgtgacga gccagtcgcc   1620
tcagtacagg ccacagtgga gctagaaacc agccacatag ggaaaggctg cgaccgagac   1680
acctactcag agaagtccct ccaccggctc tgtggtgcgg ccgcgggcac tgccgagctg   1740
ctgccatccc cgagtggatc cctcaactgg accatgggcc tgcccaccga caatggccac   1800
gacagcgacc aggtgtttga gttcaacggc acccaggcag tgaggatccc ggatggcgtc   1860
gtgtcggtca gccccaaaga gccgttcacc atctcggtgt ggatgagaca tgggccattc   1920
ggcaggaaga aggagacaat tctttgcagt tctgataaaa cagatatgaa tcggcaccac   1980
tactccctct atgtccacgg gtgccggctg atcttcctct tccgtcagga tccttctgag   2040
gagaagaaat acagacctgc agagttccac tggaagttga atcaggtctg tgatgaggaa   2100
tggcaccact acgtcctcaa tgtagaattc ccgagtgtga ctctctatgt ggatggcacg   2160
tcccacgagc ccttctctgt gactgaggat tacccgctcc atccatccaa gatagaaact   2220
cagctcgtgg tgggggcttg ctggcaagag ttttcaggag ttgaaaatga caatgaaact   2280
gagcctgtga ctgtggcctc tgcaggtggc gacctgcaca tgacccagtt tttccgaggc   2340
aatctggctg gcttaactct ccgttccggg aaactcgcgg ataagaaggt gatcgactgt   2400
ctgtatacct gcaaggaggg gctggacctg caggtcctcg aagacagtgg cagaggcgtg   2460
cagatccaag cacaccccag ccagttggta ttgaccttgg agggagaaga cctcggggaa   2520
ttggataagg ccatgcagca catctcgtac ctgaactccc ggcagttccc cacgcccgga   2580
attcgcagac tcaaaatcac cagcacaatc aagtgtttta acgaggccac ctgcatttcg   2640
gtcccccggg tagatggcta cgtgatggtt ttacagcccg aggagcccaa gatcagcctg   2700
agtggcgtcc accattttgc ccgagcagct tctgaatttg aaagctcaga aggggtgttc   2760
cttttccctg agcttcgcat catcagcacc atcacgagag aagtggagcc tgaaggggac   2820
ggggctgagg accccacagt tcaagaatca ctggtgtccg aggagatcgt gcacgacctg   2880
gatacctgtg aggtcacggt ggagggagag gagctgaacc acgagcagga gagcctggag   2940
gtggacatgg cccgcctgca gcagaagggc attgaagtga gcagctctga actgggcatg   3000
accttcacag gcgtggacac catggccagc tacgaggagg ttttgcacct gctgcgctat   3060
cggaactggc atgccaggtc cttgcttgac cggaagttta agctcatctg ctcagagctg   3120
aatggccgct acatcagcaa cgaatttaag gtggaagtga atgttatcca cacggccaac   3180
```

-continued

```
cccatggaac acgccaacca catggctgcc cagccacagt tcgtgcaccc ggaacaccgc   3240
tcctttgttg acctgtcagg ccacaacctg gccaaccccc acccgttcgc agtcgtcccc   3300
agcactgcga cagttgtgat cgtggtgtgc gtcagcttcc tggtgttcat gattatcctg   3360
ggggtatttc ggatccgggc cgcgtcgacg cggaccatgc gggatcagga caccgggaag   3420
gagaacgaga tggactggga cgactctgcc ctgaccatca ccgtcaaccc catggagacc   3480
tatgaggacc agcacagcag tgaggaggag gaggaagagg aagaggaaga ggaaagcgag   3540
gacggcgaag aagaggatga catcaccagc gccgagtcgg agagcagcga ggaggaggag   3600
ggggagcagg gcgaccccca gaacgcaacc cggcagcagc agctggagtg ggatgactcc   3660
accctcagct actgacccgt gcccccggcc acctcggttt ctgctttcga agactctgct   3720
gccatccgtt ctcccagtcc caagggtcca cgatgtncaa agtcatttcg gccagtaggt   3780
gtgcagaccc ctcccccgcc acgatcgtcn ctgttgcttg gtgtgtagga ccctaggctc   3840
cccgcccacc ctctgcctgg tcgcgctctt ctgtcccacg nnggagctga cnccttcctc   3900
tctggccgcc catccggctc gcacaggggc ctcccagcgc ctcaggcccc gcgtttgtgt   3960
ctggagtctc cccccgggga gaggacctgg ccccattttc cacactcctc ctccgacagc   4020
agctccctgg gcagtggcct gctctcaccg tgtgcagcct tgtggtttat gcttaaatgt   4080
acattttcct gctggtaaaa ggagaaactg agaggtgtcc tgcagaccgg ctgaccactc   4140
cttttggaga cggcaggagg cctgagctgt gctgctcaag agactggatc agggtagcta   4200
caagtggccg ggccttgcct ttgggattct acctgttcct aatttggtgt ggggtgcggg   4260
gtccctggcc ccttttccac actcctcctc cgacagcagc tccctgggca gtggcctggt   4320
ctcaccgtgt gcagccttgt ggtttatgct taaatgtaca ttttcctgct ggtaaaagga   4380
gaaactgaga ggtgtcctgc agaccggctg accactcctt ttggagacgg caggaggcct   4440
gagcgatccg tactcagaac gtccaggaga gacgcatggc ccgaagtcaa agtgctggaa   4500
ttttccaaaa cagcctgttc tctcctctct cctccccaga gcacccccctg ccatcagggg   4560
ggttgaaatc cctctccccc aggagccctg ctgctttgct tggtggtagg gcaggagagc   4620
aaacaaacag tcatggtcta aaacccacat agcactttgc tcttagttac atgtaaaatt   4680
ttagatttct aaaacaggtg ggcaatcatt ttgaatactg ttctgtgacc ctgactgcta   4740
gttctgagga cactggtggc tgtgctatgt gtggccatcc tccatgtccc gtccctgtag   4800
ctgctctgtt tagacagcgg acagacgctc acgcccaggg gatgtcctca cgctgtcgcc   4860
gcgcggtttc ccttcgcaga tgtgtatact catgataggt cagaaagtgt atccgctaca   4920
ataaagttct ggttctaact aaaaaaaaaa aaaaaaaaaa aaaaa                  4965
```

<210> SEQ ID NO 96
<211> LENGTH: 2617
<212> TYPE: DNA
<213> ORGANISM: Homo sapiens

<400> SEQUENCE: 96

```
gacttgctcc ggtttgcaga gctaggaggt ggcaggctgt gcgctcaaac tcaggctgtc     60
taactccaca ttctgtgggg tgagaggatg ggtgatgggg tgtcttttct ggaggaggga    120
ggtgctgtga gcctagcgag atggaggtac agtgggtgtg ggcctggagc gctgggccca    180
ggcaggggct tctgattagg aagccctggg gcaccagttc aggttctccc agagagtagt    240
gtgatgggat ccagtaacct gtgccctcca gatgacttct gtaggtgtgt ttagtgacat    300
```

-continued

```
gctcaacggg tgcgggaagg atgggcttgt gccaagggcc aagcccagag atgtttcaga    360
tttttccctt tatgcccctg caaccaagcc ctgctgctcc aggacatata agagacgaag    420
gctgagggct ccagcactca ccggcctggg ccctgtcact tctctgatag ctcccagctc    480
gctctctgca gccatgattg ccagacagca gtgtgtccga ggcgggcccc ggggcttcag    540
ctgtggctcg gccattgtag gcggtggcaa gagaggtgcc ttcagctcag tctccatgtc    600
tggaggtgct ggccgatgct cttctggggg atttggcagc agaagcctct acaacctcag    660
ggggaacaaa agcatctcca tgagtgtggc tgggtcacga caaggtgcct gctttggggg    720
tgctggaggc tttggcactg gtggctttgg tgccggcggc ttcggagctg gtttcggcac    780
tggtggcttt ggtggtggat ttgggggctc cttcagtggt aagggtggcc ctggcttccc    840
cgtctgcccc gctgggggaa ttcaggaggt caccatcaac cagagcttgc tcacccccct    900
ccacgtggag attgaccctg agatccagaa agtccggacg gaagagcgcg aacagatcaa    960
gctcctcaac aacaagtttg cctccttcat cgacaaggtg cagttcttag agcaacagaa   1020
taaggtcctg gagaccaaat ggaacctgct ccagcagcag acgaccacca cctccagcaa   1080
aaaccttgag cccctctttg agacctacct cagtgtcctg aggaagcagc tagatacctt   1140
gggcaatgac aaagggcgcc tgcagtctga gctgaagacc atgcaggaca gcgtggagga   1200
cttcaagact aagtatgaag aggagatcaa caaacgcaca gcagccgaga atgactttgt   1260
ggtcctaaag aaggacgtgg atgctgccta cctgaacaag gtggagttgg aggccaaggt   1320
ggacagtctt aatgacgaga tcaacttcct gaaggtcctc tatgatgcgg agctgtccca   1380
gatgcagacc catgtcagcg acacgtccgt ggtcctttcc atggacaaca accgcaacct   1440
ggacctggac agcattattg ccgaggtccg tgcccagtac gaggagattg cccagaggag   1500
caaggctgag gctgaagccc tgtaccagac caaggtccag cagctccaga tctcggttga   1560
ccaacatggt gacaacctga agaacaccaa gagtgaaatt gcagagctca acaggatgat   1620
ccagaggctg cgggcagaga tcgagaacat caagaagcag tgccagactc ttcaggtatc   1680
cgtggctgat gcagagcagc gaggtgagaa tgcccttaaa gatgcccaca gcaagcgcgt   1740
agagctggag gctgccctgc agcaggccaa ggaggagctg gcacgaatgc tgcgtgagta   1800
ccaggagctc atgagtgtga agctggcctt ggacatcgag atcgccacct accgcaaact   1860
gctggagggc gaggagtaca gaatgtctgg agaatgccag agtgccgtga gcatctctgt   1920
ggtcagcggt agcaccagca ctggaggcat cagcggagga ttaggaagtg gctccgggtt   1980
tggcctgagt agtggctttg gctccggctc tggaagtggc tttgggtttg gtggcagtgt   2040
ctctggcagt tccagcagca agatcatctc taccaccacc ctgaacaaga gacgatagag   2100
gagacgaggt ccctgcagct cactgtgtcc agctgggccc agcactggtg tctctgtgct   2160
tccttcactt cacctccatc ctctgtctct ggggctcatc ttactagtat cccctccact   2220
atcccatggg ctctctctgc cccaggatga tcttctgtgc tgggacaggg actctgcctc   2280
ttggagtttg gtagctactt cttgatttgg gcctggtgac ccacctggaa tgggaaggat   2340
gtcagctgac ctctcacctc ccatgggcag agaagaaaat gaccaggagt gtcatctcca   2400
gaattattgg ggtcacatat gtcccttccc agtccaatgc catctcccac tagatcctgt   2460
attatccatc tacatcagaa ccaaactact tctccaacac ccggcagcac ttggccctgc   2520
aagcttagga tgagaaccac ttagtgtccc attctactcc tctcattccc tcttatccat   2580
ctgcaggtga atcttcaata aaatgctttt gtcattc                            2617
```

<210> SEQ ID NO 97
<211> LENGTH: 2547
<212> TYPE: DNA
<213> ORGANISM: Homo sapiens

<400> SEQUENCE: 97

```
gcgacggagg gaggagggaa ggagatgaac gagattaaga cccaattcac cacccgggaa     60
ggtctgtaca agctgctgcc gcactcggag tacagccggc ccaaccgggt gcccttcaac    120
tcgcagggat ccaaccctgt ccgcgtctcc ttcgtaaacc tcaacgacca gtctggcaac    180
ggcgaccgcc tctgcttcaa tgtgggccgg gagctgtact tctatatcta caagggggtc    240
cgcaaggctg ctgacttgag taaaccaata gataaaagga tatacaaagg aacacagcct    300
acttgtcatg acttcaacca cctaacagcc acagcagaaa gtgtctctct cctagtgggc    360
ttttccgcag gccaagtcca gcttatagac ccaatcaaaa aagaaactag caaacttttt    420
aatgaggaaa gactaataga caagtcacga gttacctgtg tcaaatgggt tcccggttcg    480
gaaagccttt tcctagtagc ccactcgagt gggaacatgt acttatataa tgtggagcac    540
acttgtggca ccacagcccc ccactaccag cttctgaagc acggagagag ctttgccgtg    600
cacacttgca agagcaaatc cacgaggaac cctctcctta agtggacggt gggcgagggg    660
gccctcaacg agtttgcttt ctccccagat ggcaagttct tagcgtgcgt gagccaggac    720
gggtttctgc gggtgttcaa ctttgactca gtggagctgc acggtacgat gaaaagctac    780
tttgggggct tgctgtgtgt gtgctggagc ccggatggca agtacatcgt gacaggtggg    840
gaggacgact tggtgacagt ctggtccttt gtagactgcc gagtaatagc caaaggccac    900
gggcacaagt cctgggtcag tgttgtagcg tttgaccctt ataccactag tgtagaagaa    960
ggtgacccta tggagtttag tggcagcgat gaggacttcc aagaccttct tcattttggc   1020
agagatcgag caaatagtac acagtccagg ctctccaaac ggaactctac agacagccgc   1080
cccgtaagtg tcacgtatcg gtttggttcc gtgggccagg acacacagct ctgtttatgg   1140
gaccttacag aagatatcct tttccctcac caacccctct caagagcaag gacacacaca   1200
aatgtcatga atgccacgag tcctcctgct ggaagcaatg ggaacagtgt tacaacaccc   1260
gggaactctg tgccgcctcc tctgccacgg tccaacagcc ttccacattc agcagtctca   1320
aatgctggca gcaaaagcag tgtcatggac ggggccattg cttctggggt cagcaaattt   1380
gcaacacttt cactacatga ccggaaggag aggcaccacg agaaagatca caagcgaaat   1440
catagcatgg gacacatttc tagcaagagc agtgacaaac tgaatctagt taccaaaacc   1500
aaaacggacc ctgctaaaac tctgggaacg cccctgtgtc ctcgaatgga agatgttccc   1560
ttgttagagc cgctgatatg taaaaagata gcacatgaga gactgactgt actaatattt   1620
cttgaagact gtatagtcac tgcttgtcag gagggattta tttgcacatg gggaaggcct   1680
ggtaaagtgg gctcattgtc atccccaagc caggccagtt ctccaggtgg aactgtagtg   1740
tagcgacctc actgctgcgc gcacagtctc ccgggacttg gactcgaggg agtgacgagg   1800
aggagctccg agctgcgcct gagccgtgcc agccggcgga cctcaggcgg tggacgtcgg   1860
cgatagccgt gtggacggtg accggctcac tctgcggcgc cgtgctcccg ctgctcaccc   1920
aaagaagttg tttccatttt aaaccggtct tttggggctg cagtaaaaaa taagaaatgg   1980
agttttcttg ctttttactc taaaattcaa tgtaattaaa tttcatatat atataatata   2040
tacatatata catagtgtaa aataaaatgt ttcttggaca agaaatcccc tgaaattcag   2100
ctgttatagt gcttcactgt tttgcactg atttttctat accttaggtg gtcagaagac    2160
```

-continued

```
aaccttgaat gcactcatag agaaaactgt tactttctga cgtaatgtaa ttcaggaaga   2220

cagacgctgc aatcacagat tttaaaaaat tgtttgcact taaaaatagt tgaatgctgg   2280

tggaaagtta ctttgcagat gggtgtaagg actcatggcc ctctgaggtg cggcgtgaag   2340

atgccctttt taccccgttg acgtttattt tacgtaaaat aaactgttgt ttccaatgca   2400

atcaactctg tattatatgt ataaatattg taattctgca attggggaaa atagttactt   2460

cactagtaat tttcatcatt taagagtgat atttctaatt cacaaaagtt aatattaaaa   2520

ctattttgta atataaaaaa aaaaaaa                                       2547
```

<210> SEQ ID NO 98
<211> LENGTH: 14121
<212> TYPE: DNA
<213> ORGANISM: Homo sapiens

<400> SEQUENCE: 98

```
attcccaccg ggacctgcgg ggctgagtgc ccttctcggt tgctgccgct gaggagcccg     60

cccagccagc cagggccgcg aggccgaggc caggccgcag cccaggagcc gccccaccgc    120

agctggcgat ggacccgccg aggcccgcgc tgctggcgct gctggcgctg cctgcgctgc    180

tgctgctgct gctggcgggc gccagggccg aagaggaaat gctggaaaat gtcagcctgg    240

tctgtccaaa agatgcgacc cgattcaagc acctccggaa gtacacatac aactatgagg    300

ctgagagttc cagtggagtc cctgggactg ctgattcaag aagtgccacc aggatcaact    360

gcaaggttga gctggaggtt ccccagctct gcagcttcat cctgaagacc agccagtgca    420

ccctgaaaga ggtgtatggc ttcaaccctg agggcaaagc cttgctgaag aaaaccaaga    480

actctgagga gtttgctgca gccatgtcca ggtatgagct caagctggcc attccagaag    540

ggaagcaggt tttcctttac ccggagaaag atgaacctac ttacatcctg aacatcaaga    600

ggggcatcat ttctgccctc ctggttcccc cagagacaga agaagccaag caagtgttgt    660

ttctggatac cgtgtatgga aactgctcca ctcactttac cgtcaagacg aggaagggca    720

atgtggcaac agaaatatcc actgaaagag acctggggca gtgtgatcgc ttcaagccca    780

tccgcacagg catcagccca cttgctctca tcaaaggcat gacccgcccc ttgtcaactc    840

tgatcagcag cagccagtcc tgtcagtaca cactggacgc taagaggaag catgtggcag    900

aagccatctg caaggagcaa cacctcttcc tgcctttctc ctacaacaat aagtatggga    960

tggtagcaca agtgacacag actttgaaac ttgaagacac accaaagatc aacagccgct   1020

tctttggtga aggtactaag aagatgggcc tcgcatttga gagcaccaaa tccacatcac   1080

ctccaaagca ggccgaagct gttttgaaga ctctccagga actgaaaaaa ctaaccatct   1140

ctgagcaaaa tatccagaga gctaatctct tcaataagct ggttactgag ctgagaggcc   1200

tcagtgatga agcagtcaca tctctcttgc cacagctgat tgaggtgtcc agccccatca   1260

ctttacaagc cttggttcag tgtggacagc ctcagtgctc cactcacatc ctccagtggc   1320

tgaaacgtgt gcatgccaac cccccttctga tagatgtggt cacctacctg gtggccctga   1380

tccccgagcc ctcagcacag cagctgcgag agatcttcaa catggcgagg gatcagcgca   1440

gccgagccac cttgtatgcg ctgagccacg cggtcaacaa ctatcataag acaaacccta   1500

cagggaccca ggagctgctg gacattgcta attacctgat ggaacagatt caagatgact   1560

gcactgggga tgaagattac acctatttga ttctgcgggt cattggaaat atgggccaaa   1620

ccatggagca gttaactcca gaactcaagt cttcaatcct caaatgtgtc caaagtacaa   1680

agccatcact gatgatccag aaagctgcca tccaggctct gcggaaaatg gagcctaaag   1740
```

-continued

```
acaaggacca ggaggttctt cttcagactt tccttgatga tgcttctccg ggagataagc   1800
gactggctgc ctatcttatg ttgatgagga gtccttcaca ggcagatatt aacaaaattg   1860
tccaaattct accatgggaa cagaatgagc aagtgaagaa ctttgtggct tcccatattg   1920
ccaatatctt gaactcagaa gaattggata tccaagatct gaaaaagtta gtgaaagaag   1980
ctctgaaaga atctcaactt ccaactgtca tggacttcag aaaattctct cggaactatc   2040
aactctacaa atctgtttct cttccatcac ttgacccagc ctcagccaaa atagaaggga   2100
atcttatatt tgatccaaat aactaccttc ctaaagaaag catgctgaaa actaccctca   2160
ctgcctttgg atttgcttca gctgacctca tcgagattgg cttggaagga aaaggctttg   2220
agccaacatt ggaagctctt tttgggaagc aaggattttt cccagacagt gtcaacaaag   2280
ctttgtactg ggttaatggt caagttcctg atggtgtctc taaggtctta gtggaccact   2340
ttggctatac caaagatgat aaacatgagc aggatatggt aaatggaata atgctcagtg   2400
ttgagaagct gattaaagat ttgaaatcca aagaagtccc ggaagccaga gcctacctcc   2460
gcatcttggg agaggagctt ggttttgcca gtctccatga cctccagctc ctgggaaagc   2520
tgcttctgat gggtgcccgc actctgcagg ggatccccca gatgattgga gaggtcatca   2580
ggaagggctc aaagaatgac tttttcttc actacatctt catggagaat gcctttgaac   2640
tccccactgg agctggatta cagttgcaaa tatcttcatc tggagtcatt gctcccggag   2700
ccaaggctgg agtaaaactg gaagtagcca acatgcaggc tgaactggtg gcaaaaccct   2760
ccgtgtctgt ggagtttgtg acaaatatgg gcatcatcat tccggacttc gctaggagtg   2820
gggtccagat gaacaccaac ttcttccacg agtcgggtct ggaggctcat gttgccctaa   2880
aagctgggaa gctgaagttt atcattcctt ccccaaagag accagtcaag ctgctcagtg   2940
gaggcaacac attacatttg gtctctacca ccaaaacgga ggtgatccca cctctcattg   3000
agaacaggca gtcctggtca gtttgcaagc aagtctttcc tggcctgaat tactgcacct   3060
caggcgctta ctccaacgcc agctccacag actccgcctc ctactatccg ctgaccgggg   3120
acaccagatt agagctggaa ctgaggccta caggagagat tgagcagtat tctgtcagcg   3180
caacctatga gctccagaga gaggacagag ccttggtgga taccctgaag tttgtaactc   3240
aagcagaagg tgcgaagcag actgaggcta ccatgacatt caaatataat cggcagagta   3300
tgaccttgtc cagtgaagtc caaattccgg attttgatgt tgacctcgga acaatcctca   3360
gagttaatga tgaatctact gagggcaaaa cgtcttacag actcaccctg gacattcaga   3420
acaagaaaat tactgaggtc gccctcatgg gccacctaag ttgtgacaca aaggaagaaa   3480
gaaaaatcaa gggtgttatt tccatacccc gtttgcaagc agaagccaga agtgagatcc   3540
tcgcccactg gtcgcctgcc aaactgcttc tccaaatgga ctcatctgct acagcttatg   3600
gctccacagt ttccaagagg gtggcatggc attatgatga agagaagatt gaatttgaat   3660
ggaacacagg caccaatgta gataccaaaa aaatgacttc caatttccct gtggatctct   3720
ccgattatcc taagagcttg catatgtatg ctaatagact cctggatcac agagtccctg   3780
aaacagacat gactttccgg cacgtgggtt ccaaattaat agttgcaatg agctcatggc   3840
ttcagaaggc atctgggagt cttccttata cccagacttt gcaagaccac ctcaatagcc   3900
tgaaggagtt caacctccag aacatgggat tgccagactt ccacatccca gaaaacctct   3960
tcttaaaaag cgatggccgg gtcaaatata ccttgaacaa gaacagtttg aaaattgaga   4020
ttcctttgcc ttttggtggc aaatcctcca gagatctaaa gatgttagag actgttagga   4080
```

-continued

```
caccagccct ccacttcaag tctgtgggat tccatctgcc atctcgagag ttccaagtcc   4140
ctacttttac cattcccaag ttgtatcaac tgcaagtgcc tctcctgggt gttctagacc   4200
tctccacgaa tgtctacagc aacttgtaca actggtccgc ctcctacagt ggtggcaaca   4260
ccagcacaga ccatttcagc cttcgggctc gttaccacat gaaggctgac tctgtggttg   4320
acctgctttc ctacaatgtg caaggatctg gagaaacaac atatgaccac aagaatacgt   4380
tcacactatc atgtgatggg tctctacgcc acaaatttct agattcgaat atcaaattca   4440
gtcatgtaga aaaacttgga aacaacccag tctcaaaagg tttactaata ttcgatgcat   4500
ctagttcctg ggaccacag atgtctgctt cagttcattt ggactccaaa aagaaacagc   4560
atttgtttgt caaagaagtc aagattgatg ggcagttcag agtctcttcg ttctatgcta   4620
aaggcacata tggcctgtct tgtcagaggg atcctaacac tggccggctc aatggagagt   4680
ccaacctgag gtttaactcc tcctacctcc aaggcaccaa ccagataaca ggaagatatg   4740
aagatggaac cctctccctc acctccacct ctgatctgca aagtggcatc attaaaaata   4800
ctgcttccct aaagtatgag aactacgagc tgactttaaa atctgacacc aatgggaagt   4860
ataagaactt tgccacttct aacaagatgg atatgacctt ctctaagcaa aatgcactgc   4920
tgcgttctga atatcaggct gattacgagt cattgaggtt cttcagcctg ctttctggat   4980
cactaaattc ccatggtctt gagttaaatg ctgacatctt aggcactgac aaaattaata   5040
gtggtgctca caaggcgaca ctaaggattg gccaagatgg aatatctacc agtgcaacga   5100
ccaacttgaa gtgtagtctc ctggtgctgg agaatgagct gaatgcagag cttggcctct   5160
ctggggcatc tatgaaatta acaacaaatg gccgcttcag ggaacacaat gcaaaattca   5220
gtctggatgg gaaagccgcc ctcacagagc tatcactggg aagtgcttat caggccatga   5280
ttctgggtgt cgacagcaaa aacattttca acttcaaggt cagtcaagaa ggacttaagc   5340
tctcaaatga catgatgggc tcatatgctg aaatgaaatt tgaccacaca aacagtctga   5400
acattgcagg cttatcactg gacttctctt caaaacttga caacatttac agctctgaca   5460
agttttataa gcaaactgtt aatttacagc tacagcccta ttctctggta actactttaa   5520
acagtgacct gaaatacaat gctctggatc tcaccaacaa tgggaaacta cggctagaac   5580
ccctgaagct gcatgtggct ggtaacctaa aaggagccta ccaaaataat gaaataaaac   5640
acatctatgc catctcttct gctgccttat cagcaagcta taaagcagac actgttgcta   5700
aggttcaggg tgtggagttt agccatcggc tcaacacaga catcgctggg ctggcttcag   5760
ccattgacat gagcacaaac tataattcag actcactgca tttcagcaat gtcttccgtt   5820
ctgtaatggc cccgtttacc atgaccatcg atgcacatac aaatggcaat gggaaactcg   5880
ctctctgggg agaacatact gggcagctgt atagcaaatt cctgttgaaa gcagaacctc   5940
tggcatttac tttctctcat gattacaaag gctccacaag tcatcatctc gtgtctagga   6000
aaagcatcag tgcagctctt gaacacaaag tcagtgccct gcttactcca gctgagcaga   6060
caggcacctg gaaactcaag acccaattta acaacaatga atacagccag gacttggatg   6120
cttacaacac taaagataaa attggcgtgg agcttactgg acgaactctg gctgacctaa   6180
ctctactaga ctccccaatt aaagtgccac ttttactcag tgagcccatc aatatcattg   6240
atgctttaga gatgagagat gccgttgaga agccccaaga atttacaatt gttgcttttg   6300
taaagtatga taaaaaccaa gatgttcact ccattaacct cccatttttt gagaccttgc   6360
aagaatattt tgagaggaat cgacaaacca ttatagttgt agtggaaaac gtacagagaa   6420
acctgaagca catcaatatt gatcaatttg taagaaaata cagagcagcc ctgggaaaac   6480
```

```
tcccacagca agctaatgat tatctgaatt cattcaattg ggagagacaa gtttcacatg   6540
ccaaggagaa actgactgct ctcacaaaaa agtatagaat tacagaaaat gatatacaaa   6600
ttgcattaga tgatgccaaa atcaacttta atgaaaaact atctcaactg cagacatata   6660
tgatacaatt tgatcagtat attaaagata gttatgattt acatgatttg aaaatagcta   6720
ttgctaatat tattgatgaa atcattgaaa aattaaaaag tcttgatgag cactatcata   6780
tccgtgtaaa tttagtaaaa acaatccatg atctacattt gtttattgaa aatattgatt   6840
ttaacaaaag tggaagtagt actgcatcct ggattcaaaa tgtggatact aagtaccaaa   6900
tcagaatcca gatacaagaa aaactgcagc agcttaagag acacatacag aatatagaca   6960
tccagcacct agctggaaag ttaaaacaac acattgaggc tattgatgtt agagtgcttt   7020
tagatcaatt gggaactaca atttcatttg aaagaataaa tgatgttctt gagcatgtca   7080
aacactttgt tataaatctt attggggatt ttgaagtagc tgagaaaatc aatgccttca   7140
gagccaaagt ccatgagtta atcgagaggt atgaagtaga ccaacaaatc caggttttaa   7200
tggataaatt agtagagttg acccaccaat acaagttgaa ggagactatt cagaagctaa   7260
gcaatgtcct acaacaagtt aagataaaag attactttga gaaattggtt ggatttattg   7320
atgatgctgt gaagaagctt aatgaattat cttttaaaac attcattgaa gatgttaaca   7380
aattccttga catgttgata aagaaattaa agtcatttga ttaccaccag tttgtagatg   7440
aaaccaatga caaaatccgt gaggtgactc agagactcaa tggtgaaatt caggctctgg   7500
aactaccaca aaaagctgaa gcattaaaac tgtttttaga ggaaaccaag gccacagttg   7560
cagtgtatct ggaaagccta caggacacca aaataacctt aatcatcaat tggttacagg   7620
aggctttaag ttcagcatct ttggctcaca tgaaggccaa attccgagag actctagaag   7680
atacacgaga ccgaatgtat caaatggaca ttcagcagga acttcaacga tacctgtctc   7740
tggtaggcca ggtttatagc acacttgtca cctacatttc tgattggtgg actcttgctg   7800
ctaagaacct tactgacttt gcagagcaat attctatcca agattgggct aaacgtatga   7860
aagcattggt agagcaaggg ttcactgttc ctgaaatcaa gaccatcctt gggaccatgc   7920
ctgcctttga agtcagtctt caggctcttc agaaagctac cttccagaca cctgatttta   7980
tagtccccct aacagatttg aggattccat cagttcagat aaacttcaaa gacttaaaaa   8040
atataaaaat cccatccagg ttttccacac cagaatttac catccttaac accttccaca   8100
ttccttcctt tacaattgac tttgtcgaaa tgaaagtaaa gatcatcaga accattgacc   8160
agatgcagaa cagtgagctg cagtggcccg ttccagatat atatctcagg gatctgaagg   8220
tggaggacat tcctctagcg agaatcaccc tgccagactt ccgtttacca gaaatcgcaa   8280
ttccagaatt cataatccca actctcaacc ttaatgattt tcaagttcct gaccttcaca   8340
taccagaatt ccagcttccc cacatctcac acacaattga agtacctact tttggcaagc   8400
tatacagtat tctgaaaatc caatctcctc ttttcacatt agatgcaaat gctgacatag   8460
ggaatggaac cacctcagca aacgaagcag gtatcgcagc ttccatcact gccaaaggag   8520
agtccaaatt agaagttctc aattttgatt ttcaagcaaa tgcacaactc tcaaacccta   8580
agattaatcc gctggctctg aaggagtcag tgaagttctc cagcaagtac ctgagaacgg   8640
agcatgggag tgaaatgctg ttttttggaa atgctattga gggaaaatca aacacagtgg   8700
caagtttaca cacagaaaaa aatacactgg agcttagtaa tggagtgatt gtcaagataa   8760
acaatcagct taccctggat agcaacacta aatacttcca caaattgaac atccccaaac   8820
```

-continued

```
tggacttctc tagtcaggct gacctgcgca acgagatcaa gacactgttg aaagctggcc   8880
acatagcatg gacttcttct ggaaaagggt catggaaatg ggcctgcccc agattctcag   8940
atgagggaac acatgaatca caaattagtt tcaccataga aggacccctc acttcctttg   9000
gactgtccaa taagatcaat agcaaacacc taagagtaaa ccaaaacttg gtttatgaat   9060
ctggctccct caacttttct aaacttgaaa ttcaatcaca agtcgattcc cagcatgtgg   9120
gccacagtgt tctaactgct aaaggcatgg cactgtttgg agaagggaag gcagagttta   9180
ctgggaggca tgatgctcat ttaaatggaa aggttattgg aactttgaaa aattctcttt   9240
tcttttcagc ccagccattt gagatcacgg catccacaaa caatgaaggg aatttgaaag   9300
ttcgttttcc attaaggtta acagggaaga tagacttcct gaataactat gcactgtttc   9360
tgagtcccag tgcccagcaa gcaagttggc aagtaagtgc taggttcaat cagtataagt   9420
acaaccaaaa tttctctgct ggaaacaacg agaacattat ggaggcccat gtaggaataa   9480
atggagaagc aaatctggat ttcttaaaca ttcctttaac aattcctgaa atgcgtctac   9540
cttacacaat aatcacaact cctccactga aagatttctc tctatgggaa aaaacaggct   9600
tgaaggaatt cttgaaaacg acaaagcaat catttgattt aagtgtaaaa gctcagtata   9660
agaaaaacaa acacaggcat tccatcacaa atcctttggc tgtgctttgt gagtttatca   9720
gtcagagcat caaatccttt gacaggcatt ttgaaaaaaa cagaaacaat gcattagatt   9780
ttgtcaccaa atcctataat gaaacaaaaa ttaagtttga taagtacaaa gctgaaaaat   9840
ctcacgacga gctccccagg acctttcaaa ttcctggata cactgttcca gttgtcaatg   9900
ttgaagtgtc tccattcacc atagagatgt cggcattcgg ctatgtgttc ccaaaagcag   9960
tcagcatgcc tagtttctcc atcctaggtt ctgacgtccg tgtgccttca tacacattaa  10020
tcctgccatc attagagctg ccagtccttc atgtccctag aaatctcaag ctttctcttc  10080
cacatttcaa ggaattgtgt accataagcc atatttttat tcctgccatg ggcaatatta  10140
cctatgattt ctcctttaaa tcaagtgtca tcacactgaa taccaatgct gaacttttta  10200
accagtcaga tattgttgct catctccttt cttcatcttc atctgtcatt gatgcactgc  10260
agtacaaatt agagggcacc acaagattga caagaaaaag ggattgaag ttagccacag  10320
ctctgtctct gagcaacaaa tttgtggagg gtagtcataa cagtactgtg agcttaacca  10380
cgaaaaatat ggaagtgtca gtggcaaaaa ccacaaaagc cgaaattcca attttgagaa  10440
tgaatttcaa gcaagaactt aatggaaata ccaagtcaaa acctactgtc tcttcctcca  10500
tggaatttaa gtatgatttc aattcttcaa tgctgtactc taccgctaaa ggagcagttg  10560
accacaagct tagcttggaa agcctcacct cttacttttc cattgagtca tctaccaaag  10620
gagatgtcaa gggttcggtt ctttctcggg aatattcagg aactattgct agtgaggcca  10680
acacttactt gaattccaag agcacacggt cttcagtgaa gctgcagggc acttccaaaa  10740
ttgatgatat ctggaacctt gaagtaaaag aaaattttgc tggagaagcc acactccaac  10800
gcatatattc cctctgggag cacagtacga aaaaccactt acagctagag ggcctctttt  10860
tcaccaacgg agaacataca agcaaagcca ccctggaact ctctccatgg caaatgtcag  10920
ctcttgttca ggtccatgca agtcagccca gttccttcca tgatttccct gaccttggcc  10980
aggaagtggc cctgaatgct aacactaaga accagaagat cagatggaaa aatgaagtcc  11040
ggattcattc tgggtctttc cagagccagg tcgagctttc caatgaccaa gaaaaggcac  11100
accttgacat tgcaggatcc ttagaaggac acctaaggtt cctcaaaaat atcatcctac  11160
cagtctatga caagagctta tgggatttcc taaagctgga tgtaaccacc agcattggta  11220
```

-continued

```
ggagacagca tcttcgtgtt tcaactgcct ttgtgtacac caaaaacccc aatggctatt  11280
cattctccat ccctgtaaaa gttttggctg ataaattcat tactcctggg ctgaaactaa  11340
atgatctaaa ttcagttctt gtcatgccta cgttccatgt cccatttaca gatcttcagg  11400
ttccatcgtg caaacttgac ttcagagaaa tacaaatcta taagaagctg agaacttcat  11460
catttgccct caacctacca acactccccg aggtaaaatt ccctgaagtt gatgtgttaa  11520
caaaatattc tcaaccagaa gactccttga ttcccttttt tgagataacc gtgcctgaat  11580
ctcagttaac tgtgtcccag ttcacgcttc caaaaagtgt ttcagatggc attgctgctt  11640
tggatctaaa tgcagtagcc aacaagatcg cagactttga gttgcccacc atcatcgtgc  11700
ctgagcagac cattgagatt ccctccatta agttctctgt acctgctgga attgtcattc  11760
cttcctttca agcactgact gcacgctttg aggtagactc tcccgtgtat aatgccactt  11820
ggagtgccag tttgaaaaac aaagcagatt atgttgaaac agtcctggat tccacatgca  11880
gctcaaccgt acagttccta gaatatgaac taaatgtttt gggaacacac aaaatcgaag  11940
atggtacgtt agcctctaag actaaaggaa cacttgcaca ccgtgacttc agtgcagaat  12000
atgaagaaga tggcaaattt gaaggacttc aggaatggga aggaaaagcg cacctcaata  12060
tcaaaagccc agcgttcacc gatctccatc tgcgctacca gaaagacaag aaaggcatct  12120
ccacctcagc agcctcccca gccgtaggca ccgtgggcat ggatatggat gaagatgacg  12180
acttttctaa atggaacttc tactacagcc ctcagtcctc tccagataaa aaactcacca  12240
tattcaaaac tgagttgagg gtccgggaat ctgatgagga aactcagatc aaagttaatt  12300
gggaagaaga ggcagcttct ggcttgctaa cctctctgaa agacaacgtg cccaaggcca  12360
caggggtcct ttatgattat gtcaacaagt accactggga acacacaggg ctcaccctga  12420
gagaagtgtc ttcaaagctg agaagaaatc tgcagaacaa tgctgagtgg gtttatcaag  12480
gggccattag gcaaattgat gatatcgacg tgaggttcca gaaagcagcc agtggcacca  12540
ctgggaccta ccaagagtgg aaggacaagg cccagaatct gtaccaggaa ctgttgactc  12600
aggaaggcca agccagtttc cagggactca aggataacgt gtttgatggc ttggtacgag  12660
ttactcaaaa attccatatg aaagtcaagc atctgattga ctcactcatt gattttctga  12720
acttccccag attccagttt ccggggaaac ctgggatata cactagggag gaactttgca  12780
ctatgttcat aagggaggta gggacggtac tgtcccaggt atattcgaaa gtccataatg  12840
gttcagaaat actgttttcc tatttccaag acctagtgat tacacttcct ttcgagttaa  12900
ggaaacataa actaatagat gtaatctcga tgtataggga actgttgaaa gatttatcaa  12960
aagaagccca agaggtattt aaagccattc agtctctcaa gaccacagag gtgctacgta  13020
atcttcagga ccttttacaa ttcattttcc aactaataga agataacatt aaacagctga  13080
aagagatgaa atttacttat cttattaatt atatccaaga tgagatcaac acaatcttca  13140
atgattatat cccatatgtt tttaaattgt tgaaagaaaa cctatgcctt aatcttcata  13200
agttcaatga atttattcaa aacgagcttc aggaagcttc tcaagagtta cagcagatcc  13260
atcaatacat tatggccctt cgtgaagaat attttgatcc aagtatagtt ggctggacag  13320
tgaaatatta tgaacttgaa gaaaagatag tcagtctgat caagaacctg ttagttgctc  13380
ttaaggactt ccattctgaa tatattgtca gtgcctctaa ctttacttcc caactctcaa  13440
gtcaagttga gcaatttctg cacagaaata ttcaggaata tcttagcatc cttaccgatc  13500
cagatggaaa agggaaagag aagattgcag agctttctgc cactgctcag gaaataatta  13560
```

-continued

```
aaagccaggc cattgcgacg aagaaaataa tttctgatta ccaccagcag tttagatata  13620

aactgcaaga tttttcagac caactctctg attactatga aaaatttatt gctgaatcca  13680

aaagattgat tgacctgtcc attcaaaact accacacatt tctgatatac atcacggagt  13740

tactgaaaaa gctgcaatca accacagtca tgaaccccta catgaagctt gctccaggag  13800

aacttactat catcctctaa ttttttaaaa gaaatcttca tttattcttc ttttccaatt  13860

gaactttcac atagcacaga aaaaattcaa actgcctata ttgataaaac catacagtga  13920

gccagccttg cagtaggcag tagactataa gcagaagcac atatgaactg gacctgcacc  13980

aaagctggca ccagggctcg gaaggtctct gaactcagaa ggatggcatt ttttgcaagt  14040

taaagaaaat caggatctga gttattttgc taaacttggg ggaggaggaa caaataaatg  14100

gagtctttat tgtgtatcat a                                            14121
```

<210> SEQ ID NO 99
<211> LENGTH: 1890
<212> TYPE: DNA
<213> ORGANISM: Homo sapiens

<400> SEQUENCE: 99

```
atctgaagcc agtaaacatg gccgtcaccg acagcctcag ccgggctgcg actgtcttgg    60

caactgtgtt gctcttgtcc ttcggcagcg tggccgctag tcatatcgag gatcaagcag   120

aacaattctt tagaagtggc catacaaaca actgggctgt tctggtgtgt acatcccgat   180

tctggtttaa ttatcgacat gttgcaaata ccctttctgt ttatagaagt gtcaagaggc   240

taggtattcc tgacagtcac attgtcctaa tgcttgcaga tgatatggcc tgtaatccta   300

gaaatcccaa accagctaca gtgtttagtc acaagaatat ggaactaaat gtgtatggag   360

atgatgtgga agtggattat agaagttatg aggtaactgt ggagaatttt ttacgggtat   420

taactgggag gatcccacct agtactcctc ggtcaaaacg tcttctttct gatgacagaa   480

gcaatattct aatttatatg acagggcatg gtggaaatgg tttcttaaaa tttcaagatt   540

ctgaagaaat taccaacata gaactcgcgg atgcttttga acaaatgtgg cagaaaagac   600

gctacaatga gctactgttt attattgata cttgccaagg agcatccatg tatgaacgat   660

tttattctcc taacataatg gctctagcta gtagtcaagt gggagaagat tcactctcgc   720

atcaacctga tcctgcaatt ggagtccatc ttatggatag atacacattt tatgtcttgg   780

aatttttgga agaaattaac ccagctagcc aaactaatat gaatgacctt tttcaggtat   840

gtcccaaaag tctgtgtgtg tctactcctg gacatcgcac tgatcttttt cagagggatc   900

ctaaaaatgt actgataact gatttctttg gaagtgtacg gaaagtggaa attacaacag   960

agactattaa attgcaacag gattcagaaa tcatggaaag cagctataag gaagaccaga  1020

tggatgagaa actaatggaa cctctgaaat atgctgaaca acttcctgta gctcagataa  1080

tacaccagaa accgaagctg aaagactggc atcctcctgg gggctttatt ctgggattat  1140

gggcacttat tatcatggtt ttcttcaaaa cttatggaat taagcatatg aagttcattt  1200

tttagacttg atgatgaatg aagaatgcat ggaggactgc aaacttggat aataatttat  1260

gtcattatat atttttaaaa atgtgtttct cttgtatgaa ttggaaataa gtataaggaa  1320

actaaatttg aatcaactat taattttata acttaaagaa aaataattgt taatgcaact  1380

gcttaatggc actaaatata ttccagtttt gtattttgtg tattataaaa gcgaatgaga  1440

cagagatcag aatacattga ctgtttttga aaatagtaat ttccccttat ccccttttca  1500

tttggaaaag aaacaattgt gaagacatta aattctcact aacagaagta actttggtta  1560
```

-continued

```
attatttttt gtatatcctc ccaatctttt gacttatgca catatttttt cccaatatgg   1620

agatcatatg gaatgtacta ttttgtaatg tcttttttca ttttacaatg tattatcaac   1680

cttttccctc tcaaaaatac attgtgaatg actgcatagt attcacttta tgaatattta   1740

attcatttca cagtcttcta ttgttggacc acttacattg taccaaatgt tttcctttgg   1800

tttattcttt aatgtattaa tattttactg ctggtcactc atggaatcct gcagctttaa   1860

ttaaaagcaa agatgaaaaa aaaaaaaaaa                                     1890
```

```
<210> SEQ ID NO 100
<211> LENGTH: 1976
<212> TYPE: DNA
<213> ORGANISM: Homo sapiens

<400> SEQUENCE: 100

ggtaccagag gtggcagtgc tgccgacttc gcgtttgcct tgctggatga ttccgcttgt     60

ttgccggctg cgtgagtgct tagagctttt cggtggaaga tgccggacag taacttcgca    120

gagcgcagcg aggagcaggt gtctggtgct aaagtcatcg ctcaggccct gaaaacgcaa    180

gatgtggagt acatatttgg catcgtaggc atcccagtga ccgaaatcgc cattgctgcc    240

cagcagctag gcatcaagta catcgggatg aggaatgagc aagcggcttg ttatgctgcc    300

tccgcgattg gatatctgac aagcaggcca ggagtctgcc ttgttgtttc tggcccaggt    360

ctcatccatg ccttgggcgg tatggcaaat gcaaacatga actgctggcc cttgcttgtg    420

attggtggtt cctctgaaag aaaccaagaa acaatgggag ctttccagga gtttcctcag    480

gttgaagctt gtagattata taccaagttc tctgcccgcy caagcagcat agaagctatt    540

ccttttgtta ttgaaaaggc agtgagaagc agtatctatg gtcgtccagg tgcttgctat    600

gttgacatac cagcagattt tgtgaacctt caggtgaatg tgaattctat aaagtacatg    660

gaacgctgca tgtcacctcc tattagcatg gcagaaacct ctgctgtgtg cacggcggct    720

tctgttatta ggaatgccaa acaacccctt cttatcatcg ggaaaggtgc tgcttacgct    780

catgcagaag agagtatcaa gaaattggtg gagcaatata aactgccatt tttgcccacc    840

cctatgggaa agggtgttgt ccctgacaac catccatact gtgtaggtgc agccagatcc    900

agggctttgc aatttgctga tgtaattgtg ttatttggtg ccagactaaa ttggatttta    960

cattttggac tgcctccaag atatcagcca gatgtgaagt ttatccaggt tgatatctgt   1020

gcagaagaat tggggaataa tgtaaagccc gctgttactt tgctaggaaa catacatgct   1080

gtcactaagc agcttttaga ggaacttgat aaaacaccat ggcagtatcc tccagagagc   1140

aagtggtgga aaactctgag agaaaaaatg aagagcaatg aagctgcatc caaggaacta   1200

gcttctaaaa aatccctgcc tatgaattat tacacagtat tctaccatgt tcaagaacaa   1260

ctacctagag actgtttcgt ggtaagtgaa ggagcaaata ctatggacat tggacggact   1320

gtgcttcaga actaccttcc tcgtcacagg cttgatgctg gtactttcgg aacaatggga   1380

gttggtttgg gatttgctat tgcagctgcc gtggtggcta aagatagaag ccctgggcat   1440

tggatcatct gtgtggaagg agacagtgca tttgggtttt ctggcatgga ggtagaaacc   1500

atctgcaggt acaacttgcc aatcatactg ttggtagtga ataacaatgg aatttaccaa   1560

ggttttgata cagatacttg gaaagaaatg ttaaaatttc aagatgctac tgcagtggtc   1620

cctccaatgt gtttgctgcc aaattcacat tatgagcaag tcatgactgc atttggaggc   1680

aaagggtatt ttgtacaaac accagaagaa ctccaaaaat ccctggagca gagcctagca   1740
```

-continued

```
gacacaacta aaccttctct tatcaacatc atgattgagc cacaagccac acggaaggcc   1800

caggattttc attggctgac ccgctctaat atgtaaataa agacgccagt tggtggtctt   1860

gagttttctc tttcttgcaa gatgaaattt tattttccac agcaaaatta ctctactgtt   1920

aaaattgtgc aaaataaaat aaacatttaa aatgacattt tacagtaaaa aaaaaa       1976
```

<210> SEQ ID NO 101
<211> LENGTH: 1019
<212> TYPE: DNA
<213> ORGANISM: Homo sapiens

<400> SEQUENCE: 101

```
acggcgcccg ccgcccgccc ggagcccgcg agcaacccca gtccccccca cccgcgcgtg     60

gcggcgccgg ctccctagcc accgcggccc caccctcttc cggcctcagc tgtccgggct    120

gctttcgcct ccgcctgtgg atgctgcgcc tctccgaacg caacatgaag gtgctccttg    180

ccgccgccct catcgcgggg tccgtcttct tcctgctgct gccgggacct tctgcggccg    240

atgagaagaa gaaggggccc aaagtcaccg tcaaggtgta ttttgaccta cgaattggag    300

atgaagatgt aggccgggtg atctttggtc tcttcggaaa gactgttcca aaaacagtgg    360

ataattttgt ggccttagct acaggagaga aaggatttgg ctacaaaaac agcaaattcc    420

atcgtgtaat caaggacttc atgatccagg gcggagactt caccagggga gatggcacag    480

gaggaaagag catctacggt gagcgcttcc ccgatgagaa cttcaaactg aagcactacg    540

ggcctggctg ggtgagcatg gccaacgcag gcaaagacac caacggctcc cagttcttca    600

tcacgacagt caagacagcc tggctagatg gcaagcatgt ggtgtttggc aaagttctag    660

agggcatgga ggtggtgcgg aaggtggaga gcaccaagac agacagccgg gataaacccc    720

tgaaggatgt gatcatcgca gactgcggca agatcgaggt ggagaagccc tttgccatcg    780

ccaaggagta gggcacaggg acatctttct ttgagtgacc gtctgtgcag gccctgtagt    840

ccgccacagg gctttgagct gcactggccc cggtgctggc atctggtgga gcggacccac    900

tcccctcaca ttccacaggc ccatggactc acttttgtaa caaactccta ccaaccctga    960

ccaataaaaa aaaatgtggg tttttttttt tttttaataa aaaaaaaaaa aaaaaaaaa    1019
```

<210> SEQ ID NO 102
<211> LENGTH: 1541
<212> TYPE: DNA
<213> ORGANISM: Homo sapiens

<400> SEQUENCE: 102

```
cgcgcgagcg gcgccagctc ggggcagcgg aacccagaga agctgagggg gcggtagcgg     60

cggcgacggc gacgacgacg actcccgcgc gtgtgcccag cctcttcccg ccgcagccgc    120

ccttttcctc cctcccttac gtccccgagt gcggcagtac cgcctccttc ccagccgcgc    180

ggcttcctcc agacctctcg gcgcgggtga gccctattcc cagaggcagg tggtgctgac    240

cctgtaaccc aaaggaggaa acagctggct aagctcatca ttgttactgg tgggcaccat    300

gtccttgaag cttcaggcaa gcaatgtaac caacaagaat gaccccaagt ccatcaactc    360

tcgagtcttc attggaaacc tcaacacagc tctggtgaag aaatcagatg tggagaccat    420

cttctctaag tatggccgtg tggccggctg ttctgtgcac aagggctatg cctttgttca    480

gtactccaat gagcgccatg cccgggcagc tgtgctggga gagaatgggc gggtgctggc    540

cgggcagacc ctggacatca acatggctgg agagcctaag cctgacagac ccaaggggct    600

aaagagagca gcatctgcca tatacaggct cttcgactac cggggccgtc tgtcgcccgt    660
```

-continued

```
gccagtgccc agggcggtcc ctgtgaagcg accccgggtc acagtccctt tggtccggcg    720

tgtcaaaact aacgtacctg tcaagctctt tgcccgctcc acagctgtca ccaccagctc    780

agccaagatc aagttaaaga gcagtgagct gcaggccatc aagacggagc tgacacagat    840

caagtccaat atcgatgccc tgctgagccg cttggagcag atcgctgcgg agcaaaaggc    900

caatccagat ggcaagaaga agggtgatgg aggtggcgcc ggcggcggcg gcggtggtgg    960

tggcagcggt ggcggtggca gtggtggtgg cggtggcggt ggcagcagcc ggccaccagc   1020

cccccaagag aacacaactt ctgaggcagg cctgccccag gggaagcac ggacccgaga   1080

cgacggcgat gaggaagggc tcctgacaca cagcgaggaa gagctggaac acagccagga   1140

cacagacgcg gatgatgggg ccttgcagta agcagcctga caggagcaat ggccaccagc   1200

aggtgaaggg catcgctgcc ccaggcctca agccgggcac ccaaccctgg atgccacccc   1260

ccagcgggta ccagaggaaa gctggcagca ggcgcctcct cccccaacgc atcccagcca   1320

gtgccatgtc ctctgcaggt ggagttactg gcctactcct tccccatgag ccctccctgt   1380

ctgcactgcc caggccagag ggtagagcac aggggtttcc ccatactacc tcccctcccc   1440

aggacactcc caggcttggg ttttttctat aggtttggcg gggggccaca gggaggggac   1500

cctgacaata aagagattgg atcccaaaaa aaaaaaaaaa a                       1541
```

```
<210> SEQ ID NO 103
<211> LENGTH: 2834
<212> TYPE: DNA
<213> ORGANISM: Homo sapiens

<400> SEQUENCE: 103

gcccactccc accgccagct ggaaccctgg ggactacgac gtccctcaaa ccttgcttct     60

aggagataaa aagaacatcc agtcatggat aaaaatgagc tggttcagaa ggccaaactg    120

gccgagcagg ctgagcgata tgatgacatg gcagcctgca tgaagtctgt aactgagcaa    180

ggagctgaat tatccaatga ggagaggaat cttctctcag ttgcttataa aaatgttgta    240

ggagcccgta ggtcatcttg gagggtcgtc tcaagtattg aacaaaagac ggaaggtgct    300

gagaaaaaac agcagatggc tcgagaatac agagagaaaa ttgagacgga gctaagagat    360

atctgcaatg atgtactgtc tcttttggaa aagttcttga tccccaatgc ttcacaagca    420

gagagcaaag tcttctattt gaaaatgaaa ggagattact accgttactt ggctgaggtt    480

gccgctggtg atgacaagaa agggattgtc gatcagtcac aacaagcata ccaagaagct    540

tttgaaatca gcaaaaagga aatgcaacca acacatccta tcagactggg tctggccctt    600

aacttctctg tgttctatta tgagattctg aactccccag agaaagcctg ctctcttgca    660

aagacagctt ttgatgaagc cattgctgaa cttgatacat taagtgaaga gtcatacaaa    720

gacagcacgc taataatgca attactgaga gacaacttga cattgtggac atcggatacc    780

caaggagacg aagctgaagc aggagaagga ggggaaaatt aaccggcctt ccaacttttg    840

tctgcctcat tctaaaattt acacagtaga ccatttgtca tccatgctgt cccacaaata    900

gtttttttgtt tacgatttat gacaggttta tgttacttct atttgaattt ctatatttcc    960

catgtggttt ttatgtttaa tattagggga gtagagccag ttaacattta gggagttatc   1020

tgttttcatc ttgaggtggc caatatgggg atgtggaatt tttatacaag ttataagtgt   1080

ttggcatagt acttttggta cattgtggct tcaaaagggc cagtgtaaaa ctgcttccat   1140

gtctaagcaa agaaaactgc ctacatactg gtttgtcctg gcggggaata aaagggatca   1200
```

-continued

```
ttggttccag tcacaggtgt agtaattgtg ggtactttaa ggtttggagc acttacaagg   1260

ctgtggtaga atcatacccc atggatacca catattaaac catgtatatc tgtggaatac   1320

tcaatgtgta cacctttgac tacagctgca gaagtgttcc tttagacaaa gttgtgaccc   1380

attttactct ggataagggc agaaacggtt cacattccat tatttgtaaa gttacctgct   1440

gttagctttc attattttg ctacactcat tttatttgta tttaaatgtt ttaggcaacc   1500

taagaacaaa tgtaaaagta aagatgcagg aaaaatgaat tgcttggtat tcattacttc   1560

atgtatatca agcacagcag taaaacaaaa acccatgtat ttaacttttt tttaggattt   1620

ttgcttttgt gatttttttt ttttttttt gatacttgcc taacatgcat gtgctgtaaa   1680

aatagttaac agggaaataa cttgagatga tggctagctt tgtttaatgt cttatgaaat   1740

tttcatgaac aatccaagca taattgttaa gaacacgtgt attaaattca tgtaagtgga   1800

ataaaagttt tatgaatgga cttttcaact actttctcta cagcttttca tgtaaattag   1860

tcttggttct gaaacttctc taaaggaaat tgtacatttt ttgaaattta ttccttattc   1920

cctcttggca gctaatgggc tcttaccaag tttaaacaca aaatttatca taacaaaaat   1980

actactaata taactactgt ttccatgtcc catgatcccc tctcttcctc cccaccctga   2040

aaaaaatgag ttcctatttt ttctgggaga ggggggggatt gattagaaaa aaatgtagtg   2100

tgttccattt aaaattttgg catatggcat tttctaactt aggaagccac aatgttcttg   2160

gcccatcatg acattgggta gcattaactg taagttttgt gcttccaaat cactttttgg   2220

tttttaagaa tttcttgata ctcttatagc ctgccttcaa ttttgatcct ttattctttc   2280

tatttgtcag gtgcacaaga ttaccttcct gttttagcct tctgtcttgt caccaaccat   2340

tcttacttgg tggccatgta cttggaaaaa ggccgcatga tctttctggc tccactcagt   2400

gtctaaggca ccctgcttcc tttgcttgca tcccacagac tatttccctc atcctattta   2460

ctgcagcaaa tctctcctta gttgatgaga ctgtgtttat ctccctttaa aaccctacct   2520

atcctgaatg gtctgtcatt gtctgccttt aaaatccttc ctctttcttc ctcctctatt   2580

ctctaaataa tgatggggct aagttatacc caaagctcac tttacaaaat atttcctcag   2640

tactttgcag aaaacaccaa acaaaaatgc cattttaaaa aaggtgtatt ttttctttta   2700

gaatgtaagc tcctcaagag cagggacaat gttttctgta tgttctattg tgcctagtac   2760

actgtaaatg ctcaataaat attgatgatg ggaggcagtg agtcttgatg ataagggtga   2820

gaaactgaaa tccc                                                      2834
```

<210> SEQ ID NO 104
<211> LENGTH: 1637
<212> TYPE: DNA
<213> ORGANISM: Homo sapiens

<400> SEQUENCE: 104

```
ggcaagacgc ctcttcagtt gtctgctact cagaggaagg ggcggttggt gcggcctcca     60

ttgttcgtgt tttaaggcgc catgaggggt gacagaggcc gtggtcgtgg tgggcgcttt    120

ggttccagag gaggcccagg aggagggttc aggccccttg taccacatat cccatttgac    180

ttctatttgt gtgaaatggc ctttccccgg gtcaagccag cacctgatga aacttccttc    240

agtgaggcct tgctgaagag gaatcaggac ctggctccca attctgctga acaggcatct    300

atcctttctc tggtgacaaa aataaacaat gtgattgata atctgattgt ggctccaggg    360

acatttgaag tgcaaattga agaagttcga caggtgggat cctataaaaa ggggacaatg    420

actacaggac acaatgtggc tgacctggtg gtgatactca agattctgcc aacgttggaa    480
```

```
gctgttgctg ccctggggaa caaagtcgtg gaaagcctaa gagcacagga tccttctgaa    540

gttttaacca tgctgaccaa cgaaactggc tttgaaatca gttcttctga tgctacagtg    600

aagattctca ttacaacagt gccacccaat cttcgaaaac tggatccaga actccatttg    660

gatatcaaag tattgcagag tgccttagca gccatccgac atgcccgctg gttcgaggaa    720

aatgcttctc agtccacagt taaagttctc atcagactac tgaaggactt gaggattcgt    780

tttcctggct ttgagcccct cacaccctgg atccttgacc tactaggcca ttatgctgtg    840

atgaacaacc ccaccagaca gcctttggcc ctaaacgttg catacaggcg ctgcttgcag    900

attctggctg caggactgtt cctgccaggt tcagtgggta tcactgaccc ctgtgagagt    960

ggcaacttta gagtacacac agtcatgacc ctagaacagc aggacatggt ctgctataca   1020

gctcagactc tcgtccgaat cctctcacat ggtggcttta ggaagatcct tggccaggag   1080

ggtgatgcca gctatcttgc ttctgaaata tctacctggg atggagtgat agtaacacct   1140

tcagaaaagg cttatgagaa gccaccagag aagaaggaag gagaggaaga agaggagaat   1200

acagaagaac cacctcaagg agaggaagaa gaaagcatgg aaactcagga gtgacattcc   1260

cttcactcct tttcctaccc aagggggaag actggagcct aagctgcctg ctactgggct   1320

ttacatggtg acagacattt ccgtgggata gggaagatag caggaagaaa agtaaactcc   1380

atagaagtgt cattccactg ggttttgata ttggcttagc tgccagtctc ccatttgtga   1440

cctatgccat ccatctataa tggaggatac caacatttct tcctaatatt ctataatctc   1500

caactcctga aaccccctct ctcaactaat actttgctgt tgaaatgttg tgaaatgtta   1560

agtgtctgga aatttttttt tctaagaaaa actattaaag tacttcctag taaaaaaaaa   1620

aaaaaaaaaa aaaaaaa                                                  1637
```

<210> SEQ ID NO 105
<211> LENGTH: 1591
<212> TYPE: DNA
<213> ORGANISM: Homo sapiens

<400> SEQUENCE: 105

```
tagaatcggg ggtttcagct cactgctcct tttctttttt ttctttctct cccccgccca     60

ccccccccaaa aataattgat ttgctttaca atcatccaca ctgtgttttg tggatcttta   120

attatatata acaatagtag tcattttaaa tatatattct gaaatctttg caaattttaa   180

cagaagagtc gaagctctgc gagacccaat atttgccaat aagaatggtt atgataatta   240

gcaccatgga gcctcaggtg tcaaatggtc cgacatccaa tacaagcaat ggaccctcca   300

gcaacaacag aaactgtcct tctcccatgc aaacaggggc aaccacagat gacagcaaaa   360

ccaacctcat cgtcaactat ttaccccaga atatgaccca agaagaattc aggagtctct   420

tcgggagcat tggtgaaata gaatcctgca aacttgtgag agacaaaatt acaggacaga   480

gtttagggta tggatttgtt aactatattg atccaaagga tgcagagaaa gccatcaaca   540

ctttaaatgg actcagactc cagaccaaaa ccataaaggt ctcatatgcc cgtccgagct   600

ctgcctcaat cagggatgct aacctctatg ttagcggcct tcccaaaacc atgacccaga   660

aggaactgga gcaacttttc tcgcaatacg gccgtatcat cacctcacga atcctggttg   720

atcaagtcac aggagtgtcc agaggggtgg gattcatccg ctttgataag aggattgagg   780

cagaagaagc catcaaaggg ctgaatggcc agaagcccag cggtgctacg gaaccgatta   840

ctgtgaagtt tgccaacaac cccagccaga agtccagcca ggccctgctc tcccagctct   900
```

-continued

```
accagtcccc taaccggcgc tacccaggtc cacttcacca ccaggctcag aggttcaggc     960

tggacaattt gcttaatatg gcctatggcg taaagagact gatgtctgga ccagtccccc    1020

cttctgcttg ttcccccagg ttctccccaa ttaccattga tggaatgaca agccttgtgg    1080

gaatgaacat ccctggtcac acaggaactg ggtggtgcat ctttgtctac aacctgtccc    1140

ccgattccga tgagagtgtc ctctggcagc tctttggccc ctttggagca gtgaacaacg    1200

taaaggtgat tcgtgacttc aacaccaaca agtgcaaggg attcggcttt gtcaccatga    1260

ccaactatga tgaggcggcc atggccatcg ccagcctcaa cgggtaccgc ctgggagaca    1320

gagtgttgca agtttccttt aaaaccaaca aagcccacaa gtcctgaatt tcccattctt    1380

acttactaaa atatatatag aaatatatac gaacaaaaca cacgcgcgca cacacacaca    1440

tacacgaaag agagagaaac aaacttttca aggcttatat tcaaccatgg actttataag    1500

ccagtgttgc ctaagtatta aaacattgga ttatcctgag gtgtaccagg aaaggatttt    1560

ataatgctta gaaaaaaaaa aaaaaaaaaa a                                   1591
```

```
<210> SEQ ID NO 106
<211> LENGTH: 1923
<212> TYPE: DNA
<213> ORGANISM: Homo sapiens

<400> SEQUENCE: 106

gactgtctac attagtaatt cccaacttgg gtccgaaagt gaacttttgc tgaagcgaag      60

tagctaaccg cttccatgtg caaggcaggt tccagacttc ggggtgagga ggattaactg     120

aaggacccca ggggaaccgg tgtgctcact gatccgcctc cagggccacc gccatgtcga     180

gccgcggtgg gaagaagaag tccaccaaga cgtccaggtc tgccaaagca ggagtcatct     240

ttcccgtggg gcggatgctg cggtacatca agaaaggcca ccccaagtac aggattggag     300

tgggggcacc cgtgtacatg gccgccgtcc tggaatacct gacagcggag attctggagc     360

tggctggcaa tgcagcgaga gacaacaaga agggacgggt cacaccccgg cacatcctgc     420

tggctgtggc caatgatgaa gagctgaatc agctgctaaa aggagtcacc atagccagtg     480

ggggtgtgtt acccaacatc caccccgagt tgctagcgaa gaagcgggga tccaaaggaa     540

agttggaagc catcatcaca ccacccccag ccaaaaaggc caagtctcca tcccagaaga     600

agcctgtatc taaaaaagca ggaggcaaga aaggggcccg gaaatccaag aagcagggtg     660

aagtcagtaa ggcagccagc gccgacagca caaccgaggg cacacctgcc gacggcttca     720

cagtcctctc caccaagagc ctcttccttg gccagaagct gaaccttatt cacagtgaaa     780

tcagtaattt agccggcttt gaggtggagg ccataatcaa tcctaccaat gctgacattg     840

accttaaaga tgacctagga aacacgctgg agaagaaagg tggcaaggag tttgtggaag     900

ctgtcctgga actccggaaa aagaacgggc ccttggaagt agctggagct gctgtcagcg     960

caggccatgg cctgcctgcc aagtttgtga tccactgtaa tagtccagtt tggggtgcag    1020

acaagtgtga agaacttctg gaaaagacag tgaaaaactg cttggccctg gctgatgata    1080

agaagctgaa atccattgca tttccatcca tcggcagcgg caggaacggt tttccaaagc    1140

agacagcagc tcagctgatt ctgaaggcca tctccagtta cttcgtgtct acaatgtcct    1200

cttccatcaa aacggtgtac ttcgtgcttt ttgacagcga gagtataggc atctatgtgc    1260

aggaaatggc caagctggac gccaactagg ctgagcaatg acagaaccag ctgcaccatg    1320

taccccacct tcagtttaaa agaaaaaaaa aatccccttc actcctactg ggaggtggga    1380

ccccttcat tttcagtttt gctcatctag ggaaaataag gctttggttt ccagtttaat    1440
```

```
tgtttttgac cttctaaaat gtttttatgt tagcactgat agttggcatt actgttgtta   1500

agcactgtgt tccagaccgt gtctgactta gtgtaaccta ggagatttta tagttttatt   1560

ttaatgaaac cctgattgac gcacagcagt ggggagaaca gcgtctttta cctgtcaccg   1620

aagccaggaa gccccgtttg taagcgtgtg ttgtggtgct ttattgtaca tcctccagtg   1680

gcgttctttt tactctaatg ttcttttggt ttccccctc agaagaatca tgaatttgca    1740

acagacctaa tttttggtta ctttttgtct tattgatgga tttgaaaatg aaagatttaa   1800

taaggcaaag cagaatctgt tgtccttaat tatatttgca atttggaatt tgtgtgagtt   1860

gatttagtaa aatgttaaac cgttaaaaaa aaaaaaaaaa aaaaaaaaaa aaaaaaaaaa   1920

aaa                                                                 1923
```

<210> SEQ ID NO 107
<211> LENGTH: 799
<212> TYPE: DNA
<213> ORGANISM: Homo sapiens

<400> SEQUENCE: 107

```
cactcccaaa gaactgggta ctcaacactg agcagatctg ttctttgagc taaaaaccat     60

gtgctgtacc aagagtttgc tcctggctgc tttgatgtca gtgctgctac tccacctctg    120

cggcgaatca gaagcagcaa gcaactttga ctgctgtctt ggatacacag accgtattct    180

tcatcctaaa tttattgtgg gcttcacacg gcagctggcc aatgaaggct gtgacatcaa    240

tgctatcatc tttcacacaa agaaaaagtt gtctgtgtgc gcaaatccaa aacagacttg    300

ggtgaaatat attgtgcgtc tcctcagtaa aaaagtcaag aacatgtaaa aactgtggct    360

tttctggaat ggaattggac atagcccaag aacagaaaga accttgctgg ggttggaggt    420

ttcacttgca catcatggag ggtttagtgc ttatctaatt tgtgcctcac tggacttgtc    480

caattaatga agttgattca tattgcatca tagtttgctt tgtttaagca tcacattaaa    540

gttaaactgt attttatgtt atttatagct gtaggttttc tgtgtttagc tatttaatac    600

taattttcca taagctattt tggtttagtg caaagtataa aattatattt ggggggggaat    660

aagattatat ggactttctt gcaagcaaca agctattttt taaaaaaact atttaacatt    720

cttttgttta tattgttttg tctcctaaat tgttgtaatt gcattataaa ataagaaaaa    780

cattaataag acaaatatt                                                 799
```

<210> SEQ ID NO 108
<211> LENGTH: 1023
<212> TYPE: DNA
<213> ORGANISM: Homo sapiens

<400> SEQUENCE: 108

```
gttggctgcc ggtgagttgg gtgccggtgg agtcgtgttg gtcctcagaa tccccgcgta     60

gccgctgcct cctcctaccc tcgccatgtt tcttacccgg tctgagtacg acaggggcgt    120

gaatactttt tctcccgaag gaagattatt tcaagtggaa tatgccattg aggctatcaa    180

gcttggttct acagccattg ggatccagac atcagagggt gtgtgcctag ctgtggagaa    240

gagaattact tccccactga tggagcccag cagcattgag aaaattgtag agattgatgc    300

tcacataggt tgtgccatga gtgggctaat tgctgatgct aagactttaa ttgataaagc    360

cagagtggag acacagaacc actggttcac ctacaatgag acaatgacag tggagagtgt    420

gacccaagct gtgtccaatc tggctttgca gtttggagaa gaagatgcag atccaggtgc    480
```

-continued

```
catgtctcgt ccctttggag tagcattatt atttggagga gttgatgaga aaggacccca    540

gctgtttcat atggacccat ctgggacctt tgtacagtgt gatgctcgag caattggctc    600

tgcttcagag ggtgcccaga gctccttgca agaagtttac cacaagtcta tgactttgaa    660

agaagccatc aagtcttcac tcatcatcct caaacaagta atggaggaga agctgaatgc    720

aacaaacatt gagctagcca cagtgcagcc tggccagaat ttccacatgt tcacaaagga    780

agaacttgaa gaggttatca aggacattta aggaatcctg atcctcagaa cttctctggg    840

acaatttcag ttctaataat gtccttaaat tttatttcca gctcctgttc cttggaaaat    900

ctccattgta tgtgcatttt ttaaatgatg tctgtacata aaggcagttc tgaaataaag    960

aaaattttaa aataaaaaaa aaaaaaaaaa aaaaaaaaaa aaaaaaaaaa aaaaaaaaaa   1020

aaa                                                                 1023
```

<210> SEQ ID NO 109
<211> LENGTH: 2533
<212> TYPE: DNA
<213> ORGANISM: Homo sapiens

<400> SEQUENCE: 109

```
ccaagcccat gagggccgcg cgcccggccg ccggtgctga cgagacggag ctcctggccc     60

ccgaggagga gcagaggatc aatgcggttc aagaatcgat tccagcggtt catgaaccat    120

cgagctccag ccaatggccg ctacaagcca acttgctatg aacatgctgc taactgttac    180

acacacgcat tcctcattgt tccggccatc gtgggcagtg ccctcctcca tcggctgtct    240

gatgactgct gggaaaagat aacagcatgg atttatggaa tgggactctg tgccctcttc    300

atcgcttcta cagtatttca cattgtatca tggaaaaaga gccacttaag gacagcggag    360

cattgttttc acatgtgtga tagaatggtt atctatttct tcattgctgc ttcttatgct    420

ccatggttaa atcttcgtga acttggaccc ctggcatctc atatgcgttg gtttatctgg    480

ctcatggcag ctggaggaac catttatgta tttctctacc atgaaaaata taaggtggtt    540

gaactctttt tctatctcac aatgggattc tctccagcct tggtggtgac atcaatgaac    600

aacaccgatg gacttcagga acttgcctgt gggggcttaa tttattgctt gggagttgtg    660

ttcttcaaga gtgatggcat cattccattt gcccacgcca tctggcacct gtttgtggcc    720

acggcagctg cagtgcatta ctacgccatt tggaaatacc tttaccgaag tcctacggac    780

tttatgcggc atttatgacc aatctgtact aattctccaa accagtatta tttcaattat    840

ggcacttggg agtggggtga gagctaaaca ttgcacaggg caaagaaaaa aaataactgc    900

actgacttta tatcttttga atataattac tgtgaaagta taaaggctgt gttctggaat    960

tttctgcctc acagcaaata aataaggtag tgaattaatt attcattcca ttccactatc   1020

atgaaggact ctgaatagac ttggccaact gatgtttaca aaccagactt ttatatttta   1080

attttacaga ttttactaca tgatttttct aaattactat gtcaggttgt aaaagtcagt   1140

gcaataacaa accttccttt ttaagaagaa aattgtttct attactttcc cattcactag   1200

gtaaagaatc atggacagaa cttacactac tttttaccat gtttcatctt ggcataacat   1260

ggttcttttt taaatagaaa ctttagtttt ttgtaaattt ttaaaaaaat atttcattga   1320

tatgcatctc tgcaggtcct cattcatgtt gtaaattttt ggagcaagca gtcaacattc   1380

cacaaacgaa caaacattat acctcttctg atagttttat taagcatgga gaaattgcca   1440

atttttaaaa actgcagttt tccaaacttt tctgccaacc tcttactctg aattcagtgc   1500

tgctttggga catatacttg acctagcttg gtttaccagt gatggaaaag tattttgata   1560
```

-continued

```
tcattaactt tttcaaaaga tccaactttt tctctatgcc tttgccacat tctcttcagg   1620
gtctctttcc acagcggata aatgtttttt ctgtattatg acagtattgt tgtgatggcc   1680
atctgctgga aactcctgaa gagcattatg tattacagtg agcagttgta ttgcctgttt   1740
ggtgcccaat ggttaagtca ttgtcactta gctttatatt gtcagtttga tatttatttt   1800
aaattgtgga actagatgca taaattcaca tttctgcctt tcctttgcat cttctcatat   1860
attgtgtttt tttttttttt cctagaaaaa atatttaaag cattgtttga caggtagaaa   1920
ctcatgtatc tgtagtccat gagttatatc ctggctcagt ggagtgatat ttatgtatta   1980
tttttacttt tctctcagtg tcttatatta agattaacat gttgttaata gttgctttgt   2040
tgattaatct ctcttgttgg tgttttaata aatgaaatag gcttgccttt agatcgggtg   2100
ctgatattgc ctgtttccta gtaatgggct gatcaaatga tcagtggaat tcttggtttg   2160
atgataacct tattaattga aattttttac tgatgtggct ttaaaagagg tttattttgt   2220
atatgtttag aactctctga ttttgatgaa ttatatggga gtgagaaaca gaagaagtgg   2280
tatttgctgg cgagttaaat aggcaaggta cccagtgata acaccaacca aaccactcct   2340
atctgcatga ttctgaacat ctggatgcct gttgttttac tgtgtatatt ttatttttaa   2400
tatattaact ttgtggattc atttaaggtc tactcaaaag taacactgtc caaaccacta   2460
atatgtatgt aaaaattgtg ctgtatacta caataaagtt gttacttgga tttgttccaa   2520
aaaaaaaaaa aaa                                                      2533
```

<210> SEQ ID NO 110
<211> LENGTH: 2899
<212> TYPE: DNA
<213> ORGANISM: Homo sapiens

<400> SEQUENCE: 110

```
cagacggcgc tgagcgcggc ggcggcggga gcggcgtcga gtgtctccgt gcgcccgtct     60
gtggccaagc agccagcagc ctagcagcca gtcagcttgc cgccggcggc caagcagcca    120
accatgctca acttcggtgc ctctctccag cagactgcgg aggaaagaat ggaaatgatt    180
tctgaaaggc caaaagagag tatgtattcc tggaacaaaa ctgcagagaa aagtgatttt    240
gaagctgtag aagcacttat gtcaatgagc tgcagttgga agtctgattt taagaaatac    300
gttgaaaaca gacctgttac accagtatct gatttgtcag aggaagagaa tctgcttccg    360
ggaacacctg attttcatac aatcccagca ttttgtttga ctccacctta cagtccttct    420
gactttgaac cctctcaagt gtcaaatctg atggcaccag cgccatctac tgtacacttc    480
aagtcactct cagatactgc caaacctcac attgccgcac ctttcaaaga ggaagaaaag    540
agcccagtat ctgcccccaa actccccaaa gctcaggcaa caagtgtgat tcgtcataca    600
gctgatgccc agctatgtaa ccaccagacc tgcccaatga aagcagccag catcctcaac    660
tatcagaaca attcttttag aagaagaacc cacctaaatg ttgaggctgc aagaaagaac    720
ataccatgtg ccgctgtgtc accaaacaga tccaaatgtg agagaaacac agtggcagat    780
gttgatgaga aagcaagtgc tgcactttat gacttttctg tgccttcctc agagacggtc    840
atctgcaggt ctcagccagc ccctgtgtcc ccacaacaga agtcagtgtt ggtctctcca    900
cctgcagtat ctgcaggggg agtgccacct atgccggtca tctgccagat ggttcccctt    960
cctgccaaca accctgttgt gacaacagtc gttcccagca ctcctcccag ccagccacca   1020
gccgtttgcc cccctgttgt gttcatgggc acacaagtcc ccaaaggcgc tgtcatgttt   1080
```

-continued

```
gtggtacccc agcccgttgt gcagagttca aagcctccgg tggtgagccc gaatggcacc   1140
agactctctc ccattgcccc tgctcctggg ttttcccctt cagcagcaaa agtcactcct   1200
cagattgatt catcaaggat aaggagtcac atctgtagcc acccaggatg tggcaagaca   1260
tactttaaaa gttcccatct gaaggcccac acgaggacgc acacaggaga aaagcctttc   1320
agctgtagct ggaaaggttg tgaaaggagg tttgcccgtt ctgatgaact gtccagacac   1380
aggcgaaccc acacgggtga gaagaaattt gcgtgcccca tgtgtgaccg gcggttcatg   1440
aggagtgacc atttgaccaa gcatgcccgg cgccatctat cagccaagaa gctaccaaac   1500
tggcagatgg aagtgagcaa gctaaatgac attgctctac ctccaacccc tgctcccaca   1560
cagtgacaga ccggaaagtg aagagtcaga actaactttg gtctcagcgg gagccagtgg   1620
tgatgtaaaa atgcttccac tgcaagtctg tggccccaca acgtgggctt aaagcagaag   1680
ccccacagcc tggcacgaag gccccgcctg ggttaggtga ctaaaagggc ttcggccaca   1740
ggcaggtcac agaaaggcag gtttcatttc ttatcacata agagagatga gaaagctttt   1800
attcctttga atatttttg aaggtttcag atgaggtcaa cacaggtagc acagattttg   1860
aatctgtgtg catatttgtt actttacttt tgctgtttat acttgagacc aacttttcaa   1920
tgtgattctt ctaaagcact ggtttcaaga atatggaggc tggaaggaaa taaacattac   1980
ggtacagaca tggagatgta aaatgagttt gtattattac aaatattgtc atctttttct   2040
agagttatct tctttattat tcctagtctt tccagtcaac atcgtggatg tagtgattaa   2100
atatatctag aactatcatt tttacactat tgtgaatatt tggaattgaa cgactgtata   2160
ttgctaagag ggcccaaaga attggaatcc tccttaattt aattgctttg aagcatagct   2220
acaatttgtt tttgcatttt tgttttgaaa gtttaacaaa tgactgtatc taggcatttc   2280
attatgcttt gaactttagt ttgcctgcag tttcttgtgt agatttgaaa attgtatacc   2340
aatgtgtttt ctgtagactc taagatacac tgcactttgt ttagaaaaaa aactgaagat   2400
gaaatatata ttgtaaagaa gggatattaa gaatcttaga taacttcttg aaaaagatgg   2460
cttatgtcat cagtaaagta cctttatgtt atgaggatat aatgtgtgct ttattgaatt   2520
agaaaattag tgaccattat tcacaggtgg acaaatgttg tcctgttaat ttataggagt   2580
tttttgggga tgtggaggta gttgggtaga aaaattatta gaacattcac ttttgttaac   2640
agtatttctc ttttattctg ttatatagtg gatgatatac acagtggcaa aacaaaagta   2700
cattgcttaa aatatatagt gaaaaatgtc actatatctt cccatttaac attgtttttg   2760
tatattgggt gtagatttct gacatcaaaa cttggaccct tggaaaacaa aagttttaat   2820
taaaaaaaat ccttgtgact tacaatttgc acaatatttc ttttgttgta ctttatatct   2880
tgtttacaat aaagaattc                                                2899
```

<210> SEQ ID NO 111
<211> LENGTH: 1159
<212> TYPE: DNA
<213> ORGANISM: Homo sapiens

<400> SEQUENCE: 111

```
agtgccccag gagctatgac aagcaaagga acatacttgc ctggagatag cctttgcgat     60
atttaaatgt ccgtggatac agaaatctct gcaggcaagt tgctccagag catattgcag    120
gacaagcctg taacgaatag ttaaattcac ggcatctgga ttcctaatcc ttttccgaaa    180
tggcaggtgt gagtgcctgt ataaaatatt ctatgtttac cttcaacttc ttgttctggc    240
tatgtggtat cttgatccta gcattagcaa tatgggtacg agtaagcaat gactctcaag    300
```

-continued

```
caatttttgg ttctgaagat gtaggctcta gctcctacgt tgctgtggac atattgattg    360
ctgtaggtgc catcatcatg attctgggct tcctgggatg ctgcggtgct ataaaagaaa    420
gtcgctgcat gcttctgttg tttttcatag gcttgcttct gatcctgctc ctgcaggtgg    480
cgacaggtat cctaggagct gttttcaaat ctaagtctga tcgcattgtg aatgaaactc    540
tctatgaaaa cacaaagctt ttgagcgcca caggggaaag tgaaaaacaa ttccaggaag    600
ccataattgt gtttcaagaa gagtttaaat gctgcggttt ggtcaatgga gctgctgatt    660
ggggaaataa ttttcaacac tatcctgaat tatgtgcctg tctagataag cagagaccat    720
gccaaagcta taatggaaaa caagtttaca aagagacctg tatttctttc ataaaagact    780
tcttggcaaa aaatttgatt atagttattg gaatatcatt tggactggca gttattgaga    840
tactgggttt ggtgttttct atggtcctgt attgccagat cgggaacaaa tgaatctgtg    900
gatgcatcaa cctatcgtca gtcaaacccc tttaaaatgt tgctttggct ttgtaaattt    960
aaatatgtaa gtgctatata agtcaggagc agctgtcttt ttaaaatgtc tcggctagct   1020
agaccacaga tatcttctag acatattgaa cacatttaag atttgaggga tataagggaa   1080
aatgatatga atgtgtattt ttactcaaaa taaaagtaac tgtttacgtt aaaaaaaaaa   1140
aaaaaaaaaa aaaaaaaaa                                                1159
```

<210> SEQ ID NO 112
<211> LENGTH: 2500
<212> TYPE: DNA
<213> ORGANISM: Homo sapiens

<400> SEQUENCE: 112

```
gtgtcgctcc agctcagagc tcccggagcc gcccggccag cgtccggcct ccctgatcgt     60
ctctggccgg cgccctcgcc ctcgcccggc gcgcaccgag cagccgcggg cgccgagcag    120
ccaccgtccc gaccaagcgc cggccctgcc cgcagcggca ggatgaatga tttcggaatc    180
aagaatatgg accaggtagc ccctgtggct aacagttaca gagggacact caagcgccag    240
ccagcctttg acacctttga tgggtccctg tttgctgttt ttccttctct aaatgaagag    300
caaacactgc aagaagtgcc aacaggcttg gattccattt ctcatgactc cgccaactgt    360
gaattgcctt tgttaacccc gtgcagcaag gctgtgatga gtcaagcctt aaaagctacc    420
ttcagtggct tcaaaaagga acagcggcgc ctgggcattc caaagaaccc ctggctgtgg    480
agtgagcaac aggtatgcca gtggcttctc tgggccacca atgagttcag tctggtgaac    540
gtgaatctgc agaggttcgg catgaatggc cagatgctgt gtaaccttgg caaggaacgc    600
tttctggagc tggcacctga ctttgtgggt gacattctct gggaacatct ggagcaaatg    660
atcaaagaaa accaagaaaa gacagaagat caatatgaag aaaattcaca cctcacctcc    720
gttcctcatt ggattaacag caatacatta ggttttggca cagagcaggc gccctatgga    780
atgcagacac agaattaccc caaaggcggc ctcctggaca gcatgtgtcc ggcctccaca    840
cccagcgtac tcagctctga gcaggagttt cagatgttcc ccaagtctcg gctcagctcc    900
gtcagcgtca cctactgctc tgtcagtcag gacttcccag gcagcaactt gaatttgctc    960
accaacaatt ctgggacgcc caaagaccac gactcccctg agaacggtgc ggacagcttc   1020
gagagctcag actccctcct ccagtcctgg aacagccagt cgtccttgct ggatgtgcaa   1080
cgggttcctt ccttcgagag cttcgaagat gactgcagcc agtctctctg cctcaataag   1140
ccaaccatgt ctttcaagga ttacatccaa gagaggagtg acccggtgga gcaaggcaaa   1200
```

-continued

```
ccagttatac ctgcagctgt gctggccggc ttcacaggaa gtggacctat tcagctgtgg   1260

cagtttctcc tggagctgct atcagacaaa tcctgccagt cattcatcag ctggactgga   1320

gacggatggg agtttaagct cgccgacccc gatgaggtgg cccgccggtg gggaaagagg   1380

aaaaataagc ccaagatgaa ctacgagaag ctgagccggg gcttacgcta ctattacgac   1440

aagaacatca tccacaagac gtcggggaag cgctacgtgt accgcttcgt gtgcgacctc   1500

cagaacttgc tggggttcac gcccgaggaa ctgcacgcca tcctgggcgt ccagcccgac   1560

acggaggact gaggtcgccg ggaccaccct gagccggccc caggctcgtg gactgagtgg   1620

gaagcccatc ctgaccagct gctccgagga cccaggaaag gcaggattga aaatgtccag   1680

gaaagtggcc aagaagcagt ggccttattg catcccaaac cacgcctctt gaccaggctg   1740

cctcccttgt ggcagcaacg gcacagctaa ttctactcac agtgctttta agtgaaaatg   1800

gtcgagaaag aggcaccagg aagccgtcct ggcgcctggc agtccgtggg acgggatggt   1860

tctggctgtt tgagattctc aaaggagcga gcatgtcgtg gacacacaca gactattttt   1920

agattttctt ttgccttttg caaccaggaa cagcaaatgc aaaaactctt tgagagggta   1980

ggagggtggg aaggaaacaa ccatgtcatt tcagaagtta gtttgtatat attattataa   2040

tcttataatt gttctcagaa tcccttaaca gttgtattta acagaaattg tatattgtaa   2100

tttaaaataa ttatataact gtatttgaaa taagaattca gacatctgag gttttatttc   2160

atttttcaat agcacatatg gaattttgca aagatttaat ctgccaaggg ccgactaaga   2220

gaagttgtaa agtatgtatt atttacattt aatagactta cagggataag gcctgtgggg   2280

ggtaatccct gctttttgtg tttttttgtt tgtttgtttg tttgtttttg gggggttttc   2340

ttgccttggt tgtctggcaa ggactttgta catttgggag tttttatgag aaacttaaat   2400

gttattatct gggcttatat ctggcctctg ctttctcctt taattgtaaa gtaaaagcta   2460

taaagcagta tttttcttga caaaaaaaaa aaaaaaaaaa                         2500


<210> SEQ ID NO 113
<211> LENGTH: 2391
<212> TYPE: DNA
<213> ORGANISM: Homo sapiens

<400> SEQUENCE: 113

atgctgcgag gcggacggcg cgggcagctt ggctggcaca gctgggctgc ggggccgggc     60

agcctgctgg cttggctgat actggcatct gcgggcgccg caccctgccc cgatgcctgc    120

tgcccccacg gctcctcggg actgcgatgc acccgggatg gggccctgga tagcctccac    180

cacctgcccg gcgcagagaa cctgactgag ctctacatcg agaaccagca gcatctgcag    240

catctggagc tccgtgatct gaggggcctg ggggagctga gaaacctcac catcgtgaag    300

agtggtctcc gtttcgtggc gccagatgcc ttccatttca ctcctcggct cagtcgcctg    360

aatctctcct tcaacgctct ggagtctctc tcctggaaaa ctgtgcaggg cctctcctta    420

caggaactgg tcctgtcggg gaaccctctg cactgttctt gtgccctgcg ctggctacag    480

cgctgggagg aggagggact gggcggagtg cctgaacaga agctgcagtg tcatgggcaa    540

gggcccctgg cccacatgcc caatgccagc tgtggtgtgc ccacgctgaa ggtccaggtg    600

cccaatgcct cggtggatgt gggggacgac gtgctgctgc ggtgccaggt ggaggggcgg    660

ggcctggagc aggccggctg gatcctcaca gagctggagc agtcagccac ggtgatgaaa    720

tctgggggtc tgccatccct ggggctgacc ctggccaatg tcaccagtga cctcaacagg    780

aagaacgtga cgtgctgggc agagaacgat gtgggccggg cagaggtctc tgttcaggtc    840
```

-continued

```
aacgtctcct tcccggccag tgtgcagctg cacacggcgg tggagatgca ccactggtgc    900
atccccttct ctgtggatgg gcagccggca ccgtctctgc gctggctctt caatggctcc    960
gtgctcaatg agaccagctt catcttcact gagttcctgg agccggcagc caatgagacc   1020
gtgcggcacg ggtgtctgcg cctcaaccag cccacccacg tcaacaacgg caactacacg   1080
ctgctggctg ccaacccctt cggccaggcc tccgcctcca tcatggctgc cttcatggac   1140
aacccctttcg agttcaaccc cgaggacccc atccctgtct ccttctcgcc ggtggacact  1200
aacagcacat ctggagaccc ggtggagaag aaggacgaaa caccttttgg ggtctcggtg   1260
gctgtgggcc tggccgtctt tgcctgcctc ttcctttcta cgctgctcct tgtgctcaac   1320
aaatgtggac ggagaaacaa gtttgggatc aaccgcccgg ctgtgctggc tccagaggat   1380
gggctggcca tgtccctgca tttcatgaca ttgggtggca gctccctgtc ccccaccgag   1440
ggcaaaggct ctgggctcca aggccacatc atcgagaacc cacaatactt cagtgatgcc   1500
tgtgttcacc acatcaagcg ccgggacatc gtgctcaagt gggagctggg ggagggcgcc   1560
tttgggaagg tcttccttgc tgagtgccac aacctcctgc ctgagcagga caagatgctg   1620
gtggctgtca aggcactgaa ggaggcgtcc gagagtgctc ggcaggactt ccaacgtgag   1680
gctgagctgc tcaccatgct gcagcaccag cacatcgtgc gcttcttcgg cgtctgcacc   1740
gagggccgcc ccctgctcat ggtcttcgag tatatgcggc acggggacct caaccgcttc   1800
ctccgatccc atggacccga tgccaagctg ctggctggtg gggaggatgt ggctccaggc   1860
cccctgggtc tggggcagct gctggccgtg gctagccagg tcgctgcggg gatggtgtac   1920
ctggcgggtc tgcattttgt gcaccgggac ctggccacac gcaactgtct agtgggccag   1980
ggactggtgg tcaagattgg tgattttggc atgagcaggg atatctacag caccgactat   2040
taccgtgtgg gaggccgcac catgctgccc attcgctgga tgccgcccga gagcatcctg   2100
taccgtaagt tcaccaccga gagcgacgtg tggagcttcg gcgtggtgct ctgggagatc   2160
ttcacctacg gcaagcagcc ctggtaccag ctctccaaca cggaggcaat cgactgcatc   2220
acgcagggac gtgagttgga gcggccacgt gcctgcccac cagaggtcta cgccatcatg   2280
cggggctgct ggcagcggga gccccagcaa cgccacagca tcaaggatgt gcacgcccgg   2340
ctgcaagccc tggcccaggc acctcctgtc tacctggatg tcctgggcta g            2391

<210> SEQ ID NO 114
<211> LENGTH: 3609
<212> TYPE: DNA
<213> ORGANISM: Homo sapiens

<400> SEQUENCE: 114

cagcccgtcg tggatgacta gagccaacca cctgccttcc gtcttccagg cagaaccaca     60
gagaggctac agccgtcctg gcctccctcc ggccctgaga gctcctctgg cctgtctcaa    120
gtcttaacgt ctcaagcgca gactgccggc tccgaacggg gagaccaggc ttctgcaccg    180
gaaacaaggc accggttgtg acgtcacagc cgcagagcgc ccgacttccc agaaggcacc    240
gagtccctgc cgttctcctc aactggcggc ggcgcgaacg aatagtcgcc ggcgacctgt    300
gagggcactc ggaagggcga ggggagggct cgaccgctcg cgcctagttt ttctatctct    360
cccggagcct gagtctctga gccgtcccca gcaaacgctc aggggctgca gaggccccga    420
gaggtgaggg gctccgtgag ggcgggaacc aggctgaggc cgcctctggg gagcggagcg    480
tgtccgttgc tgagggagca aggccgggta gggagcctgg tgagcgcctc aggcaggggc    540
```

-continued

```
gcacgctgag ctttacggta aaggtgttcc ttgaccagcg gaagaggccc cagagtgagc    600
ctggcccggc ggtccttagt gggatgtcgc ctgccgctct cagcagagct ttgacggcgg    660
agaggagtcg gcaggcggtg tgtggacacc tcctcggcct tgcatctgct ccccgggaga    720
gtcaccaacc gcctccccgc ccaaagggca ccggagggag cttcggttcg agggcttggc    780
tctctggcag atttcctcta gtaagaggtg gctctggagg ccccgcgaaa cgagtgtggt    840
gtgtggttgc aaggcatgat ggctgcaaaa gtggttccta tgccccccaaa gccaaagcag    900
tcctttatac tgagagttcc gccagactcc aagctgggcc aagacctact tcgagatgcc    960
actaacgggc ccaagaccat ccaccagcta gtgctggagc acttcctcac cttcttgccc   1020
aagccaagcc tggtccagcc cagtcagaaa gtcaaggaga ccttggttat tatgaaagat   1080
gtgagctcaa gccttcagaa cagagtgcat cctcgtccct tggtgaagct tctgcccaaa   1140
ggagtccaaa aggaacaaga gacagtgtct ctgtatttga aagctaaccc tgaggagctg   1200
gtggtctttg aggatttgaa tgtatttcac tgccaggaag aatgtgtgag cttggatcct   1260
actcaacaac tcacgtcaga gaaggaagat gacagcagtg tcggggaaat gatgttactg   1320
gcagtcaatg gcagtaatcc tgaaggtgaa gatcctgaga gggaacctgt agaaaatgaa   1380
gattatagag aaaagtcttc agatgatgat gaaatggatt cttccttggt ctctcagcag   1440
cctcccgata accaggaaaa ggaacgacta aatacatcca ttccacaaaa aaggaaaatg   1500
agaaatctgt tagttaccat tgagaatgat actcctctag aggaactctc aaaatatgta   1560
gacatcagta ttattgccct tactcgaaat cggaggacaa ggagatggta cacttgtcca   1620
ctgtgtggga aacagtttaa tgaaagttct tacctcattt ccccaccagag gacccacact   1680
ggagaaaaac cctatgactg taatcactgt gggaaaagct tcaatcataa aacaaacctc   1740
aataaacatg agcgaattca tacaggagag aaaccttatt cctgttctca gtgtggaaaa   1800
aacttccgtc agaattctca tcggagtcgt catgaaggaa tccatataag ggagaagata   1860
tttaagtgtc cagaatgtgg gaaaaccttc ccaaagaatg aggagtttgt gcttcatctg   1920
cagagtcatg aggctgagag accatatggt tgcaaaaaat gtgggagaag atttggtcgg   1980
ctgtcaaact gtacccggca tgagaaaacc cactcagcct gtaagacccg aaagcagaag   2040
taatactggg aaccctttct gggtctgatg gtgctgcctc aacctgagag ctttcataag   2100
tagttctgaa ttcccaagct gcctaaaaag gtataaatgt gtaaaaatct cattattgcc   2160
aaaattggat aaatgcccat cttagctaaa acctcaaatt gctagaaaat tcacagggaa   2220
gaaaacattt caagggctat acctcagcat ctaggctttt tggactaagg agctttcctt   2280
tttgaagtta tatgataatg tacaggtcac agatcccctt tcccaacact ttgaagatga   2340
atctggagtc tgcttacttg gaaggcaaag agtgacttgt gtctattgaa agtatatccg   2400
ttttcccccc acatggggat tcatacttga gaaatagtgc aaagatgctt atctggaact   2460
gtgttctggt gaaagaacca aattactggc ttgttagcca acagcttctg atagcaattc   2520
atataaccct ctaagaatac ctgtttaagt cttgagtgtt gaaaggaatt gtttactttg   2580
gaatatagga aaacagttga atgtcagact ctcatttgta tgtgatctaa atttgcaatc   2640
aatttcaata atatttacaa tttgtgataa aactgacttt tacagattcc ttttcacaac   2700
ataatttagg tgtctactgt tcttattgta ttttgttctg ctgttgatct ctccagcagc   2760
cgtctcatgc ttctcccttg ctaaaagaag tttggattac tcaggcaggg ccatccagcc   2820
ccaccactag aaaagctctt cagaatcttg tccctctgtt gagcccagat ctcatgtgct   2880
acgaaggaaa ccccaagacc cagagaggaa gggtcaacct ggaggcagga aaaagttggc   2940
```

-continued

```
ttggatccat gtctcatcaa taaccttacc atatgcttag gtcccctcta tgctgtcatc   3000

agacctttgg caatggggtg gtcactacct cacaaggcaa agtgttgtat gattagaaat   3060

tacgtctcca gtggttagct cacattgcct ctcaagagac aggtttccag gtgtcttcat   3120

tgtagtgggt attaattgtc ttcagcctct tgatatccat accttcctgt cctctgccta   3180

gaagcaaggc cagcggtgcc tttacggact gatcgtgtgg tgcgatttag ggattcttca   3240

gttttgcttg ctttaggttt ccaaaagtta tacattggtg ttttgattgg aataaagaaa   3300

tcctataagc tatttgggaa aaattatagt gtatgtttcc catccagaaa catgcctttc   3360

tatttattag agtattatat tcctgtgaaa atttttctaa ttttcttcac ttgttttaca   3420

caattttgtt attgtagttt tttccattat atttttatag ttgattattg cttttacatg   3480

ggaaagttat ttttaattat atatttgtat agtcatctca ctgttgttaa ttttcaatag   3540

tttgttggtt tagttctgtt aacttttggt aaaatgacac catctacaaa gaaaaaaaaa   3600

aaaaaaaaa                                                           3609
```

```
<210> SEQ ID NO 115
<211> LENGTH: 1386
<212> TYPE: DNA
<213> ORGANISM: Homo sapiens

<400> SEQUENCE: 115

gctcctcgcc ccgcgcctgc ccccaggatg gtccgcgcga ggcaccagcc gggtgggctt     60

tgcctcctgc tgctgctgct ctgccagttc atggaggacc gcagtgccca ggctgggaac    120

tgctggctcc gtcaagcgaa gaacggccgc tgccaggtcc tgtacaagac cgaactgagc    180

aaggaggagt gctgcagcac cggccggctg agcacctcgt ggaccgagga ggacgtgaat    240

gacaacacac tcttcaagtg gatgattttc aacgggggcg cccccaactg catcccctgt    300

aaagaaacgt gtgagaacgt ggactgtgga cctgggaaaa aatgccgaat gaacaagaag    360

aacaaacccc gctgcgtctg cgccccggat tgttccaaca tcacctggaa gggtccagtc    420

tgcgggctgg atgggaaaac ctaccgcaat gaatgtgcac tcctaaaggc aagatgtaaa    480

gagcagccag aactggaagt ccagtaccaa ggcagatgta aaaagacttg tcgggatgtt    540

ttctgtccag gcagctccac atgtgtggtg gaccagacca ataatgccta ctgtgtgacc    600

tgtaatcgga tttgcccaga gcctgcttcc tctgagcaat atctctgtgg gaatgatgga    660

gtcacctact ccagtgcctg ccacctgaga aaggctacct gcctgctggg cagatctatt    720

ggattagcct atgagggaaa gtgtatcaaa gcaaagtcct gtgaagatat ccagtgcact    780

ggtgggaaaa aatgtttatg ggatttcaag gttgggagag gccggtgttc cctctgtgat    840

gagctgtgcc ctgacagtaa gtcggatgag cctgtctgtg ccagtgacaa tgccacttat    900

gccagcgagt gtgccatgaa ggaagctgcc tgctcctcag gtgtgctact ggaagtaaag    960

cactccggat cttgcaactg aatctgcccg taaaacctga gccattgatt cttcagaact   1020

ttctgcagtt tttgacttca tagattatgc tttaaaaaat tttttttaac ttattgcata   1080

acagcagatg ccaaaaacaa aaaaagcatc tcactgcaag tcacataaaa atgcaacgct   1140

gtaatatggc tgtatcagag ggctttgaaa acatacactg agctgcttct gcgctgttgt   1200

tgtccgtatt taaacaacag ctcccctgta ttcccccatc tagccatttc ggaagacacc   1260

gaggaagagg aggaagatga agaccaggac tacagctttc ctatatcttc tattctagag   1320

tggtaaactc tctataagtg ttcagtgttc acatagcctt tgtgcaaaaa aaaaaaaaaa   1380
```

```
aaaaaa                                                              1386

<210> SEQ ID NO 116
<211> LENGTH: 3163
<212> TYPE: DNA
<213> ORGANISM: Homo sapiens

<400> SEQUENCE: 116

agcgggaaag aaagcttgcc ccagaggact taaacaggca agaaggactt ggttaaagac     60

tattgcaata gtcaacttcc aatacaacag cagctggaga tttatagcta acgggctggg    120

tgaaggagtt aaaggatgct aaattactaa gaggaagtga tgggcagtag gggctgagca    180

aagataactt ctgacatagt caaaccaact ccctctcaga agaacctgat gtttcctgac    240

tgctttctcc ttcctcagcc ctgccctgct tggatagagg cctccgaaca ggagtaaaga    300

atggctgttg aacatccaca aggcacctgc aagactatga atcaaagttg agaccaagaa    360

attatttctg aaaaaggata tggaaaacct tacaaaacac agcattgagt gttcaagttt    420

cagaggtgat tgggaatgta aaaaccagtt tgagagaaaa cagggatctc aggaaggaca    480

tttcagtgaa atgatattta ctcctgaaga catgcccact ttcagtatcc agcatcagag    540

aattcatact gatgagaaac tccttgaatg taaggaatgt gggaaggatt ttagttttgt    600

atcagtcctt gttcgacatc agcgaattca tactggtgag aaaccttatg aatgcaaaga    660

atgtggcaag gcctttggta gtggtgcaaa ccttgcttac catcaaagaa ttcatactgg    720

tgagaagcct tttgaatgta aagaatgtgg gaaggccttt ggtagtggct caaaccttac    780

tcaccatcag agaattcata ctggtgagaa accctatgag tgtaaggaat gtgggaaagc    840

ctttagtttt ggatcaggcc ttattcgaca tcagatcatt cacagtggtg agaagcctta    900

tgagtgtaag gaatgtggga agtcctttag ttttgaatca gcccttattc ggcatcacag    960

aattcacaca ggtgagaaac cttatgaatg tatagattgt ggtaaagcct ttggcagtgg   1020

ttcaaacctt actcaacatc ggcggattca tactggtgag aaaccttatg aatgcaaagc   1080

atgtggaatg gcctttagca gtggttcggc tcttactcgg catcagagaa ttcataccgg   1140

tgagaaacca tatatatgta atgaatgtgg taaggccttt agttttggat cagcccttac   1200

tcgacatcaa agaattcata ctggtgagaa accttatgta tgtaaggaat gtgggaaggc   1260

ttttaatagt ggctcagatc tcactcagca tcagagaatt cacactggtg agaaacccta   1320

tgagtgtaag gagtgtgaga aagcctttag aagtggttca aaacttattc agcatcaaag   1380

aatgcatact ggagagaaac cttatgaatg taaggaatgt gggaagacct ttagtagtgg   1440

ttcagacctt actcaacatc acagaattca tactggtgag aaaccctatg aatgtaagga   1500

atgtgggaag gcctttggta gtggctcaaa acttatccaa caccagctaa tccatactgg   1560

tgaaagaccc tatgaatgta aagaatgtgg aaagtccttt agtagtggtt cagctcttaa   1620

tcggcaccag agaatacaca ctggtgagaa accctatgaa tgtaaggagt gtgggaaggc   1680

tttttatagt ggctcaagcc ttactcagca tcagagaatt catacaggtg agaaacttta   1740

tgaatgtaag aactgtggga aggcttatgg gagggattca gagtttcagc aacataagaa   1800

aagtcataat ggtaagaaac tctgcgaatt ggaaactata aattgaaatt atgtgctgaa   1860

ggaaggactc taaacatatg acttaagaaa attcatagtg gtgaaaatct ctacaaatag   1920

aactaaggta caaatgcctt acttatgctt cacaggttag tcagtctaag aatatttata   1980

caggaaaaaa atcaccccaa ataaaataaa tatttgaaga tccttatcta tattcattcc   2040

ttcattactt ttggaaaatt cttacttgtg aatgttaaaa atgaaaaaaa aatcatttat   2100
```

-continued

```
tatattttgc ctcaacttta aacattggaa aactcatttc tgggttaatc ctactatatt   2160

ttttcaatgg tctttttttt ttgtattata cagaattact gattcattga aaaattattt   2220

tatttattgc aagtctaaat ttatcctttt tttctttcct gattatccta acaccattta   2280

ttcaataacc ttgtccattt tcatattttt tttattgact atttgatggt aagttacatt   2340

tttattcaca taaagcttgg atatcaggtc agtgtttttt tgtttttgtt tttgtttttg   2400

tttttttgag atggagtctc actgtcacca ggctggagtg cagtggtgca atctcggttc   2460

actgcaacct ccacctcccg agttcaagtg attttcctgc ctcagctccc cagtagctgg   2520

gactacaggc gcccgccacc acgcccagct aatttttttgt attttcatta gagatggggt   2580

ttcaccacgt tggccaggat ggtctcgatc tcttgacctc gtgatccatc tgcctcggcc   2640

tcccaacgtg ctggaattac aggcatgagc caccatgcct ggcccagtgt ttgtttttta   2700

aatttatata tatgtatcta tgtctcatcc tgtttatggt caataactgt tacttttaag   2760

tatcctttaa tacctgtacc ttttgtttta gaagattgtt tactttcctt ttataaaatt   2820

atactctcca ttttagcaaa acagctttcc ctcatcataa tgtagataaa aagaaaaaaa   2880

ggatatggtt acctgtaatc ttaccaatca tagataatca ctgtcaaact tttggagcaa   2940

atcctttaat actatctctc attgttttgg aaacaaggtg tgattatgct atactataac   3000

cagcccttaa tattttttgt ctgtaaatat gttgttacca ttttattggc tttatagtat   3060

tcacctgtct ttatcaaacc ccaattttgt caaatattaa aaattttgcc attataaaaa   3120

aaaaaaaaaa aaaaaaaaaa aaaaaaaaga aaaaaaaaaa aaa                      3163
```

<210> SEQ ID NO 117
<211> LENGTH: 1632
<212> TYPE: DNA
<213> ORGANISM: Homo sapiens

<400> SEQUENCE: 117

```
atagatacta gattgtattg aattctgttt taattattct ctaggtaagt atgttttagg     60

attaaatacc ttttacagat actgaaagtg cctccttttg tggtgtaaaa aacaaattat    120

ggtgcaaaaa gtaatcacta gattgaaata catgaaggtt ttttgctttt tgacatacga    180

aaatgtcaag agaaaggcca aagatttgta ctttttcact tacaaagcac tcctttttcc    240

cttaaacttc tttctgtcaa attagattta atgagagagt actattttta aggagctatc    300

tgtttatgta gaatgatttt gttaagagta atgtaaacta ttattgagta gaggcctaaa    360

gaggactgtg ccatttttgc tatttaaagg aatcacaaat gatcatactt aagtgagcaa    420

aaatgacaag ttttactagc taagtagaga aataaatctc aaatgcagcg ctacaatttt    480

cattatctta agtacattgt acatttctac agaacctgtg attattctcg catgataagg    540

atggtacttg catatggtga attactactg ttgacagttt ccgcagaaat cctatttcag    600

tggaccaaca ttgtggcatg gcagcaaatg ccaacatttt gtggaatagc agcaaatcta    660

caagagaccc tggttggttt ttcgttttgt tttctttgtt ttttcccccct tctcctgaat    720

cagcagggat ggaaggaggg tagggaagtt atgaattact ccttccagta gtagctctga    780

agtgtcacat ttaatatcag tttttttttaa acatgattct agttaaatgt agaagagaga    840

agaaagagga agtgttcact tttttaatac actgatttag aaatttgatg tcttatatca    900

gtagttctga ggtattgata gcttgcttta tttctgcctt tacgttgaca gtgttgaagc    960

agggtgaata actagggcat atattttttt ttttttttgt aagctgtttc atgatgtttt   1020
```

```
ctttggaatt tccggataag ttcaggaaaa cattctgcat gttgtatcta gtctgatgta   1080

cttatccatc tcattacaaa caaaaacaca cagaactgca tttgtagctc tgtaatcctt   1140

gaatacggaa gtaaatttc ttctttcctg actttgacat tgtagctata ctgtttccat    1200

ttttgttttt acaaatcctt tgggtctaat tctgtgagcc tacctatagc actggattaa   1260

aatgtctgca tcatttcttt agttatccag ttaactttaa aactgttgta aaagtgtaaa   1320

ccagcccatg acaggttttt gtacatgtta aagaacttca ttgttcagtt ttcatgatta   1380

ttgtgtaagg aagactgatg tagatgttct gtgctgtcct ggaccatgtt aattacactt   1440

acgacgtatt ttagttccac atcacaatga tttgtcccca gtgacccttt tatcctttct   1500

aggcacattt cttgttgttg ttgttgttgc agttcccctt tgcattgtat tgctttgaca   1560

actgtaattt gaatcagatc tgaaagaggt ccagaataaa atatattttg atattaaaaa   1620

aagaaaaaaa at                                                       1632
```

<210> SEQ ID NO 118
<211> LENGTH: 2202
<212> TYPE: DNA
<213> ORGANISM: Homo sapiens

<400> SEQUENCE: 118

```
gggactgtcg cgtcggcgcc cgacgcggag tcagcagggg cgaaaagcgg tagatcatgg     60

caaccataga agaaattgca catcaaatta ttgaacaaca gatgggagag attgttacag    120

agcagcaaac tgggcagaaa atccagattg tgacagcact tgatcataat acccaaggca    180

agcagttcat tctgacaaat cacgacggct ctactccaag caaagtcatt ctggccaggc    240

aagattccac tccgggaaaa gttttcctta caactccaga tgcagcaggt gtcaaccagt    300

tattttttac cactcctgat ctgtctgcac aacacctgca gctcctaaca gataattctc    360

cagaccaagg accaaataag gtttttgatc tttgcgtagt atgtggagac aaagcatcag    420

gacgtcatta tggagcagta acttgtgaag gctgcaaagg atttttttaaa agaagcatcc   480

gaaaaaattt agtatattca tgtcgaggat caaaggattg tattattaat aagcaccacc    540

gaaaccgctg tcaatactgc aggttacaga gatgtattgc gtttggaatg aagcaagact    600

ctgtccaatg tgaaagaaaa cccattgaag tatcacgaga aaaatcttcc aactgtgccg    660

cttcaacaga aaaaatctat atccgaaagg accttcgtag cccattaact gcaactccaa    720

cttttgtaac agatagtgaa agtacaaggt caacaggact gttagattca ggaatgttca    780

tgaatattca tccatctgga gtaaaaactg agtcagctgt gctgatgaca tcagataagg    840

ctgaatcatg tcagggagat ttaagtacat tggccaatgt ggttacatca ttagcgaatc    900

ttggaaaaac taaagatctt tctcaaaata gtaatgaaat gtctatgatt gaaagcttaa    960

gcaatgatga tacctctttg tgtgaatttc aagaaatgca gaccaacggt gatgtttcaa   1020

gggcatttga cactcttgca aaagcattga atcctggaga gagcacagcc tgccagagct   1080

cagtagcggg catggaagga agtgtacacc taatcactgg agattcaagc ataaattaca   1140

ccgaaaaaga ggggccactt ctcagcgatt cacatgtagc tttcaggctc accatgcctt   1200

ctcctatgcc tgagtacctg aatgtgcact acattgggga gtctgcctcc agactgctgt   1260

tcttatcaat gcactgggca ctttcgattc cttctttcca ggctctaggg caagaaaaca   1320

gcatatcact ggtgaaagct tactggaatg aacttttttac tcttggtctt gcccagtgct  1380

ggcaagtgat gaatgtagca actatattag caacatttgt caattgtctt cacaatagtc   1440

ttcaacaaga taaaatgtca acagaaagaa gaaaattatt gatggagcac atcttcaaac   1500
```

-continued

```
tacaggagtt ttgtaacagc atggttaaac tctgcattga tggatacgaa tatgcctacc   1560

tgaaggcaat agtactcttc agtccagatc atccaagcct agaaaacatg gaactgatag   1620

agaaatttca ggaaaaggct tatgtggaat tccaagatta tataaccaaa acatatccag   1680

atgacaccta caggttatcc agactactac tcagattgcc agctttaaga ctgatgaatg   1740

ctaccatcac tgaagaattg tttttcaaag gtctcattgg caatatacga attgacagtg   1800

ttatcccaca tattttgaaa atggagcctg cagattataa ctctcaaata attggtcaca   1860

gcatttgaaa actgtgactg cagtgctgta aacttaactg ttctttgcca gaacacaaga   1920

caccaaattg aactcactgc ttttgaggca tctggaaatt tttactttaa aaagtaacca   1980

gaatccaagg tatttttatt ttagcttccc ttaagaattt ttgaagtgac tgggcaggca   2040

gcagaaatta aatgaatttt tcttcctgat tcctttaaat gaatatgaaa cactacaaat   2100

ttattcttgg tgaagatgat acctgaagct gtcacctctt gattatctaa actaagcgct   2160

cattctattt tataaaacaa ataaattagt ctcttttttc tg                      2202
```

<210> SEQ ID NO 119
<211> LENGTH: 2716
<212> TYPE: DNA
<213> ORGANISM: Homo sapiens

<400> SEQUENCE: 119

```
aggctgaggg gcggttgttg ttggcagctg tggctaagga ggggagaacc tctgctcccc     60

gcccgtcttc tcttctgcgt ttcccgggct agggggcgtg gggagtggtt ttaggcggcg    120

aagccgctcg gcagcacctt ccttctttgc caggcagacg cccgttgtag ccgttgggga    180

accgttgaga atccgccatg gagccagaga gggaagggac cgagagacac cccaggaagg    240

tcagggaagg caggcaggcc ccaaataagc tggtcggggc agctgaggcg atgaaagccg    300

gttgggatct cgaggagagt cagcccgagg ccaagaaagc ccgcttatct accattttat    360

ttactgacaa ctgtgaagta acccatgacc agctgtgtga attgctgaag tatgcagttc    420

tgggcaaatc caatgttcca aaacccagct ggtgccagct tttcatcaa aaccacctaa    480

acaacgtagt ggtttttgtt ctgcagggaa tgagtcagct acacttttac aggttctatt    540

tggagtttgg atgtcttcga aaagcattca gacataaatt ccgcttgcct ccaccatcat    600

ctgattttct agctgatgtt gttgggctac aaactgaaca aagagctgga gatctgccca    660

agacaatgga agggccttta ccttctaatg caaaagccgc catcaacctt caggatgatc    720

ccatcattca aaagtatggc tctaagaaag tgggcttgac cagatgcctt ctgacaaagg    780

aggaaatgag aacgtttcac tttccattac aaggttttcc tgattgtgaa aactttttac    840

ttaccaaatg taatggttct atagcagaca atagtcctct ctttggactt gactgtgaaa    900

tgtgcctcac atccaagggg agagagctaa cacgcatctc actggttgct gaaggaggct    960

gctgtgttat ggatgaactg gtcaaacctg aaaacaagat tctggactac ctcaccagct   1020

tttcgggaat cacgaagaag attcttaacc cagtgacgac caaactcaaa gatgtacaga   1080

ggcagttaaa agcactgctt cctcctgatg ctgtgttagt gggccactcc ttagatttgg   1140

atctcagagc actgaaaatg atacatccat atgttattga tacatcgttg ctttatgtca   1200

gagagcaggg cagaagattt aagctcaagt tcttagccaa agttattttg gggaaggata   1260

tacagtgtcc agacagactt ggtcatgatg ccacagaaga tgctagaaca atccttgaat   1320

tggctcggta tttccttaag catggcccaa aaaagattgc agaactaaat ctagaagcac   1380
```

```
tagctaatca ccaagaaata caagcagcag gccaagagcc taaaaacaca gcagaagtac   1440

ttcagcaccc aaacacaagt gttttagaat gcttggattc agtgggtcag aagcttcttt   1500

ttttgacccg ggagacagat gctggtgaac ttccatcttc cagaaattgt caaactatta   1560

agtgtctttc aaataaagag gttcttgagc aggccagagt ggaaatcccc ctgtttccct   1620

tcagcattgt tcagttctct tttaaggcct tttcacctgt cctcactgag gagatgaaca   1680

aaaggatgag gatcaagtgg acagagatat caactgtcta tgctgggcca tttagcaaaa   1740

attgcaatct cagggctctg aagaggctgt ttaaaagctt tggcccagtc cagtcaatga   1800

cttttgttct tgaaacccgt cagcctcatc tctgtataca gtatgaagtc ctagaagctg   1860

cccagctggc catagagtcc ttggatggta ttctggtaga tggtatctgc atcaaggtgc   1920

agaggcctgt gacagagctc acgcttgatt gtgacaccct cgtgaatgag ctggaaggag   1980

attctgaaaa ccaaggctct atatatctgt ctggagtgag tgaaaccttc aaagaacagc   2040

tattgcagga gccccgcctc tttcttggcc tggaagctgt gatcttgcct aaagatctta   2100

aaagtggaaa gcagaaaaaa tactgtttcc tgaaattcaa aagttttggc agtgcccagc   2160

aggccctcaa cattctcaca ggcaaggact ggaagctgaa aggcaggcat gccctaaccc   2220

ccaggcacct ccatgcctgg ctcagaggct taccacctga atcaacaagg ctcccagggc   2280

ttcgtgttgt acctccccca tttgaacagg aggccttgca gactctgaaa ctggaccacc   2340

cgaagatagc agcctggcgc tggagccgga agattggaaa gctctacaac agcttgtgcc   2400

cgggcactct ctgcctcatc ctgctgccag gaaccaagag cactcatggt tcactctctg   2460

gtctaggact gatgggaata aaagaggaag aagaaagcgc tggcccaggc ctgtgttcgt   2520

gagtcggcct gccatgtttc catgtgccat ttcttacccc ttgtaggcaa tggcaaagaa   2580

tgtggtcagg ctgtagcctc cccaaccagc agacagtttt atggaaactt ggtatagcag   2640

ctaaaagagt ttagtttgtt tatatggcat gtataagttt tcaataaatg cctaaagttc   2700

aagcataaaa aaaaaa                                                    2716
```

<210> SEQ ID NO 120
<211> LENGTH: 7825
<212> TYPE: DNA
<213> ORGANISM: Homo sapiens

<400> SEQUENCE: 120

```
ccttttcgtt cgccctctcg ggcggcttc gccgaaggta gcgccgaatc cggcaaccgg      60

agcctgggcg cgaagcgaag aagccggaac aaagtgaggg ggagccggcc ggctggcccg    120

ggaagcccca ggggcgcagg ggaagcggga ctcgcgccgg gcggggtttc cctgcgcccc    180

ggcgccccgc gggcagcatg cccctgcggg caggggggagc tgggctgaac tggccctccc   240

gggggctcag cttgcgccct agagcccacc agatgtgccc ccgccggggc ccccgggttg    300

cgtgaggaca cctcctctga ggggcgccgc ttgcccctct ccggatcgcc cggggccccg    360

gctggccaga ggatggacga ggaggaggat ggagcgggcg ccgaggagtc gggacagccc    420

cggagcttca tgcggctcaa cgacctgtcg ggggccgggg gccggccggg gccggggtca    480

gcagaaaagg acccgggcag cgcggactcc gaggcggagg ggctgccgta cccggcgctg    540

gccccggtgg ttttcttcta cttgagccag gacagccgcc cgcggagctg gtgtctccgc    600

acggtctgta acccctggtt tgagcgcatc agcatgttgg tcatccttct caactgcgtg    660

accctgggca tgttccggcc atgcgaggac atcgcctgtg actcccagcg ctgccggatc    720

ctgcaggcct ttgatgactt catctttgcc ttctttgccg tggagatggt ggtgaagatg    780
```

-continued

```
gtggccttgg gcatctttgg gaaaaagtgt tacctgggag acacttggaa ccggcttgac    840
tttttcatcg tcatcgcagg gatgctggag tactcgctgg acctgcagaa cgtcagcttc    900
tcagctgtca ggacagtccg tgtgctgcga ccgctcaggg ccattaaccg ggtgcccagc    960
atgcgcatcc ttgtcacgtt gctgctggat acgctgccca tgctgggcaa cgtcctgctg   1020
ctctgcttct tcgtcttctt catcttcggc atcgtcggcg tccagctgtg ggcagggctg   1080
cttcggaacc gatgcttcct acctgagaat ttcagcctcc ccctgagcgt ggacctggag   1140
cgctattacc agacagagaa cgaggatgag agccccttca tctgctccca gccacgcgag   1200
aacggcatgc ggtcctgcag aagcgtgccc acgctgcgcg gggacggggg cggtggccca   1260
ccttgcggtc tggactatga ggcctacaac agctccagca acaccacctg tgtcaactgg   1320
aaccagtact acaccaactg ctcagcgggg gagcacaacc ccttcaaggg cgccatcaac   1380
tttgacaaca ttggctatgc ctggatcgcc atcttccagg tcatcacgct ggagggctgg   1440
gtcgacatca tgtactttgt gatggatgct cattccttct acaatttcat ctacttcatc   1500
ctcctcatca tcgtgggctc cttcttcatg atcaacctgt gcctggtggt gattgccacg   1560
cagttctcag agaccaagca gcgggaaagc cagctgatgc gggagcagcg tgtgcggttc   1620
ctgtccaacg ccagcaccct ggctagcttc tctgagcccg gcagctgcta tgaggagctg   1680
ctcaagtacc tggtgtacat ccttcgtaag gcagcccgca ggctggctca ggtctctcgg   1740
gcagcaggtg tgcgggttgg gctgctcagc agcccagcac ccctcggggg ccaggagacc   1800
cagcccagca gcagctgctc tcgctcccac cgccgcctat ccgtccacca cctggtgcac   1860
caccaccacc accatcacca ccactaccac ctgggcaatg ggacgctcag ggcccccggg   1920
gccagcccgg agatccagga cagggatgcc aatgggtccc gccggctcat gctgccacca   1980
ccctcgacgc ctgccctctc cggggccccc cctggtggcg cagagtctgt gcacagcttc   2040
taccatgccg actgccactt agagccagtc cgctgccagg cgccccctcc caggtcccca   2100
tctgaggcat ccggcaggac tgtgggcagc gggaaggtgt atcccaccgt gcacaccagc   2160
cctccaccgg agacgctgaa ggagaaggca ctagtagagg tggctgccag ctctgggccc   2220
ccaaccctca ccagcctcaa catcccaccc gggccctaca gctccatgca caagctgctg   2280
gagacacaga gtacaggtgc ctgccaaagc tcttgcaaga tctccagccc ttgcttgaaa   2340
gcagacagtg gagcctgtgg tccagacagc tgcccctact gtgcccgggc cggggcaggg   2400
gaggtggagc tcgccgaccg tgaaatgcct gactcagaca gcgaggcagt ttatgagttc   2460
acacaggatg cccagcacag cgacctccgg gacccccaca gccggcggca acggagcctg   2520
ggcccagatg cagagcccag ctctgtgctg gccttctgga ggctaatctg tgacaccttc   2580
cgaaagattg tggacagcaa gtactttggc cggggaatca tgatcgccat cctggtcaac   2640
acactcagca tgggcatcga ataccacgag cagcccgagg agcttaccaa cgccctagaa   2700
atcagcaaca tcgtcttcac cagcctcttt gccctggaga tgctgctgaa gctgcttgtg   2760
tatggtccct ttggctacat caagaatccc tacaacatct tcgatggtgt cattgtggtc   2820
atcagcgtgt gggagatcgt gggccagcag gggggcggcc tgtcggtgct gcggaccttc   2880
cgcctgatgc gtgtgctgaa gctggtgcgc ttcctgccgg cgctgcagcg gcagctggtg   2940
gtgctcatga agaccatgga caacgtggcc accttctgca tgctgcttat gctcttcatc   3000
ttcatcttca gcatcctggg catgcatctc ttcggctgca agtttgcctc tgagcgggat   3060
ggggacaccc tgccagaccg gaagaatttt gactccttgc tctgggccat cgtcactgtc   3120
```

-continued

```
tttcagatcc tgacccagga ggactggaac aaagtcctct acaatggtat ggcctccacg   3180
tcgtcctggg cggcccttta tttcattgcc ctcatgacct tcggcaacta cgtgctcttc   3240
aatttgctgg tcgccattct ggtggagggc ttccaggcgg aggaaatcag caaacgggaa   3300
gatgcgagtg gacagttaag ctgtattcag ctgcctgtcg actcccaggg gggagatgcc   3360
aacaagtccg aatcagagcc cgatttcttc tcacccagcc tggatggtga tggggacagg   3420
aagaagtgct tggccttggt gtccctggga gagcacccgg agctgcggaa gagcctgctg   3480
ccgcctctca tcatccacac ggccgccaca cccatgtcgc tgcccaagag caccagcacg   3540
ggcctgggcg aggcgctggg ccctgcgtcg cgccgcacca gcagcagcgg gtcggcagag   3600
cctggggcgg cccacgagat gaagtcaccg cccagcgccc gcagctctcc gcacagcccc   3660
tggagcgctg caagcagctg gaccagcagg cgctccagcc ggaacagcct cggccgtgca   3720
cccagcctga agcggagaag cccaagtgga gagcggcggt ccctgttgtc gggagaaggc   3780
caggagagcc aggatgaaga ggagagctca gaagaggagc gggccagccc tgcgggcagt   3840
gaccatcgcc acaggggggtc cctggagcgg gaggccaaga gttcctttga cctgccagac   3900
acactgcagg tgccagggct gcatcgcact gccagtggcc gagggtctgc ttctgagcac   3960
caggactgca atggcaagtc ggcttcaggg cgcctggccc gggccctgcg gcctgatgac   4020
cccccactgg atggggatga cgccgatgac gagggcaacc tgagcaaagg ggaacgggtc   4080
cgcgcgtgga tccgagcccg actccctgcc tgctgcctcg agcgagactc ctggtcagcc   4140
tacatcttcc ctcctcagtc caggttccgc ctcctgtgtc accggatcat cacccacaag   4200
atgttcgacc acgtggtcct tgtcatcatc ttccttaact gcatcaccat cgccatggag   4260
cgccccaaaa ttgacccccca cagcgctgaa cgcatcttcc tgaccctctc caattacatc   4320
ttcaccgcag tctttctggc tgaaatgaca gtgaaggtgg tggcactggg ctggtgcttc   4380
ggggagcagg cgtacctgcg gagcagttgg aacgtgctgg acgggctgtt ggtgctcatc   4440
tccgtcatcg acattctggt gtccatggtc tctgacagcg gcaccaagat cctgggcatg   4500
ctgagggtgc tgcggctgct gcggaccctg cgcccgctca gggtgatcag ccgggcgcag   4560
gggctgaagc tggtggtgga gacgctgatg tcctcactga aacccatcgg caacattgta   4620
gtcatctgct gtgccttctt catcattttc ggcatcttgg gggtgcagct cttcaaaggg   4680
aagtttttcg tgtgccaggg cgaggatacc aggaacatca ccaataaatc ggactgtgcc   4740
gaggccagtt accggtgggt ccggcacaag tacaactttg acaaccttgg ccaggccctg   4800
atgtccctgt tcgttttggc ctccaaggat ggttgggtgg acatcatgta cgatgggctg   4860
gatgctgtgg gcgtggacca gcagcccatc atgaaccaca acccctggat gctgctgtac   4920
ttcatctcgt tcctgctcat tgtggccttc tttgtcctga acatgtttgt gggtgtggtg   4980
gtggagaact tccacaagtg tcggcagcac caggaggaag aggaggcccg gcggcgggag   5040
gagaagcgcc tacgaagact ggagaaaaag agaaggaatc taatgctgga cgatgtaatt   5100
gcttccggca gctcagccag cgctgcgtca gaagcccagt gcaaacctta ctactccgac   5160
tactcccgct tccggctcct cgtccaccac ttgtgcacca gccactacct ggacctcttc   5220
atcacaggtg tcatcgggct gaacgtggtc accatggcca tggagcacta ccagcagccc   5280
cagattctgg atgaggctct gaagatctgc aactacatct tcactgtcat ctttgtcttg   5340
gagtcagttt tcaaacttgt ggcctttggt ttccgtcggt tcttccagga caggtggaac   5400
cagctggacc tggccattgt gctgctgtcc atcatgggca tcacgctgga ggaaatcgag   5460
gtcaacgcct cgctgcccat caaccccacc atcatccgca tcatgagggt gctgcgcatt   5520
```

-continued

```
gcccgagtgc tgaagctgct gaagatggct gtgggcatgc gggcgctgct ggacacggtg   5580
atgcaggccc tgccccaggt ggggaacctg ggacttctct tcatgttgtt gtttttcatc   5640
tttgcagctc tgggcgtgga gctctttgga gacctggagt gtgacgagac acacccctgt   5700
gagggcctgg gccgtcatgc cacctttcgg aactttggca tggccttcct aaccctcttc   5760
cgagtctcca caggtgacaa ttggaatggc attatgaagg acaccctccg ggactgtgac   5820
caggagtcca cctgctacaa cacggtcatc tcgcctatct actttgtgtc cttcgtgctg   5880
acggcccagt tcgtgctagt caacgtggtg atcgccgtgc tgatgaagca cctggaggag   5940
agcaacaagg aggccaagga ggaggccgag ctagaggctg agctggagct ggagatgaag   6000
accctcagcc cccagcccca ctcgccactg ggcagcccct tcctctggcc tggggtcgag   6060
ggccccgaca gccccgacag ccccaagcct ggggctctgc acccagcggc ccacgcgaga   6120
tcagcctccc acttttccct ggagcacccc acggacaggc agctgtttga caccatatcc   6180
ctgctgatcc agggctccct ggagtgggag ctgaagctga tggacgagct ggcaggccca   6240
gggggccagc cctctgcctt cccttctgcc cccagcctgg gaggctccga cccacagatc   6300
cctctagctg agatggaggc tctgtctctg acgtcagaga ttgtgtctga accgtcctgc   6360
tctctagctc tgacggatga ctctttgcct gatgacatgc acacactctt acttagtgcc   6420
ctggagagca atatgcagcc ccaccccacg gagctgccag gaccagactt actgactgtg   6480
cggaagtctg ggtcagccg aacgcactct ctgcccaatg acagctacat gtgtcggcat   6540
gggagcactg ccgaggggcc cctgggacac aggggctggg ggctccccaa agctcagtca   6600
ggctccgtct tgtccgttca ctcccagcca gcagatacca gctacatcct gcagcttccc   6660
aaagatgcac ctcatctgct ccagccccac agcgccccaa cctggggcac catccccaaa   6720
ctgcccccac caggacgctc cccttggct cagaggccac tcaggcgcca ggcagcaata   6780
aggactgact ccttggacgt tcagggtctg ggcagccggg aagacctgct ggcagaggtg   6840
agtgggccct ccccgcccct ggcccgggcc tactctttct ggggccagtc aagtacccag   6900
gcacagcagc actcccgcag ccacagcaag atctccaagc acatgacccc gccagcccct   6960
tgcccaggcc cagaacccaa ctggggcaag ggccctccag agaccagaag cagcttagag   7020
ttggacacgg agctgagctg gatttcagga gacctcctgc cccctggcgg ccaggaggag   7080
cccccatccc cacgggacct gaagaagtgc tacagcgtgg aggcccagag ctgccagcgc   7140
cggcctacgt cctggctgga tgagcagagg agacactcta tcgccgtcag ctgcctggac   7200
agcggctccc aaccccacct gggcacagac ccctctaacc ttgggggcca gcctcttggg   7260
gggcctggga gccggcccaa gaaaaaactc agcccgccta gtatcaccat agaccccccc   7320
gagagccaag gtcctcggac cccgcccagc cctggtatct gcctccggag gagggctccg   7380
tccagcgact ccaaggatcc cttggcctct ggcccccctg acagcatggc tgcctcgccc   7440
tccccaaaga aagatgtgct gagtctctcc ggtttatcct ctgacccagc agacctggac   7500
ccctgagtcc tgccccactt tcccactcac ctttctccac tgggtgccaa gtcctagctc   7560
ctcctcctgg gctatattcc tgacaaaagt tccatataga caccaaggag gcggaggcgc   7620
tcctccctgc ctcagtggct ctgggtacct gcaagcagaa cttccaaaga gagttaaaag   7680
cagcagcccc ggcaactctg gctccaggca gaaggagagg cccggtgcag ctgaggttcc   7740
cgacaccaga agctgttggg agaaagcaat acgtttgtgc agaatctcta tgtatattct   7800
attttattaa attaattgaa tctag                                         7825
```

-continued

<210> SEQ ID NO 121
<211> LENGTH: 3497
<212> TYPE: DNA
<213> ORGANISM: Homo sapiens

<400> SEQUENCE: 121

```
cggacgcggc cgccgccgtc gccgccatct gtcacctcca ctccggcatc agcagccagt     60
cgcccgtgtc ccgcctgtct cctcggcgga gcctgctgcc cgtcctgcca cctctctgct    120
ctgttcttgt ctctgccttc attcccgaat ggatctggta ggagtggcat cgcctgagcc    180
cgggacggca gcggcctggg gacccagcaa gtgtccatgg gctattcctc aaaatacaat    240
atcttgttct ttggctgatg taatgagtga acagctggcc aaagaattgc agttagaaga    300
agaagctgcc gtttttcctg aagttgctgt tgctgaagga ccatttatta ctggagaaaa    360
cattgatact tccagtgacc ttatgctggc tcagatgcta cagatggaat atgacagaga    420
atatgatgca cagcttaggc gtgaagaaaa aaaattcaat ggagatagca aagtttccat    480
ttcctttgaa aattatcgaa aagtgcatcc ttatgaagac agcgatagct ctgaagatga    540
ggttgactgg caggatactc gtgatgatcc ctacagacca gcaaaaccgg ttcccactcc    600
taaaaagggc tttattggaa aaggaaaaga tatcaccacc aaacatgatg aagtagtatg    660
tgggagaaag aacacagcaa gaatggaaaa ttttgcacct gagtttcagg taggagatgg    720
aattggaatg gatttaaaac tatcaaacca tgttttcaat gctttaaaac aacatgccta    780
ctcagaagaa cgtcgaagtg cccgcctaca tgagaaaaag gagcattcta cagcagaaaa    840
agcagttgat cctaagacac gtttacttat gtataaaatg gtcaactctg gaatgttgga    900
gacaatcact ggctgtatta gtacaggaaa ggagtctgtt gtctttcatg catatggagg    960
gagcatggag gatgaaaagg aagatagtaa agttatacct acagaatgtg ccatcaaggt   1020
atttaaaaca acccttaatg aatttaagaa tcgtgacaaa tatattaaag atgatttcag   1080
gtttaaagat cgcttcagta aactaaatcc acgtaagatc atccgcatgt gggcagaaaa   1140
agaaatgcac aatctcgcaa gaatgcagag agctggaatt ccttgtccaa cagttgtact   1200
actgaagaaa cacattttag ttatgtcttt tattggccat gatcaagttc cagcccctaa   1260
attaaaagaa gtaaagctca atagtgaaga aatgaaagaa gcctactatc aaactcttca   1320
tttgatgcgg cagttatatc atgaatgtac gcttgtccat gctgacctca gtgagtataa   1380
catgctgtgg catgctggaa aggtctggtt gatcgatgtc agtcagtcag tagaacctac   1440
ccaccctcac ggcctggagt tcttgttccg ggactgcagg aatgtctcgc agtttttcca   1500
gaaaggagga gtcaaggaag cccttagtga acgagaactc ttcaatgctg tttcaggctt   1560
aaacatcaca gcagataatg aagctgattt tttagctgag atagaagctt tggagaaaat   1620
gaatgaagat cacgttcaga agaatggaag gaaagctgct tcattttttga aagatgatgg   1680
agacccacca ctactatatg atgaatagca ctaataccca ctgcttcagt gttaacacag   1740
cagtgattgt cagctgccaa tagcaaatga agttatgggt gacttgaaat accaaaacct   1800
gaggagtggg caatggtgct tctgtgcttt tcccccttgt aacccatgtg ccagatgtgt   1860
ggaattttta gctcagcatt gagagaataa aatgtcacta cctctcatct tatgaacagg   1920
ataatataat tctttaacag ctataggtta tctggctgaa gtagacctaa ttttatgtga   1980
cttgtggtgt aaaatgtctt gatgataatt tttaaaactt gggtaacact tccaaatatg   2040
ggaggaaagg acagatgtgt ttacaaggga ggattttaca acatacttgc tttattcacc   2100
tccctgtttt gtgttgcgtc tttccttgaa tattttattg gcccagagtt agcctttctc   2160
```

```
aattatgttt ccagactgtg gccgtgattc taaaggaaaa tgtgtgctct ttagtgggta   2220

gaacaaatgg aaatttggtt tcagaatggc tgacagaaat cgacataagt catgtaattt   2280

ttgttgatat atcatgaaaa tgaacagaat tctttttcca tacttatatc taagaaaagg   2340

catcataggt ttctgaaaga gataactata taacagcttt ttaactatcc agtcaacttt   2400

cagcttttct acatttaggt aaaatggtta ggatataact catggtgtgg ctaatctaca   2460

tttatcaata aaatgtaaat tatctgaaag gacagaatat aagatttaac catgtttgac   2520

gtattttaat ttagttaatg aagcaaaatt cagtttatat ttcactagaa ctgtgtactt   2580

gattgatttt cagagaaata tcacaaatta gaaatattaa atctaaggat gaaaggtata   2640

tataaaacaa tttgggggcc aggcacgatg gctcaaacct gtaatcccag cactttggga   2700

gaccaaggcg ggtggatcac ttgaggtcag gagttcaaga ccagcctggg caacatggcg   2760

aaaccctgtc tctactaaaa atacaaaaat tagccgggtg tggtggcact tctctgtaat   2820

ctcagcttct caggaggctg agacaggaga atcgcttgaa cccgggaggc agaggttgca   2880

gtgagctgag atcatgccac tgcactccgg cctaggtgac agagggaaac tccatctcca   2940

ggaaaaaaaa aaaaaaaccc aatttggata ccaaattaat caactaattt gagctatctg   3000

gccttactct tagtagtttt tagtacgtgc tggacaccac ttttaaaaag caatcactgt   3060

gctagaaaag tatattggct ttgttaggat taaagttcat taacttcaat gtaatcatgc   3120

ctcctattac tgaagtcaga ttggaaccac taaagatcca aactttctgt ctggtaatag   3180

aaagtaaaaa tctagacatc atttacattt gagaagctgt ttttaacatt attttaaaat   3240

gccaaatatg ttctttctag aaaaatattt atttttgttt ttgttggata gcttttaatt   3300

acatttcaga gaggtgtaat tttgggtaga tgctcattac atttttgaaa ggtttatgat   3360

tccaaaataa agatttatat gactggtgat actggcttta cagaaatttc agagaactaa   3420

tttttaaaat ctttagcatt taaaactttt tttgttttgt tttctgacat attctgacaa   3480

agagcagcaa accactg                                                  3497
```

<210> SEQ ID NO 122
<211> LENGTH: 1966
<212> TYPE: DNA
<213> ORGANISM: Homo sapiens

<400> SEQUENCE: 122

```
gaggggcgaa aggacatttt ttttttcttt gctcccgcct ctgttcttcc cccacctgcc     60

acgtacagag cccaagttct cgctaggctt gttgggtcag cgcgattggc cggggcccgc    120

gcgagcctgc gagcgaggtg cggcggtcgc gaagggcaac cgagggggcc gtgaccaccg    180

cctccccgcg acgccccagt ccagtggcct cgcgtccgcc cattcagcgg agacctgcgg    240

agaggcggcg gccgcggcct ccgcaagccg tctttctcta gagttgtata tatagaacat    300

cctggagtcc accatgaacg gacagttgga tctaagtggg aagctaatca tcaaagctca    360

acttggggag gatattcggc gaattcctat tcataatgaa gatattactt atgatgaatt    420

agtgctaatg atgcaacgag ttttcagagg aaaacttctg agtaatgatg aagtaacaat    480

aaagtataaa gatgaagatg gagatcttat aacaattttt gatagttctg acctttcctt    540

tgcaattcag tgcagtagga tactgaaact gacattattt gttaatggcc agccaagacc    600

ccttgaatca agtcaggtga aatatctccg tcgagaactg atagaacttc gaaataaagt    660

gaatcgttta ttggatagct tggaaccacc tggagaacca ggaccttcca ccaatattcc    720
```

-continued

```
tgaaaatgat actgtggatg gtagggaaga aaagtctgct tctgattctt ctggaaaaca    780

gtctactcag gttatggcag caagtatgtc tgcttttgat cctttaaaaa accaagatga    840

aatcaataaa aatgttatgt cagcgtttgg cttaacagat gatcaggttt cagggccacc    900

cagtgctcct gcagaagatc gttcaggaac acccgacagc attgcttcct cctcctcagc    960

agctcaccca ccaggcgttc agccacagca gccaccatat acaggagctc agactcaagc   1020

aggtcagatt gaaggtcaga tgtaccaaca gtaccagcaa caggccggct atggtgcaca   1080

gcagccgcag gctccacctc agcagcctca acagtatggt attcagtatt cagcaagcta   1140

tagtcagcag actggacctc aacaacctca gcagttccag ggatatggcc agcaaccaac   1200

ttcccaggca ccagctcctg ccttttctgg tcagcctcaa caactgcctg ctcagccgcc   1260

acagcagtac caggcgagca attatcctgc acaaacttac actgcccaaa cttctcagcc   1320

tactaattat actgtggctc ctgcctctca acctggaatg gctccaagcc aacctggggc   1380

ctatcaacca agaccaggtt ttacttcact tcctggaagt accatgaccc ctcctccaag   1440

tgggcctaat ccttatgcgc gtaaccgtcc tccctttggt cagggctata cccaacctgg   1500

acctggttat cgataaggag gctcctctac accaattaat gtagctgcta gctattggcc   1560

tcccaaaaga ctccagtact attttaattt gtattgaaga agttcagaaa tttaaaagca   1620

gagcattttt tatgatatca ttgttggtgt taattgaaag tataatttgc tggaacacaa   1680

agaccaaaat gaaagttttt tcctccctgc ttaaaaatgt agcagcttct tagttacttt   1740

ggaacactac tcttacatgt ataaagtgat tgacttgact ttctagcttc ccttgtccgg   1800

aggatattaa aatgctaggg tgaggtttag ccatcttact tggcttttta ctattaacat   1860

gatgtactaa agtagagccc tttgagaata caagatatta tgtataaaat gtaacactga   1920

tgataggtta ataaagatga ttgaatccaa aaaaaaaaaa aaaaaa                  1966


<210> SEQ ID NO 123
<211> LENGTH: 419
<212> TYPE: DNA
<213> ORGANISM: Homo sapiens

<400> SEQUENCE: 123

aagggcccct cattttggca gaacttacca tgtcgaccag ccgcaaatta aagagtcatg     60

gcatgaggag gagcaagagc cgatctcctc acaagggagt caagagaggt ggcagcaaaa    120

gaaaataccg taagggcaac ctgaaaagta ggaaacgggg cgatgacgcc aatcgcaatt    180

accgctccca cttgtgagcc cccagcgggc tctgccctgg tgcgcttcac acagcaccaa    240

gcagcaacaa gaacagcaga aggggaactg ccaaggagac ctgatgttag atcaaagcca    300

gagaggagcc tatggaatgt ggatcaaatg ccagttgtga cgaaatgagg aatgtatatg    360

ttggctgttt ttccccaaca tctcaataaa actttgaaag cagaaaaaaa aaaaaaaaa     419


<210> SEQ ID NO 124
<211> LENGTH: 2679
<212> TYPE: DNA
<213> ORGANISM: Homo sapiens

<400> SEQUENCE: 124

cggaccgtgc aatggcccag cgtaagaatg ccaagagcag cggcaacagc agcagcagcg     60

gctccggcag cggtagcacg agtgcgggca gcagcagccc cggggcccgg agagagacaa    120

agcatggagg acacaagaat gggaggaaag gcggactctc aggaacttca ttcttcacgt    180

ggtttatggt gattgcattg ctgggcgtct ggacatctgt agctgtcgtt tggtttgatc    240
```

```
ttgttgacta tgaggaagtt ctaggaaaac taggaatcta tgatgctgat ggtgatggag    300
attttgatgt ggatgatgcc aaagttttat taggacttaa agagagatct acttcagagc    360
cagcagtccc gccagaagag gctgagccac acactgagcc cgaggagcag gttcctgtgg    420
aggcagaacc ccagaatatc gaagatgaag caaaagaaca aattcagtcc cttctccatg    480
aaatggtaca cgcagaacat gttgagggag aagacttgca acaagaagat ggacccacag    540
gagaaccaca acaagaggat gatgagtttc ttatggcgac tgatgtagat gatagatttg    600
agaccctgga acctgaagta tctcatgaag aaaccgagca tagttaccac gtggaagaga    660
cagtttcaca agactgtaat caggatatgg aagagatgat gtctgagcag gaaaatccag    720
attccagtga accagtagta gaagatgaaa gattgcacca tgatacagat gatgtaacat    780
accaagtcta tgaggaacaa gcagtatatg aacctctaga aaatgaaggg atagaaatca    840
cagaagtaac tgctccccct gaggataatc ctgtagaaga ttcacaggta attgtagaag    900
aagtaagcat ttttcctgtg gaagaacagc aggaagtacc accagatact taaagcttca    960
aaaagactgc ccctaccacc acaggaggac cagcctaacc atacgctcca aaagatggct   1020
gtgatagatc ttgtgaagca attactgagc agatcaagat ctttgggaag gaacactaaa   1080
gatgttttga atgaattata gtccactggc attttagtgt attttttttt ctttttacaa   1140
acacacattt ctaaaaatgt catgttacat tcctgcatgt ccctttttgat agcattagtg   1200
gatccattgg atttcttttt tctttttgtg agacagcttt tagtcttacc tgaatttatg   1260
tgtgtttttc cgacagtggt taataattat attggtgatg tagcagcaat tgtgttggca   1320
gggtttttcat atattattag taattaacac taactgttgg actgacttgt gtacactgtg   1380
ttaaacatga tttaaaagct attaagagta ctttgtgtta gcactcttaa aaacgctaac   1440
agagatcatc attagctgtg aagatttgag ttgtatatac ctgcactgat attcttatca   1500
aaaatttcta cattagcttt aagtgttcag attaacactt ttgaaatttt tgtagctttt   1560
agctgattaa ttagaaaaat taatatttca gtgaaagttt taaattatca ttatttattt   1620
ttttaaatga gaggggaaag ctgaaattcc ttgttaagac acaaggaaaa agaatggccc   1680
tactattatc atgcaaaaat gctttgttgg cacctcagat taatcatata atagctatag   1740
tctcttcagc atttgtttaa attttagaaa acctgtataa attactggtg cataacttaa   1800
agattattct gcctttggct aattgagtaa ttcccctcca gcactagaga ccgctcagtg   1860
ctcttactag atgaactcag taacgccttg agctgggttg attgaggatg tgtgaaaagc   1920
tcacagagcc cgatgcctgc tgctatttca cggcaatgag ccttttttctt tctacactga   1980
agattttctt cttatttaat gtggtttatt ttgggctcag aaataattgc tctgttgaaa   2040
ataatccttt gtcagaaaag aaggtagcta ccacatcatt ttgaaaggac catgagcaac   2100
tataagcaaa gccataagaa gtggtttgat cgatatatta ggggtagctc ttgattttgt   2160
taacattaag ataaggtgac tttttccccc tgcttttagg attaaaatca aagatacttc   2220
tatattttta tcactataga tcatagttat tatacaatgt agtgagtcct gcatgggtac   2280
tcgatgtgta atgaaacctg aaataataag ataataagaa aagcaataat tttctaaagc   2340
tgtgctgtcg gtgatacaga gacgatactc aaattataat aaaactcttc attttgtgaa   2400
ttatagaagc tactttttat aaagccatat ttttttaggg aaactaagga gtgacataga   2460
actgatgaat gagcaaaagt aagttttgct ggatttttgt agaactctgg acgttgagga   2520
ttcattatgc tgtggttaac tttaaatatt tttgaattcc aaatatctga attaatgagc   2580
```

-continued

```
cttgtgttta caaatatgtg ccattgtgca acatcggtgg attttctaaa aataatgtaa   2640

atgtcttcta ttaaatgttg agtgcaataa aatccagaa                          2679


<210> SEQ ID NO 125
<211> LENGTH: 1279
<212> TYPE: DNA
<213> ORGANISM: Homo sapiens

<400> SEQUENCE: 125

gcggccgcgt cgacatgcag tgtgcctaaa acctgccagc agtacttttg agtttttttt     60

tttgttttgt tttactttag catttattat tcatggattg aagaaatcaa aatggctgaa    120

gataaagaga caaagcatgg aggacacaag aatgggagga aaggcggact ctcaggaact    180

tcattcttca cgtggtttat ggtgattgca ttgctgggcg tctggacatc tgtagctgtc    240

gtttggtttg atcttgttga ctatgaggaa gttctaggaa aactaggaat ctatgatgct    300

gatggtgatg gagattttga tgtggatgat gccaaagttt tattagaagg acccagtggg    360

gtagccaaga gaaaaactaa ggctaaagtt aaagaactca ctaaagaaga gctcaagaag    420

gagaaagaga aacctgagtc aaggaaggaa agtaagaatg aagagagaaa aaaggggaag    480

aaagaggatg tccgaaagga taagaaaatt gctgatgcag acctatccag gaaggagtct    540

cctaagggta aaaaggacag agaaaaagag aaagtggacc tagaaaaaag tgctaaaacc    600

aaggaaaata ggaaaaaatc aacaaatatg aaggatgttt ctagtaaaat ggcatcccga    660

gacaaagatg acagaaagga aagtagaagt tctaccagat atgcacactt aacaaaggga    720

aatacccaga aaagaaacgg ctaaagctct ggcatcatca tcccagaaca tggtcatgtt    780

ccagattgca gtttgttaca aaaaagcatg gaaaatgtaa tattgctctg attggtgagg    840

gtgtgtaaat tagccattga atgtatcatt ggtgcttagc aagtaaatta cctgaaattt    900

aaatataccg tctcatactt ctaaatgtaa aaacatttta aaaatgtcac agaatatgat    960

gtaataactt ctatttattg atcatttatt gatcatgtat tcagataaat gtatatgtat   1020

catgaatttt tatggattaa tatattgaat actttcattg acgttaaata agaatattaa   1080

gattttaaat gttaccctgt gcataatgcc ttgtaacttt ttcaagtatg ctaaatactc   1140

agggagatgg atttgctcgt tgttttcttc cctccttccc cttcctgctt ccctgttttc   1200

tctttcgtgg acacctcccc aggctcatgt gccaccacct tccctcctct ccagccctcc   1260

cagccctccc gcagcctttt                                               1279


<210> SEQ ID NO 126
<211> LENGTH: 5119
<212> TYPE: DNA
<213> ORGANISM: Homo sapiens

<400> SEQUENCE: 126

ccccagccgc atgacgcgcg gaggaggcag cgggacgagc gcgggagccg ggaccgggta     60

gccgcgcgct gggggtgggc gccgctcgct ccgccccgcg aagcccctgc gcgctcaggg    120

acgcggcccc cccgcggcag ccgcgctagg ctccggcgtg tggccgcggc cgccgccgcc    180

gctgccatgt ctccggggaa gcccggggcg ggcggagcgg ggacgaggcg gaccggctgg    240

cggaggagga ggcgaaggag acggcaggag gcggcgacga cggtgcccgg gctcgggcgc    300

acggcggggc ccgattcgcg cgtccggggc acgttccagg gcgcgcgggg catgaagccg    360

gcggcgcggg aggcgcggct gcctccgcgc tcgcccgggc tgcgctgggc gctgccgctg    420

ctgctgctgc tgctgcgcct gggccagatc ctgtgcgcag gtggcacccc tagtccaatt    480
```

-continued

```
cctgaccctt cagtagcaac tgttgccaca ggggaaaatg gcataacgca gatcagcagt    540
acagcagaat cctttcataa acagaatgga actggaacac ctcaggtgga aacaaacacc    600
agtgaggatg gtgaaagctc tggagccaac gatagtttaa gaacacctga acaaggatct    660
aatgggactg atggggcatc tcaaaaaact cccagtagca ctgggcccag tcctgtgttt    720
gacattaaag ctgtttccat cagtccaacc aatgtgatct taacttggaa aagtaatgac    780
acagctgctt ctgagtacaa gtatgtagta aagcataaga tggaaaatga gaagacaatt    840
actgttgtgc atcaaccatg gtgtaacatc acaggcttac gtccagcgac ttcatatgta    900
ttctccatca ctccaggaat aggcaatgag acttggggag atcccagagt cataaaagtc    960
atcacagagc cgatcccagt ttctgatctc cgtgttgccc tcacgggtgt gaggaaggct   1020
gctctctcct ggagcaatgg caatggcact gcctcctgcc gggttcttct tgaaagcatt   1080
ggaagccatg aggagttgac tcaagactca agacttcagg tcaatatctc gggcctgaag   1140
ccaggggttc aatacaacat caacccgtat cttctacaat caaataagac aaagggagac   1200
cccttgggca cagaaggtgg cttggatgcc agcaatacag agagaagccg ggcagggagc   1260
cccaccgccc ctgtgcatga tgagtccctc gtgggacctg tggacccatc ctccggccag   1320
cagtcccgag acacggaagt cctgcttgtc gggttagagc ctggcacccg atacaatgcc   1380
accgtttatt cccaagcagc gaatggcaca gaaggacagc cccaggccat agagttcagg   1440
acaaatgcta ttcaggtttt tgacgtcacc gctgtgaaca tcagtgccac aagcctgacc   1500
ctgatctgga aagtcagcga taacgagtcg tcatctaact atacctacaa gatacatgtg   1560
gcgggggaga cagattcttc caatctcaac gtcagtgagc ctcgcgctgt catccccgga   1620
ctccgctcca gcaccttcta caacatcaca gtgtgtcctg tcctaggtga catcgagggc   1680
acgccgggct tcctccaagt gcacaccccc cctgttccag tttctgactt ccgagtgaca   1740
gtggtcagca cgacggagat cggcttagca tggagcagcc atgatgcaga atcatttcag   1800
atgcatatca cacaggaggg agctggcaat tctcgggtag aaataaccac caaccaaagt   1860
attatcattg gtggcttgtt ccctggaacc aagtattgct ttgaaatagt tccaaaagga   1920
ccaaatggga ctgaaggggc atctcggaca gtttgcaata gaactgttcc cagtgcagtg   1980
tttgacatcc acgtggtcta cgtcaccacc acggagatgt ggctggactg gaagagccct   2040
gacggtgctt ccgagtatgt ctaccattta gtcatagagt ccaagcatgg ctctaaccac   2100
acaagcacgt atgacaaagc gattactctc cagggcctga ttccgggcac cttatataac   2160
atcaccatct ctccagaagt ggaccacgtc tgggggggacc ccaactccac tgcacagtac   2220
acacggccca gcaatgtgtc caacattgat gtaagtacca acaccacagc agcaacttta   2280
agttggcaga actttgatga cgcctctccc acgtactcct actgccttct tattgagaag   2340
gctggaaatt ccagcaacgc aacacaagta gtcacggaca ttggaattac tgacgctaca   2400
gtcactgaat taatacctgg ctcatcatac acagtggaga tctttgcaca agtaggggat   2460
gggatcaagt cactggaacc tggccggaag tcattctgta cagatcctgc gtccatggcc   2520
tccttcgact gcgaagtggt ccccaaagag ccagccctgg ttctcaaatg gacctgccct   2580
cctggcgcca atgcaggctt tgagctggag gtcagcagtg gagcctggaa caatgcgacc   2640
cacctggaga gctgctcctc tgagaatggc actgagtata gaacggaagt cacgtatttg   2700
aatttttcta cctcgtacaa catcagcatc accactgtgt cctgtggaaa gatggcagcc   2760
cccacccgga acacctgcac tactggcatc acagatcccc ctcctccaga tggatcccct   2820
```

-continued

```
aatattacat ctgtcagtca caattcagta aaggtcaagt tcagtggatt tgaagccagc   2880

cacggaccca tcaaagccta tgctgtcatt ctcaccaccg gggaagctgg tcacccttct   2940

gcagatgtcc tgaaatacac gtatgacgat ttcaaaaagg gagcctcaga tacttatgtg   3000

acatacctca taagaacaga agaaaaggga cgttctcaga gcttgtctga agttttgaaa   3060

tatgaaattg acgttgggaa tgagtcaacc acacttggtt attacaatgg gaagctggaa   3120

cctctgggct cctaccgggc ttgtgtggct ggcttcacca acattacctt ccaccctcaa   3180

aacaaggggc tcattgatgg ggctgagagc tatgtgtcct tcagtcgcta ctcagatgct   3240

gtttccttgc cccaggatcc aggtgtcatc tgtggagcgg tttttggctg tatctttggt   3300

gccctggtta ttgtgactgt gggaggcttc atcttctgga gaaagaagag gaaagatgca   3360

aagaataatg aagtgtcctt ttctcaaatt aaacctaaaa aatctaagtt aatcagagtg   3420

gagaattttg aggcctactt caagaagcag caagctgact ccaactgtgg gttcgcagag   3480

gaatacgaag atctgaagct tgttggaatt agtcaaccta aatatgcagc agaactggct   3540

gagaatagag gaaagaatcg ctataataat gttctgccct atgatatttc ccgtgtcaaa   3600

ctttcggtcc agacccattc aacggatgac tacatcaatg ccaactacat gcctggctac   3660

cactccaaga aagattttat tgccacacaa ggacctttac cgaacacttt gaaagatttt   3720

tggcgtatgg tttgggagaa aaatgtatat gccatcatta tgttgactaa atgtgttgaa   3780

cagggaagaa ccaaatgtga ggagtattgg ccctccaagc aggctcagga ctatggagac   3840

ataactgtgg caatgacatc agaaattgtt cttccggaat ggaccatcag agatttcaca   3900

gtgaaaaata tccagacaag tgagagtcac cctctgagac agttccattt cacctcctgg   3960

ccagaccacg gtgttcccga caccactgac ctgctcatca acttccggta cctcgttcgt   4020

gactacatga agcagagtcc tcccgaatcg ccgattctgg tgcattgcag tgctggggtc   4080

ggaaggacgg gcactttcat tgccattgat cgtctcatct accagataga gaatgagaac   4140

accgtggatg tgtatgggat tgtgtatgac cttcgaatgc ataggccttt aatggtgcag   4200

acagaggacc agtatgtttt cctcaatcag tgtgttttgg atattgtcag atcccagaaa   4260

gactcaaaag tagatcttat ctaccagaac acaactgcaa tgacaatcta tgaaaacctt   4320

gcgcccgtga ccacatttgg aaagaccaat ggttacatcg cctaattcca aaggaataac   4380

ctttctggag tgaaccagac cgtcgcaccc acagcgaagg cacatgcccc gatgtcgaca   4440

tgtttttata tgtctaatat cttaattctt tgttctgttt tgtgagaact aattttgagg   4500

gcatgaagct gcatatgata gatgacaaat tggggctgtc gggggctgtg gatgggtggg   4560

gagcaaatca tctgcattcc tgatgaccaa tgggatgagg tcactttttt tttttttcccc   4620

cttgaggatt gcggaaaacc aggaaaaggg atctatgatt tttttttcca aaacaatttc   4680

tttttttaaaa agactatttt atatgattca catgctaaag ccaggattgt gttgggttga   4740

atatatttta agtatcagag gtctattttt acctactgtg tcttggaatc tagccgatgg   4800

aaaataccta attgtggatg atgattgcgc agggaggggt acgtggcacc tcttccgaat   4860

gggttttcta tttgaacatg tgccttttct gaattatgct tccacaggca aaactcagta   4920

gagatctata tttttgtact gaatctcata attggaatat acggaatatt taaacagtag   4980

cttagcatca gaggtttgct tcctcagtaa catttctgtt ctcatttgat caggggaggc   5040

ctctttgccc cggccccgct tcccctgccc ccgtgtgatt tgtgctccat tttttcttcc   5100

cttttccctc ccagttttc                                                 5119
```

-continued

<210> SEQ ID NO 127
<211> LENGTH: 4009
<212> TYPE: DNA
<213> ORGANISM: Homo sapiens

<400> SEQUENCE: 127
gagtccggaa gcgcctgcgc gcgctcctcc gtacgagaac tagttttgtt ccgtgccctc 60
tggactggaa ccttttggag agaacccccg gcaggaccaa ccccgcaccc gccagcaccg 120
cggcaatgtc cagcaatagt tttccttaca atgagcagtc cggaggaggg gaggcgacgg 180
agctgggtca ggaggcgacc tcaaccattt ccccctcggg ggccttcggc ctctttagca 240
gcgatttgaa gaagaatgaa gatctaaagc aaatgttaga gagcaacaaa gattctgcta 300
aactggatgc tatgaagcgg attgttggga tgattgcaaa agggaaaaat gcatctgaac 360
tgtttcctgc tgttgtgaag aatgtggcca gtaaaaatat tgagatcaag aagttggtat 420
atgtttacct ggttcgatat gctgaagaac agcaggatct tgcactcctg tccataagca 480
cttttcagcg agctctgaag gacccaaacc aactaattcg tgcaagcgct ttgagagttc 540
tgtcaagtat tagagtgcca attattgtac ctatcatgat gcttgctatt aaggaagctt 600
ctgctgactt atcaccatat gttaggaaga atgcagccca tgcaatacaa aaattataca 660
gccttgatcc agagcagaag gaaatgttaa ttgaagtaat tgaaaaactt ctgaaagata 720
aaagcacatt ggtagctggc agtgttgtga tggcttttga agaagtatgc ccggacagaa 780
tagatctgat tcataaaaat taccgcaagc tatgtaactt actagtggat gttgaagagt 840
gggggcaggt tgtcataatc cacatgctaa ctcgatatgc tcggacacag tttgtcagcc 900
cttggaaaga gggtgatgaa ttagaagaca atggaaagaa tttctacgaa tctgatgatg 960
atcagaagga aaagactgac aaaaagaaga agccgtatac tatggatcca gatcatagac 1020
tcttaattag aaatacaaag cctttgcttc agagcaggaa tgctgcggtg gttatggcag 1080
ttgctcagct gtattggcac atatcaccaa aatctgaagc tggcataatt tctaaatcac 1140
tagtgcgttt acttcgtagc aatagggagg tgcagtatat tgtcctacaa aatatagcaa 1200
ctatgtcaat tcaaagaaag ggatgtttg aaccttatct gaagagtttc tatgttaggt 1260
caactgatcc aactatgatc aagacactga agcttgaaat tttgacaaac ttggcaaatg 1320
aagccaacat atcaactctt cttcgagaat ttcagaccta tgtgaaaagc caggataaac 1380
aatttgcagc agccactatt cagactatag gcagatgtgc aaccaacatc ttggaagtca 1440
ctgacacgtg cctcaatggc ttggtctgtc tgctgtccaa cagggatgaa atagttgttg 1500
ctgaaagtgt ggttgttata aagaaattac tgcaaatgca acctgcacaa catggtgaaa 1560
ttattaaaca tatggccaaa ctcctggaca gtatcactgt tcctgttgct agagcaagta 1620
ttctttggct aattggagaa aactgtgaac gagttcctaa aattgcccct gatgttttga 1680
ggaagatggc taaaagcttc actagtgaag atgatctggt aaaactgcag atattaaatc 1740
tgggagcaaa attgtattta accaactcca aacagacaaa attgcttacc cagtacatat 1800
taaatctcgg caagtatgat caaaactacg acatcagaga ccgtacaaga tttattaggc 1860
agcttattgt tccgaatgta aagagtggag ctttaagtaa atatgccaaa aaaatattcc 1920
tagcacaaaa gcctgcacca ctgcttgagt ctccttttaa agatagagat catttccagc 1980
ttggcacctt atctcatact ctcaacatta aagctactgg gtacctggaa ttatctaatt 2040
ggccagaggt ggcgcccgac ccatcagttc gaaatgtaga agtaatagag ttggcaaaag 2100
aatggacccc agcaggaaaa gcaaagcaag agaattctgc taagaagttt tattctgaat 2160

-continued

```
ctgaggaaga ggaggactct tctgatagta gcagtgacag tgagagtgaa tctggaagtg   2220

aaagtggaga acaaggcgaa agtggggagg aaggagacag caatgaggac agcagtgagg   2280

actcctccag tgagcaggac agtgagagtg gacgggagtc aggcctagaa aacaaaagaa   2340

cagccaagag gaactcaaaa gccaaaggaa aaagtgattc tgaagatggg gagaaggaaa   2400

atgaaaaatc taaaacttca gattcttcaa atgacgaatc tagttcaata gaagacagtt   2460

cttccgattc tgaatcagag tcagaacctg aaagtgaatc tgaatccaga agagtcacta   2520

aggagaaaga aaagaaaaca aagcaagata gaactcctct taccaaagat gtttcacttc   2580

tagatctgga tgattttaac ccagtatcca ctccagttgc acttcccaca ccagctcttt   2640

ctccaagttt gatggctgat cttgaaggtt tacacttgtc aacttcctct tcagtcatca   2700

gtgtcagtac tcctgcattt gtaccaacga aaactcacgt gctgcttcat cgaatgagtg   2760

gaaaaggact agctgcccat tatttctttc caagacagcc ttgcattttt ggtgataaga   2820

tggtctctat acaaataaca ctgaataaca ctactgatcg aaagatagaa aatatccaca   2880

taggggaaaa aaaacttcct ataggcatga aaatgcatgt ttttaatcca atagactctc   2940

ttgagcctga gggatccatt acagtttcaa tgggtattga cttttgtgat tctactcaga   3000

ctgccagttt ccagttgtgt accaaggatg attgcttcaa tgttaatatt cagccacctg   3060

ttggagaact gcttttacct gtggccatgt cagagaaaga ttttaagaaa gagcaaggag   3120

tgctaacagg aatgaatgaa acttctgctg taatcattgc tgcaccacag aatttcactc   3180

cctctgtgat ctttcagaag gttgtaaatg tagccaatgt aggtgcagtc ccttctggcc   3240

aggataatat acacaggttt gcagctaaaa ctgtgcacag tgggtcattg atgctagtca   3300

cagtggaact gaaggaaggc tctacagccc agcttatcat aaacactgag aaaactgtga   3360

ttggctctgt tctgctgcgg gaactgaagc ctgtcctgtc tcaggggtaa cctgcttaca   3420

tctggacttt agaatctggc acacaacaaa agtgcctggc atccactact gctgcctttc   3480

atttataata atagcccttc catctggcag tgggggtaga atacactctt gacattcttg   3540

tctcctgctt tagaatgcta gtgtgtatct atcatgtatg caatactttc ccccttttg    3600

ctttgctaac caaagagcat atattttact gtcagttgtc tcaactcttg aatccatgtg   3660

gcgttttctc tgtcctgctg cttcttttgg cctcctcgtt ttccttctct tttcgacaa    3720

tggtagacat gaatgagata tttaaagttc attggaaatc ttcttcccta cagcagtaag   3780

caaaaattag caaagagata gtctaaatgg cctctcagct tggtatgtga aaatgagatc   3840

acatactttt taaatccaaa tacaaaagca tagtctctgc aagattttgt tctttgaatt   3900

tcttgatatt gtaattgatt attgataact gtcatcatga aattatctct caataataag   3960

ataaataaac tagcatatga atcataaaaa aaaaaaaaaa aaaaaaaaa               4009
```

<210> SEQ ID NO 128
<211> LENGTH: 3863
<212> TYPE: DNA
<213> ORGANISM: Homo sapiens

<400> SEQUENCE: 128

```
gagatggaga ctcgctctgt cacccaggct ggagtgcaat ggtgagatct cggctcactg     60

caacctccac ctcctgggtt caggcgattc tcctgcctcc caatcctagt agctgggagt    120

atcaggtgag tcgcagcccc aacgcacgcc cggcataatt tttttatttt tagtcgagac    180

gggtttcacc acgttggcca ggatggtctc gaactcctga cctcaggtga tccacccgcc    240

tcggcctccc aaagcactgg gattacaggc gtgagccacc gcgcccggcc tccatatcca    300
```

-continued

```
ttcttgggaa cacttgttgc ttagctgaac ggagcccgca tcctgctgtg gcggcactcg    360
ccccggtgct ggtctgagca gacgcctcct ttctcttgca gaagaagtaa gtgaggaaga    420
aatgagtgaa gatgaagaac gagaaaatga aaaccacctc ttggttgttc cagagtcacg    480
gttcgaccga gattccgggg agagtgaaga agcagaggaa gaagtgggtg agggaacgcc    540
gcagagcagc gccctgacag agggcgacta tgtgcccgac tcccctgccc tgtcgcccat    600
cgagctcaag caggagctgc ccaagtacct gccggccctg cagggctgcc ggagcgtcga    660
ggagttccag tgcctgaaca ggatcgagga gggcacctat ggagtggtct acagagcaaa    720
agacaagaaa acagatgaaa ttgtggctct aaagcggctg aagatggaga aggagaagga    780
gggcttcccg atcacgtcgc tgagggagat caacaccatc ctcaaggccc agcatcccaa    840
catcgtcacc gttagagaga ttgtggtggg cagcaacatg gacaagatct acatcgtgat    900
gaactatgtg gagcacgacc tcaagagcct gatggagacc atgaaacagc ccttcctgcc    960
aggggaggtg aagaccctga tgatccagct gctgcgtggg gtgaaacacc tgcacgacaa   1020
ctggatcctg caccgtgacc tcaagacgtc caacctgctg ctgagccacg ccggcatcct   1080
caaggtgggt gacttcgggc tggcgcggga gtacggatcc cctctgaagg cctacacccc   1140
ggtcgtggtg accctgtggt accgcgcccc agagctgctg cttggtgcca aggaatactc   1200
cacggccgtg gacatgtggt cagtgggttg catcttcggg gagctgctga ctcagaagcc   1260
tctgttcccc gggaagtcag aaatcgatca gatcaacaag gtgttcaagg atctggggac   1320
ccctagtgag aaaatctggc ccggctacag cgagctccca gcagtcaaga agatgacctt   1380
cagcgagcac ccctacaaca acctccgcaa gcgcttcggg gctctgctct cagaccaggg   1440
cttcgacctc atgaacaagt tcctgaccta cttccccggg aggaggatca gcgctgagga   1500
cggcctcaag catgagtatt tccgcgagac cccccctccc atcgacccct ccatgttccc   1560
cacgtggccc gccaagagcg agcagcagcg tgtgaagcgg ggcaccagcc cgaggccccc   1620
tgagggaggc ctgggctaca gccagctggg tgacgacgac ctgaaggaga cgggcttcca   1680
ccttaccacc acgaaccagg gggcctctgc cgcgggcccc ggcttcagcc tcaagttctg   1740
aaggtcagag tggaccccgt catggggaga actcagccgg gaccacaggc gtggctactg   1800
cggctggagc tgcgatgaga ctcggaactc ctcgtcttac tttgtgctcc atgttttgtt   1860
tttgtatttt ggtttgtaaa tttgtagaat taaatcattt tccttgtaaa cccgaattcg   1920
ggaccatcac agtttgatta gcctcagcct caagagctgg cacatgcttg tgaacttgtg   1980
ctttcatatt ttcctaacct gtgtgctctt tgtgggagga ataacccaga ctaggaatgc   2040
cagcatctgc caagcagttg ggataattct tcactattcc acccttgcca cagtactatg   2100
ggtaggagtg acagctcgaa atatctacaa acaagtcact aaaaaagcta aaagatgcca   2160
ggatcctgat gaaccaccac ctccaccaag accaatgctc agattttacc tgattggtgg   2220
tggtatcccc atcattgttt gcggcataac tgcaggcagc gaacattaag aattacggca   2280
gtcggccaaa cgcaccctat tgctggatgg catgggaacc ctccttggga gccttctatg   2340
ggccagccag cttcagcact tttgtaaact gcatgtactt tctgagcata tttattcagt   2400
tgaaaagaca ccctgagcgc aaatatgagc ttaaggagcc cactggccag caacagagat   2460
tggcatgcca atgaaaatgg cgaaataaat catcaggaaa tcatttcttt gtctctgatt   2520
tctacatcag ccttggaaaa tgagcacact tttcattctc agctcttggg gccagcctta   2580
ctttgctctt atatgttgca ctgtggatgt ttggggcttt ggctgtttct ttgtattacc   2640
```

-continued

```
ctttggactt ggtttttagc ttcgtttttg gagccacaag tttaagcttc agtgcattct   2700

tcatggtcca ccattgtgtt aatagggagg atcttagact tgcgtggatc atgacttgct   2760

gcccaggacg gagctcgtat tcagtgcaag tcaacgtcca gcccccccaac tctaatggga   2820

cgaatggaga ggcacccaaa tgccccaata gcagtgcgga gtcttcatgc acaaacaaaa   2880

gtgattcaag cttcaaaatt cctcccaggg ctgcaaatta acaaacttgc aggcggctgc   2940

agctcagtgc catgccaatt ctttaccttt gaactccacc cctcagcttg ataatagtct   3000

gacagaacat tcaatggaca atgatattaa aatgcacgct ggcgccttta gaagttcagt   3060

ttcgaacaaa tgtgcactca agccgccacc ataaaaacag aagtaaagga caccgggcaa   3120

gccgactcac agtcctgaga gaatatgcct acgatgtccc aacgagcgtg gaaggaagcg   3180

tgcagaacgg cttacctaaa agccggctgg gcaataacga aggacactcg aggagccgaa   3240

gagcttattt agcctacaga gagagacagt acaacccacc ccagcaagac agcagcgatg   3300

cttgtagcac acttcccaaa agtagcagaa attttgaaaa gccagtttca accactagta   3360

aaaagatgcg ttaagggaag ccagctgtgg ttgaacttca aaatcagcaa aaatcttatg   3420

gcctcaactt ggccattcag aatggaccaa ttaaaagcaa tgggcaggag ggacccttgc   3480

tcggtaccga tagcactggc aatgttacca ctggattatg gaaacacgaa actactgtgt   3540

aacattgctg ggcttcctag gcagaaattc atataaactg tgatactcac attccttgaa   3600

gctatgagca tttaaaaact gtttacagcc accataggga ttcaaaagaa tttggaataa   3660

actttgaagt tttggatttt acttattttt atccccaaat tgttgctatt ttttaggatc   3720

tgaaacaaaa tctttctaaa acattgtttt agttgtcaaa gcaccaacag gacattttgg   3780

gatgtgaaat gtaatttctt ggaatctgta atttgtactt aatatttcag gcttgtattt   3840

aatataataa ataggtgttt gtt                                           3863
```

<210> SEQ ID NO 129
<211> LENGTH: 2165
<212> TYPE: DNA
<213> ORGANISM: Homo sapiens

<400> SEQUENCE: 129

```
aaatgactct aatctggaga catttgctga gacccttgtg cctggtcact tccgctccca     60

ggatccttga gatgcatcct ttcctgagcc taggtacttc ccggacatca gtaaccaagc    120

tcagtcttca tacaaagccc agaatgcctc catgtgactt catgcctgaa agataccagt    180

cccttggcta caaccgtgtc ctggaaatcc acaaggaaca tctttctcct gtggtgacgg    240

catatttcca gaaacccctg ctgctccacc aggggcacat ggagtggctc tttgatgctg    300

aaggaagcag atacctggat ttcttttccg ggattgttac tgtcagtgtt ggccattgcc    360

acccaaaggt gaatgcagtg gcacaaaagc agctcggccg cctgtggcat acaagcaccg    420

tcttcttcca ccctccaatg catgaatatg cagagaagct tgccgcactt cttcctgagc    480

ctcttaaggt cattttcttg gtgaacagtg gctcagaagc caatgagctg gccatgctga    540

tggccagggc gcactcaaac aacatagaca tcatttcttt cagaggagcc taccatggat    600

gcagtcctta cacacttggc ttgacaaacg tagggaccta caagatggaa ctccctggtg    660

ggacaggttg ccaaccaaca atgtgtccag atgtttttcg tggcccttgg ggaggaagcc    720

actgtcgaga ttctccagtg caaacaatca ggaagtgcag ctgtgcacca gactgctgcc    780

aagctaaaga tcagtatatt gagcaattca aagatacgct gagcacatct gtggccaagt    840

caattgctgg atttttcgca gaacctattc aaggtgtgaa tggagttgtc cagtacccaa    900
```

-continued

```
aggggtttct aaaggaagcc tttgagctgg tgcgagcaag gggaggcgtg tgcattgcag    960
atgaagtgca gacaggattt ggaaggttgg gctctcactt ctggggcttc caaacccacg   1020
atgtcctgcc tgacattgtc accatggcta aagggattgg gaatggcttt cccatggcag   1080
cagtcataac cactccagag attgccaaat ctttggcgaa atgcctgcag cacttcaaca   1140
cctttggagg gaaccccatg gcctgtgcca ttggatctgc tgtgcttgag gtgattaaag   1200
aagaaaatct acaggaaaac agtcaagaag ttgggaccta catgttacta aagtttgcta   1260
agctgcggga tgaatttgaa attgttggag acgtccgagg caaaggtctc atgataggca   1320
tagaaatggt gcaggataag ataagctgtc ggcctcttcc ccgtgaagaa gtaaatcaga   1380
tccatgagga ctgcaagcac atgggactcc tcgttggcag aggcagcatt ttttctcaga   1440
catttcgcat tgcgccctca atgtgcatca ctaaaccaga agttgatttt gcagtagaag   1500
tatttcgttc tgccttaacc caacacatgg aaagaagagc taagtaacat tgtcagaaat   1560
aaataaaacc acaagtctca agaatttgcc acgtatgttc aagggtgaat ttgaagaatt   1620
tcagaaccac tggtatccag agaaagcctg cagctctcca caggagctgt aaaagtcatg   1680
gttgactgcc taccaaccat atttgttagc agagcccctc ttatcttgag aactccattc   1740
ttcagggaaa ggatctccct agctcagaga ataaatccta attagtttat gttaggtatg   1800
gtaatttgat tccccttgc agtgattggt ttatgcatga atatgtgatg tatttttgtc    1860
cagtgaatct tgaagaaaaa tcttttggtg gaggtgcctt cagggaaagt tttcttcacc   1920
ctcactcttc agttcaagaa gagatgtctt cttgttgcgc tgagaacacc atatgttcat   1980
gacgagattc ctggcaccat gtcagccggc ttgtagtcat gaggacaacc ctttttggtg   2040
aggttggaag atggatggaa gccaagtgct tagtgatgtc aaagaagcac tcacttaagc   2100
attcctggag ccaccctacc tcagggcctc ttgatatttg aggtaataaa ttcattgttc   2160
tgtat                                                               2165
```

<210> SEQ ID NO 130
<211> LENGTH: 2279
<212> TYPE: DNA
<213> ORGANISM: Homo sapiens

<400> SEQUENCE: 130

```
aggtggagcc ttttttgctc acggcagcaa gttcccttct cctttctctc ccccggcggc     60
gtgtgcattg gctcttcaag ctgcctgtgc tgctccgtgg agtgaaaaag gcagggtgtg    120
ctcgcagact gtgctataaa ctgcaatttc tatttggggt cctcacggag aagaacacca    180
ggaaagacag acaggaccag tgccatgggc cagctttgct gctttccttt ctcaagagat    240
gaaggaaaaa tcagtgaaaa gaacggaggg gagcccgatg acgctgaact agtaaggctc    300
agtaagaggc tggtggagaa cgcggtgctc aaggctgtcc agcagtatct ggaggaaaca    360
cagaataaaa acaagccggg ggaggggagc tctgtgaaaa ccgaagcagc tgatcagaat    420
ggcaatgaca atgagaacaa caggaaatga gcccggaacg caggccccca tgtctctgtg    480
caaagcctcc ctgcttccct ctgctgagtc tagggactga cttgcagcgt gctgtttaag    540
ttaagtttct ctggtgcaat ctgtgaagat tgcctaatac ttttcatgat cgatgtgttc    600
gcattgctga aacacaacag aagaaaaatg gagtgctggg actggcagag gaaattaatt    660
gatgaaagaa gaatggccca agtttcattc gccctcagcc acgcacaagg gaaagggaac    720
tttgggttat gcctcctgga cgcaaattaa aggccgagaa agaggccttg ccatcaatgg    780
```

-continued

```
aatactgcca tttatattgc ttagcagggc atttgactac tttatctgag gccagaactc    840

tcacacacag ctatcaagtg ctaagtttaa aataatcact gttggaattg tcatctgtac    900

aattagtcca taatgtttca tgtttgtcct aagtgtgctg ttgctatgca gtgtgatctt    960

tatttatagt aaattatgtt tcatgtaaat gatatatttt tggtgaaatg caacctttc    1020

tataaaatgt gggcaacatt ttaaagtttt tttaaaatcc tattttgata agtcagtatg   1080

ccatatttaa tgaaatgtta ttatataatt tttttttctt aggcaagaaa cctattggaa   1140

ttcgagactt aattaatgaa gctttgcatc gagaaacgat gggtctgaag tccaaagtga   1200

aacagataaa ggaactttta ttaaagcctg agactcaggc cagaattagg agggagcttt   1260

ttgaaggaag acttattaac aacagtaatt cagcaaatga cgttgatttc agcacaactt   1320

tgacataagc tctacattgc gattgtgaca acatagctta tgaaatcttt tcagcttatt   1380

aagtagctct ttggtaaaca ccaaagaagt ttctgatagt gtctgcacaa cagcaaacca   1440

acatttggtg aggaattagc aatttcttgc caaagaaaat tgattctgcc caattatttt   1500

ttgagctaca cttgtgtttt agaatatctg tttctgtaat attgagagtt attttataga   1560

aatgatttct taattagctg ttgtgagata tttctcgggt ccttgcagaa aaaaacatac   1620

agactgtgaa caaatcattc acaaacagaa taaaacagag ccaacaacag tattttaagg   1680

gtcacttgcc tcctgttgac acaattgttg ctaaatcaaa agaagcgttg tccaggtgtg   1740

tctacatcta gtgttacttt taatgagaat ttgaatgttt attgaacaat agtacttgaa   1800

tgaacattta taaatgtaat tattgcgatc actggttaag aatgttttat atatccttat   1860

aatatttttc actgatcaaa atgttgttct gctttttcat ttcttaagga atacatgttt   1920

gggattttta ttttttacgt gtccgaagat aagctccagg tcttatcgta tcccttgcca   1980

tctgaacttg tttgcactgc ttctgtttga aagagcatct tgaaaaactt ccccggtatg   2040

atgattgttg gtaacaactt tttctatagt cattgatgga gtagatcatg atggagggga   2100

aatcactgga gatcaaatat gtaaaatcat ttcaaatata aaatccagtt tactcatgga   2160

ttttagctat tttttcactg ggtaaattat actacattta tttacaaatg agtttatgca   2220

ttttcatggc tcttaataaa catattgttt tcccttgaaa aaaaaaaaaa aaaaaaaaa    2279
```

```
<210> SEQ ID NO 131
<211> LENGTH: 2881
<212> TYPE: DNA
<213> ORGANISM: Homo sapiens

<400> SEQUENCE: 131

atccactcag gtctacaggc tcttagaact agaacttaga actttatctt gaaaatgtac     60

cactgttgca gaagctcctc acagagtatg tgtcaggcat ttttaacctg ctaaaggcaa    120

gaagaagtgt tcaccacata gttgcaaagg tcttcaactt gccacagcca acagaaaaat    180

caaaatgatt gaaccctttg ggaatcagta tattgtggcc aggccagtgt attctacaaa    240

tgcttttgag gaaaatcata aaaagacagg aagacatcat aagacatttc tggatcatct    300

caaagtgtgt tgtagctgtt ccccacaaaa ggccaagaga attgtcctct ctttgttccc    360

catagcatct tggttgccag cataccggct taaagaatgg ttgctcagtg atattgtttc    420

tggtatcagc acagggattg tggccgtact acaaggttta gcatttgctc tgctggtcga    480

cattccccca gtctatgggt tgtatgcatc ctttttccca gccataatct accttttctt    540

cggcacttcc agacacatat ccgtgggtcc gtttccgatt ctgagtatga tggtgggact    600

agcagtttca ggagcagttt caaaagcagt cccagatcgc aatgcaacta ctttgggatt    660
```

-continued

```
gcctaacaac tcgaataatt cttcactact ggatgacgag agggtgaggg tggcggcggc    720
ggcatcagtc acagtgcttt ctggaatcat ccagttggct tttgggattc tgcggattgg    780
atttgtagtg atatacctgt ctgagtccct catcagtggc ttcactactg ctgctgctgt    840
tcatgttttg gtttcccaac tcaaattcat ttttcagttg acagtcccgt cacacactga    900
tccagtttca attttcaaag tactatactc tgtattctca caaatagaga agactaatat    960
tgcagacctg gtgacagctc tgattgtcct tttggttgta tccattgtta aagaaataaa   1020
tcagcgcttc aaagacaaac ttccagtgcc cattccaatc gaattcatta tgaccgtgat   1080
tgcagcaggt gtatcctacg gctgtgactt taaaaacagg tttaaagtgg ctgtggttgg   1140
ggacatgaat cctggatttc agccccctat tacacctgac gtggagactt tccaaaacac   1200
cgtaggagat tgcttcggca tcgcaatggt tgcatttgca gtggcctttt cagttgccag   1260
cgtctattcc ctcaaatacg attatccact tgatggcaat caggagttaa tagccttggg   1320
actgggtaac atagtctgtg gagtattcag aggatttgct gggagtactg ccctctccag   1380
atcagcagtt caggagagca caggaggcaa aacacagatt gctgggctta ttggtgccat   1440
catcgtgctg attgtcgttc tagccattgg atttctcctg gcgcctctac aaaagtccgt   1500
cctggcagct ttagcattgg gaaacttaaa gggaatgctg atgcagtttg ctgaaatagg   1560
cagattgtgg cgaaaggaca aatatgattg tttaatttgg atcatgacct tcatcttcac   1620
cattgtcctg ggactcgggt taggcctggc agctagtgtg gcatttcaac tgctaaccat   1680
cgtgttcagg acccaatttc caaaatgcag cacgctggct aatattggaa gaaccaacat   1740
ctataagaat aaaaaagatt attatgatat gtatgagcca gaaggagtga aaattttcag   1800
atgtccatct cctatctact ttgcaaacat tggtttcttt aggcggaaac ttatcgatgc   1860
tgttggcttt agtccacttc gaattctacg caagcgcaac aaagctttga ggaaaatccg   1920
aaaactgcag aagcaaggct tgctacaagt gacaccaaaa ggatttatat gtactgttga   1980
caccataaaa gattctgacg aagagctgga caacaatcag atagaagtac tggaccagcc   2040
aatcaatacc acagacctgc ctttccacat tgactggaat gatgatcttc ctctcaacat   2100
tgaggtcccc aaaatcagcc tccacagcct cattctcgac ttttcagcag tgtcctttct   2160
tgatgtttct tcagtgaggg gccttaaatc gattttgcaa gaatttatca ggatcaaggt   2220
agatgtgtat atcgttggaa ctgatgatga cttcattgag aagcttaacc ggtatgaatt   2280
ttttgatggt gaagtgaaaa gctcaatatt tttcttaaca atccatgatg ctgttttgca   2340
tattttgatg aagaaagatt acagtacttc aaagtttaat cccagtcagg aaaaagatgg   2400
aaaaattgat tttaccataa atacaaatgg aggattacgt aatcgggtat atgaggtgcc   2460
agttgaaaca aaattctaat caacatataa ttcagaagga tcttcatctg actatgacat   2520
aaaaacaact ttatacccag aaagttattg ataagttcat acattgtacg aagagtattt   2580
ttgacagaat atgtttcaaa ctttggaaca agatggttct agcatggcat atttttcaca   2640
tatctagtat gaaattatat aagtattcta aattttatat cttgtagctt tatcaaaggg   2700
tgaaaattat tttgttcata catatttttg tagcactgac agatttccat cctagtcact   2760
accttcatgc ataggtttag cagtatagtg gcgccactgt tttgaatctc ataatttata   2820
caggtcatat taatatattt ccattaaaaa atcagttgta cagtgaaaaa aaaaaagaaa   2880
a                                                                    2881
```

<210> SEQ ID NO 132

-continued

<211> LENGTH: 2832
<212> TYPE: DNA
<213> ORGANISM: Homo sapiens

<400> SEQUENCE: 132
aggaagctga accatctatc tccagaaatg tcttcagaaa gtaaagagca acataacgtt 60
tcacccagag actcagctga aggaaatgac agttatccat ctgggatcca tctggaactt 120
caaagggaat caagtactga cttcaagcaa tttgagacca atgatcaatg cagaccttat 180
cataggatcc ttattgagcg tcaagagaaa tcagatacaa acttcaagga gtttgttatt 240
aaaaagctgc agaagaattg ccagtgcagt ccagccaaag ccaaaaatat gattttaggt 300
ttccttcctg ttttgcagtg gctcccaaaa tacgacctaa agaaaaacat tttaggggat 360
gtgatgtcag gcttgattgt gggcatatta ttggtgcccc agtccattgc ttattccctg 420
ctggctggcc aagaacctgt ctatggtctg tacacatctt tttttgccag catcatttat 480
tttctcttgg gtacctcccg tcacatctct gtgggcattt ttggagtact gtgccttatg 540
attggtgaga cagttgaccg agaactacag aaagctggct atgacaatgc ccatagtgct 600
ccttccttag gaatggtttc aaatgggagc acattattaa atcatacatc agacaggata 660
tgtgacaaaa gttgctatgc aattatggtt ggcagcactg taacctttat agctggagtt 720
tatcaggtag cgatgggctt ctttcaagtg ggttttgttt ctgtctacct ctcagatgcc 780
ttgctgagtg gatttgtcac tggtgcctcc ttcactattc ttacatctca ggccaagtat 840
cttcttgggc tcaaccttcc tcggactaat ggtgtgggct cactcatcac tacctggata 900
catgtcttca gaaacatcca taagaccaat ctctgtgatc ttatcaccag ccttttgtgc 960
cttttggttc ttttgccaac caaagaactc aatgaacact tcaaatccaa gcttaaggca 1020
ccgattccta ttgaacttgt tgttgttgta gcagccacat tagcctctca ttttggaaaa 1080
ctacatgaaa attataattc tagtattgct ggacatattc ccactgggtt tatgccaccc 1140
aaagtaccag aatggaacct aattcctagt gtggctgtag atgcaatagc tatttccatc 1200
attggttttg ctatcactgt atcactttct gagatgtttg ccaagaaaca tggttacaca 1260
gtcaaagcaa accaggaaat gtatgccatt ggcttttgta atatcatccc ttccttcttc 1320
cactgtttta ctactagtgc agctcttgca aagacattgg ttaaagaatc aacaggctgc 1380
catactcagc tttctggtgt ggtaacagcc ctggttcttt tgttggtcct cctagtaata 1440
gctcctttgt tctattccct tcaaaaaagt gtccttggtg tgatcacaat tgtaaatcta 1500
cggggagccc ttcgtaaatt tagggatctt cccaaaatgt ggagtattag tagaatggat 1560
acagttatct ggtttgttac tatgctgtcc tctgcactgc taagtactga aataggccta 1620
cttgttgggg tttgtttttc tatattttgt gtcatcctcc gcactcagaa gccaaagagt 1680
tcactgcttg gcttggtgga agagtctgag gtctttgaat ctgtgtctgc ttacaagaac 1740
cttcagacta agccaggcat caagattttc cgctttgtag cccctctcta ctacataaac 1800
aaagaatgct ttaaatctgc tttatacaaa caaactgtca acccaatctt aataaaggtg 1860
gcttggaaga aggcagcaaa gagaaagatc aaagaaaaag tagtgactct tggtggaatc 1920
caggatgaaa tgtcagtgca actttcccat gatcccttgg agctgcatac tatagtgatt 1980
gactgcagtg caattcaatt tttagataca gcagggatcc acacactgaa agaagttcgc 2040
agagattatg aagccattgg aatccaggtt ctgctggctc agtgcaatcc cactgtgagg 2100
gattccctaa ccaacggaga atattgcaaa aaggaagaag aaaaccttct cttctatagt 2160
gtgtatgaag cgatggcttt tgcagaagta tctaaaaatc agaaaggagt atgtgttccc 2220
aatggtctga gtcttagtag tgattaattg agaaggtaga tagaagaatg tctagccaat 2280
aggttaaaat ttcaagtgtc caacatttcc cagttccaca gtgggaaatt ttgcacactt 2340
gaaattttaa ccaagtggct agatattatt cctcctttga agctaatggc atttgtatat 2400
acacactgca gcagagcttg tagctggaca gagtcaaaaa gaagaaaata cggtttcagg 2460
ctttcttgca gatatgaagt attcttggaa tgcaataagt atgtattgaa ctgtactgta 2520
aagtagctcc aaaacttaat tactctcctg ttttaggggt tatacatttg gactgtgcat 2580
tctccaagag atgaagcggt gaagttggga tttacattgg aagtgctgta gacttcttta 2640
tgtggctcag tggagagagg gaaagaatgt tgcacctgct ctagtaccat aggtcaagag 2700
gcttctggat cacaaagtca taactagaca ggtttgttct tgtagttttc tatccccagt 2760
ctttgctccc cagatggcag tagtttttag taggaaagtg ccattcctgt ccttaaggca 2820
cagtctcatc ag 2832

<210> SEQ ID NO 133
<211> LENGTH: 1702
<212> TYPE: DNA
<213> ORGANISM: Homo sapiens

<400> SEQUENCE: 133
tgaaagggag tgagggagga gagatgagtg gctattccag aacgacataa agaatttcca 60
gccttggacg gacagctggg aacgtcttcc aatttggact ggtgtttaca agcgggaagc 120
taggtggacc ttggattttg gcgggtgaag aggctaggtt gtttaaggag gtggggcgcg 180
tttcagtggc tctctttgaa aaagcccagc aagatgtcag acctgctctc agtcttcctc 240
cacctcctcc ttctcttcaa gttggttgcc ccggtgacct ttcgccacca ccgctatgat 300
gatcttgtgc ggacgctgta caaggtgcaa aacgaatgcc ccggcatcac gcgggtctac 360
agcattgggc gcagcgtgga ggggagacac ctctacgtgc tggagttcag cgaccaccct 420
ggaatccacg agcccttgga accagaggtc aagtatgtgg ggaacatgca cggcaacgaa 480
gcgttgggcc gcgagctgat gctgcagctg tcggagtttc tgtgcgagga gttccggaac 540
aggaaccagc gcatcgtcca gctcatccag gacacgcgca ttcacatcct gccatccatg 600
aaccccgacg gctacgaggt ggctgctgcc cagggcccaa acaagcctgg gtatctagtt 660
ggcaggaaca atgcaaatgg agtggacctg aaccgcaact tccctgatct caatacctat 720
atctactata acgagaagta cggaggcccc aaccaccacc tgccccttcc agacaactgg 780
aaaagtcagg tggaacccga gacccgggcg gtgatccggt ggatgcactc cttcaacttt 840
gttctttcag ccaatctcca cggaggggcg gtggtggcca attacccgta tgacaagtcc 900
tttgagcacc gggtccgagg ggtccgccgc accgccagca cccccacgcc tgacgacaag 960
ctcttccaga agctggccaa ggtctactcc tatgcacatg gatggatgtt ccaaggttgg 1020
aactgcggag attacttccc agatggcatc accaatgggg cttcctggta ttctctcagc 1080
aagggaatgc aagactttaa ttatctccat accaactgct ttgagatcac gctggaactg 1140
agttgcgaca agtttccccc cgaagaggag ttacagcggg agtggctggg taatcgggaa 1200
gccctaatcc agttcctgga acaggttcac cagggcatca agggaatggt gcttgatgag 1260
aattacaata atctcgccaa tgctgtcatt tctgtcagtg ggattaacca tgatgtcact 1320
tcaggtgacc atggtgatta cttccggctg ctgcttccag gtatctacac tgttagtgcc 1380
acagcacctg ggtatgaccc agagacagta actgtgaccg tgggtcctgc ggaaccaacg 1440

-continued

```
ttggttaact tccacctcaa aagaagcatc cctcaagtaa gccctgtgag gagagctccc   1500

agcagaaggc acggagtcag agccaaagtg cagccccaag ccagaaagaa agaaatggag   1560

atgaggcagc tgcagagagg ccctgcctga aacccacagt gccaggcaac ccttcagaaa   1620

ggctttgctc ctgctctcag atcagatcaa gcattctttc tattttatta tctgggacat   1680

atttaaatac aaacatattc ag                                            1702
```

<210> SEQ ID NO 134
<211> LENGTH: 4139
<212> TYPE: DNA
<213> ORGANISM: Homo sapiens

<400> SEQUENCE: 134

```
ggcggcgcag gggcggggct ttacggacgc aagcacgtcg aagcgctgct cctggagccg     60

cggagggtgc gggtttggct gcggtggttt ctgtggcggt tgctgtggcg gagtttggag    120

gttggagaga aatccaggta ctcactagac tggtaccttc tgccaccatg gggagagcttt    180

tccggagtga agaaatgaca ctggcccagc tttttctaca gtcagaggct gcttattgtt    240

gtgtcagtga attaggagaa cttggaaagg ttcagtttcg tgacttaaat ccagatgtga    300

atgttttcca acggaaattt gtgaatgaag ttagaagatg tgaagaaatg gatcgaaagc    360

ttcgatttgt tgagaaagag ataagaaaag ctaacattcc gattatggac accggtgaaa    420

acccagaggt tcccttcccc cgggacatga ttgacttaga ggccaatttt gagaagattg    480

aaaatgaact gaaggaaatc aacacaaacc aggaagctct gaagagaaac ttcctggaac    540

tgaccgaatt aaaatttata cttcgcaaaa ctcagcaatt ttttgatgag atggcggatc    600

cagacttgtt ggaagagtcc tcatccctct tggagccaag tgagatggga agaggcactc    660

ctttaagact tggcttcgtg gctggtgtca ttaaccggga gcgcatccct acttttgagc    720

gcatgctttg gcgggtatgc cggggaaatg tgttcctgcg acaggctgaa atcgagaacc    780

ccctggagga tcctgtgact ggcgactacg tgcacaagtc tgtgtttatc attttcttcc    840

aaggcgatca gctgaaaaac agagtcaaga aatctgtgga agggttccga gcctcactct    900

atccctgtcc tgagacacca caggagagga aggaaatggc ttctggagtg aataccagga    960

ttgatgatct ccaaatggtt ctgaatcaaa cggaggatca ccgccagagg gttctgcagg   1020

cagctgctaa gaacatccgt gtctggttca tcaaagtgcg gaagatgaag gccatctatc   1080

acaccctgaa cctgtgcaac atagatgtga ctcagaaatg cttgattgca gaggtctggt   1140

gccctgtcac cgaccttgac tccatccagt ttgcactcag aaggggcacg gaacacagtg   1200

gttccactgt accttccatt ttgaacagga tgcagacaaa ccagactccc ccaacctata   1260

acaaaaccaa caagtttacc tatggctttc agaacatagt agatgcttat ggaattggaa   1320

cttaccgaga gataaatcca gctccgtata ctattatcac gttccctttt ctatttgctg   1380

tgatgtttgg agacttcggt catggcattt taatgaccct tttgctgtg tggatggtac   1440

tgagggagag ccggatcctt tcccagaaga atgagaatga gatgtttagc actgtgttca   1500

gtggtcgata cattatttta ttgatgggtg tgttctccat gtacactggc ctcatctaca   1560

atgattgctt ttccaagtct cttaatatct ttgggtcatc ctggagtgta cggccgatgt   1620

ttacttataa ttggactgaa gagacgcttc gggggaaccc tgttctacag ctgaacccag   1680

ccctccctgg agtgtttggt ggaccatacc cttttggcat tgatccaatt tggaacattg   1740

ctaccaataa actgacgttc ttgaactcct ttaagatgaa gatgtctgtt atccttggta   1800

tcatccatat gctgtttgga gtcagcctga gtctgttcaa ccatatctat ttcaagaagc   1860
```

```
ccctgaatat ctactttgga tttattcctg aaataatctt catgacctct ttgtttggct   1920
atttggttat ccttattttt tacaagtgga cggcctatga tgctcatacc tctgagaatg   1980
caccaagcct tctgatccat ttcataaaca tgttcctctt ttcctaccca gagtctggtt   2040
attcaatgtt gtattctgga cagaaaggaa ttcagtgttt cctggtagtg gttgcactac   2100
tgtgtgtacc ttggatgctg ctgtttaaac cattggtcct tcgccgtcag tatttgagga   2160
gaaagcattt gggaactctc aactttggtg ggatcagggt gggcaacgga ccgacagagg   2220
aggatgctga gattattcag catgaccagc tctccaccca ctcagaggac gcagacgagt   2280
ttgactttgg ggacaccatg gtccaccagg ccatccacac catcgagtac tgcctgggct   2340
gcatctccaa cactgcctcc tacttgcggc tctgggccct cagcctcgct catgcgcagc   2400
tgtctgaggt gctttggacc atggtgatcc acatcggcct gagcgtgaag agcttggcgg   2460
gaggtttggt gctgttcttc ttcttcactg cctttgccac cctgaccgtg gccatcctcc   2520
tgatcatgga gggcctctcg gcctttctcc acgcactgcg cttacactgg gttgagttcc   2580
agaataaatt ctacagcggg accggtttca agttcttacc cttctccttc gagcatattc   2640
gggaagggaa gtttgaagag tgagtccctg tgagggccgt gtgccccatg ctaccctccc   2700
cgcctccctc cacagtgatc agctgtgcct ctctgcctgt tggttgtgat ctgtgggcac   2760
cagctcattc gtgtcaccct gtctgtgagt catttagata gaatagtcct ccttgggtct   2820
cccaccaccc ctagctttgt gtgtagtgta gtgattttct ggctgtcact catactcact   2880
gggcaccagc cttgccctct tagcctccat ccatccagac agcccttccc acctcctggt   2940
ggtgagccag tctgcattcc cacgccatcc caaagccctt tcatcttccc cgtgcattgt   3000
agatggaagg agcacccatg ccattcaccc atctagactt tgagttccct gcatctgcca   3060
ccgtagtttc tagcaggagt agtgggggga gtaatacaga ttcttcccta gaaggggaca   3120
ctggtaacat gtcccactct tggattagca ggggtgggtc caggaagatg atatttgcgt   3180
cttttgccca ccccccctggc attcagctgg acccaactag gccatcatga gtggcttctc   3240
cctgtcatcc ccaggggtca taggatatct acaccgcctt tctgacccca ccctgcactc   3300
ccatcctttc ctctctcccc gttcatgccc tgcactacat agcacagccg ggatgcttgg   3360
aacagaggcc ttggctgctc cgcagtgcac agggcttccc tctctcgggg ttggcttctt   3420
cccaggcctt gcatgggccc tgcccacaag cacaccctca ggccgagggt gcagactgat   3480
gctcttccct gatggagacc ctgagatctt ccccaccccc aatcatgatg tcttcagtgt   3540
gggactgggg tcctcttggt tctgcctgca gcctgcctgg ctccgcccct agtgccccct   3600
cctcaccaca ctggccccag gtctcaggag gggtgtcctg ggcagggaag gtcagtgtca   3660
ctgatggttt gctgtttgga agccattggc agggctgccg tgcatgtggc tgtgagggct   3720
gcacagtcct gccaaggggc ttcctccttg tcaccccgaa ccttgtaatc gtgtgctggc   3780
gtggcagccc tggctaagtt aatccccacc gctttcagtg gtagaaagaa ttccctgagt   3840
gggccaggct ggtgccctcc tcctaccctg gcttttctga gtgagctgcc tggagccctc   3900
atcccctctc ccaggctggg ctggccctgg gcggggccac tgtgtgctgg cccactgtga   3960
cctgacccga ccttgtgcag ccccccctgcc ctggtgtcct gggttttcgt gatgatcttt   3020
gctctgtttc cagtggggtt tgaagcagag ttcagggaac cctgcccaag gtcctcctgt   4080
tcagacattc ctatgttgaa taaagtatgt ttgacttccc cggaaaaaaa aaaaaaaaa    4139
```

<210> SEQ ID NO 135

-continued

<211> LENGTH: 2808
<212> TYPE: DNA
<213> ORGANISM: Homo sapiens

<400> SEQUENCE: 135

```
cggcatgaga ggccagcctg ccagggaaat ccaggaatct gcaacaaaaa cgatgacagt     60
ctgaaatact ctctggtgcc aacctccaaa ttctcgtctg tcacttcaga cccccactag    120
ttgacagagc agcagaatat caactccagt agacttgaat gtgcctctgg gcaaagaagc    180
agagctaacg aggaaaggga tttaaagagt tttcttgggg tgtttgtcaa acttttattc    240
cctgtctgtg tgcagagggg attcaacttc aattttctgc agtggctctg ggtccagccc    300
cttacttaaa gatctggaaa gcatgaagac tgggcctttt ttcctatgtc tcttgggaac    360
tgcagctgca atcccgacaa atgcaagatt attatctgat cattccaaac caactgctga    420
aacggtagca cctgacaaca ctgcaatccc cagtttatgg gctgaagctg aagaaaatga    480
aaaagaaaca gcagtatcca cagaagacga ttcccaccat aaggctgaaa aatcatcagt    540
actaaagtca aaagaggaaa gccatgaaca gtcagcagaa cagggcaaga gttctagcca    600
agagctggga ttgaaggatc aagaggacag tgatggtcac ttaagtgtga atttggagta    660
tgcaccaact gaaggtacat tggacataaa agaagatatg attgagcctc aggagaaaaa    720
actctcagag aacactgatt ttttggctcc tggtgttagt tccttcacag attctaacca    780
acaagaaagt atcacaaaga gagaggaaaa ccaagaacaa cctagaaatt attcacatca    840
tcagttgaac aggagcagta aacatagcca aggcctaagg gatcaaggaa accaagagca    900
ggatccaaat atttccaatg gagaagagga agaagaaaaa gagccaggtg aagttggtac    960
ccacaatgat aaccaagaaa gaaagacaga attgcccagg gagcatgcta acagcaagca   1020
ggaggaagac aatacccaat ctgatgatat tttggaagag tctgatcaac caactcaagt   1080
aagcaagatg caggaggatg aatttgatca gggtaaccaa gaacaagaag ataactccaa   1140
tgcagaaatg gaagaggaaa atgcatcgaa cgtcaataag cacattcaag aaactgaatg   1200
gcagagtcaa gagggtaaaa ctggcctaga agctatcagc aaccacaaag agacagaaga   1260
aaagactgtt tctgaggctc tgctcatgga acctactgat gatggtaata ccacgcccag   1320
aaatcatgga gttgatgatg atggcgatga tgatggcgat gatggcggca ctgatggccc   1380
caggcacagt gcaagtgatg actacttcat cccaagccag gcctttctgg aggccgagag   1440
agctcaatcc attgcctatc acctcaaaat tgaggagcaa agagaaaaag tacatgaaaa   1500
tgaaaatata ggtaccactg agcctggaga gcaccaagag gccaagaaag cagagaactc   1560
atcaaatgag gaggaaacgt caagtgaagg caacatgagg gtgcatgctg tggattcttg   1620
catgagcttc cagtgtaaaa gaggccacat ctgtaaggca gaccaacagg gaaaacctca   1680
ctgtgtctgc caggatccag tgacttgtcc tccaacaaaa ccccttgatc aagtttgtgg   1740
cactgacaat cagacctatg ctagttcctg tcatctattc gctactaaat gcagactgga   1800
ggggaccaaa aaggggcatc aactccagct ggattatttt ggagcctgca aatctattcc   1860
tacttgtacg gactttgaag tgattcagtt tcctctacgg atgagagact ggctcaagaa   1920
tatcctcatg cagctttatg aagccaactc tgaacatgct ggttatctaa atgagaagca   1980
gagaaataaa gtcaagaaaa tttacctgga tgaaaagagg cttttggctg gggaccatcc   2040
cattgatctt ctcttaaggg actttaagaa aaactaccac atgtatgtgt atcctgtgca   2100
ctggcagttt agtgaacttg accaacaccc tatggataga gtcttgacac attctgaact   2160
tgctcctctg cgagcatctc tggtgcccat ggaacactgc ataacccgtt tctttgagga   2220
```

```
gtgtgacccc aacaaggata agcacatcac cctgaaggag tggggccact gctttggaat   2280

taaagaagag gacatagatg aaaatctctt gttttgaacg aagattttaa agaactcaac   2340

tttccagcat cctcctctgt tctaaccact tcagaaatat atgcagctgt gatacttgta   2400

gatttatatt tagcaaaatg ttagcatgta tgacaagaca atgagagtaa ttgcttgaca   2460

acaacctatg caccaggtat ttaacattaa ctttggaaac aaaaatgtac aattaagtaa   2520

agtcaacata tgcaaaatac tgtacattgt gaacagaagt ttaattcata gtaatttcac   2580

tctctgcatt gacttatgag ataattaatg attaaactat taatgataaa aataatgcat   2640

ttgtattgtt cataatatca tgtgcacttc aagaaaatgg aatgctactc ttttgtggtt   2700

tacgtgtatt attttcaata tcttaatacc ctaataaaga gtccataaaa atccaaaaaa   2760

aaaaaaaaaa aaaaaaaaaa aaaaaaaaaa aaaaaaaaaa aaaaaaaa                2808
```

```
<210> SEQ ID NO 136
<211> LENGTH: 1479
<212> TYPE: DNA
<213> ORGANISM: Homo sapiens

<400> SEQUENCE: 136

gcgaggcgcg gggaaggcgc acctggggtg gccctggcgt gcgggcggcg acatggagga     60

cggcgtgctc aaggagggct tcctggtcaa gaggggccac attgtccaca actggaaggc    120

gcgatggttc atccttcggc agaacacgct ggtgtactac aagcttgagg ggggtcggag    180

agtgacccct cccaagggcc ggatcctcct ggatggctgc accatcacct gcccctgcct    240

ggagtatgaa aaccgaccgc tcctcattaa gctgaagact caaacatcca cggagtactt    300

cctggaggcc tgttctcgag aggagcggga tgcctgggcc tttgagatca ccggggctat    360

tcatgcaggg cagccgggga aggtccagca gctgcacagc ctgagaaact ccttcaagct    420

gcccccgcac atcagcctgc atcgcattgt ggacaagatg cacgatagca acaccggaat    480

ccgttcaagc cccaacatgg agcagggaag cacctataaa aagaccttcc tcggctcctc    540

cctggtggac tggctcatct ccaacagctt cacggccagc cgtctggagg cggtgaccct    600

ggcctccatg ctcatggagg agaacttcct caggcctgtg ggtgtccgaa gcatgggagc    660

cattcgctct ggggatctgg ccgagcagtt cctggatgac tccacagccc tgtacacttt    720

tgctgagagc tacaaaaaga agataagccc caaggaagaa attagcctga gcactgtgga    780

gttaagtggc acggtggtga aacaaggcta cctggccaag cagggacaca agaggaaaaa    840

ctggaaggtg cgtcgctttg ttctaaggaa ggatccagct ttcctgcatt actatgaccc    900

ttccaaagaa gagaacaggc cagtgggtgg gttttctctt cgtggttcac tcgtgtctgc    960

tctggaagat aatggcgttc ccactggggt taaagggaat gtccagggaa acctcttcaa   1020

agtgattact aaggatgaca cacactatta cattcaggcc agcagcaagg ctgagcgagc   1080

cgagtggatt gaagctatca aaaagctaac atgacaagga cctgagggaa ccaggattcc   1140

tccctcctac cagatgacac agacaagagt tcctggagaa tgggagtgtt aagacttttg   1200

acttctttgt aagttttgta ctgctttgga gagtgaatgc tgccaagagt tcctcagatt   1260

acaaacagca gtggtgccat ttccttcccc atcttcatgt tacaaacctg gaaaggctag   1320

aacagccatt aggcgtcagc atcttgactt ttccccagca tcacaaacag ccatttcctc   1380

gggcaccaaa gtaggttccc tttgttggaa caattacact ggccatgcca taatgttgaa   1440

taaaactctc ttcttatgag aaaaaaaaaa aaaaaaaaa                          1479
```

<210> SEQ ID NO 137
<211> LENGTH: 2828
<212> TYPE: DNA
<213> ORGANISM: Homo sapiens

<400> SEQUENCE: 137

```
agcagccggc acggggacag ccggccgcac aacggatctg caggcgcgga gcaaaatgca     60
cccgccgcgc cgcgcggtcc tgcagccccg ccacggcccc gcggcccgca cccccccggg    120
gcgacagtga gcctctcccg ccaccaccgg gggccgagcg gagggctctc gggtgggaga    180
gcgggaccag atctcgacag ctgttcattt ccaggaagcc accgcagcca gagcgaaagg    240
ggaccttctg ccaccagcgg ggcatcagcc agcggcgcgc atggatttat gaagacactc    300
atgcaagaag tgggcaggac ttggacaaac ttttccaccg gctccgcgtc cgccgctccc    360
cgcgcctcgt ctcctttccc ctcctctccc ggcggccgcc gctgcccgcg atggtggccg    420
cgctgctggg cggcggcggc gaggcccgcg gggggacagt gccgggcgcc tggctgtgcc    480
tgatggcgct gctgcagctg ctgggctcgg cgccgcgggg atcggggctg gcgcacggcc    540
gccgcctcat ctgctggcag gcgctgctgc agtgccaggg ggagccggag tgcagctacg    600
cctacaacca gtacgccgag gcgtgcgcgc cggtgctggc gcagcacggc gggggcgacg    660
cgcccggggc cgccgccgcc gctttcccgg cctcggccgc ctctttctcg tcgcgctggc    720
gctgcccgag tcactgcatc tcggccctca ttcagctcaa ccacacgcgc cgcgggcccg    780
ccctggagga ctgtgactgc gcgcaggacg agaactgcaa gtccaccaag cgcgccattg    840
agccgtgcct gccccggacg agcggcggcg gcgcgggcgg ccccggcgcg ggcggggtca    900
tgggctgcac cgaggcccgg cggcgctgcg accgcgacag ccgctgcaac ctggcgctga    960
gccgctacct gacctactgc ggcaaagtct tcaacgggct gcgctgcacg gacgaatgcc   1020
gcaccgtcat tgaggacatg ctggctatgc ccaaggtggc gctgctcaac gactgcgtgt   1080
gcgacggcct cgagcggccc atctgcgagt cggtcaagga gaacatggcc cgcctgtgct   1140
tcggcgccga gctgggcaac ggccccggca gcagcggctc ggacgggggc ctggacgact   1200
actacgatga ggactacgat gacgagcagc gcaccggggg cgcgggtggt gagcagccgc   1260
tggacgacga cgacggcgtc ccgcacccac cgcgcccggg cagcggcgct gctgcatcgg   1320
gcggccgcgg ggacctgccc tatgggcctg ggcgcaggag cagcggcggc ggcggccgct   1380
tggcgccccg gggcgcctgg accccactcg cctccatctt gctgctgctg cttgggccgc   1440
tcttttagcc ctcgcgcccc ccgccgttgg ctgcgggaga gcccgcgtcc cactcccgtg   1500
ctcgcctcga ccccgcgccg ggcacctgtg gcttgggaca gatagaaggg atggttgggg   1560
atacttccca aaactttttc caagtcaact tggtgtagcc ggttccccgg ccacgactct   1620
gggcacttcc cctgaagctc ctctccggag cttgacttct tggacctcct cccccgcccc   1680
aattccaagc tccagaaact cccaactcgt ctgccgtcca gaaagctagc tgcagtgttc   1740
aggacgtccg ggaggaagca agcatgtggg ggacagaaca gtagtcctgg actcgaaagg   1800
gaaggtgctg accagtgggg ccttagcaat ttgaagggtt gggaaggagg aattatattt   1860
gcaaaggggc tgtctattag catatttcct ttgagggggc aaaaaaaagt gccagtatcg   1920
acttttacag attgtggcca gtgaggatat tataatccta tgtaaacaga aaagtcccac   1980
ttaccgattc attctttcac tgtttgtatc tgcgcccaga attctcagtg acgtgggggt   2040
gagggtgggt ggcgattgcc ttagagggaa cccctaaatt ggttttggat aagtttgagc   2100
ccttgacctt aatttcattg ctaccactct gatctcttag cacatttctt aggattaagg   2160
```

```
gtccaaaaat gctgatctaa ggggttgcca tggtgttgaa caatgcaact ttttatttaa   2220

aaaagctctg cactgccatg tatgaaagtc tctttatgat gtttgttttt ttgtcatttt   2280

tgttctttac atcaagaaat tttatgttta aatatgcgga gaatgtatat tgcctctgct   2340

cctatcaggg ttgctaaacc ctggtacatc gtatataaaa tgtattaaaa ctggggtttg   2400

ttaccagttg ctgtactttg tatatagaat ttttataaat tgtatgcttc agaaataatt   2460

tatttttaaa aagaaattaa aagttttaaa ctcacatcca tattacacct ttcccccctg   2520

aaatgtatag aatccatttg tcatcaggaa tcaaaaccca cagtccattg tgaagtgtgc   2580

tatatttaga acagtcttaa aatgtacagt gtattttata gaattgaagt taacattctt   2640

attttcaaga gaatttatgg acgttgtaga aatgtacaaa tgcatttcca aactgcctta   2700

aacgttgtat ttttatagac atgttttttt aaaaatccta agtttttaaa taactatgga   2760

tttgtgtatt ttttttggtt atttgtttta ttaaaacatg tacatcagta aagagtttta   2820

aacaatga                                                            2828
```

<210> SEQ ID NO 138
<211> LENGTH: 1741
<212> TYPE: DNA
<213> ORGANISM: Homo sapiens

<400> SEQUENCE: 138

```
ttggaacacc tggcgagtcc tcggtgtcgg tggccggcag tcatctcgcg gccgttcaga     60

attataaggc tgtctgcaga gatttgaaaa atggcaacaa atgaaagtgt cagcatcttt    120

agttcagcat ccttggctgt ggaatatgta gattcacttt tacctgagaa tcctctgcaa    180

gaaccattta aaaatgcttg gaactatatg ttgaataatt atacaaagtt ccagattgca    240

acatggggat cccttatagt tcatgaagcc ctttatttct tattctgttt acctggattt    300

ttatttcaat ttataccta tatgaaaaaa tacaaaattc aaaaggataa gccagagaca    360

tgggaaaacc aatggaagtg tttcaaagtt cttctcttta atcacttctg tatccagctg    420

cctttgattt gtggaaccta ttattttaca gagtatttca atattcctta tgattgggaa    480

agaatgccaa gatggtattt tcttttggca agatgctttg gttgtgcagt cattgaagat    540

acttggcact attttctgca tagactctta caccacaaaa gaatatacaa gtatattcat    600

aaagttcatc atgagtttca ggctccattt ggaatggaag ctgaatatgc acatcctttg    660

gagactctaa ttcttggaac tggatttttc attggaatcg tgcttttgtg tgatcatgta    720

attcttcttt gggcatgggt gaccattcgt ttattagaaa ctattgatgt ccatagtggt    780

tatgatattc ctctcaaccc tttaaatctg atccctttct atgctggttc tcggcatcat    840

gatttccacc acatgaactt cattggaaac tatgcttcaa catttacatg gtgggatcga    900

atttttggaa cagactctca gtataatgcc tataatgaaa agaggaagaa gtttgagaaa    960

aagactgaat aaatatctca cgtaaacctt cctgaaagat aaacgttttc ctgaattcag   1020

aaactagtag ctaacattgc ttctggagag cagaaataag catgtcttct ggctactaag   1080

tgataaaaag aacattaaca acctttaatt accttcctag tgggaacttt ttctacttta   1140

cctacaagtt ctatatatgt agaaatgaat aaatatatat ttaagtacag ttttcatgag   1200

gaagttttaa aagaccatgt tcctaagctt ccaagaaggt tttggatact agaagtatta   1260

atctatggct tttctcccag taaaaccata ggcctgaagt tcacattggg tctttaaatc   1320

ttttagatat atactggtca tttcagaaaa ttcttcatag tggtattggc cttatattta   1380
```

-continued

```
acttttttt tatttttttt ttgagacaaa gccacactct gtctccttgt ctggagtgtg   1440
gtggcacagt ctcagctcac tgcaacctct gcctcccagt tcaagcaatt cttctgcctc   1500
agcctcccaa gtagctggga ttacaggcac ccgccaccac gcccagctaa tttttgtatt   1560
tttgtagaga tggggtttct cgatgttggc caggctggtc tcaaacttct gacctcaagt   1620
gatctgccca ccttggcctc ccaaagtgct gggattacag gtgtaagcca ctgcgcccgg   1680
ccttttttaac tttaaacatg ttttagaatt cacctaaaga tcaaaatatc atggattgaa   1740
c                                                                   1741
```

```
<210> SEQ ID NO 139
<211> LENGTH: 904
<212> TYPE: DNA
<213> ORGANISM: Homo sapiens

<400> SEQUENCE: 139

ggaattccgt cgacggcagc ggcggcggcg ggtgggaaat ggcggagtat ctggcctcca     60
tcttcggcac cgagaaagac aaagtcaact gttcatttta tttcaaaatt ggagcatgtc    120
gtcatggaga caggtgctct cggttgcaca ataaaccgac gtttagccag accattgccc    180
tcttgaacat ttaccgtaac cctcaaaact cttcccagtc tgctgacggt ttgcgctgtg    240
ccgtgagcga tgtggagatg caggaacact atgatgagtt ttttgaggag gtttttacag    300
aaatggagga gaagtatggg gaagtagagg agatgaacgt ctgtgacaac ctgggagacc    360
acctggtggg gaacgtgtac gtcaagtttc gccgtgagga agatgcggaa aaggctgtga    420
ttgacttgaa taaccgttgg tttaatggac agccgatcca cgccgagctg tcacccgtga    480
cggacttcag agaagcctgc tgccgtcagt atgagatggg agaatgcaca cgaggcggct    540
tctgcaactt catgcatttg aagcccattt ccagagagct gcggcgggag ctgtatggcc    600
gccgtcgcaa gaagcataga tcaagatccc gatcccggga gcgtcgttct cggtctagag    660
accgtggtcg tggcggtggc ggtggcggtg gtggaggtgg cggcggacgg gagcgtgaca    720
ggaggcggtc gagagatcgt gaaagatctg ggcgattctg agccatgcca tttttacctt    780
atgtctgcta gaaagtgttg tagttgattg accaaaccag ttcataaggg gaattttta    840
aaaaacaaca aaaaaaaaac atacaaagat gggtttctga ataaaaattt gtagtgataa    900
cagt                                                                 904
```

```
<210> SEQ ID NO 140
<211> LENGTH: 2037
<212> TYPE: DNA
<213> ORGANISM: Homo sapiens

<400> SEQUENCE: 140

cgccccccgag cagcgcccgc gccctccgcg ccttctccgc cgggacctcg agcgaaagac     60
gcccgcccgc cgcccagccc tcgcctccct gcccaccggg cccaccgcgc cgccaccccg    120
accccgctgc gcacggcctg tccgctgcac accagcttgt tggcgtcttc gtcgccgcgc    180
tcgccccggg ctactcctgc gcgccacaat gagctcccgc atcgccaggg cgctcgcctt    240
agtcgtcacc cttctccact tgaccaggct ggcgctctcc acctgccccg ctgcctgcca    300
ctgcccccctg gaggcgccca agtgcgcgcc gggagtcggg ctggtccggg acggctgcgg    360
ctgctgtaag gtctgcgcca agcagctcaa cgaggactgc agcaaaacgc agccctgcga    420
ccacaccaag ggctggaat gcaacttcgg cgccagctcc accgctctga aggggatctg    480
cagagctcag tcagagggca gaccctgtga atataactcc agaatctacc aaaacgggga    540
```

-continued

```
aagtttccag cccaactgta aacatcagtg cacatgtatt gatggcgccg tgggctgcat    600

tcctctgtgt ccccaagaac tatctctccc caacttgggc tgtcccaacc ctcggctggt    660

caaagttacc gggcagtgct gcgaggagtg ggtctgtgac gaggatagta tcaaggaccc    720

catggaggac caggacggcc tccttggcaa ggagctggga ttcgatgcct ccgaggtgga    780

gttgacgaga aacaatgaat tgattgcagt tggaaaaggc agctcactga agcggctccc    840

tgtttttgga atggagcctc gcatcctata caacccttta caaggccaga aatgtattgt    900

tcaaacaact tcatggtccc agtgctcaaa gacctgtgga actggtatct ccacacgagt    960

taccaatgac aaccctgagt gccgccttgt gaaagaaacc cggatttgtg aggtgcggcc   1020

ttgtggacag ccagtgtaca gcagcctgaa aaagggcaag aaatgcagca agaccaagaa   1080

atcccccgaa ccagtcaggt ttacttacgc tggatgtttg agtgtgaaga aataccggcc   1140

caagtactgc ggttcctgcg tggacggccg atgctgcacg ccccagctga ccaggactgt   1200

gaagatgcgg ttccgctgcg aagatgggga gacattttcc aagaacgtca tgatgatcca   1260

gtcctgcaaa tgcaactaca actgcccgca tgccaatgaa gcagcgtttc ccttctacag   1320

gctgttcaat gacattcaca aatttaggga ctaaatgcta cctgggtttc cagggcacac   1380

ctagacaaac aagggagaag agtgtcagaa tcagaatcat ggagaaaatg ggcgggggtg   1440

gtgtgggtga tgggactcat tgtagaaagg aagccttgct cattcttgag gagcattaag   1500

gtatttcgaa actgccaagg gtgctggtgc ggatggacac taatgcagcc acgattggag   1560

aatactttgc ttcatagtat tggagcacat gttactgctt cattttggag cttgtggagt   1620

tgatgacttt ctgttttctg tttgtaaatt atttgctaag catattttct ctaggctttt   1680

ttccttttgg ggttctacag tcgtaaaaga gataataaga ttagttggac agtttaaagc   1740

ttttattcgt cctttgacaa aagtaaatgg gagggcattc catcccttcc tgaagggggga   1800

cactccatga gtgtctgtga gaggcagcta tctgcactct aaactgcaaa cagaaatcag   1860

gtgttttaag actgaatgtt ttatttatca aaatgtagcc tttggggagg gaggggaaat   1920

gtaatactgg aataatttgt aaatgatttt aattttatat tcagtgaaaa gattttattt   1980

atggaattaa ccatttaata aagaaatatt tacctaataa aaaaaaaaaa aaaaaaa      2037
```

<210> SEQ ID NO 141
<211> LENGTH: 3186
<212> TYPE: DNA
<213> ORGANISM: Homo sapiens

<400> SEQUENCE: 141

```
ggaactggca gcggggagga ggctctagcg aggcctgaaa ggctgcgtaa ccaggcagga     60

gtaggggttg gggttcgggg ttgggggaca gccagggatc gcgtctgata tgctgttggg    120

gtcgtgaccg tctgggggcc gaggcaggca ctggccagac ccagccaggg atcctcgtat    180

tcgtcgagcc taatttccag cagccgggta ggcctcacca gaggctcctt tccgtgaggc    240

cgcccccaat tcctgcccct attctctgcc tgggagatgg cttccccgag ccccccgccg    300

gagtcgaagg ggttgctgac atttgaggat gtggctgtgt tttttaccca ggaggagtgg    360

gattatctgg acccagctca gagaagcctg tataaagatg tcatgatgga gaattatgga    420

aacctggtct cactggatgt tttgaacaga gataaggatg aggagccaac tgtaaaacaa    480

gagattgaag aaattgagga agaagtggaa ccacagggtg taatagttac aagaatcaaa    540

agtgaaattg accaggatcc tatgggtaga gaaacatttg aacttgttgg taggttagat    600
```

-continued

```
aaacaaagag ggatcttcct atgggaaata ccaagggaat ctttgaccca ggaacagaga    660
atgttcagag aaaacactaa cattatccgt aaaagaccaa actcagaaga gaaatgccat    720
aaatgtgaag aatgtggaaa gggttttgtc cgcaaggccc atttcattca acatcaaagg    780
gtccatactg gtgagaaacc ttttcagtgc aatgaatgtg ggaaaagttt tagtcgcagt    840
tcatttgtta ttgaacatca gagaattcac actggggaaa ggccctatga gtgtaattac    900
tgtggaaaaa cctttagtgt gagctcaacc cttattagac atcagagaat ccacactgga    960
gaaagaccct atcagtgtaa tcagtgtaaa cagagcttca gccagagaag gagccttgtt   1020
aaacatcaaa ggattcatac aggtgagaaa ccccataaat gtagtgactg tgggaaagcc   1080
ttcagttgga aatcacacct tattgagcat caaagaactc acactggtga gaaaccttat   1140
cactgtacca aatgtaagaa gagctttagt cgaaattcat tgcttgttga gcatcaaaga   1200
attcacactg ggaaagaccc ccataaatgt ggtgaatgtg ggaaagcctt tcgattaagc   1260
acataccta tacaacacca aaaaattcac actggcgaga agccttttct ttgtattgag    1320
tgtggaaaaa gtttcagtcg gagctcattc cttattgaac atcagaggat ccatactggt   1380
gaaagacctt atcagtgcaa agagtgtggg aaaagtttca gtcagctttg caaccttact   1440
cgtcatcaga gaattcacac aggagacaag ccccataaat gtgaggaatg tggaaaagcc   1500
tttagtagaa gctcaggtct tattcagcat cagagaattc acaccaggga gaagacttat   1560
ccatacaatg aaactaagga aagttttgat ccaaattgca gtcttgttat acagcaggaa   1620
gtctacccta aggagaaatc ttataaatgt gatgaatgtg ggaaaacttt tagtgttagt   1680
gctcatcttg tacaacatca aagaatccac actggtgaaa agccctatct atgtactgtc   1740
tgtgggaaaa gcttcagccg gagctcattt cttattgaac atcagagaat ccacactggt   1800
gagagaccct atctgtgcag acagtgtgga aaaagcttta gtcagctttg taatcttatt   1860
cgacatcagg gtgttcacac aggtaataaa ccccataaat gtgatgaatg tggaaaggcc   1920
tttagccgga actcgggtct tattcagcat cagagaatac acacaggaga gaaaccttat   1980
aagtgtgaga agtgcgacaa aagtttcagt caacagcgca gtcttgtcaa ccatcagaag   2040
atccatgcag aggtgaaaac ccaagaaacc catgaatgtg acgcttgtgg tgaagccttt   2100
aattgccgta tttctcttat tcagcatcag aaattgcaca cagcatggat gcaataaatg   2160
tagagcaata cataagctca atttgatttg agactagtac ccaagtgcag ttttagtatg   2220
gctcaacatg ggtcagattt agtgataaag caaattctcc ttggcctcag gcaaatagtt   2280
tctaaagatt ctgtgaatag tggacaactg cccatgagca tttgacttcc cttactcttt   2340
gatgatcgta gagaaagact tggtaattta tctaagtatc tttaataaat ctttcagcag   2400
agagattaaa cctaggttca gagcatgggt gctctgaggg acaaagttgg attagtataa   2460
gggagctgga gcagctgata gtggaaaaca gaataatgat tcaaagagtc ttctgtcacc   2520
atgtcatatt gtggttcttt cagttccatg atatgtttgg ctctgcatgc caaagtccag   2580
tgattaagca tatataagtt gtcaaggaaa caaagcccaa atgtttttaa aacaagtata   2640
cagtttttgt cattgtttaa gaaagccagt tgtttggcat gtgagttaaa ggcagttcca   2700
atgcctgatg gttcccagat ctatgaaatg agtggaccat taaccttaca tgtaaagatt   2760
atgttagtaa ttaagaaacc taacaaaggt gttaccaagg aacctttggg agtgcctttt   2820
ttgtttttca agatggaccc aaaaaagtgg aggaagatat tgttcttttg tgccctccta   2880
cctgtgagag atatttgtag tcctatgtga atgagcttat ccctccacaa ccaggtgcat   2940
atgaaagtgt acatattatg actgccaagt attggaaatg aaaagacctg gagtctatgc   3000
```

-continued taggaagctg agatattttg gtattgcatt ggtttttatg gtaactaggt tttgcatgca 3060
attaaaaatc cttatttctt gttctagggc ttcccttagt taatggttat tataaaccta 3120
ttaattcatc tgttttaacc attaaaacct gttttgtttt tagctttgaa aaaaaaaaaa 3180
aaaaaa 3186

<210> SEQ ID NO 142
<211> LENGTH: 1903
<212> TYPE: DNA
<213> ORGANISM: Homo sapiens

<400> SEQUENCE: 142
gggcaacgga ggggaaataa aagggaacgg ctccgaatct gccccagcgg ccgctgcgag 60
acctcggcgc cgacatcgcg acagcgaagc gctttgcacg ccaggaaggt cccctctatg 120
tgctgctgag ccggtcctgg acgcgacgag cccgccctcg gtcttcggag cagaattcgc 180
aaaaacggaa ggactggaaa tggcagacca tatgatggca atgaaccacg ggcgcttccc 240
cgacggcacc aatgggctgc accatcaccc tgcccaccgc atgggcatgg ggcagttccc 300
gagcccccat caccaccagc agcagcagcc ccagcacgcc ttcaacgccc taatgggcga 360
gcacatacac tacggcgcgg gcaacatgaa tgccacgagc ggcatcaggc atgcgatggg 420
gccggggact gtgaacggag ggcacccccc gagcgcgctg gcccccgcgg ccaggtttaa 480
caactcccag ttcatgggtc ccccggtggc cagccaggga ggctccctgc cggccagcat 540
gcagctgcag aagctcaaca accagtattt caaccatcac ccctaccccc acaaccacta 600
catgccggat ttgcaccctg ctgcaggcca ccagatgaac gggacaaacc agcacttccg 660
agattgcaac cccaagcaca gcggcggcag cagcaccccc ggcggctcgg gcggcagcag 720
cacccccggc ggctctggca gcagctcggg cggcggcgcg ggcagcagca acagcggcgg 780
cggcagcggc agcggcaaca tgcccgcctc cgtggcccac gtccccgctg caatgctgcc 840
gcccaatgtc atagacactg atttcatcga cgaggaagtt cttatgtcct tggtgataga 900
aatgggtttg gaccgcatca aggagctgcc cgaactctgg ctggggcaaa acgagtttga 960
ttttatgacg gacttcgtgt gcaaacagca gcccagcaga gtgagctgtt gactcgatcg 1020
aaaccccggc gaaagaaatc aaacccccaa cttcttcggc gtgaattaaa agaaacattc 1080
ccttagacac agtatctcac ttttcagatc ttgaaaggtt tgagaacttg gaaacaaagt 1140
aaactataaa cttgtacaaa ttggttttaa aaaaaattgc tgccactttt tttcctgttt 1200
ttgtttcgtt tttgtagcct tgacattcac ccacctccct tatgtagttg aaatatctag 1260
ctaacttggt ctttttcgtt gtttgttttt actcctttcc ctcactttct ccagtgctca 1320
actgttagat attaatcttg gcaaactgct taatcttgtg gattttgtag atggtttcaa 1380
atgactgaac tgcattcaga tttacgagtg aaaggaaaaa ttgcattagt tggttgcatg 1440
aacttcgaag ggcagatatt actgcacaaa ctgccatctc gcttcatttt tttaactatg 1500
catttgagta cagactaatt tttaaaatat gctaaactgg aagattaaac agatgtgggc 1560
caaactgttc tggatcagga aagtcatact gttcactttc aagttggctg tcccccccgc 1620
cgcccccccc acccccatat gtacagatga taatagggtg tggaatgtcg tcagtggcaa 1680
acatttcaca gatttttatt ttgtttctgt cttcaacatt tttgacactg tgctaatagt 1740
tatattcagt acatgaaaag atactactgt gttgaaagct ttttaggaaa ttttgacagt 1800

-continued

```
atttttgtac aaaacatttt tttgaaaaaa tacttgttaa tttattctat tttaatttgc   1860

caatgtcaat aaaaagttaa gaaaaaaaaa aaaaaaaaaa aaa                     1903
```